(12) United States Patent
Yao et al.

(10) Patent No.: US 6,576,664 B1
(45) Date of Patent: Jun. 10, 2003

(54) INHIBITORS OF AGGRECANASE AND MATRIX METALLOPROTEINASES FOR THE TREATMENT OF ARTHRITIS

(75) Inventors: Wenqing Yao, Kennett Square, PA (US); Carl P. Decicco, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/134,484

(22) Filed: Aug. 14, 1998

Related U.S. Application Data

(60) Provisional application No. 60/055,944, filed on Aug. 18, 1997, and provisional application No. 60/068,335, filed on Dec. 19, 1997.

(51) Int. Cl.[7] .................... A61K 31/235; A61K 31/205; C07C 381/00; C07C 233/00
(52) U.S. Cl. ................. 514/533; 514/555; 562/428; 564/169; 564/170
(58) Field of Search ................. 564/169, 170; 562/428; 514/533, 555

(56) References Cited

U.S. PATENT DOCUMENTS

| | | | | |
|---|---|---|---|---|
| 5,413,999 A | * | 5/1995 | Vacca et al. | 514/231.5 |
| 5,508,404 A | * | 4/1996 | Askin et al. | 544/365 |
| 6,008,243 A | * | 12/1999 | Bender et al. | 514/422 |

FOREIGN PATENT DOCUMENTS

| | | |
|---|---|---|
| EP | 574758 | 12/1993 |
| GB | 2268935 | 1/1994 |
| WO | 9005716 | 5/1990 |
| WO | 9213831 | 8/1992 |
| WO | 9221360 | 12/1992 |
| WO | 9402446 | 2/1994 |
| WO | 9424140 | 10/1994 |
| WO | 9509841 | 4/1995 |
| WO | 9817643 | 4/1998 |

OTHER PUBLICATIONS

Holloway et al., 1995, J. Med. Chem., 38(2), 305–17.
Robinson et al., Jul. 23, 1996, Bioorganic & Medicinal Chemistry Letters, 6(4), 1719–1724.
Mankin et al. 1970, J. Bone Joint Surg.. 52A, 424–434.
Mankin et al. 1978, Arthritis Rheum., 21, 761–766.
Woessner et al. 1983, Arthritis Rheum., 26, 63–68.
Woessner et al. 1984, Arthritis Rheum., 27, 305–312.
Lohmander et al. 1993, Arthritis Rheum., 36, 1214–1222.
Wahl et al. 1990, Ann. Rep. Med. Chem., 25, 177–184.
Feldman et al. 1994, Lancet, 344, 1105.
Macdonald et al. 1990, Clin. Exp. Immunol., 81, 301.
Gearing et al., 1994, Nature, 370, 555.
Remington's Pharm. Sci. 1985, 17th Ed., Mack Pub. Co., p. 1418.
Wolfe et al., 1996, Tetrahedron, 5, 7525–7546.
Hartwig, J. F. *Synlett*, 1996, 329.
Ghosh et al 1997 *Synthesis*, 541–544.
Jacobsen et al., 1991, J. Am. Chem. Soc. 113, 7163–7064.
Sharpless et al 1996,. Angew. Chem. Int. Ed. Engl., 35, 2813.
Sudo et al., 1996, Tetrahedron Asymetry, 7, 2939–2956.
Roberts and Vellaccio, 1983, The Peptides, 5: 342–429.

* cited by examiner

Primary Examiner—Mukund J. Shah
Assistant Examiner—Tamthom N. Truong

(57) ABSTRACT

This invention relates to molecules which inhibit metalloproteinases, including aggrecanase, and the production of tumor necrosis factor (TNF). In particular, the compounds are inhibitors of metalloproteinases involved in tissue degradation and inhibitors of the release of tumor necrosis factor. The present invention also relates to pharmaceutical compositions comprising such compounds and to methods of using these compounds for the treatment of inflammatory diseases.

36 Claims, No Drawings

INHIBITORS OF AGGRECANASE AND MATRIX METALLOPROTEINASES FOR THE TREATMENT OF ARTHRITIS

This application claims the benefit of U.S. Provisional Application No. 60/055,944 filed Aug. 18, 1997 and U.S. Provisional Application No. 60/068,335 filed on Dec. 19, 1997.

FIELD OF THE INVENTION

The present invention relates to novel molecules which inhibit metalloproteinases, including aggrecanase, and the production of tumor necrosis factor (TNF), pharmaceutical preparations containing them and to their use as pharmaceutical agents. In particular the compounds are inhibitors of metalloproteinases involved in tissue degradation and inhibitors of the release of tumor necrosis factor.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

This invention describes novel molecules that inhibit aggrecanase and other metalloproteinases. These novel molecules are provided as cartilage protecting therapeutics. The inhibition of aggrecanase and other metalloproteinases by these novel molecules prevent the degradation of cartilage by these enzymes, thereby alleviating the pathological conditions of osteo- and rheumatoid arthritis.

Tumor necrosis factor (TNF) is a cell associated cytokine that is processed from a 26 kD precursor form to a 17 kD active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L.S. et al. Arthritis Rheum. 36, 1993, 1214–22) and Crohn's disease (Macdonald T. et al. Clin. Exp. Immunol. 81, 1990, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes novel molecules that inhibit this conversion and hence the secretion of active TNF-α from cells. These novel molecules provide a means of mechanism based therapeutic intervention for diseases including but not restricted to septic shock, haemodynamic shock, sepsis syndrome, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, rheumatoid arthritis, multiple sclerosis, radiation damage, hyperoxic alveolar injury, HIV and non-insulin dependent diabetes melitus.

Since excessive TNF production has been noted in several disease conditions also characterized by MMP-mediated tissue degradation, compounds which inhibit both MMPs and TNF production may also have a particular advantage in diseases where both mechanisms are involved.

There are several patents which disclose hydroxamate and carboxylate based MMP inhibitors.

PCT International Publication No. WO 92/213260 describes N-carboxyalkylpeptidyl compounds of general formula:

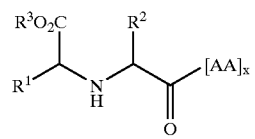

wherein AA is an amino acid, as inhibitors of matrix metallproteinase mediated diseases.

PCT International Publication No. WO 90/05716 discloses hydroxamic acid based collagenase inhibitors having the general formula:

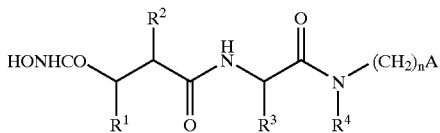

PCT International Publication No. WO 92/13831 describes related hydroxamic acids having collagenase inhibiting activity with the general formula:

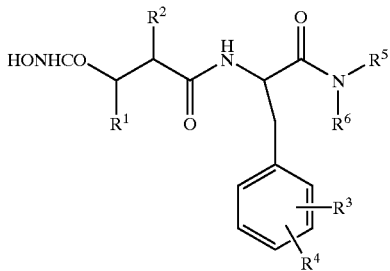

PCT International Publication No. WO 94/02446 discloses metalloproteinase inhibitors which are natural amino acid derivatives of general formula:

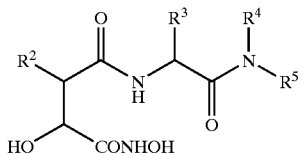

WO95/09841 describes compounds that are hydroxamic acid derivatives and are inhibitors of cytokine production.

European Patent Application Publication No. 574,758 A1, discloses hydroxamic acid derivatives as collagenase inhibitors having the general formula:

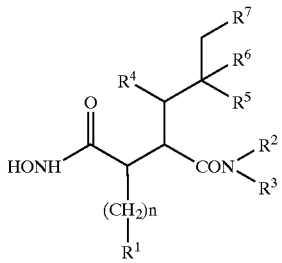

GB 2 268 934 A and WO 94/24140 claim hydroxamate inhibitors of MMPs as inhibitors of TNF production.

The compounds of the current invention act as inhibitors of MPs, in particular aggrecanase and TNF-C, thereby preventing cartilage loss and destruction and inflammatory disorders involving TNF. The hydroxamic and carboxylic acids and derivatives contain a cyclic peptide mimic attached to a succinate peptide mimic, and thus the inhibitors are non-peptide in nature. A selection of these molecules are water soluble and are orally bioavailable.

SUMMARY OF THE INVENTION

This invention provides novel hydroxamic acids and carboxylic acids and derivatives thereof of formula (I) (described below) which are useful as inhibitors of metalloproteinases, such as aggrecanase and TNF-C. The present invention also includes pharmaceutical compositions comprising such compounds of formula (I) and methods of using such compounds for the treatment of arthritis and other inflammatory disorders as described previously, in a patient.

Also included in the present invention are pharmaceutical kits comprising one or more containers containing pharmaceutical dosage units comprising a compound of formula (I), for the treatment of arthritis and other inflammatory disorders as described previously.

The present invention also includes methods of inhibiting metalloproteinases, such as aggrecanase and TNF-C, and for the treatment of arthritis by administering a compound of formula (I) in combination with one or more second therapeutic agents selected from other inhibitors of metalloproteinases, such as aggrecanase and TNF-C and/or therapeutic agents for the treatment of arthritis and inflammation.

DETAILED DESCRIPTION OF THE INVENTION

This invention provides novel hydroxamic acids and carboxylic acids and derivatives thereof of formula (I) (described below) which are useful as inhibitors of metalloproteinases, such as aggrecanase and TNF-C. The present invention also includes pharmaceutical compositions comprising such compounds of formula (I) and methods of using such compounds for the treatment of arthritis and other inflammatory disorders as described previously, in a patient.

Also included in the present invention are pharmaceutical kits comprising one or more containers containing pharmaceutical dosage units comprising a compound of formula (I), for the treatment of arthritis and other inflammatory disorders as described previously.

The present invention also includes methods of inhibiting metalloproteinases, such as aggrecanase and tumor necrosis factor alpha, and for the treatment of arthritis by administering a compound of formula (I) in combination with one or more second therapeutic agents selected from other inhibitors of metalloproteinases, such as aggrecanase and tumor necrosis factor alpha and/or therapeutic agents for the treatment of arthritis and inflammation.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "H" is intended to include substitutions with deuterium or tritium. Where "H" is not indicated but is part of a bond then substitutions with deuterium or tritium are also intentded.

As used herein, "$C_{1-10}$ alkyl" or "$C_{1-10}$ alkylene" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl;

"Alkenyl" or "alkenylene" is intended to include hydrocarbon chains of either a straight or branched configuration and one or more unsaturated carbon-carbon bonds which may occur in any stable point along the chain, such as ethenyl, propenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, and the like.

As used herein, "aryl" or "aromatic residue" is intended to include phenyl or naphthyl as well as commonly referred to "heterocycle" or "heteroaryl" or "heterocyclic" compounds.

As used herein the term "alkylaryl" represents an aryl group attached through an alkyl bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle",or "heterocyclic system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

As used herein, the term "aromatic heterocyclic system" is intended to mean a stable 5- to 7-membered monocyclic or bicyclic or 7- to 14-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent. compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" and "prodrug derivatives" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

[1] There is provided by this invention a compound of the formula (I):

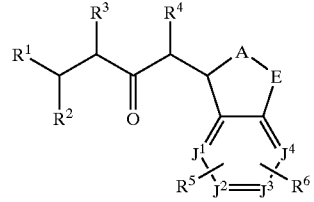

Formula I or a pharmaceutically acceptable salt form or a steroisomer thereof, wherein:

$R^1$ is selected from:
—$CO_2H$, —C(O)NHOH, —C(O)NHOR$^7$, —SH, —$CH_2CO_2R^7$, —COR$^7$, —N(OH)COR$^7$, —$SN_2H_2R^7$, —SONHR$^7$, —$CH_2CO_2H$, —PO(OH)$_2$, —PO(OH)NHR$^7$, —$CH_2SH$, —C(O)NHOR$^7$, —CO$_2R^7$, and common prodrug derivatives;

$R^2$ is selected from the formula:

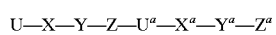

U—X—Y—Z—U$^a$—X$^a$—Y$^a$—Z$^a$ wherein:
U is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X is absent or selected from H, $C_{1-10}$ alkylene, $C_{2-10}$ alkenylene, $C_{2-10}$ alkynylene;

Y is absent or selected from H, O, NR$^a$, S(O)$_p$, and C(O);

Z is absent or selected from H, a $C_{3-13}$ carbocyclic residue substituted with 0–5 R$^b$ and a 5–14 membered heterocyclic system containing from 1–4 heteroatoms selected from the group consisting of N, O, and S substituted with 0–5 R$^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^{a'}$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^3$ is selected from the formula:

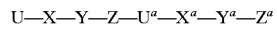

wherein:

U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^{a'}$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^4$ is selected from:
hydrogen, ($C_1$–$C_5$)alkyl, ($C_1$–$C_5$)alkyl-aryl, $R^5$ and $R^6$ are independently selected from:

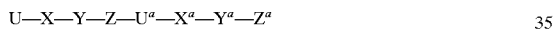

wherein:

U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^{a'}$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

R⁷ is selected from: $C_1$–$C_{10}$ alkyl, alkylaryl, and common prodrug derivatives A is selected from:
  $SO_2$, SO, CHOH;

E is $(CR^8R^9)_m$—W—$(CR^8R^9)_n$,
  wherein W can be absent or selected from:
    $CH_2$, CO, O, $S(O)_m$ and $NR^{10}$,
    m is 0–2,
    n is 0–2;
    with the proviso that when W is O, S or $NR^{10}$ then m must not be 0;

$R^8$ and $R^9$ is independently selected from:
  H,
  $C_1$–$C_8$ alkyl substituted with 0–5 $R^b$,
  $C_1$–$C_8$ alkenyl,
  $C_1$–$C_8$ alkylaryl substituted with 0–5 $R^b$,
  $C_{3-13}$ carbocyclic residue substituted with 0–5 $R^b$,
  5–14 membered heterocyclic system containing from 1–4 heteroatoms selected from the group consisting of N, O, and S substituted with 0–5 $R^b$;
  amino,
  $C_1$–$C_8$ alkyl-$NR^{10}$
  hydroxyl,
  $R^8$ and $R^9$ can also form a ring interrupted by $NR^{10}$, O, S(O)m.

$R^{10}$ is selected from:
  hydrogen,
  $C_1$–$C_8$ alkyl
  $C_1$–$C_8$ alkylaryl $J^1$, $J^2$, $J^3$, $J^4$ are independently selected from:
  CH, or N.
  with no more than two N in the cycle.

[2] The present invention includes compounds of formula (I) wherein:
  $R^1$ is selected from: —$CO_2H$, —C(O)NHOH, —C(O)NHOR⁷, —SH, —$CH_2CO_2R^7$, —COR⁷, —N(OH)COR⁷, —$SN_2H_2R^7$, —SONHR⁷, —$CH_2CO_2H$, —PO(OH)₂, —PO(OH)NHR⁷, —$CH_2SH$, —C(O)NHOR⁷, —$CO_2R^7$, and common prodrug derivatives;

$R^2$ is selected from the formula:

U—X—Y—Z—$U^a$—$X^a$—$Y^a$—$Z^a$ wherein:
  U is absent or is selected from: O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;
  X is absent or selected from H, $C_{1-10}$ alkylene, $C_{2-10}$ alkenylene, $C_{2-10}$ alkynylene;
  Y is absent or selected from H, O, $NR^a$, $S(O)_p$, and C(O);
  Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;
  $U^a$ is absent or is selected from: H, O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;
  $X^a$ is absent or selected from H, $C_{1-10}$ alkylene, $C_{2-10}$ alkenylene, $C_{2-10}$ alkynylene;
  $Y^a$ is absent or selected from H, O, $NR^a$, $S(O)_p$, and C(O);
  $Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;
  $R^a$, at each occurrence, is independently selected from H, $C_{1-4}$ alkyl, phenyl or benzyl;
  $R^{a'}$, at each occurrence, is independently selected from H, $C_{1-4}$ alkyl, phenyl or benzyl;
  alternatively, $R^a$ and $R^{a'}$ taken together with the nitrogen to which they are attached form a 5 or 6 membered ring containing from 0–1 additional heteroatoms selected from the group consisting of N, O, and S;
  $R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;
  , at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^3$ is selected from the formula:

U—X—Y—Z—$U^a$—$X^a$—$Y^a$—$Z^a$ wherein:
  U is absent or is selected from: O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;
  X is absent or selected from H, $C_{1-10}$ alkylene, $C_{2-10}$ alkenylene, $C_{2-10}$ alkynylene;
  Y is absent or selected from H, O, $NR^a$, $S(O)_p$, and C(O);
  Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;
  $U^a$ is absent or is selected from: H, O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;
  $X^a$ is absent or selected from H, $C_{1-10}$ alkylene, $C_{2-10}$ alkenylene, $C_{2-10}$ alkynylene;
  $Y^a$ is absent or selected from H, O, $NR^a$, $S(O)_p$, and C(O);
  $Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;
  $R^a$, at each occurrence, is independently selected from H, $C_{1-4}$ alkyl, phenyl or benzyl;
  $R^{a'}$, at each occurrence, is independently selected from H, $C_{1-4}$ alkyl, phenyl or benzyl;
  alternatively, $R^a$ and $R^{a'}$ taken together with the nitrogen to which they are attached form a 5 or 6 membered ring containing from 0–1 additional heteroatoms selected from the group consisting of N, O, and S;
  $R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;
  , at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^4$ is selected from:
hydrogen, $R^5$ and $R^6$ are independently selected from:

$$U—X—Y—Z—U^a—X^a—Y^a—Z^a$$

wherein:

U is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^7$ is selected from: $C_1$–$C_{10}$ alkyl, alkylaryl, and common prodrug derivatives A is selected from:
$SO_2$, SO, CHOH;

E is $(CR^8R^9)_m$—W—$(CR^8R^9)_n$,
wherein W can be absent or selected from:
$CH_2$, CO, O, $S(O)_m$ and $NR^{10}$,
m is 0–2,
n is 0–2;

with the proviso that when w is O, S or $NR^{10}$ then m must not be 0;

$R^8$ and $R^9$ is independently selected from:
H,
$C_1$–$C_8$ alkyl substituted with 0–5 $R^b$,
$C_1$–$C_8$ alkenyl,
$C_1$–$C_8$ alkylaryl substituted with 0–5 $R^b$,
$C_{3-13}$ carbocyclic residue substituted with 0–5 $R^b$,
5–14 membered heterocyclic system containing from 1–4 heteroatoms selected from the group consisting of N, O, and S substituted with 0–5 $R^b$;
amino,
$C_1$–$C_8$ alkyl-$NR^{10}$
hydroxyl, $R^8$ and $R^9$ can also form a ring interrupted by $NR^{10}$, O, S(O)m.

$R^{10}$ is selected from:
hydrogen,
$C_1$–$C_8$ alkyl
$C_1$–$C_8$ alkylaryl $J^1$, $J^2$, $J^3$, $J^4$ are independently selected from:
CH, or N.
with no more than two N in the cycle.

[3] The present invention includes preferred compounds of formula (I) wherein:

$R^1$ is selected from:
—$CO_2H$, —C(O)NHOH, —C(O)NHOR$^7$, —SH, —$CH_2CO_2R^7$,
and common prodrug derivatives;

$R^2$ is selected from the formula:

$$U—X—Y—Z—U^a—X^a—Y^a—Z^a$$

wherein:

U is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^a$, $S(O)_2 NR^aR^{a'}$, $S(O)_p R^a$, $CF_3$, $CF_2CF_3$, and a 5–14 membered heterocyclic system containing from 1–4 heteroatoms selected from the group consisting of N, O, and S;

$R^3$ is selected from the formula:

$$U{-}X{-}Y{-}Z{-}U^a{-}X^a{-}Y^a{-}Z^a$$

wherein:

U is absent or is selected from: O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2 NR^aR^{a'}$, $S(O)_p R^a$, $CF_3$, $CF_2CF_3$, and a 5–14 membered heterocyclic system containing from 1–4 heteroatoms selected from the group consisting of N, O, and S;

$R^4$ is selected from:
hydrogen, $R^5$ and $R^6$ are independently selected from:

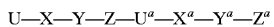

$$U{-}X{-}Y{-}Z{-}U^a{-}X^a{-}Y^a{-}Z^a$$

wherein:

U is absent or is selected from: O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^aC(O)$, OC(O)O, OC(O)$NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p R^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2 NR^aR^{a'}$, $S(O)_p R^a$, $CF_3$, $CF_2CF_3$, and a 5–14 membered heterocyclic system containing from 1–4 heteroatoms selected from the group consisting of N, O, and S;

$R^7$ is selected from: $C_1$–$C_{10}$ alkyl, alkylaryl, and common prodrug derivatives A is selected from:
$SO_2$, SO, CHOH;

E is $(CR^8R^9)_m$—W—$(CR^8R^9)_n$,
wherein W can be absent or selected from:
$CH_2$, CO, O, $S(O)_m$ and $NR^{10}$,
m is 0–2,
n is 0–2;
with the proviso that when W is O, S or $NR^{10}$ then m must not be 0;

$R^8$ and $R^9$ is independently selected from:
H,
$C_1$–$C_8$ alkyl substituted with 0–5 $R^b$,
$C_1$–$C_8$ alkenyl,
$C_1$–$C_8$ alkylaryl substituted with 0–5 $R^b$;
$C_{3-13}$ carbocyclic residue substituted with 0–5 $R^b$,
5–14 membered heterocyclic system containing from 1–4 heteroatoms selected from the group consisting of N, O, and S substituted with 0–5 $R^b$;
amino,
$C_1$–$C_8$ alkyl-$NR^{10}$
hydroxyl,
$R^8$ and $R^9$ can also form a ring interrupted by $NR^{10}$, O, $S(O)_m$.
$R^{10}$ is selected from:
hydrogen,
$C_1$–$C_8$ alkyl
$C_1$–$C_8$ alkylaryl
$J^1$, $J^2$, $J^3$, $J^4$ are independently selected from:
CH, or N.
with no more than two N in the cycle.

[4] There is provided by this invention preferred compounds of the formula (II):

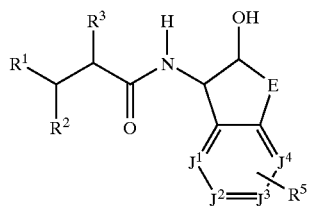

Formula II or a pharmaceutically acceptable salt form or a steroisomer thereof, wherein:

$R^1$ is selected from:
—$CO_2H$, —C(O)NHOH, —C(O)$NHOR^7$, —SH, —$CH_2CO_2R^7$,
and common prodrug derivatives;

$R^2$ is selected from the formula:

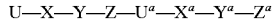

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, $S(O)_p$, $S(O)_p NR^a$, $NR^a$S $(O)_p$, and $NR^a SO_2 NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, $S(O)_p$, $S(O)_p NR^a$, $NR^a$S $(O)_p$, and $NR^a SO_2 NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^a R^{a'}$, C(O)$R^a$, C(O)$OR^a$, C(O)$NR^a R^{a'}$, $S(O)_2 NR^a R^{a'}$, $S(O)_p R^a$, $CF_3$, and $CF_2 CF_3$;

$R^c$, at each occurrence, is independently selected from $C_{1-6}$ alkyl, $OR^a$, Cl, F, Br, I, =O, CN, $NO_2$, $NR^a R^{a'}$, C(O)$R^a$, C(O)$OR^a$, C(O)$NR^a R^{a'}$, $NR^a S(O)_2 R^a$, $S(O)_2$ $NR^a R^{a'}$, $S(O)_p R^a$, $CF_3$, $CF_2 CF_3$, and a 5–14 membered heterocyclic system containing from 1–4 heteroatoms selected from the group consisting of N, O, and S;

$R^3$ is selected from the formula:

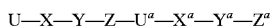

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, $S(O)_p$, $S(O)_p NR^a$, $NR^a$S $(O)_p$, and $NR^a SO_2 NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(OO, OC(O), C(O)$NR^a$, $NR^a$C(O), OC(O)O, OC(O)$NR^a$, $NR^a$C(O)O, $NR^a$C(O)$NR^a$, $S(O)_p$, $S(O)_p NR^a$, $NR^a$S $(O)_p$, and $NR^a SO_2 NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^a R^a$, C(O)$R^a$, C(O)$OR^a$, C(O)$NR^a R^{a'}$, $S(O)_2 NR^a R^{a'}$, $S(O)_p$ $R^a$, $CF_3$, and $CF_2 CF_3$;

$R^c$, at each occurrence, is independently selected from $C_{1-6}$ alkyl, $OR^a$, Cl, F, Br, I, =O, CN, $NO_2$, $NR^a R^{a'}$, C(O)$R^a$, C(O)$OR^a$, C(O)$NR^a R^{a'}$, $NR^a S(O)_2 R^a$, $S(O)_2$ $NR^a R^{a'}$, $S(O)_p R^a$, $CF_3$, $CF_2 CF_3$, and a 5–14 membered heterocyclic system containing from 1–4 heteroatoms selected from the group consisting of N, O, and S;

$R^5$ is selected from:

wherein:
U is absent or is selected from: O, $NR^a$, C(O), C(O)O, OC(O), $C(O)NR^a$, $NR^aC(O)$, OC(O)O, $OC(O)NR^a$, $NR^aC(O)O$ $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^7$ is selected from: $C_1-C_{10}$ alkyl, alkylaryl, and common prodrug derivatives E is $(CR^8R^9)_m$—W—$(CR^8R^9)_n$,
wherein W can be absent or selected from:
$CH_2$, CO, O, $S(O)_m$ and $NR^{10}$,
m is 0–2,
n is 0–2;
with the proviso that when W is O, S or $NR^{10}$ then m must not be 0;

$R^8$ and $R^9$ is independently selected from:
H,
$C_1-C_8$ alkyl substituted with 0–5 $R^b$,
$C_1-C_8$ alkenyl,
$C_1-C_8$ alkylaryl substituted with 0–5 $R^b$,
$C_{3-13}$ carbocyclic residue substituted with 0–5 $R^b$,
5–14 membered heterocyclic system containing from 1–4 heteroatoms selected from the group consisting of N, O, and S substituted with 0–5 $R^b$;
amino,
$C_1-C_8$ alkyl-$NR^{10}$
hydroxyl, $R^8$ and $R^9$ can also form a ring interrupted by $NR^{10}$, O, $S(O)_m$.

$R^{10}$ is selected from:
hydrogen,
$C_1-C_8$ alkyl
$C_1-C_8$ alkylaryl $J^1$, $J^2$, $J^3$, $J^4$ are independently selected from:
CH, or N.
with no more than two N in the cycle.

[5] Preferred compounds of the present invention include compounds of formula (II) wherein:

$R^1$ is selected from:
—C(O)NHOH,
and common prodrug derivatives;

$R^2$ is selected from the formula:

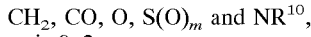

wherein:
U is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from H, $C_{1-10}$ alkylene, $C_{2-10}$ alkenylene, $C_{2-10}$ alkynylene;

Y is absent or selected from H, O, $NR^a$, $S(O)_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, $S(O)_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^a$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^3$ is selected from the formula:

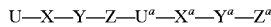

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p NR^a$, $NR^a$S(O)$_p$, and $NR^a SO_2 NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p NR^a$, $NR^a$S(O)$_p$, and $NR^a SO_2 NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, $C_1$, F, Br, I, =O, CN, $NO_2$, $NR^a R^{a'}$, $C(O)R^a$, $C(O)OR^a$, $C(O)NR^a R^{a'}$, $S(O)_2 NR^a R^{a'}$, $S(O)_p R^a$, $CF_3$, and $CF_2 CF_3$;

$R^c$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $NR^a S(O)_2 R^{a'}$, $S(O)_2 NR^a R^{a'}$, $S(O)_p R^a$, $CF_3$, $_{CF2} CF_3$, and a 5–14 membered heterocyclic system containing from 1–4 heteroatoms selected from the group consisting of N, O, and S;

$R^5$ is selected from:

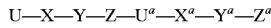

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p NR^a$, $NR^a$S(O)$_p$, and $NR^a SO_2 NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p NR^a$, $NR^a$S(O)$_p$, and $NR^a SO_2 NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $S(O)_2 NR^a R^{a'}$, $S(O)_p R^a$, $CF_3$, and $CF_2 CF_3$;

$R^c$, at each occurrence, is independently selected from $C_{1-6}$ alkyl, $OR^a$, Cl, F, Br, I, =O, CN, $NO_2$, $NR^a R^{a'}$, $C(O)R^a$, $C(O)OR^a$, $C(O)NR^a R^{a'}$, $NR^a S(O)_2 R^a$, $S(O)_2 NR^a R^{a'}$, $S(O)_p R^a$, $CF_3$, $CF_2 CF_3$, and a 5–14 membered heterocyclic system containing from 1–4 heteroatoms selected from the group consisting of N, O, and S;

$R^7$ is selected from: $C_1$–$C_{10}$ alkyl, alkylaryl, and common prodrug derivatives E is $(CR^8 R^9)_m$—W—$(CR^8 R^9)_n$,
wherein W can be absent or selected from:
$CH_2$, CO, O, S(O)$_m$ and $NR^{10}$,
m is 0–2,
n is 0–2;
with the proviso that when W is O, S or $NR^{10}$ then m must not be 0;

$R^8$ and $R^9$ is independently selected from:
H,
$C_1$–$C_8$ alkyl substituted with 0–5 $R^b$,
$C_1$–$C_8$ alkenyl,
$C_1$–$C_8$ alkylaryl substituted with 0–5 $R^b$,
$C_{3-13}$ carbocyclic residue substituted with 0–5 $R^b$,
5–14 membered heterocyclic system containing from 1–4 heteroatoms selected from the group consisting of N, O, and S substituted with 0–5 $R^b$;
amino,
$C_1$–$C_8$ alkyl-$NR^{10}$
hydroxyl, $R^8$ and $R^9$ can also form a ring interrupted by $NR^{10}$, O, S(O)$_m$.

$R^{10}$ is selected from:
hydrogen,
$C_1$–$C_8$ alkyl
$C_1$–$C_8$ alkylaryl $J^1$, $J^2$, $J^3$, $J^4$ are independently selected from:
CH, or N.
with no more than two N in the cycle.

[6] More preferred compounds of the present invention are compounds of the formula (III):

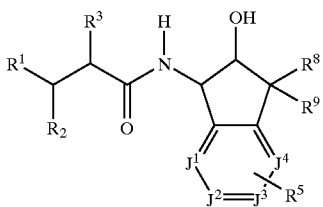

Formula III or a pharmaceutically acceptable salt form or a steroisomer thereof, wherein:
$R^1$ is selected from:
—C(O)NHOH
and common prodrug derivatives;
$R^2$ is selected from the formula:

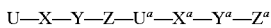

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^a$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^3$ is selected from the formula:

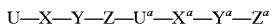

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H; a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, $OR^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^a$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^5$ is selected from:

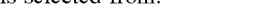

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$, X is absent or selected from H, $C_{1-10}$ alkylene, $C_{2-10}$ alkenylene, $C_{2-1}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, OR$^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, OR$^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^{a'}$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^8$ and $R^9$ is independently selected from:
H,
$C_1$–$C_8$ alkyl substituted with 0–5 $R^b$,
$C_1$–$C_8$ alkenyl,
$C_1$–$C_8$ alkylaryl substituted with 0–5 $R^b$,
$C_{3-13}$ carbocyclic residue substituted with 0–5 $R^b$,
5–14 membered heterocyclic system containing from 1–4 heteroatoms selected from the group consisting of N, O, and S substituted with 0–5 $R^b$;
amino, $C_1$–$C_8$ alkyl-$NR^{10}$
hydroxyl, $R^8$ and $R^9$ can also form a ring interrupted by $NR^{10}$, O, S(O)$_m$.

$R^{10}$ is selected from:
hydrogen,
$C_1$–$C_8$ alkyl
$C_1$–$C_8$ alkylaryl $J^1$, $J^2$, $J^3$, $J^4$ are independently selected from:
CH, or N.
with no more than two N in the cycle.

[7] The more preferred compounds provided by this invention are compounds of the formula (IV):

Formula IV

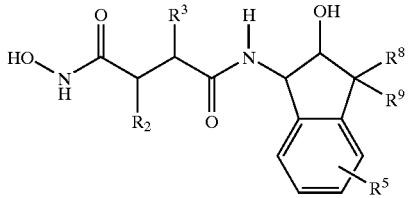

or a pharmaceutically acceptable salt form or a steroisomer therof, wherein:

$R^2$ is selected from the formula:

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, 01–10 alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

$X^a$ is absent or selected from H, $C_{1-10}$ alkylene, $C_{2-10}$ alkenylene, $C_{2-10}$ alkynylene;

$Y^a$ is absent or selected from H, O, $NR^a$, S(O)$_p$, and C(O);

$Z^a$ is absent or selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, OR$^a$, Cl, F, Br, I, =O, CN, NO$_2$, $NR^aR^{a'}$, C(O)$R^a$, C(O)O$R^a$, C(O)$NR^aR^{a'}$, S(O)$_2$$NR^aR^{a'}$, S(O)$_p$$R^a$, CF$_3$, and CF$_2$CF$_3$;

$R^c$, at each occurrence, is independently selected from $C_{1-6}$ alkyl, OR$^a$, Cl, F, Br, I, =O, CN, NO$_2$, $NR^aR^{a'}$, C(O)$R^a$, C(O)O$R^a$, C(O)$NR^aR^{a'}$, $NR^a$S(O)$_2$$R^{a'}$, S(O)$_2$$NR^aR^{a'}$, S(O)$_p$$R^a$, CF$_3$, CF$_2$CF$_3$, and a 5–14 membered heterocyclic system containing from 1–4 heteroatoms selected from the group consisting of N, O, and S;

$R^3$ is selected from the formula:

wherein:
U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, S(O)$_p$, S(O)$_p$$NR^a$, $NR^a$S(O)$_p$, and $NR^a$SO$_2$$NR^a$;

X is absent or selected from H, $C_{1-10}$ alkylene, $C_{2-10}$ alkenylene, $C_{2-10}$ alkynylene;

Y is absent or selected from H, O, $NR^a$, S(O)$_p$, and C(O);

Z is absent or selected from H, a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: H, O, $NR^a$, C(O), C(O)O, OC(O), C(O)$NR^a$, $NR^a$C(O), OC(O)O, OC(O)$NR^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X$^a$ is absent or selected from H, C$_{1-10}$ alkylene, C$_{2-10}$ alkenylene, C$_{2-10}$ alkynylene;

Y$^a$ is absent or selected from H, O, NR$^a$, S(O)$_p$, and C(O);

Z$^a$ is absent or selected from H, a C$_{3-13}$ carbocyclic residue substituted with 0–5 R$^c$ and a 5–14 membered heterocyclic system containing from 1–4 heteroatoms selected from the group consisting of N, O, and S substituted with 0–5 R$^c$;

R$^a$, at each occurrence, is independently selected from H, C$_{1-4}$ alkyl, phenyl or benzyl;

R$^{a'}$, at each occurrence, is independently selected from H, C$_{1-4}$ alkyl, phenyl or benzyl;

alternatively, R$^a$ and R$^{a'}$ taken together with the nitrogen to which they are attached form a 5 or 6 membered ring containing from 0–1 additional heteroatoms selected from the group consisting of N, O, and S;

R$^b$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, and CF$_2$CF$_3$;

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$S(O)$_2$R$^{a'}$, S(O)$_2$NR$^a$R$^{a'}$, S(O)$_p$R$^a$, CF$_3$, CF$_2$CF$_3$, and a 5–14 membered heterocyclic system containing from 1–4 heteroatoms selected from the group consisting of N, O, and S;

R$^5$ is selected from:

U—X—Y—Z—U$^a$—X$^a$—Y$^a$—Z$^a$ wherein:

U is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X is absent or selected from H, C$_{1-10}$ alkylene, C$_{2-10}$ alkenylene, C$_{2-10}$ alkynylene;

Y is absent or selected from H, O, NR$^a$, S(O)$_p$, and C(O);

Z is absent or selected from H, a C$_{3-13}$ carbocyclic residue substituted with 0–5 R$^b$ and a 5–14 membered heterocyclic system containing from 1–4 heteroatoms selected from the group consisting of N, O, and S substituted with 0–5 R$^b$;

U$^a$ is absent or is selected from: H, O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X$^a$ is absent or selected from H, C$_{1-10}$ alkylene, C$_{2-10}$ alkenylene, C$_{2-10}$ alkynylene;

Y$^a$ is absent or selected from H, O, NR$^a$, S(O)$_p$, and C(O);

Z$^a$ is absent or selected from H, a C$_{3-13}$ carbocyclic residue substituted with 0–5 R$^c$ and a 5–14 membered heterocyclic system containing from 1–4 heteroatoms selected from the group consisting of N, O, and S substituted with 0–5 R$^c$;

R$^a$, at each occurrence, is independently selected from H, C$_{1-4}$ alkyl, phenyl or benzyl;

R$^{a'}$, at each occurrence, is independently selected from H, C$_{1-4}$ alkyl, phenyl or benzyl;

alternatively, R$^a$ and R$^{a'}$ taken together with the nitrogen to which they are attached form a 5 or 6 membered ring containing from 0–1 additional heteroatoms selected from the group consisting of N, O, and S;

R$^b$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, and CF$_2$CF$_3$;

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$S(O)$_2$R$^{a'}$, S(O)$_2$NR$^a$R$^{a'}$, S(O)$_p$R$^a$, CF$_3$, CF$_2$CF$_3$, and a 5–14 membered heterocyclic system containing from 1–4 heteroatoms selected from the group consisting of N, O, and S;

R$^8$ and R$^9$ is independently selected from:
H,
C1–C8 alkyl substituted with 0–5 R$^b$,
C1–C8 alkenyl,
C1–C8 alkylaryl substituted with 0–5 R$^b$,
C$_{3-13}$ carbocyclic residue substituted with 0–5 R$^b$,
5–14 membered heterocyclic system containing from 1–4 heteroatoms selected from the group consisting of N, O, and S substituted with 0–5 R$^b$;
amino, C1–C8 alkyl-NR$^{10}$
hydroxyl,
R$^8$ and R$^9$ can also form a ring interrupted by NR$^{10}$, O, S(O)m.

R$^{10}$ is selected from:
hydrogen,
C1–C8 alkyl
C1–C8 alkylaryl

[8] Most preferred compounds of the present invention include compounds selected from the group consisting of:

N1-(2(R)-hydroxy-1(S)-indanyl)-N4-hydroxy-2(R)-isobutyl-butanediamide;

N1-(2(R)-hydroxy-1(S)-indanyl)-N4-hydroxy-2(R)-isobutyl-3(S)-(5-hydroxycarbonyl)-pentanamide;

N1-(2(R)-hydroxy-1(S)-indanyl)-N4-hydroxy-2(R)-isobutyl-3(S)-methyl-butanediamide;

N1-(2(R)-hydroxy-1(S)-indanyl)-N4-hydroxy-2(R)-isobutyl-3(S)-propyl-butanediamide;

N1-(2(R)-hydroxy-1(S)-indanyl)-N4-hydroxy-2(R)-hexyl-3(S)-propyl-butanediamide;

N1-[2(R)-hydroxy-1(S)-indanyl]-N4-hydroxy-2(R)-[4-hydroxy-phenyl)methyl]butanediamide;

N1-[2(R)-hydroxy-1(S)-indanyl]-N4-hydroxy-2(R)-[4-methoxy-phenyl)methyl]butanediamide;

N1-[1(S)-indanyl]-N4-hydroxy-2(R)-[4-(hydroxy-phenyl)methyl]butanediamide;

N1-[2(R)-hydroxy-1(S)-indanyl]-N4-hydroxy-2(R)-[3-phenyl-propyl]butanediamide;

N1-[2(R)-hydroxy-1(S)-indanyl]-N4-hydroxy-2(R)-[[4-(benzyloxy)-phenyl]methyl]butanediamide;

N1-[2(R)-hydroxy-1(S)-indanyl]-N4-hydroxy-2(R)-[[3-(benzyloxy)-phenyl]methyl]butanediamide;

N1-[2(R)-hydroxy-1(S)-indanyl]-N4-hydroxy-2(R)-[3-(hydroxy-phenyl)methyl]butanediamide;

N1-[2(R)-hydroxy-1(S)-indanyl]-N4-hydroxy-2(R)-[4-(fluoro-phenyl)methyl]butanediamide;

N1-[2(R)-hydroxy-1(S)-indanyl]-N4-hydroxy-2(R)-[3,4-(methylenedioxy-phenyl)methyl]butanediamide;

N1-[2(R)-hydroxy-1(S)-indanyl]-N4-hydroxy-2(R)-[3-(methoxy-phenyl)methyl]butanediamide;

N1-[2(R)-hydroxy-1(S)-indanyl]-N4-hydroxy-2(R)-[[4-(3-trifluoromethyl-phenyl)phenyl]methyl]butanediamide;

N1-[2(R)-hydroxy-1(S)-indanyl]-N4-hydroxy-2(R)-[[4-(2-tert-butylaminosulfonyl-phenyl)phenyl]methyl]-butanediamide;

N1-[2(R)-hydroxy-1(S)-indanyl]-N4-hydroxy-2(R)-[[4-(2-methoxy-phenyl)phenyl]methyl]butanediamide;

N1-[2(R)-hydroxy-1(S)-indanyl]-N4-hydroxy-2(R)-[[4-(phenyl)phenyl]methyl]butanediamide;

N1-[2(R)-hydroxy-1(S)-indanyl]-N4-hydroxy-2(R)-[(3-hydroxy-4-methoxy-phenyl)methyl]butanediamide;

N1-[2(R)-hydroxy-1(S)-indanyl]-N4-hydroxy-2(R)-[[3-(3-thiophene)isoxazoline]methyl]butanediamide;

N1-[2(R)-hydroxy-1(S)-indanyl]-N4-hydroxy-2(R)-[[4-(2-chloro-phenyl)phenyl]methyl]butanediamide;

N1-[2(R)-hydroxy-1(S)-indanyl]-N4-hydroxy-2(R)-[[4-(2-benzofuran)phenyl]methyl]butanediamide;

N1-[2(R)-hydroxy-1(S)-indanyl]-N4-hydroxy-2(R)-[[4-(2-methyl-phenyl)phenyl]methyl]butanediamide;

N1-[2(R)-hydroxy-1(S)-indanyl]-N4-hydroxy-2(R)-[[3,4-(methylenedioxy-phenyl)phenyl]methyl]butanediamide;

N1-[2(R)-hydroxy-1(S)-indanyl]-N4-hydroxy-2(R)-[[4-(2-tetrazole-phenyl)phenyl]methyl]butanediamide;

N1-[2(R)-hydroxy-1(S)-indanyl]-N4-hydroxy-2(R)-[[3-phenyl)phenyl]methyl]butanediamide;

N1-[2(R)-hydroxy-1(S)-indanyl]-N4-hydroxy-2(R)-[[3-methyl-phenyl)phenyl]methyl]butanediamide;

N1-[2(R)-hydroxy-1(S)-indanyl]-N4-hydroxy-2(R)-[4-(amino-phenyl)methyl]butanediamide;

N1-[2(R)-hydroxy-1(S)-indanyl]-N4-hydroxy-2(R)-[[4-(benzyloxy-carbonyl)amino]phenyl)methyl]butanediamide;

N1-[2(R)-hydroxy-1(S)-indanyl]-N4-hydroxy-2(R)-[[4-(2-hydroxymethlene)phenyl)phenyl]methyl]butanediamide;

N1-[2(R)-hydroxy-1(S)-indanyl]-N4-hydroxy-2(R)-[[4-(3,4,5-trimethoxy-phenyl)phenyl]methyl]butanediamide;

N1-[2(R)-hydroxy-1(S)-indanyl]-N4-hydroxy-2(R)-[[4-(2,4-di-methoxy-phenyl)phenyl]methyl]butanediamide;

N1-[2(R)-hydroxy-1(S)-indanyl]-N4-hydroxy-2(R)-[[4-(3,5-di-chloro-phenyl)phenyl]methyl]butanediamide;

N1-[2(R)-hydroxy-1(S)-indanyl]-N4-hydroxy-2(R)-[[4-(2-trifluoromethyl-phenyl)phenyl]methyl]butanediamide;

N1-[2(R)-hydroxy-1(S)-indanyl]-N4-hydroxy-2(R)-[[4-(3-isopropyl-phenyl)phenyl]methyl]butanediamide;

N1-[2(R)-hydroxy-1(S)-indanyl]-N4-hydroxy-2(R)-[[4-(2,4-dichloro-phenyl)phenyl]methyl]butanediamide;

N1-[2(R)-hydroxy-1(S)-indanyl]-N4-hydroxy-2(R)-[[4-(3-chloro-4-fluoro-phenyl)phenyl]methyl]butanediamide;

N1-[2(R)-hydroxy-1(S)-indanyl]-N4-hydroxy-2(R)-[[4-(p-toluenesulfonyl-amino)phenyl]methyl]butanediamide;

N1-[2(R)-hydroxy-1(S)-indanyl]-N4-hydroxy-2(R)-phenylmethyl-3(S)-(tert-butyloxy-carbonyl-amino)-butanediamide;

N1-[2(R)-hydroxy-1(S)-indanyl]-N4-hydroxy-2(R)-[[4-(3,4-methylenedioxyphenyl)phenyl]methyl]-3(S)-(tert-butyloxy-carbonyl-amino)-butanediamide;

N1-[2(R)-hydroxy-1(S)-indanyl]-N4-hydroxy-2(R)-[[4-(3-methoxyphenyl)phenyl]methyl]butanediamide;

N1-[2(R)-hydroxy-1(S)-indanyl]-N4-hydroxy-2(R)-[[4-(3-fluorophenyl)phenyl]methyl]butanediamide;

N1-[2(R)-hydroxy-1(S)-indanyl]-N4-hydroxy-2(R)-[3-(fluoro-phenyl)methyl]-3(S)-(tert-butyloxy-carbonyl-amino)-butanediamide;

N1-[2(R)-hydroxy-1(S)-indanyl]-N4-hydroxy-2(R)-[3-(hydroxy-phenyl)methyl]-3(S)-(tert-butyloxy-carbonyl-amino)-butanediamide;

N1-[2(R)-hydroxy-1(S)-indanyl]-N4-hydroxy-2(R)-[[4-(3-nitrophenyl)phenyl]methyl]butanediamide;

N1-[2(R)-hydroxy-1(S)-indanyl]-N4-hydroxy-2(R)-[[4-(3-(methylsulfonyl-amino)-phenyl)phenyl]methyl]-butanediamide;

N1-[2(R)-hydroxy-1(S)-indanyl]-N4-hydroxy-2(R)-[3-(hydroxy-phenyl)methyl]-3(S)-(3-trimethylsilyl-propyl)-butanediamide;

N1-[2(R)-hydroxy-1(S)-indanyl]-N4-hydroxy-2(R)-[3-(hydroxy-phenyl)methyl]-3(S)-(2,2-dimethyl-propionamido)-butanediamide;

N1-[2(R)-hydroxy-1(S)-indanyl]-N4-hydroxy-2(R)-[3-(hydroxy-phenyl)methyl]-3(S)-(ethyloxy-carbonyl-amino)-butanediamide;

N1-[2(R)-hydroxy-1(S)-indanyl]-N4-hydroxy-2(R)-[3-(hydroxy-phenyl)methyl]-3(S)-(iso-butyloxy-carbonyl-amino)-butanediamide;

N1-[2(R)-hydroxy-1(S)-indanyl]-N4-hydroxy-2(R)-[3-(hydroxy-phenyl)methyl]-3(S)-(propionamido)-butanediamide;

N1-[2(R)-hydroxy-1(S)-indanyl]-N4-hydroxy-2(R)-[3-(hydroxy-phenyl)methyl]-3(S)-(1-methyl-cyclopropane carboxamido-1-yl)-butanediamide;

N1-[2(R)-hydroxy-1(S)-indanyl]-N4-hydroxy-2(R)-[3-(hydroxy-phenyl)methyl]-3(S)-(2,2-dimethylpropyl-amino)-butanediamide;

N1-[2(R)-hydroxy-1(S)-indanyl]-N4-hydroxy-2(R)-[3-(hydroxy-phenyl)methyl]-3(S)-(methylsulfonyl-amino)-butanediamide;

N1-[2(R)-hydroxy-1(S)-indanyl]-N4-hydroxy-2(R)-[3-(hydroxy-phenyl)methyl]-3(S)-amino-butanediamide;

N1-[2(R)-hydroxy-1(S)-indanyl]-N4-hydroxy-2(R)-[4-(methylsulfonylamino)-phenyl)methyl]-butanediamide N1-[2(R)-hydroxy-1(S)-indanyl]-N4-hydroxy-2(R)-[3-(hydroxy-phenyl)methyl]-3(S)-(cyclobutane carboxamido-1-yl)-butanediamide N1-[2(R)-hydroxy-1(S)-indanyl]-N4-hydroxy-2(R)-[3-(hydroxy-phenyl)methyl]-3(S)-(2-hydroxymethyl-isobutanamide)-butanediamide N1-[2(R)-hydroxy-1(S)-indanyl]-N4-hydroxy-2(R)-[3-(hydroxy-phenyl)methyl]-3(S)-(1-hydroxyl-cyclopropane carboxamido-1-yl)-butanediamide N1-[2(R)-hydroxy-1(S)-indanyl]-N4-hydroxy-2(R)-[3-(hydroxy-phenyl)methyl]-3(S)-(1-phenyl-cyclopropane carboxamido-1-yl)-butanediamide N1-[2(R)-hydroxy-1(S)-indanyl]-N4-hydroxy-2(R)-[3-(hydroxy-phenyl)methyl]-3(S)-(bezene carboxamido-1-yl)-butanediamide N1-[2(R)-hydroxy-1(S)-indanyl]-N4-hydroxy-2(R)-[3-(hydroxy-phenyl)methyl]-3(S)-(1-cyano-cyclopropane carboxamido-1-yl)-butanediamide N1-[2(R)-hydroxy-1(S)-indanyl]-N4-hydroxy-2(R)-[3-(hydroxy-phenyl)methyl]-3(S)-(1-phenyl-cyclopentane carboxamido-1-yl)-butanediamide N1-[2(R)-hydroxy-1(S)-indanyl]-N4-hydroxy-2(R)-[3-(hydroxy-phenyl)methyl]-3(S)-(1-methyl-cyclohexane carboxamido-1-yl)-butanediamide N1-[2(R)-hydroxy-1(S)-indanyl]-N4-hydroxy-2(R)-[3-(hydroxy-phenyl)methyl]-3(S)-(2-indole carboxamido)-butanediamide
N1-[2(R)-hydroxy-1(S)-indanyl]-N4-hydroxy-2(R)-[3-(hydroxy-phenyl)methyl]-3(S)-(2-furan carboxamido)-butanediamide
N1-[2(R)-hydroxy-1(S)-indanyl]-N4-hydroxy-2(R)-[3-(hydroxy-phenyl)methyl]-3(S)-(2-quinoline carboxamido)-butanediamide
N1-[2(R)-hydroxy-1(S)-indanyl]-N4-hydroxy-2(R)-[3-(hydroxy-phenyl)methyl]-3(S)-(3,4,5-trimethoxy benzene carboxamido-1-yl)-butanediamide
N1-[2(R)-hydroxy-1(S)-indanyl]-N4-hydroxy-2(R)-[3-(hydroxy-phenyl)methyl]-3(S)-(2-methyl-3-amino-benzene carboxamido-1-yl)-butanediamide
N1-[2(R)-hydroxy-1(S)-indanyl]-N4-hydroxy-2(R)-[3-(hydroxy-phenyl)methyl]-3(S)-(2-methyl-6-amino-benzene carboxamido-1-yl)-butanediamide
N1-[2(R)-hydroxy-1(S)-indanyl]-N4-hydroxy-2(R)-[3-(hydroxy-phenyl)methyl]-3(S)-(3-pyridine carboxamido-1-yl)-butanediamide
N1-[2(R)-hydroxy-1(S)-indanyl]-N4-hydroxy-2(R)-[3-(hydroxy-phenyl)methyl]-3(S)-(1-(2,4-dichloro-phenyl)-cyclopropane carboxamido-1-yl)-butanediamide
N1-[2(R)-hydroxy-1(S)-indanyl]-N4-hydroxy-2(R)-[3-(hydroxy-phenyl)methyl]-3(S)-(1-(4-chloro-phenyl)-cyclopropane carboxamido-1-yl)-butanediamide
N1-[2(R)-hydroxy-1(S)-indanyl]-N4-hydroxy-2(R)-[3-(hydroxy-phenyl)methyl]-3(S)-(3-methylsulfonyl)-benzene carboxamido-1-yl)-butanediamide
N1-[2(R)-hydroxy-1(S)-indanyl]-N4-hydroxy-2(R)-[3-(hydroxy-phenyl)methyl]-3(S)-(2-methylsulfonyl-benzene carboxamido-1-yl)-butanediamide
N1-[2(R)-hydroxy-1(S)-indanyl]-N4-hydroxy-2(R)-[3-(hydroxy-phenyl)methyl]-3(S)-(3-cyano-benzene carboxamido-1-yl)-butanediamide
N1-[2(R)-hydroxy-1(S)-indanyl]-N4-hydroxy-2(R)-[(3-hydroxy-phenyl)methyl]-3(S)-(6-quinoline carboxamido)-butanediamide
N1-[2(R)-hydroxy-1(S)-indanyl]-N4-hydroxy-2(R)-[(3-hydroxy-phenyl)methyl]-3(S)-(1-ethyl, 3-methyl-pyrazole 5-carboxamido)-butanediamide
N1-[2(R)-hydroxy-1(S)-indanyl]-N4-hydroxy-2(R)-[(3-hydroxy-phenyl)methyl]-3-(4-morpholino-benzene carboxamido-1-yl)-butanediamide
N1-[2(R)-hydroxy-1(S)-indanyl]-N4-hydroxy-2(R)-[(3-hydroxy-phenyl)methyl]-3(S)-(2-chloro-4-methylsulfonyl-benzene carboxamido-1-yl)-butanediamide
N1-[2(R)-hydroxy-1(S)-indanyl]-N4-hydroxy-2(R)-[(3-hydroxy-phenyl)methyl]-3(S)-(4-(imidazol-1-yl)benzene carboxamido-1-yl)-butanediamide
N1-[2(R)-hydroxy-1(S)-indanyl]-N4-hydroxy-2(R)-[(3-hydroxy-phenyl)methyl]-3(S)-(2-thiophene carboxamido-1-yl)-butanediamide
N1-[2(R)-hydroxy-1(S)-indanyl]-N4-hydroxy-2(R)-[(3-hydroxy-phenyl)methyl]-3(S)-(1-tert-butyl, 3-methyl-pyrazole 5-carboxamido)-butanediamide
N1-[2(R)-hydroxy-1(S)-indanyl]-N4-hydroxy-2(R)-[(3-hydroxy-phenyl)methyl]-3(S)-(4-aminomethyl benzene carboxamido-1-yl)-butanediamide
N1-[2(R)-hydroxy-1(S)-indanyl]-N4-hydroxy-2(R)-[(3-hydroxy-phenyl)methyl]-3(S)-(2-hydroxyl-isobutanamido)-butanediamide
N1-[2(R)-hydroxy-1(S)-indanyl]-N4-hydroxy-2(R)-[3-(hydroxy-phenyl)methyl]-3(S)-(cyclopropane carboxamido-1-yl)-butanediamide
N1-[2(R)-hydroxy-1(S)-indanyl]-N4-hydroxy-2(R)-[3-(hydroxy-phenyl)methyl]-3(S)-(cyclopentane carboxamido-1-yl)-butanediamide
N1-[2(R)-hydroxy-1(S)-indanyl]-N4-hydroxy-2(R)-(3-(hydroxy-phenyl)methyl-3(S)-(2cyclopentyl acetamido)-butanediamide
N1-[2(R)-hydroxy-1(S)-indanyl]-N4-hydroxy-2(R)-[3-(hydroxy-phenyl)methyl]-3(S)-(cyclohexane carboxamido-1-yl)-butanediamide
N1-[2(R)-hydroxy-1(S)-indanyl]-N4-hydroxy-2(R)-[3-(hydroxy-phenyl)methyl]-3(S)-(4-(4-N-Boc-piperazinyl-1-yl)benzene carboxamido-1-yl) butanediamide
N1-[2(R)-hydroxy-1(S)-indanyl]-N4-hydroxy-2(R)-[3-(hydroxy-phenyl)methyl]-3(S)-(4-(piperazinyl-1-yl) benzene carboxamido-1-yl)-butanediamide
N1-[2(R)-hydroxy-1(S)-indanyl]-N4-hydroxy-2(R)-[3-(hydroxy-phenyl)methyl]-3(S)-(2-Fluoro-6-chloro-benzene carboxamido-1-yl)-butanediamide
N1-[2(R)-hydroxy-1(S)-indanyl]-N4-hydroxy-2(R)-[3-(hydroxy-phenyl)methyl]-3(S)-(1-amino-cyclohexane carboxamido-1-yl)-butanediamide
N1-[2(R)-hydroxy-1(S)-indanyl]-N4-hydroxy-2(R)-[3-(hydroxy-phenyl)methyl]-3(S)-(2-methylthio-acetamido)-butanediamide
N1-[2(R)-hydroxy-1(S)-indanyl]-N4-hydroxy-2(R)-[3-(hydroxy-phenyl)methyl]-3(S)-(2-methoxy-acetamido)-butanediamide
N1-[2(R)-hydroxy-1(S)-indanyl]-N4-hydroxy-2(R)-[3-(hydroxy-phenyl)methyl]-3(S)-(1-allyl-cyclopentane carboxamido-1-yl)-butanediamide
N1-[2(R)-hydroxy-1(S)-indanyl]-N4-hydroxy-2(R)-[3-(hydroxy-phenyl)methyl]-3(S)-(1-n-propyl-cyclopentane carboxamido-1-yl)-butanediamide
N1-[2(R)-hydroxy-1(S)-indanyl]-N4-hydroxy-2(R)-[3-(hydroxy-phenyl)methyl]-3(S)-(1-allyl-cyclopropane carboxamido-1-yl)-butanediamide
N1-[2(R)-hydroxy-1(S)-indanyl]-N4-hydroxy-2(R)-[3-(hydroxy-phenyl)methyl]-3(S)-(8-quinoline-sulfonamido)-butanediamide
N1-[2(R)-hydroxy-1(S)-indanyl]-N4-hydroxy-2(R)-[3-(hydroxy-phenyl)methyl]-3(S)-(4-nitro-benzene sulfonamido)-butanediamide
N1-[2(R)-hydroxy-1(S)-indanyl]-N4-hydroxy-2(R)-[3-(hydroxy-phenyl)methyl]-3(S)-(1,4-di-methyl-2-chloro-pyrazole-3-sulfonamido)-butanediamide
N1-[2(R)-hydroxy-1(S)-indanyl]-N4-hydroxy-2(R)-[3-(hydroxy-phenyl)methyl-3(S)-(1,5-dimethyl-isooxazole-3-sulfonamido)-butanediamide
N1-[2(R)-hydroxy-1(S)-indanyl]-N4-hydroxy-2(R)-[3-(hydroxy-phenyl)methyl]-3(S)-(1-methyl-imidazole 3-sulfonamido)-butanediamide
N1-[2(R)-hydroxy-1(S)-indanyl]-N4-hydroxy-2(R)-[3-(hydroxy-phenyl)methyl]-3(S)-(benzene sulfonamido)-butanediamide
N1-[2(R)-hydroxy-1(S)-indanyl]-N4-hydroxy-2(R)-[3-(hydroxy-phenyl)methyl]-3(S)-(1,4-dimethyl pyrazole 3-sulfonamido)-butanediamide
N1-[2(R)-hydroxy-1(S)-indanyl]-N4-hydroxy-2(R)-[3-(hydroxy-phenyl)methyl]-3(S)-(2-methylsulfonyl benzene sulfonamido-1-yl)-butanediamide N1-[2(R)-hydroxy-1(S)-indanyl]-N4-hydroxy-2(R)-[3-(hydroxy-phenyl)methyl]-3(S)-(cyclohexylamino)-butanediamide N1-[2(R)-hydroxy-1(S)-indanyl]-N4-hydroxy-2(R)-[3-(hydroxy-phenyl)methyl]-3(S)-(iso-propylamino)-butanediamide N1-[2(R)-hydroxy-1(S)-indanyl]-N4-hydroxy-2(R)-[4(2-trifluoromethylphenyl)-phenylmethyl]-3(S)-(2,2-dimethylpropyl-amino)-butanediamide N1-[2(R)-hydroxy-1(S)-indanyl]-N4-hydroxy-2(R)-[3-(hydroxy-phenyl)methyl]-3(S)-(cyclopentylamino)-butanediamide N1-[2(R)-hydroxy-1(S)-indanyl]-N4-hydroxy-2(R)-[3-(hydroxy-phenyl)methyl]-3(S)-(cyclopropylmethyl)-butanediamide N1-[2(R)-hydroxy-1(S)-indanyl]-N4-hydroxy-2(R)-[3-(hydroxy-phenyl)methyl]-3(S)-(benzylamino)-butanediamide N1-[2(R)-hydroxy-1(S)-indanyl]-N4-hydroxy-2(R)-[3-(hydroxy-phenyl)methyl]-3(S)-(2-furanmethylamino)-butanediamide N1-[2(R)-hydroxy-1(S)-indanyl]-N4-hydroxy-2(R)-[3-(hydroxy-4-methylphenyl)methyl]-3(S)-(3-cyanophenylmethylamino)-butanediamide N1-[2(R)-hydroxy-1(S)-indanyl]-N4-hydroxy-2(R)-[3-(hydroxy-phenyl)methyl]-3(S)-(2,2-dimethylpropyl-amino)-butanediamide N1-[2(R)-hydroxy-1(S)-indanyl]-N4-hydroxy-2(R)-[3-(hydroxy-phenyl)methyl]-3(S)-(2-pentylamino)-butanediamide N1-[2(R)-hydroxy-1(S)-indanyl]-N4-hydroxy-2(R)-[3-(hydroxy-phenyl)methyl]-3(S)-(bis-cyclopropylmethyamino)-butanediamide N1-[2(R)-hydroxy-1(S)-indanyl]-N4-hydroxy-2(R)-[3-(hydroxy-phenyl)methyl]-3(S)-(2-thiophenemethylamino)-butanediamide N1-[2(R)-hydroxy-1(S)-indanyl]-N4-hydroxy-2(R)-[3-(hydroxy-phenyl)methyl]-3(S)-(2-methyl-propylamino)-butanediamide The present invention also provides a pharmaceutical composition comprising a pharmaceutically acceptable carrier and a therapeutically effective amount of a compound of formula (I) as described herein.

The present invention also provides for treating an inflammatory disease in a mammal comprising administering to the mammal in need of such treatment a therapeutically effective amount of a compound of formula (I) as described herein.

The present invention also provides a method for treating a condition or disease mediated by MMPs and/or TNF and/or aggrecanase in a mammal comprising administering to the mammal in need of such treatment a therapeutically effective amount of a compound of formula (I) as described herein.

The present invention alsoprovides a method for treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of formula (I) as described herein.

The present invention also provides a method for treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) as described herein.

In the following description a (-) symbolizes the point of attachment.

SYNTHESIS

The novel compounds of the present invention may be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of compounds of formula 5 are prepared by the methods outlined in scheme 1. Coupling of carboxylic acid 1 with cis-(1S,2R-(-)-1-amino-2-indanol provided amide 2. The hydroxyl group of 2 was protected as the acetonide 3, followed by alkylation with tert-butyl 2-bromo-acetate to afford the desired diastereomer 4. Removal of the tert-butyl group of 4 with TFA in methylene chloride, followed by coupling with O-benzyl hydroxy amine, and hydrogenation afforded the target molecule 5.

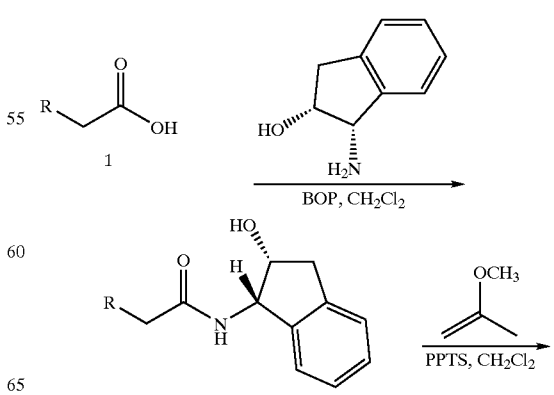

Scheme 1

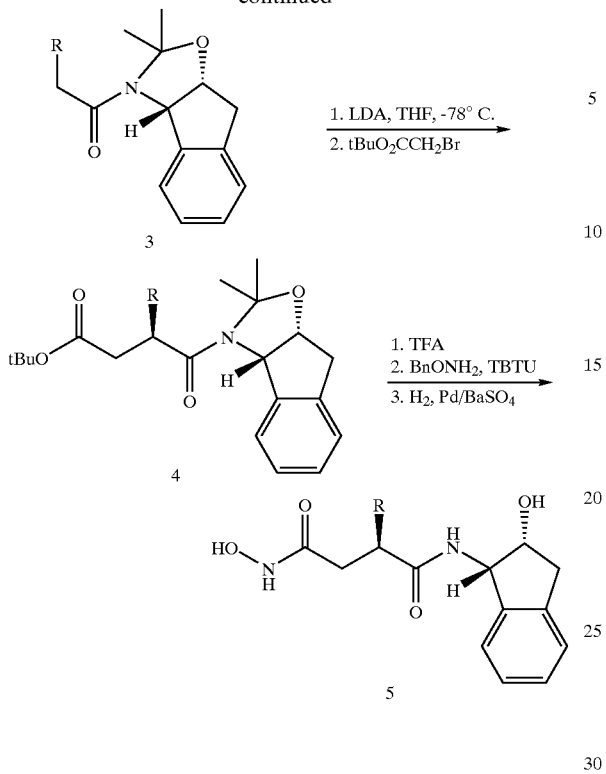

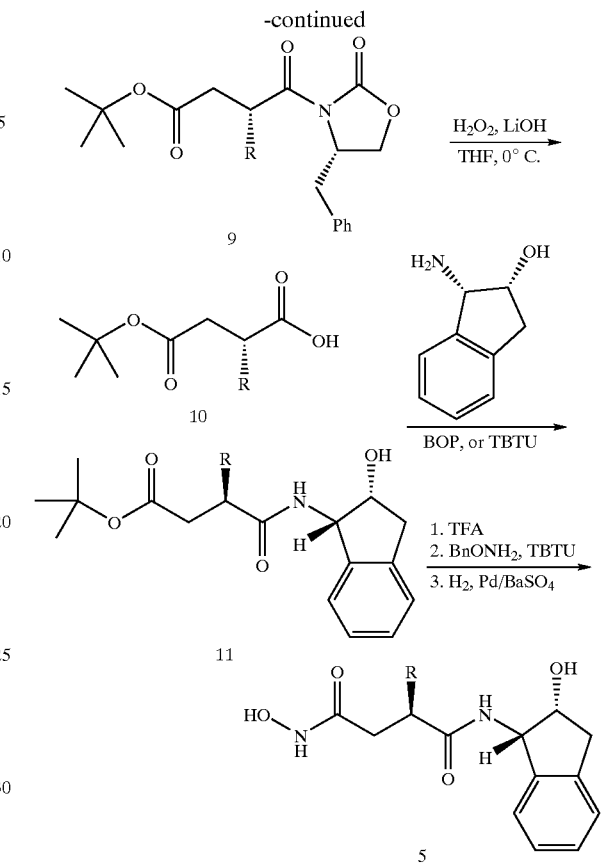

Compounds of formula 5 can also be prepared by the methods outlined in scheme 2. The 2-substituted succinic acid 10 can be prepared using standard Evans chemistry. An acid 6 (X=OH) is converted to its oxazolidinone derivative 8 using the standard chemistry. Asymmetric alkylation, followed by hydrolysis using $H_2O_2$/LiOH afforded the desired acid 10. The mono-protected succinic acid was coupled to (1S, 2R)-(−) cis-1-amino-2-indanol using standard BOP, or other peptide coupling reagents such as DCC, EDAC, TBTU. The intermediate 11 can then be readily converted into the target compounds 5 using the similar procedures to that used for the synthesis of target 5 as described in scheme 1.

Compounds of formula 12 are prepared by the methods outlined in scheme 3. Dianion reaction of the intermidate 10 with an organic halides or triflates produces the 2,3-disubstituted succinate 13. The acid 13 was coupled with cis-(1S, 2R)-(−)-1-amino-2-indanol. Following similar procedures to that used for the synthesis of target 5 as described in scheme 1, compounds of formula 12 can be readily prepared.

Scheme 2

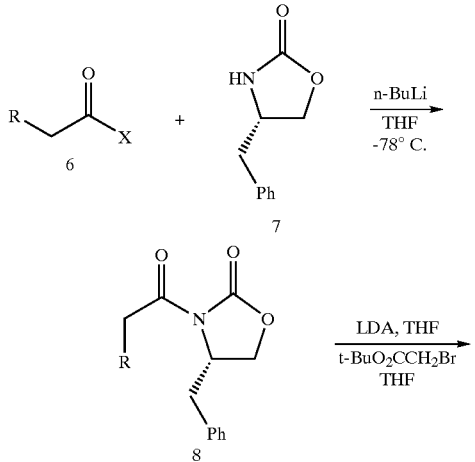

Scheme 3

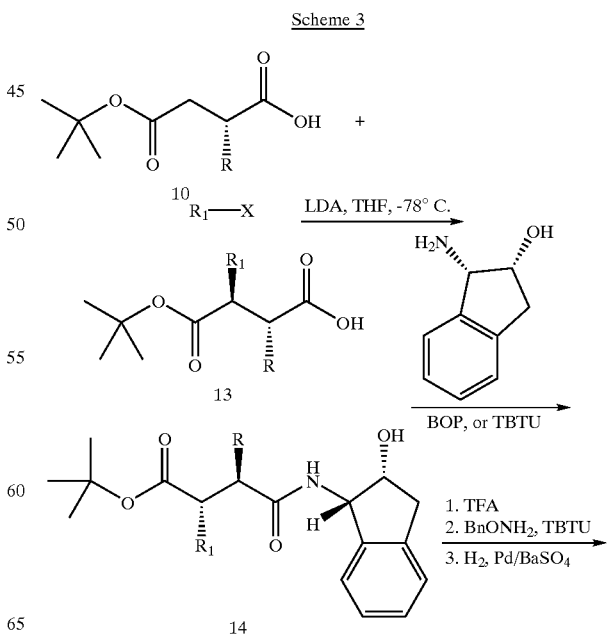

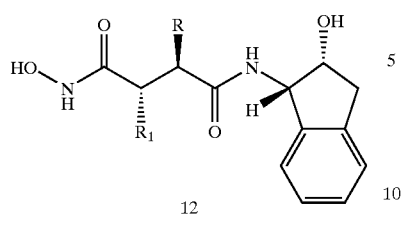

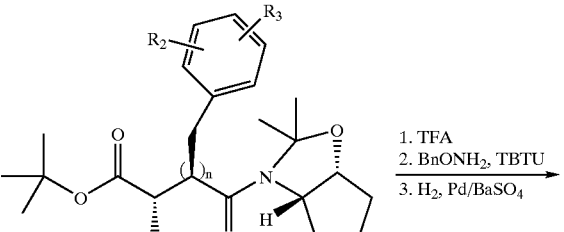

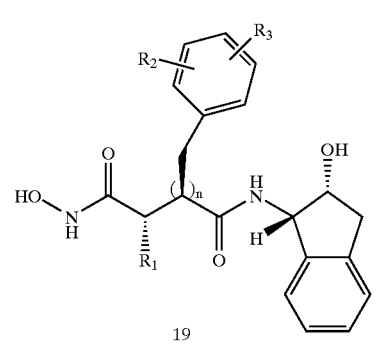

Compounds of formula 19 are prepared as shown in scheme 4. The intermediate 15 prepared using the method described in scheme 3, was hydrogenated to produce 16. Compound 16 was then converted to the triflate 17. The Pd catalyzed Suzuki or stille cross coupling of triflate 17 with either a boronic acid or organostanane afford the coupling product 18. Using the standard chemistry as described in scheme 3, 18 can be easily converted to the compounds of formula 19.

Compounds of formula 20 are prepared as shown in scheme 5. Compound 21 prepared as described in scheme 2 can be hydrogenated to give the free amine 22. The free amino group can then be protected as sulfonamides, carbamates, and amides 23. Following similar chemistry to that described in scheme 1, compound 23 can be readily converted to the target of formula 20.

Scheme 4

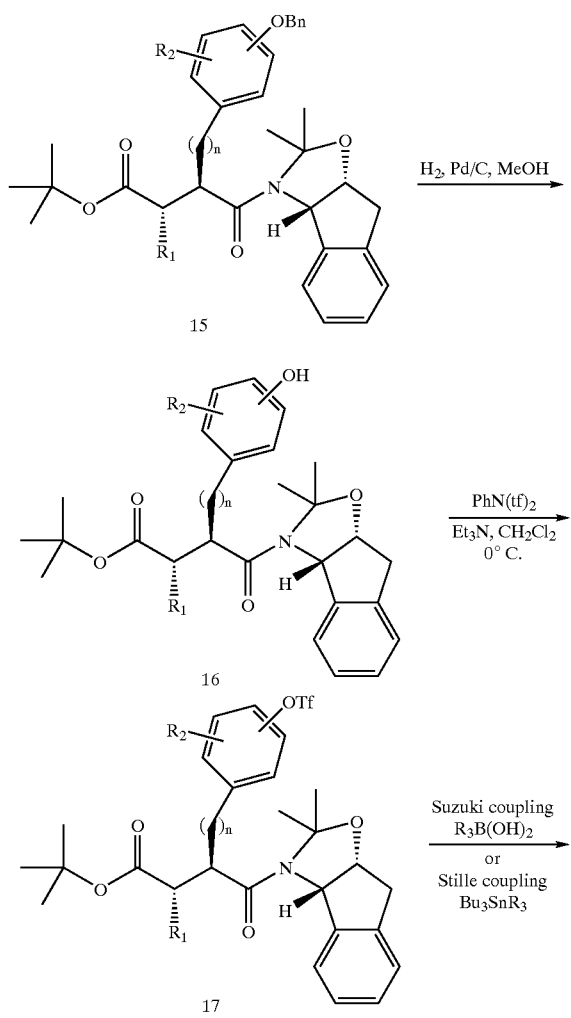

Scheme 5

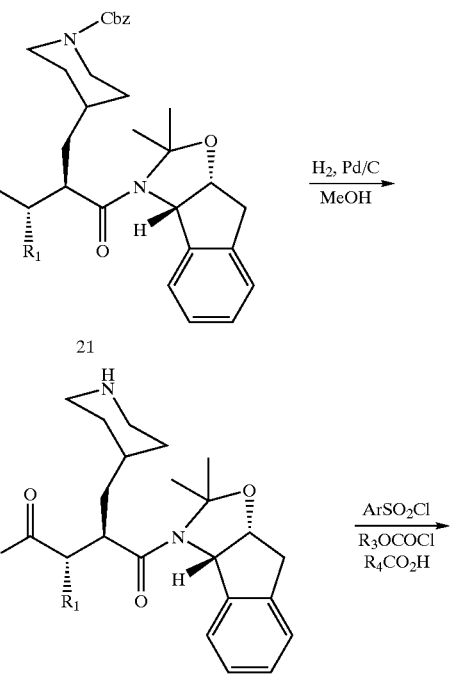

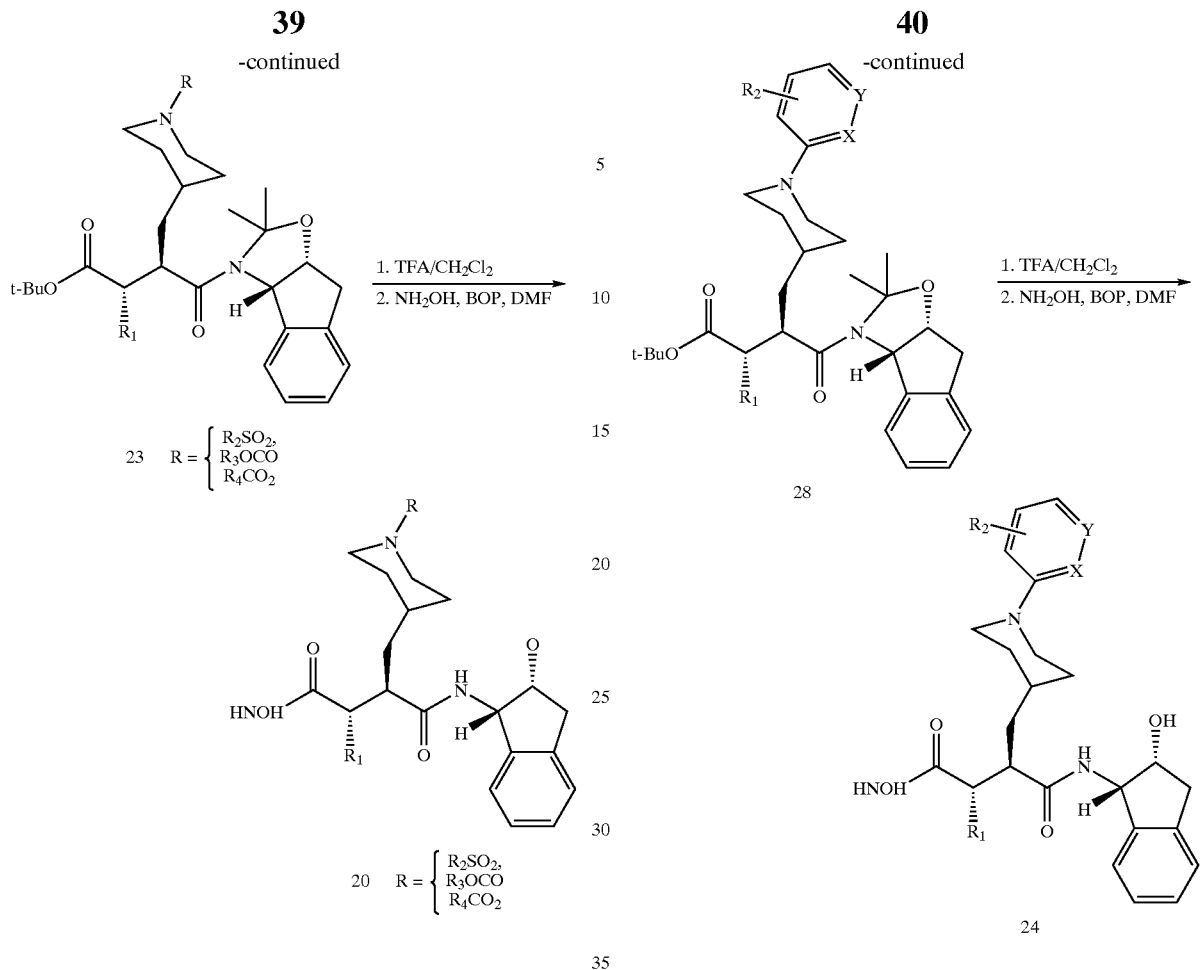

Compounds of formula 24 are prepared as shown in scheme 6. Starting from 22 prepared in scheme 5, the free amino group can be further functionalized to afford compound 28 by either palladium catalyzed aryl amination (Wolfe, J. P.; Rennels, R. A.; Buchwald, S. L. *Tetrahedron*, 1996, 52, 7525–7546, Hartwig, J. F. *Synlett*, 1996, 329), or displacement with a substituted aryl fluoride. As described in the previous scheme 5, 28 can be easily converted to the final compound 24.

Scheme 6

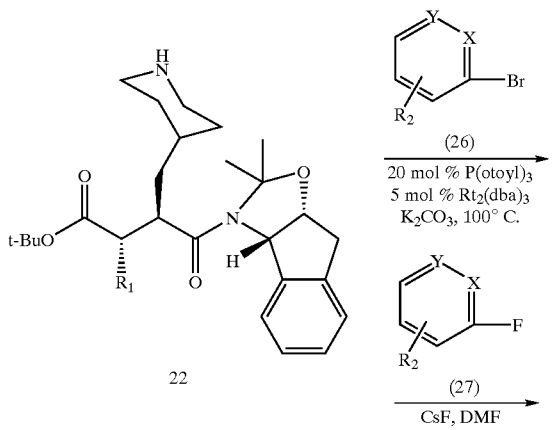

Compounds of formula 29 are prepared as shown in schemes 7–9.

The synthesis of substituted cis-1-amino-2-indanol (36) was followed by the route developed by Ghosh et al (Ghosh, A. K.; Kincaid, J. F.; Haske, M. G. *Synthesis*, 1997, 541–544) The substituted indene (30) is converted to the epoxide 31 with MCPBA, or to the optically pure epoxide of 31 with Jacobsen's highly enantioselective epoxidation catalysts (Jacobsen, E. N.; Zhang, W.; Muci, A. R.; Ecker, J. R.; Deng, L. *J. Am. Chem. Soc.* 1991, 113, 7063–7064.). The epoxide 31 is converted to the alcohol 32 by treating it with NaN$_3$. The racemic alcohol of 32 is resolved by Lipase P Sas described by Ghosh et al (Ghosh, A. K.; Kincaid, J. F.; Haske, M. G. *Synthesis*, 1997, 541–544). The azide of 33 was hydrogenated in the presence of O(CO$_2$Et)$_2$ to give 34. The compound 34 was then converted to final substituted cis-1-amino-2-indanol 36 first by mixing with SOCl$_2$, followed by hydrolysis.

Scheme 7

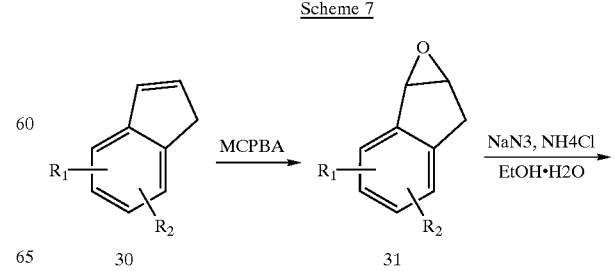

41

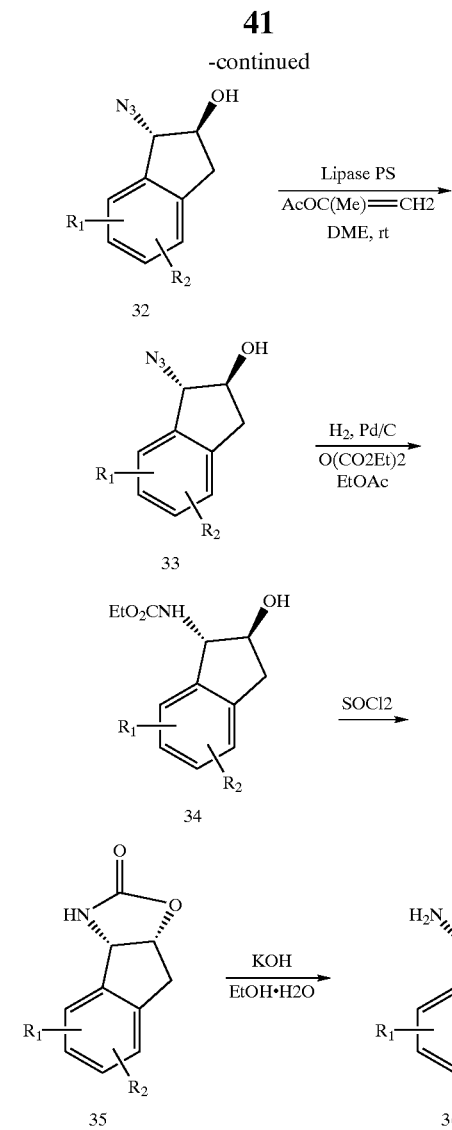

Alternatively, the substituted cis-1-amino-2-indanol 36 is directly prepared from substituted indene (30) following a method recently developed by Sharpless, K. B. et al as shown in scheme 8 (Li, G.; Angert, H. H.; Sharpless, K. B. *Angew. Chem. Int. Ed. Engl.* 1996, 35, 2813). The cbz group of 38 was removed by hydrogenation to give the free amine 36.

Scheme 8

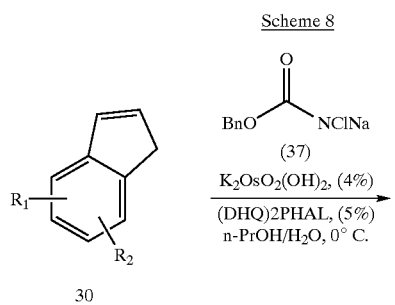

42

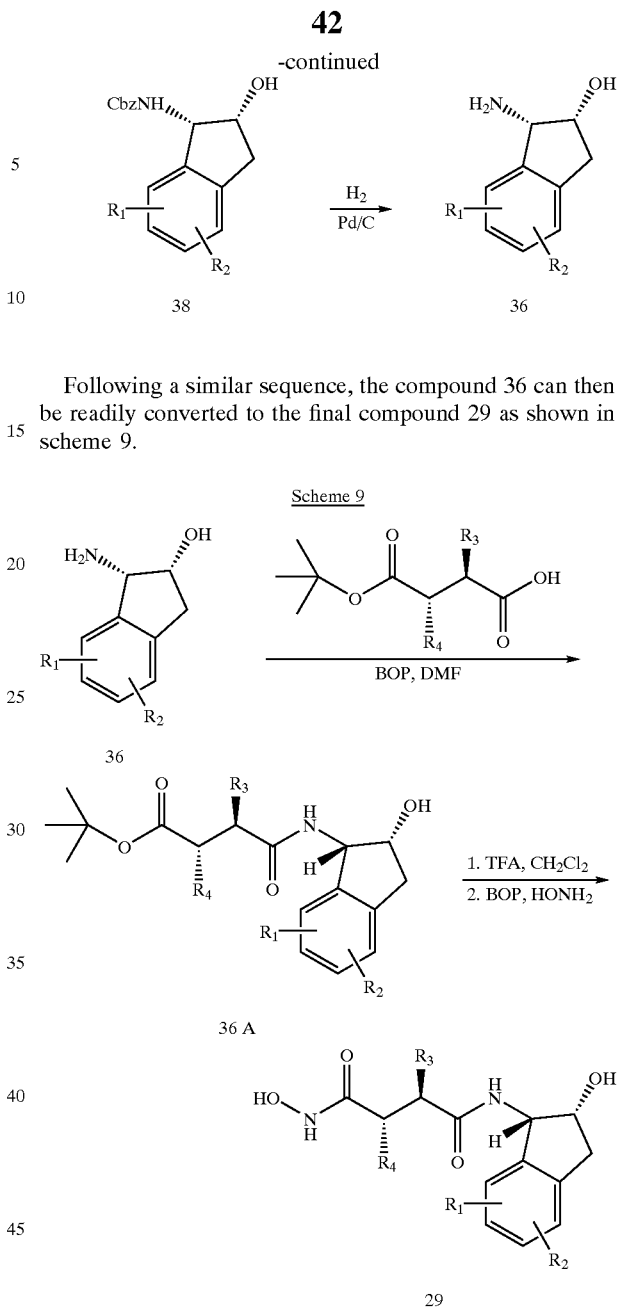

Following a similar sequence, the compound 36 can then be readily converted to the final compound 29 as shown in scheme 9.

Compounds of formula 39 can be synthesized as shown in scheme 10. Following the method developed by Sudo and Saigo (Sudo, A.; Saigo, K. Tetrahedron Asymetry, 1996, 7, 2939–2956), the racemic cis-2-amino-1-indanol can be readily synthesized from substituted indanone 40 as outlined in scheme 9. The indanone can be readily converted into oxime 41 with butyl nitrile under acidic conditions. Reduction of 41 with $NaBH_4$ in methanol could provide the hydroxy oxime, which was then treated with acetic anhydride and pyridine to give diacetate 42. Borane reduction of 42 then gives the racemic 43, which can then be directly used or resolved by co-crystalization with tartaric acid or others to provide the desired enantiomerically pure amine 43. Using similar chemistry to that used for the synthesis of target 5 as described in scheme 1, compound 44 can be readily converted to the target 39.

Scheme 10

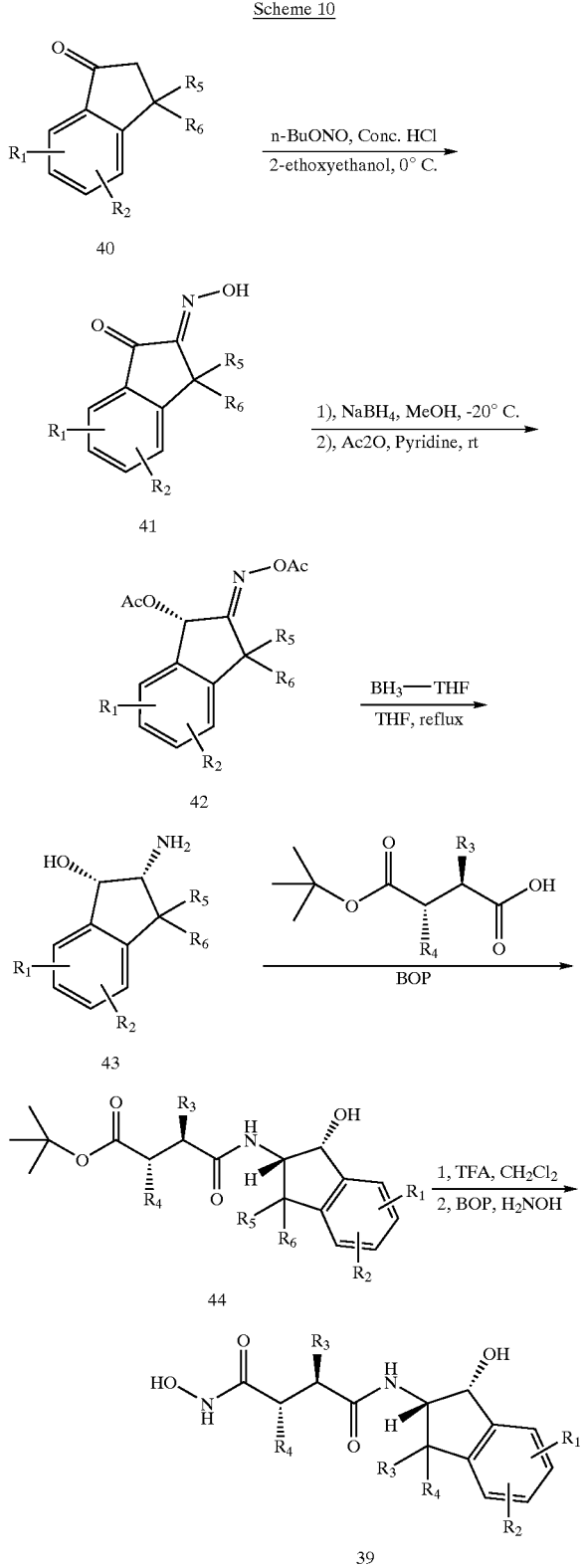

Scheme 11

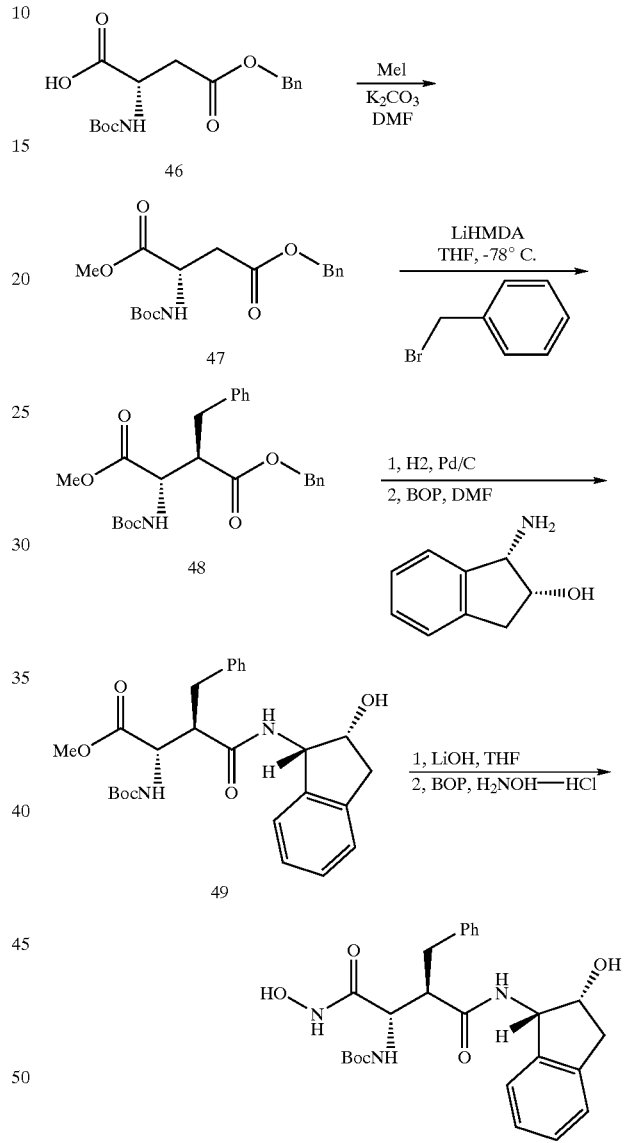

the enolate, which was reacted with benzyl bromide to afford 48. The benzyl group of 48 was removed by hydrogenation. The resulting acid was then coupled with cis-2-amino indanol to give 49. Hydrolysis of compound 49, followed by coupling with hydroxy amine to furnish the desired target 45.

Compounds of formula 45 are synthesized as shown in scheme 11. The carboxylic group of commercially available aspartic acid was protected as methyl ester 47. Compound 47 was then treated with LiHMDS in THF at −78° C. to form Compounds of formula 50 are synthesized as shown in scheme 12. Compound 51 was prepared using the similar procedure to that used for the synthesis of compound 49 (see scheme 11). The amino protecting group of 51 was removed by TFA in methylene chloride. The free amino group was converted to its corresponding amide, carbamate and sulfonamide 53 using the standard chemistry. Hydrolysis of compound 53, followed by coupling with hydroxy amine to furnish the desired target 50.

Scheme 12

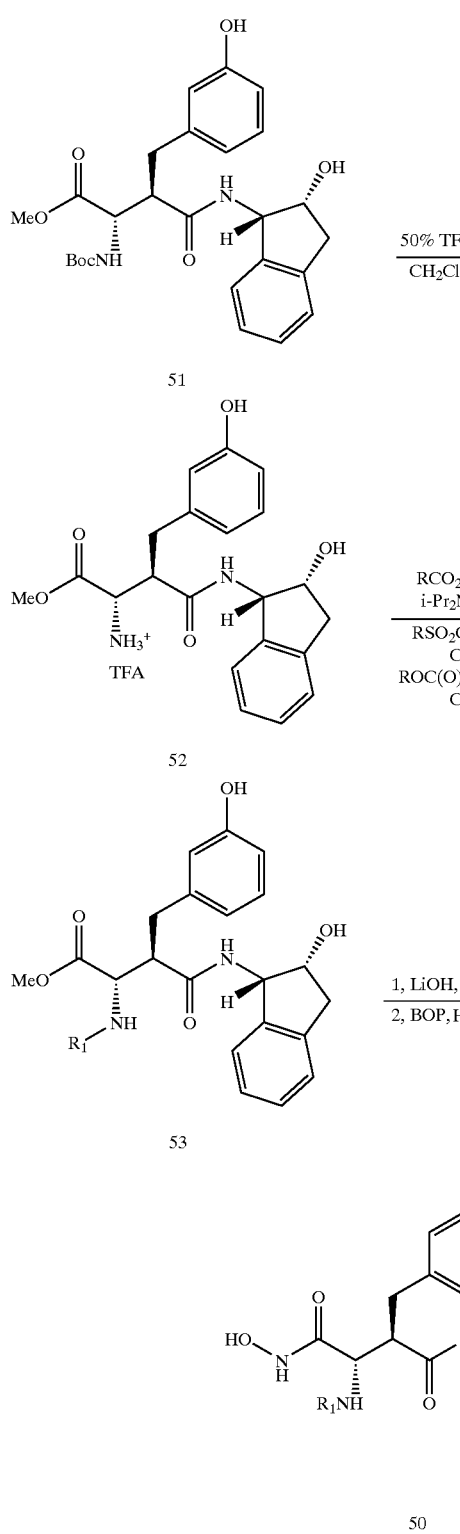

Scheme 13

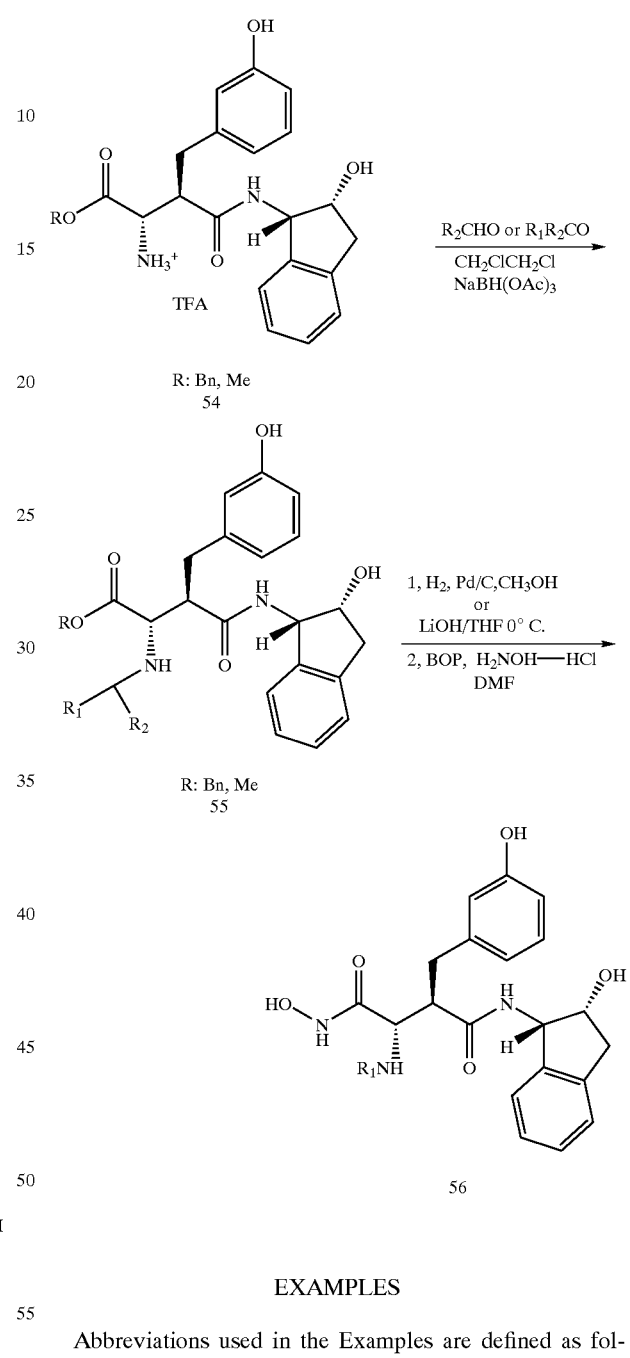

by either hydrogenation or hydrolysis. The resulting acid was then coupled with hydroxy amine to furnish the desired target 56.

Compounds of formula 56 are synthesized as shown in scheme 13. The amino TFA salt 54 can be prepared as described in scheme 11 and scheme 12. The reductive amination of 54 with either ketone or aldehyde under the reducing agent of NaBH(OAc)3 provided the desired alkyl amine 55. The, benzyl or methyl group of 55 was removed

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "R" and "S" are stereochemical designations familiar to those skilled in the art.

Example 1

N1(2(R)-Hydroxy-1(S)-indanyl)-N-4-hydroxy-2(R)-isobutyl-butanediamide

(a) N1(2R-Hydroxy-1S-indanyl)-2R-isobutyl-3-(tert-butoxycarbonyl)propanamide:

To a stirred, cooled (0° C.) solution of 500 mg (2.17 mmol) 2R-isobutyl 3-(tert-butoxycarbonyl)propinoic acid and 323.9 mg (2.17 mmol) (1S, 2R)-(–) cis-1-amino-2-indanol in 4.0 mL of anhydrous DMF was added 731.4 mg of TBTU, followed by addition of 1.19 mL of diisopropylethyl amine. The reaction was allowed to warm to room temperature. After 1 h, the reaction mixture was diluted with 15 mL 10% citric acid and 50 mL ethyl acetate, the aqueous solution was further extracted with ethyl acetate (2×25 mL). The combined organic solution was washed with water, sat. NaHCO$_3$, and brine, dried over MgSO$_4$. The solution was filtered and concentrated under reduced pressure to afford 0.685 g (87% yield) as a white solid. ESI-MS (M+H)$^+$: calcd 362, found 362.

(b) N-(2R-Hydroxy-1S-indanyl)-2R-isobutyl-3-(hydroxycarbonyl)propanamide:

To a solution of 0.635 g of N-(2R-hydroxy-1S-indanyl)-2R-isobutyl-3-(tert-butoxycarbonyl) propanamide in 4.5 mL methylene chloride and 0.5 mL water was dropwise added 5.0 mL of TFA. The reaction was stirred at room temperature for 50 min. The solution mixture was concentrated, and dried by co-evaporation with toluene (3×15 mL). The resulting material was directly used in the next step. ESI-MS (M+H)$^+$: calcd 306, found 306.

(c) N1(2(R)-Hydroxy-1(S)-indanyl)-N-4-hydroxy-2(R)-isobutyl-butanediamide:

To a cooled (0° C.) solution of 501.0 mg of N-(2R-hydroxy-1S-indanyl)-2R-isobutyl-3-(hydroxycarbonyl) propanamide in 6.4 mL DMF was added 786.5 mg of O-benzyl hydroxyamine-HCl, and 684.6 mg of TBTU, followed by addition of 1.71 mL of ethyldiisopropyl amine. The reaction was stirred at 0° C. for 15 min. and warmed to room temperature. After 4 h, the reaction mixture was poured into ethyl acetate/5% citric acid, the aqueous solution was extracted with ethyl acetate (3×25 mL). The combined organic solution was washed with 5% citric acid, water, sat. NaHCO$_3$, brine, and dried over MgSO$_4$. The solution was filtered and concentrated to afford 647 mg of desired product as a white solid.

To 323.5 mg of the above in 20 mL methanol was added 500 mg of 5% Pd/BaSO$_4$. The mixture was shaken under 50 psi H$_2$ for 16 hours. The reaction mixture was filtered and concentrated and purified by reverse HPLC to afford 110 mg of the desired hydroxamic acid as a white solid. ESI-MS (M+H)$^+$: calcd 321, found 321.

Example 2

N1(2(R)-Hydroxy-1(S)-indanyl)-N-4-hydroxy-2(R)-isobutyl-3(S)-(3-propionic Acid)-butanediamide

Following a procedure analogous to that used in example 1, 2R-isobutyl 3S-(tert-butoxycarbonyl) 5-benzoxycarbonyl pentanoic acid was coupled with (1S, 2R)-(–) cis-1-amino-2-indanol using TBTU as the coupling reagent. Removal of tert-butyl protecting group was achieved by treating with TFA as described in example 1, followed by coupling with O-benzyl hydroxyamine-HCl mediated by TBTU. The resulting material was hydrogenated to afford the desired product. ESI-MS (M+H)$^+$: calcd 393, found 393.

Example 3

N1(2(R)-Hydroxy-1(S)-indanyl)-N-4-hydroxy-2(R)-isobutyl-3(S)-methyl-butanediamide

Following a procedure analogous to that used in example 1, 2R-hexyl 3S-(tert-butoxycarbonyl) butanoic acid was coupled with (1S, 2R)-(–) cis-1-amino-2-indanol using TBTU as the coupling reagent. Removal of tert-butyl protecting group was achieved by treating with TFA as described in example 1, followed by coupling with O-benzyl hydroxyamine-HCl mediated by TBTU or BOP. The resulting material was hydrogenated to afford the desired product as a white solid. ESI-MS (M+H)+: calcd 335, found 335.

Example 4

N1(2(R)-Hydroxy-1(S)-indanyl)-N-4-hydroxy-2(R)-isobutyl-3(S)-propyl-butanediamide

Following a procedure analogous to that used in example 1, 2R-isobutyl 3S-(tert-butoxycarbonyl) hexanoic acid was coupled with (1S, 2R)-(–) cis-1-amino-2-indanol using TBTU as the coupling reagent. Removal of tert-butyl protecting group was achieved by treating with TFA as described in example 1, followed by coupling with O-benzyl hydroxyamine-HCl mediated by TBTU or BOP. The resulting material was hydrogenated to afford the desired product as a white solid. ESI-MS (M+H)$^+$: calcd 363, found 363.

Example 5

N1(2(R)-Hydroxy-1(S)-indanyl)-N-4-hydroxy-2(R)-hexyl-3(S)-propyl-butanediamide

Following a procedure analogous to that used in example 1, 2R-hexyl 3S-(tert-butoxycarbonyl) hexanoic acid was coupled with (1S, 2R)-(–) cis-1-amino-2-indanol using TBTU as the coupling reagent. Removal of tert-butyl protecting group was achieved by treating with TFA as described in example 1, followed by coupling with O-benzyl hydroxyamine-HCl mediated by TBTU or BOP. The resulting material was hydrogenated to afford the desired product as a white solid. ESI-MS (M+H)+: calcd 391, found 391.

Example 6

N1-[2(R)-Hydroxy-1(S)-indanyl]-N-4-hydroxy-2(R)-[4-hydroxy-phenyl)methyl]-butanediamide

(a) Preparation of N-(2R-Hydroxy-1S-indanyl)-3-(4-benzyloxy-phenyl)-propanamide:

To a stirred, cooled (0° C.) solution of 10 g (39.1 mmol) 3-(4-benzyloxy-phenyl)-propinoic acid and 7 g (46.92 mmol) (1S, 2R)-(–) cis-1-amino-2-indanol in 200 mL of anhydrous DMF was added 17.3 g BOP as a solid, followed by addition of 20 mL of diethylisopropyl amine. The reaction was allowed to warm to room temperature. After 5 h, the reaction mixture was diluted with 100 mL 10% citric acid and 100 mL ethyl acetate, the aqueous solution was further extracted with ethyl acetate (2×50 mL). The combined organic solution was washed with water, sat. NaHCO$_3$, and brine, dried over MgSO$_4$. The solution was filtered and concentrated under reduced pressure to afford 15.1 g desired product as a white solid. ESI-MS (M+H)$^+$: calcd 388, found 388.

(b) N-(1S,2R-N,O-Dimethyl Acetonide-indanyl)-3-(4-benzyloxy-phenyl)-propanamide:

To a stirred, cooled (0° C.) solution of 15.1 g N-(2R-hydroxy-1S-indanyl)-3-(4-benzyloxy-phenyl)-propanamide and 1.14 g of PPTS in 300 mL of methylene chloride was slowly added 30 ml of 2-methoxy propene. The solution was slowly warmed to room temperature and stirred overnight. The reaction was quenched by addition of 50 mL of sat. NaHCO$_3$, and extracted with ethyl acetate (3×50 mL). The combined solution was washed with sat NaHCO$_3$, water, brine, and dried over MgSO$_4$. The solution was filtered and concentrated. The crude material was purified by flash column (Ethyl acetate/Hexane: 40:60) to give 15.3 g desired product as a white solid. ESI-MS (M+H)$^+$: calcd 428, found 428.

(c) N-(1S, 2R-N,O-Dimethyl Acetonide-indanyl)-2R-(4-benzyloxy-phenylmethyl)-3-(tert-butoxycarbonyl-propanamide:

To a stirred and cooled (−78° C.) solution of 3.0 g (7.0 mmol) of N-(2R-hydroxy-1S-indanyl)-3-(4-benzyloxy-phenyl)-propanamide in 20 mL THF was dropwise added a freshly prepared, cooled (−78° C.) LDA (7.0 mmol) in THF. After 1.0 hour, a solution of 1.14 mL (7.7 mmol) tert-butyl 2-bromoacetate in 3.0 ml THF was added dropwise. The resulting solution was incubated at −78° C. for 4.0 h. The reaction was quenched by addition of 10% citric acid, and extracted with ethyl acetate (3×100 mL). The combined organic solution was washed with water, brine, and dried over MgSO$_4$. The solution was filtered and concentrated. The crude material was purified by flash column with (Ethyl acetate/Hexane: 15–25:85–75) to afford the desired product (2.8 g, 71% yield) as a white solid, and 0.1 g of other diastereomer. ESI-MS (M+H)$^+$: calcd 542, found 542.

(d) N-(2R-Hydroxy-1S-indanyl)-2R-(4-benzyloxy-phenylmethyl)-3-(hydroxy-carbonyl)propanamide:

To a solution of 1.13 g of N-(2R-hydroxy-1S-indanyl)-2R-(4-Benzyloxy-phenylmethyl)-3-(tert-butoxycarbonyl) propanamide in 7.6 mL methylene chloride and 0.4 mL water was dropwise added 8.0 mL of TFA. The reaction was stirred at room temperature for 50 min. The solution mixture was concentrated to half of its original volume. The residue was then dried by co-evaporation with toluene (3×15 mL) and directly used in the next step. ESI-MS (M+H)$^+$: calcd 446, found 446.

(e) N-(2R-Hydroxy-1S-indanyl)-2K-(4-benzyloxy-phenylmethyl)-3-(N-hydroxyaminocarbonyl)propan-amide:

To a cooled (0° C.) solution of 104 mg of N-(2R-hydroxy-1S-indanyl)-2R-(4-Benzyloxy-phenylmethyl)-3-(hydroxy-carbonyl) propanamide in 1.2 mL DMF was added 112 mg of O-benzyl hydroxylamine-HCl, and 78.8 mg of TBTU, followed by addition of 0.24 mL of ethyldiisopropyl amine. The reaction was stirred at 0° C. for 15 min. and warmed to room temperature. After 2 h, the reaction mixture was poured into ethyl acetate/5% citric acid, the aqueous solution was extracted with ethyl acetate (3×25 mL). The combined organic solution was washed with 5% citric acid, water, sat. NaHCO$_3$, brine, and dried over MgSO$_4$. The solution was filtered and concentrated to afford 105 mg of desired product.

To 105 mg of the above in 6 mL methanol was added 60 mg of 5% Pd/BaSO$_4$. The mixture was shaken under 50 psi H$_2$ for 4 hour. The reaction mixture was filtered and concentrated and purified by reverse HPLC to afford 47 mg of the desired hydroxamic acid as a white solid. ESI-MS (M+H)$^+$: calcd 371, found 371.

Example 7

N1-[2(R)-Hydroxy-1(S)-indanyl]-N-4-hydroxy-2(R)-[4-methoxy-phenyl)methyl]-butanediamide Prepared by the method described in example 6 to give the desired material. ESI-MS (M+H)$^+$: calcd 385, found 385.

Example 8

N1-[2(R)-Hydroxy-1(S)-indanyl]-N4-hydroxy-2(R)-[4-(hydroxy-phenyl)methyl]-butanediamide Prepared by the method described in example 6 to give the desired material. ESI-MS (M+H)$^+$: calcd 355, found 355.

Example 9

N1-[2(R)-Hydroxy-1(S)-indanyl]-N-4-hydroxy-2(R)-[3-phenyl-propyl]butanediamide

Prepared by the method described in example 6 to give the desired material. ESI-MS (M+H)$^+$: calcd 383, found 383.

Example 10

N1-[2(R)-Hydroxy-1(S)-indanyl]-N-4-hydroxy-2(R)-[[4-(benzyloxy)-phenyl]methyl]-butanediamide Prepared by the method described in example 6 to give the desired material. ESI-MS (M+H)$^+$: calcd 461, found 461.

Example 11

N1-[2(R)-Hydroxy-1(S)-indanyl]-N-4-hydroxy-2(R)-[[3-(benzyloxy)-phenyl]methyl]-butanediamide Prepared by the method described in example 6 to give the desired material. ESI-MS (M+H)$^+$: calcd 461, found 461.

Example 12

N1-[2(R)-Hydroxy-1(S)-indanyl]-N-4-hydroxy-2(R)-[(3-(hydroxy-phenyl)methyl]-butanediamide Prepared by the method described in example 6 to give the desired material. ESI-MS (M+H)$^+$: calcd 371, found 371.

Example 13

N1-[2(R)-Hydroxy-1(S)-indanyl]-N-4-hydroxy-2(R)-[4-(fluoro-phenyl)methyl]-butanediamide Prepared by the method described in example 6 to give the desired material. ESI-MS (M+H) +: calcd 373, found 373.

Example 14

N1-[2(R)-Hydroxy-1(S)-indanyl]-N-4-hydroxy-2(R)-[3,4-(methylenedioxy-phenyl)methyl]-butanediamide Prepared by the method described in example 6 to give the desired material. ESI-MS (M+H)$^+$: calcd 379, found 379.

Example 15

N1-[2(R)-Hydroxy-1(S)-indanyl]-N-4-hydroxy-2(R)-[3-(methoxy-phenyl)methyl]-butanediamide Prepared by the method described in example 6 to give the desired material. ESI-MS (M+H)$^+$: calcd 385, found 385.

Example 16

N1-[2(R)-Hydroxy-1(S)-indanyl]-N-4-hydroxy-2(R)-[[4-(phenyl)phenyl]methyl]-butanediamide (a) N-(1S,2R-N,O-Dimethyl Acetonide-indanyl)-2R-(4-phenyl)phenylmethyl-3-(tert-butoxycarbonyl)propanamide To 2.6 g N-(1S,2R-N,O-dimethyl acetonide-indanyl)-2R-(4-Benzyloxy-phenylmethyl)-3-(tert-butoxycarbonyl) propanamide in 20 mL methanol was added 300 mg of 5% Pd/C. The mixture was shaken under 50 psi H$_2$ for 17 hours. The reaction mixture was filtered and concentrated to afford 2.0 g of the desired product.

To a cooled (0° C.) solution of 1.2 g of N-(2R-hydroxy-1S-indanyl)-2R-(4-hydroxy-phenylmethyl)-3-(tert-butoxycarbonyl) propanamide and 0.95 g of PhN(tf)$_2$ in 9.0 mL of methylene chloride was dropwise added 0.77 mL Et₃N. After 45 min at 0° C., the reaction mixture was diluted in ethyl ether (60 mL), washed with sat NaHCO₃, brine, and dried over MgSO₄. The crude mater was purified by flash column with 20% ethyl acetate in hexane to afford the desired product as a colorless oil.

To a solution of 192.0 mg of above material and 22 mg of PPh₃ in 1.4 mL toluene and 1.4 mL 0.35M Na₂CO₃ aq. solution was added catalytical amount (6.0 mg) of Pd(Ac)₂. The resulting mixture was stirred at 60° C. for 10 min, followed by addition of 44 mg of benzene bornic acid as solid. The reaction was heated at 70° C. After four hours, the reaction mixture was then diluted with ethyl acetate, washed with water, brine, and dried over MgSO4. The crude material was purified by 15% ethyl acetate in hexane to afford 127.1 mg of desired product as a colorless oil. ESI-MS (M+H)⁺: calcd 431, found 431.

(b) N-(2R-Hydroxy-1S-indanyl)-2R-(4-phenyl)phenyl-methyl-3-(N-hydroxyaminocarbonyl)propanamide:

Following the method used in the synthesis of example 1, the above N-(1S ,2R-N,O-dimethyl acetonide-indanyl)-2R-(4-phenyl)phenylmethyl-3-(tert-butoxycarbonyl) propanamide was treated with TFA, followed by coupling with hydroxylamine to yield the desired N-(2R-hydroxy-1S-indanyl)-2R-(4-phenyl)-phenylmethyl-3-(N-hydroxyaminocarbonyl)-propanamide as a white solid. ESI-MS (M+H)⁺: calcd 431.2, found 431.2.

Example 17

N1-[2(R)-Hydroxy-1(S)-indanyl]-N-4-hydroxy-2(R)-[[4-(2-tert-butylaminosulfonyl-phenyl)phenyl]methyl]butanediamide Prepared by the method described in example 16 to give the desired material. ESI-MS (M+H)⁺: calcd 566, found 566.

Example 18

N1-[2(R)-Hydroxy-1(S)-indanyl]-N-4-hydroxy-2(R)-[[4-(2-methoxy-phenyl)phenyl]methyl]butanediamide Prepared by the method described in example 16 to give the desired material. ESI-MS (M+H)⁺: calcd 461, found 461.

Example 19

N1-[2(R)-Hydroxy-1(S)-indanyl]-N-4-hydroxy-2(R)-[[4-(3-trifluoromethyl-phenyl)-phenyl]methyl]butanediamide Prepared by the method described in example 16 to give the desired material. ESI-MS (M+H)⁺: calcd 499, found 499.

Example 20

N1-[2(R)-Hydroxy-1(S)-indanyl]-N-4-hydroxy-2(R)-[(3-hydroxy-4-methylphenyl)-methyl]butanediamide Prepared by the method described in example 6 to give the desired material. ESI-MS (M+H)⁺: calcd 401, found 401.

Example 21

N1-[2(R)-Hydroxy-1(S)-indanyl]-N-4-hydroxy-2(R)-[[3-(3-thiophene-isoxazoline]-methyl]butanediamide Prepared by the method described in example 6 to give the desired material. ESI-MS (M+H)⁺: calcd 429, found 429.

Example 22

N1-[2(R)-Hydroxy-1(S)-indanyl]-N-4-hydroxy-2(R)-[[4-(2-chloro-phenyl)-phenyl]-methyl]butanediamide Prepared by the method described in example 16 to give the desired material. ESI-MS (M+H)⁺: calcd 465.5, found 465.5.

Example 23

N1-[2(R)-Hydroxy-1(S)-indanyl]-N-4-hydroxy-2(R)-[[4-(2-benzofuran)-phenyl]-methyl]butanediamide Prepared by the method described in example 16 to give the desired material. ESI-MS (M+H)⁺: calcd 471, found 471.

Example 24

N1-[2(R)-Hydroxy-1(S)-indanyl]-N-4-hydroxy-2(R)-[[4-(2-methyl-phenyl)-phenyl]-methyl]butanediamide Prepared by the method described in example 16 to give the desired material. ESI-MS (M+H)⁺: calcd 445, found 445.

Example 25

N1-[2(R)-Hydroxy-1(S)-indanyl]-N-4-hydroxy-2(R)-[[(3,4-(methylenedioxy-phenyl)-phenyl]methyl]butanediamide Prepared by the method described in example 16 to give the desired material. ESI-MS (M+H)⁺: calcd 475, found 475.

Example 26

N1-[2(R)-Hydroxy-1(S)-indanyl]-N-4-hydroxy-2(R)-[[4-(2-tetrazole-phenyl)-phenyl]-methyl]butanediamide Prepared by the method described in example 16 to give the desired material. ESI-MS (M+H)⁺: calcd 499, found 499.

Example 27

N1-[2(R)-Hydroxy-1(S)-indanyl]-N-4-hydroxy-2(R)-[[3-phenyl)phenyl]methyl]-butanediamide Prepared by the method described in example 16 to give the desired material. ESI-MS (M+H)⁺: calcd 431, found 431.

Example 28

N1-[2(R)-Hydroxy-1(S)-indanyl]-N-4-hydroxy-2(R)-[[3-methyl-phenyl)phenyl]methyl]-butanediamide Prepared by the method described in example 16 to give the desired material. ESI-MS (M+H)⁺: calcd 445, found 445.

Example 29

N1-[2(R)-Hydroxy-1(S)-indanyl]-N-4-hydroxy-2(R)-[4-(amino-phenyl)methyl]-butanediamide Prepared by the method described in example 6 to give the desired material. ESI-MS (M+H)⁺: calcd 370, found 370.

Example 30

N1-[2(R)-Hydroxy-1(S)-indanyl]-N-4-hydroxy-2(R)-[[(4-(benzyloxy-carbonyl)-amino]phenyl)methyl]butanediamide Prepared by the method described in example 6 to give the desired material. ESI-MS (M+H)⁺: calcd 504, found 504.

Example 31

N1-[2(R)-Hydroxy-1(S)-indanyl]-N-4-hydroxy-2 (R)-[[4-(2-hydroxymethlene)phenyl)-phenyl]methyl] butanediamide Prepared by the method described in example 16 to give the desired material. ESI-MS (M+H)$^+$: calcd 461, found 461.

Example 32

N1-[2(R)-Hydroxy-1(S)-indanyl]-N-4-hydroxy-2 (R)-[[4-(3,4,5-trimethoxy-phenyl)phenyl]methyl] butanediamide Prepared by the method described in example 16 to give the desired material. ESI-MS (M+H)$^+$: calcd 521, found 521.

Example 33

N1-[2(R)-Hydroxy-1(S)-indanyl]-N-4-hydroxy-2 (R)-[[4-(2,4-di-methoxy-phenyl)-phenyl]methyl] butanediamide Prepared by the method described in example 16 to give the desired material. ESI-MS (M+H)$^+$: calcd 491, found 491.

Example 34

N1-[2(R)-Hydroxy-1(S)-indanyl]-N-4-hydroxy-2 (R)-[[4-(3,5-di-chloro-phenyl)-phenyl]methyl] butanediamide Prepared by the method described in example 16 to give the desired material. ESI-MS (M+H)$^+$: calcd 499, found 499.

Example 35

N1-[2(R)-Hydroxy-1(S)-indanyl]-N-4-hydroxy-2 (R)-[[4-(2-trifluoromethyl-phenyl)-phenyl]methyl] butanediamide Prepared by the method described in example 16 to give the desired material. ESI-MS (M+H)$^+$: calcd 499, found 499.

Example 36

N1-[2(R)-Hydroxy-1(S)-indanyl]-N-4-hydroxy-2 (R)-[[4-(3-isopropyl-phenyl)-phenyl]methyl] butanediamide Prepared by the method described in example 16 to give the desired material. ESI-MS (M+H)$^+$: calcd 473, found 473.

Example 37

N1-[2(R)-Hydroxy-1(S)-indanyl]-N-4-hydroxy-2 (R)-[[4-(2,4-dichloro-phenyl)-phenyl]methyl] butanediamide Prepared by the method described in example 16 to give the desired material. ESI-MS (M+H)$^+$: calcd 499, found 499.

Example 38

N1-[2(R)-Hydroxy-1(S)-indanyl]-N-4-hydroxy-2 (R)-[[4-(3-chloro-4-fluoro-phenyl)-phenyl]methyl] butanediamide Prepared by the method described in example 16 to give the desired material. ESI-MS (M+H)$^+$: calcd 483, found 483.

Example 39

N1-[2(R)-Hydroxy-1(S)-indanyl]-N-4-hydroxy-2 (R)-[[4-(p-toluenesulfonylamino)-phenyl]methyl] butanediamide Prepared by the method described in example 16 to give the desired material. ESI-MS (M+H)$^+$: calcd 524, found 524.

Example 40

N1-[2(R)-Hydroxy-1(S)-indanyl]-N-4-hydroxy-2 (R)-phenylmethyl-3(S)-(tert-butyloxy-carbonyl-amino)butanediamide To a solution of 20 g of Boc-Asp(OBn)-OH and 8.9 g of K$_2$CO$_3$ in 200 mL DMF was added 4.04 mL of CH$_3$I. The reaction mixture was stirred at room temperature for 12 h. The mixture was diluted in water, extracted with diethyl ether. The combined organic layer was washed with sat. NaHCO$_3$, water and brine. The crude material was recrystalized from diethyl ether and hexane to afford 19.2 g of the desired product Boc-Asp(OBn)-OCH$_3$.

To a cooled (−78° C.) solution of 2.5 g of compound Boc-Asp(OBn)-OCH$_3$ in 49 mL toluene was added dropwise 15.2 mL of (1.0 M in THF) LiHMDS over 15 min. The resulting solution was stirred at −78° C. for 1.0 h, followed by addition of 1.4 mL benzyl bromide. The solution was stirred at −50° C overnight. The reaction was quenched with 10% citric acid, and extracted with diethyl ether. The organic layer was washed with sat. brine, dried over Na$_2$SO$_4$. The crude material was purified by 15% ethyl acetate to afford 2.1 g (64% yield) of desired product.

1.0 g (2.34 mmmol) above product and 500 mg of 10% Pd/C was hydrogenated at 32 Psi for two hour. The reaction mixture was filtered, and concentracted to afford a residue.

678 mg (2.01 mmol) above acid was coupled with 314 mg cis-2-amino indanol using 933 mg of BOP as the coupling reagent in DMF to afford 867 mg of coupling product N1-[2(R)-hydroxy-1(S)-indanyl]-N-4-hydroxy-2(R)-phenylmethyl-3(S)-(tert-butyloxy-carbonyl-amino)-4-(tert-butoxycarbonyl)-butan-amide.

To a cooled solution of 268 mg of N1-[2(R)-hydroxy-1 (S)-indanyl]-N-4-hydroxy-2(R)-phenylmethyl-3(S)-(tert-butyloxy-carbonyl-amino)-4-(tert-butoxycarbonyl)butan-amide. in 4.3 mL THF was added 0.43 mL (2.5 M in H$_2$O) LiOH solution. The reaction mixture was stirred at 0° C. for 30 min. The reaction was quenched with 10% citric acid, extracted with EtOAc, the organic layer was washed with sat. brine, and dried over Na$_2$SO$_4$. The solvent was removed to afford 252.1 mg of the product as white solid.

The above acid (252 mg, 0.555 mmol) was treated with 257 mg of BOP and 116 mg of hydroxylamine in DMF. The crude material was purified by RP-HPLC (column: 41.5× 250 mm C18 dynamax, gradient: 15 to 65% acetonitrile with 0.1% TFA over 25 min. The sample was detected at 220 nM.) to give the desired material N1-[2(R)-hydroxy-1(S)-indanyl]-N-4-hydroxy-2(R)-phenylmethyl-3(S)-(tert-butyloxy-carbonyl-amino)-butanediamide, ESI-MS (M+H)$^+$: calcd 470, found 470.

Example 41

N1-[2(R)-Hydroxy-1(S)-indanyl]-N-4-hydroxy-2 (R)-[[4-(3,4-methylenedioxyphenyl)-phenyl] methyl]-3(S)-(tert-butyloxy-carbonyl-amino)-butanediamide Prepared by the method described in example 40 to give the desired material. ESI-MS (M+H)$^+$: calcd 588, found 588.

Example 42

N1-[2(R)-Hydroxy-1(S)-indanyl]-N-4-hydroxy-2 (R)-[[4-(3-methoxyphenyl)-phenyl]methyl] butanediamide Prepared by the method described in example 16 to give the desired material. ESI-MS (M+H)$^+$: calcd 461, found 461.

Example 43

N1-[2(R)-Hydroxy-1(S)-indanyl]-N-4-hydroxy-2
(R)-[[4-(3-fluororphenyl)-phenyl]-methyl]
butanediamide Prepared by the method described in example 16 to give the desired material. ESI-MS (M+H)$^+$: calcd 449, found 449.

Example 44

N1-[2(R)-Hydroxy-1(S)-indanyl]-N-4-hydroxy-2
(R)-[3-(fluoro-phenyl)methyl]-3(S)-(tert-butyloxy-
carbonyl-amino)-butanediamide Prepared by the method described in example 40 to give the desired material. ESI-MS (M+H)$^+$: calcd 488, found 488.

Example 45

N1-[2(R)-Hydroxy-1(S)-indanyl]-N-4-hydroxy-2
(R)-[3-(hydroxy-phenyl)methyl]-3(S)-(tert-butyloxy-
carbonyl-amino)-butanediamide Prepared by the method described in example 40 to give the desired material. ESI-MS (M+H)$^+$: calcd 486, found 486.

Example 46

N1-[2(R)-Hydroxy-1(S)-indanyl]-N-4-hydroxy-2
(R)-[[4-(3-nitrophenyl)phenyl]-methyl]
butanediamide Prepared by the method described in example 16 to give the desired material. ESI-MS (M+H)$^+$: calcd 476, found 476.

Example 47

N1-[2(R)-Hydroxy-1(S)-indanyl]-N-4-hydroxy-2
(R)-[[4-(3-(methylsulfonyl-amino)-phenyl)phenyl]-
methyl]butanediamide Prepared by the method described in example 16 to give the desired material. ESI-MS (M+H)$^+$: calcd 524, found 524.

Example 48

N1-[2(R)-Hydroxy-1(S)-indanyl]-N-4-hydroxy-2
(R)-[3-(hydroxy-phenyl)methyl]-3(S)-(2,2-dimethyl-
propionamido)-butanediamide Step 1: To a solution of 1.55 g of N1-[2(R)-hydroxy-1(S)-indanyl]-2(R)-[3-(hydroxy-phenyl)methyl]-3(S)-(tert-butyloxy-carbonyl-amino)-Succinamic methyl ester was added 20 mL of 4N Hcl in dioxane at RT. The resulting solution was stirred at room temperature for 25 min. The reaction mixture was concentracted to afford 1.45 g of N1-[2(R)-hydroxy-1(S)-indanyl]-2(R)-[3-(hydroxy-phenyl)methyl]-3(S)-amino-Succinamic methyl ester as a white solid.

Step 2: To a ice cold solution of 166 mg (0.43 mmol) of N1-[2(R)-hydroxy-1(S)-indanyl]-2(R)-[3-(hydroxy-phenyl)methyl]-3(S)-amino-Succinamic methyl ester and 88 mg (0.86 mmol) of 2,2-dimethyl-propionic acid in 2.15 mL DMF was added 145 mg TBTU (0.45 mmol) as a solid, followed by addition of 0.23 mL of hunig base. The resulting solution was stirred at room temperature for two hours. The mixture was diluted in 5% NaHCO3 solution, and extracted with ethyl acetate (3×20 mL). The combined organic layer was washed with saturated brine, and dried with MgSO4. Flash column of the crude material with 50% ethyl acetate in hexane to give 189 mg (94% yield) of N1-[2(R)-hydroxy-1(S)-indanyl]-2(R)-[3-(hydroxy-phenyl)methyl]-3(S)-(2,2-dimethyl-propionamido)-Succinamic methyl ester as a off white solid.

Step 3: To a ice cold solution of 176 mg of N1-[2(R)-hydroxy-1(S)-indanyl]-2(R)-[3-(hydroxy-phenyl)methyl]-3(S)-(2,2-dimethyl-propionamido)-Succinamic methyl ester in 2.0 mL of THF was added 0.38 mL LiOH solution (2.5M). The resulting solutionon was stirred at 0° C. for 30 min. The reaction was quenched with 0.35 mL HCl (3N) solution, and extracted with ethyl acetate (3×10 mL). The combined solution was washed with saturated brine, dried over Na2SO4. The solution was then filterted and concentracted to afford 152 mg of N1-[2(R)-hydroxy-1(S)-indanyl]-2(R)-[3-(hydroxy-phenyl)methyl]-3(S)-(2,2-dimethyl-propionamido)-Succinamic acid as an off white solid.

Step 4: To an ice cold solution of 135 mg (0.297 mmol) of N1-[2(R)-hydroxy-1(S)-indanyl]-2(R)-[3-(hydroxy-phenyl)methyl]-3(S)-(2,2-dimethyl-propionamido)-Succinamic acid in 1.5 mL DMF was added 131 mg of BOP, followed by addition of 62 mg hydroxy amine and 0.15 mL hunig base. The resulting solution was stirred at room temperature for three hour. The crude material was directly purified on reverse-HPLC to afford 82 mg of the desired N1-[2(R)-hydroxy-1(S)-indanyl]-N-4-hydroxy-2(R)-[3-(hydroxy-phenyl)methyl]-3(S)-(2,2-dimethyl-propionamido)-butanediamide as white solid. ESI-MS (M+H)$^+$: calcd 470, found 470.

Example 49

N1-[2(R)-Hydroxy-1(S)-indanyl]-N-4-hydroxy-2
(R)-[3-(hydroxy-phenyl)methyl]-3(S)-(ethyloxy-
carbonyl-amino)-butanediamide Prepared by the method described in example 40 to give the desired material. ESI-MS (M+H)$^+$: calcd 458, found 458.

Example 50

N1-[2(R)-Hydroxy-1(S)-indanyl]-N-4-hydroxy-2
(R)-[3-(hydroxy-phenyl)methyl]-3(S)-(iso-butyloxy-
carbonyl-amino)-butanediamide Prepared by the method described in example 40 to give the desired material. ESI-MS (M+H)$^+$: calcd 486, found 486.

Example 51

N1-[2(R)-Hydroxy-1(S)-indanyl]-N-4-hydroxy-2
(R)-[3-(hydroxy-phenyl)methyl]-3(S)-
(propionamido)-butanediamide Prepared by the method described in example 40 to give the desired material. ESI-MS (M+H)$^+$: calcd 458, found 458.

Example 52

N1-[2(R)-Hydroxy-1(S)-indanyl]-N-4-hydroxy-2
(R)-[3-(hydroxy-phenyl)methyl]-3(S)-(1-methyl-
cyclo-propane Carboxamido-1-yl)-butanediamide Prepared by the method described in example 40 to give the desired material. ESI-MS (M+H)$^+$: calcd 452, found 452.

Example 53

N1-[2(R)-Hydroxy-1(S)-indanyl]-N-4-hydroxy-2
(R)-[3-(hydroxy-phenyl)methyl]-3(S)-(2,2-dimethyl-
propyl-amino)-butanediamide Step 1: A solution of 2.1 g of N1-[2(R)-hydroxy-1(S)-indanyl]-2(R)-[3-(hydroxy-phenyl)methyl]-3(S)-amino- Succinamic methyl ester in 18 mL 1,2-dichloroethane was mixed with 0.55 mL of pivaldehyde and 1.10 mL of hunig base for 20 min, followed by addition of 1.79 g of NaBH(OAc)3 as a solid. The resulting solution was stirred at room temperature for 3 hour. The reaction mixtur was diluted in 5% NaHCO3 and extracted with ethyl acetate (3×30 mL). The combined solution was washed with saturated brine. The crude material was purified on silica with 30–50% ethyl acetate in hexane to give 1.44 g of N1-[2(R)-hydroxy-1(S)-indanyl]-2(R)-[3-(hydroxy-phenyl)methyl]-3(S)-(2,2-dimethylpropyl-amino)-Succinamic methyl ester.

Step 2: To a ice cold solution of 290 mg of N1-[2(R)-hydroxy-1(S)-indanyl]-2(R)-[3-(hydroxy-phenyl)methyl]-3(S)-(2,2-dimethylpropyl-amino)-Succinamic methyl ester in 2.5 mL THF was added 0.63 mL of LiOH (2.5 M). The reaction mixture was stirred at 0° C. for 30 min. The reaction was quenched with 0.6 ml HCl solution (3N), tha mixture was then freeze dried.

Step 3: To an ice cold solution of above material in 1.5 mL DMF was added 295 mg of BOP, followed by addition of 264 mg hydroxyl amine and 0.8 mL hunig base. The resulting solution was stirred at room temperature for three hour. The crude material was directly purified on reverse-HPLC to afford 85 mg of the desired N1-[2(R)-hydroxy-1(S)-indanyl]-N-4-hydroxy-2(R)-[3-(hydroxy-phenyl)methyl]-3(S)-(2,2-dimethylpropyl-amino)-butanediamide as a white solid. ESI-MS (M+H)$^+$: calcd 455, found 455.

Example 54

N1-[2(R)-Hydroxy-1(S)-indanyl]-N-4-hydroxy-2(R)-[3-(hydroxy-phenyl)methyl]-3(S)-(methylsulfonyl-amino)-butanediamide Prepared by the method described in example 16 to give the desired material. ESI-MS (M+H)$^+$: calcd 464, found 464.

Example 55

N1-[2(R)-Hydroxy-1(S)-indanyl]-N-4-hydroxy-2(R)-13-(hydroxy-phenyl)methyl]-3(S)-amino-butanediamide Prepared by the method described in example 40 to give the desired material. ESI-MS (M+H)$^+$: calcd 386, found 386.

Example 56

N1-[2(R)-Hydroxy-1(S)-indanyl]-N-4-hydroxy-2(R)-[4-(methylsulfonylamino)-phenyl)methyl] butanediamide Prepared by the method described in example 16 to give the desired material. ESI-MS (M+H)$^+$: calcd 448, found 448.

Example 57

N1-[2(R)-Hydroxy-1(S)-indanyl]-N-4-hydroxy-2(R)-[3-(hydroxy-phenyl)methyl]-3(S)-(cyclobutane carboxamido-1-yl)-butanediamide Prepared by the method described in example 48 to give the desired material. ESI-MS (M+H)$^+$: calcd 468.5, found 468.5.

Example 58

N1-[2(R)-Hydroxy-1(S)-indanyl]-N-4-hydroxy-2(R)-[3-(hydroxy-phenyl)methyl]-3(S)-(2-hydroxymethyl-isobutanamide)-butanediamide Prepared by the method described in example 48 to give the desired material. ESI-MS (M+H)$^+$: calcd 486.5, found 486.5.

Example 59

N1-[2(R)-Hydroxy-1(S)-indanyl]-N-4-hydroxy-2(R)-[3-(hydroxy-phenyl)methyl]-3(S)-1-hydroxyl-cyclopropane carboxyamido-1-yl)-butanediamide Prepared by the method described in example 48 to give the desired material. ESI-MS (M+H)$^+$: calcd 470.5, found 470.5.

Example 60

N1-[2(R)-Hydroxy-1(S)-indanyl]-N-4-hydroxy-2(R)-[3-(hydroxy-phenyl)methyl]-3(S)-(1-phenyl-cycylopropane carboxamido-1-yl)-butanediamide Prepared by the method described in example 48 to give the desired material. ESI-MS (M+H)$^+$: calcd 530.6, found 530.6.

Example 61

N1-[2(R)-Hydroxy-1(S)-indanyl]-N-4-hydroxy-2(R)-[3-(hydroxy-phenyl)methyl]-3(S)-(bezene carboxamido)-butanediamide Prepared by the method described in example 48 to give the desired material. ESI-MS (M+H)$^+$: calcd 490.5, found 490.5.

Example 62

N1-[2(R)-Hydroxy-1(S)-indanyl]-N-4-hydroxy-2(R)-[3-(hydroxy-phenyl)methyl]-3(S)-(1-cyano-cyclopropane Carboxamido-1-yl)-butanediamide Prepared by the method described in example 48 to give the desired material. ESI-MS (M+H)$^+$: calcd 479.5, found 479.5.

Example 63

N1-[2(R)-hydroxy-1(S)-indanyl]-N-4-hydroxy-2(R)-[3-(hydroxy-phenyl)methyl]-3(S)-(1-phenyl-cyclopentane Carboxamido-1-yl)-butanediamide Prepared by the method described in example 48 to give the desired material. ESI-MS (M+H)$^+$: calcd 558.6, found 558.6.

Example 64

N1-[2(R)-Hydroxy-1(S)-indanyl]-N-4-hydroxy-2(R)-[3-(hydroxy-phenyl)methyl]-3(S)-(1-methyl-cyclohexane Carboxamido-1-yl)-butanediamide Prepared by the method described in example 48 to give the desired material. ESI-MS (M+H)$^+$: calcd 510.6, found 510.6.

Example 65

N1-[2(R)-Hydroxy-1(S)-indanyl]-N-4-hydroxy-2(R)-[3-hydroxy-phenyl)methyl]-3(S)-2-indole Carboxamido)-butanediamide Prepared by the method described in example 48 to give the desired material. ESI-MS (M+H)$^+$: calcd 529.6, found 529.6.

Example 66

N1-[2(R)-Hydroxy-1(S)-indanyl]-N-4-hydroxy-2(R)-[3-(hydroxy-phenyl)methyl]-3(S)-(2-furan Carboxamido)-butanediamide Prepared by the method described in example 48 to give the desired material. ESI-MS (M+H)$^+$: calcd 480.5, found 480.5.

Example 67

N1-[2(R)-Hydroxy-1(S)-indanyl]-N-4-hydroxy-2(R)-[3-(hydroxy-phenyl)methyl]-3(S)-(2-quinoline Carboxamido)-butanediamide Prepared by the method described in example 48 to give the desired material. ESI-MS (M+H)$^+$: calcd 541.6, found 541.6.

Example 68

N1-[2(R)-Hydroxy-1(S)-indanyl]-N-4-hydroxy-2(R)-[3-(hydroxy-phenyl)methyl]-3(S)-(3,4,5-trimethoxy Benzene Carboxamido-1-yl)-butanediamide Prepared by the method described in example 48 to give the desired material. ESI-MS (M+H)$^+$: calcd 580.6, found 580.6.

Example 69

N1-[2(R)-Hydroxy-1(S)-indanyl]-N-4-hydroxy-2(R)-[3-(hydroxy-phenyl)methyl]-3(S)-(2-methyl-3-amino-benzene Carboxamido-1-yl)-butanediamide Prepared by the method described in example 48 to give the desired material. ESI-MS (M+H)$^+$: calcd 519.6, found 519.6.

Example 70

N1-[2(R)-Hydroxy-1(S)-indanyl]-N-4-hydroxy-2(R)-[3-(hydroxy-phenyl)methyl]-3(S)-(2-methyl-6-amino-benzene Carboxamido-1-yl)-butanediamide Prepared by the method described in example 48 to give the desired material. ESI-MS (M+H)$^+$: calcd 519.6, found 619.6.

Example 71

N1-[2(R)-Hydroxy-1(S)-indanyl]-N-4-hydroxy-2(R)-[3-(hydroxy-phenyl)methyl]-3(S)-(3-pyridine Carboxamido-1-yl)-butanediamide Prepared by the method described in example 48 to give the desired material. ESI-MS (M+H)$^+$: calcd 491.5, found 491.5.

Example 72

N1-[2(R)-Hydroxy-1(S)-indanyl]-N-4-hydroxy-2(R)-[3-(hydroxy-phenyl)methyl]-3(S)-(1-(2,4-dichloro-phenyl)-cyclopropane Carboxamido-1-yl)-butanediamide Prepared by the method described in example 48 to give the desired material. ESI-MS (M+H)$^+$: calcd 599.6, found 599.6.

Example 73

N1-[2(R)-Hydroxy-1(S)-indanyl]-N-4-hydroxy-2(R)-[3-(hydroxy-phenyl)methyl]-3(S)-(1-(4-chloro-phenyl)-cyclopropane Carboxamido-1-yl)-butanediamide Prepared by the method described in example 48 to give the desired material. ESI-MS (M+H)$^+$: calcd 565, found 565.

Example 74

N1-[2(R)-Hydroxy-1(S)-indanyl]-N-4-hydroxy-2(R)-[3-(hydroxy-phenyl)methyl]-3(S)-(3-methylsulfonyl)-benzene Carboxamido-1-yl)-butanediamide Prepared by the method described in example 48 to give the desired material. ESI-MS (M+H)$^+$: calcd 568.6, found 568.6.

Example 75

N1-[2(R)-Hydroxy-1(S)-indanyl]-N-4-hydroxy-2(R)-[3-(hydroxy-phenyl)methyl]-3(S)-(2-methylsulfonyl-benzene Carboxamido-1-yl)-butanediamide Prepared by the method described in example 48 to give the desired material. ESI-MS (M+H)$^+$: calcd 568.6, found 568.6.

Example 76

N1-[2(R)-Hydroxy-1(S)-indanyl]-N-4-hydroxy-2(R)-[3-(hydroxy-phenyl)methyl]-3(S)-(3-cyano-benzene Carboxamido-1-yl)-butanediamide Prepared by the method described in example 48 to give the desired material. ESI-MS (M+H)$^+$: calcd 515.5, found 515.5.

Example 77

N1-[2(R)-Hydroxy-1(S)-indanyl]-N-4-hydroxy-2(R)-[3-(hydroxy-phenyl)methyl]-3(S)-(6-quinoline Carboxamido)-butanediamide Prepared by the method described in example 48 to give the desired material. ESI-MS (M+H)$^+$: calcd 541.6, found 541.6.

Example 78

N1-[2(R)-Hydroxy-1(S)-indanyl]-N-4-hydroxy-2(R)-[3-(hydroxy-phenyl)methyl]-3(S)-(1-ethyl, 3-Methyl-pyrazole 5-Carboxamido)-butanediamide Prepared by the method described in example 48 to give the desired material. ESI-MS (M+H)$^+$: calcd 522.6, found 522.6.

Example 79

N1-[2(R)-Hydroxy-1(S)-indanyl]-N-4-hydroxy-2(R)-[3-(hydroxy-phenyl)methyl]-3-(4-morpholino-benzene Carboxamido-1-yl)-butanediamide Prepared by the method described in example 48 to give the desired material. ESI-MS (M+H)$^+$: calcd 575.6, found 575.6.

Example 80

N1-[2(R)-Hydroxy-1(S)-indanyl]-N-4-hydroxy-2(R)-[3-(hydroxy-phenyl)methyl]-3(S)-(2-chloro-4-methylsulfonyl-benzene Carboxyamido-1-yl)-butanediamide Prepared by the method described in example 48 to give the desired material. ESI-MS (M+H)$^+$: calcd 603, found 603.

Example 81

N1-[2(R)-Hydroxy-1(S)-indanyl]-N-4-hydroxy-2(R)-[3-(hydroxy-phenyl)methyl]-3(S)-(4-(imidazol-1-yl)benzene Carboxamido-1-yl)-butanediamide Prepared by the method described in example 48 to give the desired material. ESI-MS (M+H)$^+$: calcd 556.6, found 556.6.

Example 82

N1-[2(R)-Hydroxy-1(S)-indanyl]-N-4-hydroxy-2(R)-[3-(hydroxy-phenyl)methyl]-3(S)-(2-thiophene Carboxamido-1-yl)-butanediamide Prepared by the method described in example 48 to give the desired material. ESI-MS (M+H)$^+$: calcd 496.6, found 496.6.

Example 83

N1-[2(R)-Hydroxy-1(S)-indanyl]-N-4-hydroxy-2 (R)-[3-(hydroxy-phenyl)methyl]-3(S)-(1-tert-butyl, 3-Methyl-pyrazole 5-Carboxamido)-butanediamide Prepared by the method described in example 40 to give the desired material. ESI-MS (M+H)$^+$: calcd 550.6, found 550.6.

Example 84

N1-[2(R)-Hydroxy-1(S)-indanyl]-N4-hydroxy-2(R)- [3-(hydroxy-phenyl)methyl]-3(S)-(4-aminomethyl benzene Carboxamido-1-yl)-butanediamide Prepared by the method described in example 48 to give the desired material. ESI-MS (M+H)$^+$: calcd 519.6, found 519.6.

Example 85

N1-[2(R)-Hydroxy-1(S)-indanyl]-N4-hydroxy-2(R)- [3-(hydroxy-phenyl)methyl]-3(S)-(2-hydroxyl- isobutanamido)-butanediamide Prepared by the method described in example 48 to give the desired material. ESI-MS (M+H)$^+$: calcd 472.6, found 472.6.

Example 86

N1-[2(R)-Hydroxy-1(S)-indanyl]-N4-hydroxy-2(R)- [3-(hydroxy-phenyl)methyl]-3(S)-(cyclopropane Carboxamido-1-yl)-butanediamide Prepared by the method described in example 48 to give the desired material. ESI-MS (M+H)$^+$: calcd 454.6, found 454.6.

Example 87

N1-[2(R)-Hydroxy-1(S)-indanyl]-N4-hydroxy-2(R)- [3-(hydroxy-phenyl)methyl]-3(S)-(cyclopentane Carboxamido-1-yl)-butanediamide Prepared by the method described in example 48 to give the desired material. ESI-MS (M+H)$^+$: calcd 482.6, found 482.6.

Example 88

N1-[2(R)-Hydroxy-1(S)-indanyl]-N4-hydroxy-2(R)- [3-(hydroxy-phenyl)methyl]-3(S)-(2-cyclopentyl Acetamido)-butanediamide Prepared by the method described in example 48 to give the desired material. ESI-MS (M+H)$^+$: calcd 496.6, found 496.6.

Example 89

N1-[2(R)-Hydroxy-1(S)-indanyl]-N4-hydroxy-2(R)- [3-(hydroxy-phenyl)methyl]-3(S)-(cyclohexane Carboxamido-1-yl)-butanediamide Prepared by the method described in example 48 to give the desired material. ESI-MS (M+H)$^+$: calcd 496.6, found 496.6.

Example 90

N1-[2(R)-Hydroxy-1(S)-indanyl]-N4-hydroxy-2(R)- [3-(hydroxy-phenyl)methyl]-3(S)-(4-(4-N-Boc- piperazinyl-1-yl)benzene Carboxamido-1-yl)- butanediamide Prepared by the method described in example 48 to give the desired material. ESI-MS (M+H)$^+$: calcd 674.8, found 674.8.

Example 91

N1-[2(R)-Hydroxy-1(S)-indanyl]-N4-hydroxy-2(R)- [3-(hydroxy-phenyl)methyl]-3(S)-[4-(piperazinyl-1- yl)benzene Carboxamido-1-yl]-butanediamide Prepared by the method described in example 48 to give the desired material. ESI-MS (M+H)$^+$: calcd 574.6, found 574.6.

Example 92

N1-[2(R)-Hydroxy-1(S)-indanyl]-N4-hydroxy-2(R)- [3-(hydroxy-phenyl)methyl]-3(S)-(2-fluoro-6- chloro-benzene Carboxamido-1-yl)-butanediamide Prepared by the method described in example 48 to give the desired material. ESI-MS (M+H)$^+$: calcd 542.9, found 542.9.

Example 93

N1-[2(R)-Hydroxy-1(S)-indanyl]-N4-hydroxy-2(R)- [3-(hydroxy-phenyl)methyl]-3(S)-(1-amino- cyclohexane Carboxamido-1-yl)-butanediamide Prepared by the method described in example 48 to give the desired material. ESI-MS (M+H)$^+$: calcd 511.6, found 511.6.

Example 94

N1-[2(R)-Hydroxy-1(S)-indanyl]-N4-hydroxy-2(R)- [3-(hydroxy-phenyl)methyl]-3(S)-(2-methylthio- acetamido)-butanediamide Prepared by the method described in example 48 to give the desired material. ESI-MS (M+H)$^+$: calcd 474.6, found 474.6.

Example 95

N1-[2(R)-Hydroxy-1(S)-indanyl]-N4-hydroxy-2(R)- [3-(hydroxy-phenyl)methyl]-3(S)-(2-methoxy- acetamido)-butanediamide Prepared by the method described in example 48 to give the desired material. ESI-MS (M+H)$^+$: calcd 458.5, found 458.5.

Example 96

N1-[2(R)-Hydroxy-1(S)-indanyl]-N4-hydroxy-2(R)- [3-(hydroxy-phenyl)methyl]-3(S)-(1-allyl- cyclopentane Carboxamido-1-yl)-butanediamide Prepared by the method described in example 48 to give the desired material. ESI-MS (M+H)$^+$: calcd 522.6, found 522.6.

Example 97

N1-[2(R)-Hydroxy-1(S)-indanyl]-N4hydroxy-2(R)- [3-(hydroxy-phenyl)methyl]-3(S)-(1-n-propyl- cyclopentane Carboxamido-1-yl)-butanediamide Prepared by the method described in example 48 to give the desired material. ESI-MS (M+H)$^+$: calcd 524.6, found 524.6.

Example 98

N1-[2(R)-Hydroxy-1(S)-indanyl]-N4-hydroxy-2(R)- [3-(hydroxy-phenyl)methyl]-3(S)-(1-allyl- cyclopropane Carboxamido-1-yl)-butanediamide Prepared by the method described in example 48 to give the desired material. ESI-MS (M+H)$^+$: calcd 494.6, found 494.6.

Example 99

N1-[2(R)-Hydroxy-1(S)-indanyl]-N4-hydroxy-2(R)-[3-(hydroxy-phenyl)methyl]-3(S)-(8-quinoline-sulfonamido)-butanediamide Prepared by the method described in example 48 to give the desired material. ESI-MS (M+H)$^+$: calcd 577.6, found 577.6.

Example 100

N1-[2(R)-Hydroxy-1(S)-indanyl]-N4-hydroxy-2(R)-[3-(hydroxy-phenyl)methyl]-3(S)-(4-nitro-benzene Sulfonamido)-butanediamide Prepared by the method described in example 48 to give the desired material. ESI-MS (M+H)$^+$: calcd 571.6, found 571.6.

Example 101

N1-[2(R)-Hydroxy-1(S)-indanyl]-N4-hydroxy-2(R)-[3-(hydroxy-phenyl)methyl]-3(S)-(1,4-di-methyl-2-chloro-pyrazole-3-sulfonamido)-butanediamide Prepared by the method described in example 48 to give the desired material. ESI-MS (M+H)$^+$: calcd 579, found 579.

Example 102

N1-[2(R)-Hydroxy-1(S)-indanyl]-N4-hydroxy-2(R)-[3-(hydroxy-phenyl)methyl]-3(S)-(1,5-dimethyl-isooxazole 3-sulfonamido)-butanediamide Prepared by the method described in example 48 to give the desired material. ESI-MS (M+H)$^+$: calcd 545.6, found 545.6.

Example 103

N1-[2(R)-Hydroxy-1(S)-indanyl]-N4-hydroxy-2(R)-[3-(hydroxy-phenyl)methyl]-3(S)-(1-methyl-imidazole 3-sulfonamido)-butanediamide Prepared by the method described in example 48 to give the desired material. ESI-MS (M+H)$^+$: calcd 530.6, found 530.6.

Example 104

N1-[2(R)-(Hydroxy-1(S)-indanyl]-N4-hydroxy-2(R)-[3-(hydroxy-phenyl)methyl]-3(S)-(benzene Sulfonamido)-butanediamide Prepared by the method described in example 48 to give the desired material. ESI-MS (M+H)$^+$: calcd 526.6, found 526.6.

Example 105

N1-[2(R)-Hydroxy-1(S)-indanyl]-N4-hydroxy-2(R)-[3-(hydroxy-phenyl)methyl]-3(S)-(1,4-dimethyl Pyrazole 3-Sulfonamido)-butanediamide Prepared by the method described in example 48 to give the desired material. ESI-MS (M+H)$^+$: calcd 544.6, found 544.6.

Example 106

N1-[2(R)-Hydroxy-1(S)-indanyl]-N4-hydroxy-2(R)-[3-(hydroxy-phenyl)methyl]-3(S)-(2-methylsulfonyl Benzene Sulfonamido-1-yl)-butanediamide Prepared by the method described in example 48 to give the desired material. ESI-MS (M+H)$^+$: calcd 604.7, found 604.7.

Example 107

N1-[2(R)-Hydroxy-1(S)-indanyl]-N4-hydroxy-2(R)-[3-(hydroxy-phenyl)methyl]-3(S)-(cyclohexylamino)-butanediamide Prepared by the method described in example 53 to give the desired material. ESI-MS (M+H)$^+$: calcd 468, found 468.

Example 108

N1-[2(R)-Hydroxy-1(S)-indanyl]-N4-hydroxy-2(R)-[3-(hydroxy-phenyl)methyl]-3(S)-(iso-propylamino)-butanediamide Prepared by the method described in example 53 to give the desired material. ESI-MS (M+H)$^+$: calcd 428, found 428.

Example 109

N1-[2(R)-Hydroxy-1(S)-indanyl]-N4-hydroxy-2(R)-[4(2-trifluoromethylphenyl)-phenylmethyl]-3(S)-(2,2-dimethylpropyl-amino)-butanediamide Prepared by the method described in example 53 to give the desired material. ESI-MS (M+H)$^+$: calcd 584, found 584.

Example 110

N1-[2(R)-Hydroxy-1(S)-indanyl]-N4-hydroxy-2(R)-[3-(hydroxy-phenyl)methyl]-3(S)-(cyclopentylamino)-butanediamide Prepared by the method described in example 53 to 10 give the desired material. ESI-MS (M+H)$^+$: calcd 454.5, found 454.5.

Example 111

N1-[2(R)-Hydroxy-1(S)-indanyl]-N4-hydroxy-2(R)-[3-(hydroxy-phenyl)methyl]-3(S)-(cyclopropylmethylamino)-butanediamide Prepared by the method described in example 53 to give the desired material. ESI-MS (M+H)$^+$: calcd 440.5, found 440.5.

Example 112

N1-[2(R)-Hydroxy-1(S)-indanyl]-N4-hydroxy-2(R)-[3-(hydroxy-phenyl)methyl]-3(S)-(benzylamino)-butanediamide Prepared by the method described in example 53 to give the desired material. ESI-MS (M+H)$^+$: calcd 476.5, found 476.5.

Example 113

N1-[2(R)-Hydroxy-1(S)-indanyl]-N4-hydroxy-2(R)-[3-(hydroxy-phenyl)methyl]-3(S)-(2-furanmethylamino)-butanediamide Prepared by the method described in example 53 to give the desired material. ESI-MS (M+H)$^+$: calcd 466.5, found 466.5.

Example 114

N1-[2(R)-Hydroxy-1(S)-indanyl]-N4-hydroxy-2(R)-[3-(hydroxy-4-methylphenyl)methyl]-3(S)-(3-cyanophenylmethylamino)-butanediamide Prepared by the method described in example 53 to give the desired material. ESI-MS (M+H)$^+$: calcd 501.5, found 501.5.

Example 115

N1-[2(R)-Hydroxy-1(S)-indanyl]-N4-hydroxy-2(R)-[3-(hydroxy-4-methylphenyl)methyl]-3(S)-(2,2-dimethylpropyl-amino)-butanediamide Prepared by the method described in example 53 to give the desired material. ESI-MS (M+H)$^+$: calcd 470.6, found 470.6.

Example 116

N1-[2(R)-Hydroxy-1(S)-indanyl]-N4-hydroxy-2(R)-[3-(hydroxy-phenyl)methyl]-3(S)-(2-pentylamino)-butanediamide Prepared by the method described in example 53 to give the desired material. ESI-MS (M+H)$^+$: calcd 456.6, found 456.6.

Example 117

N1-[2(R)-Hydroxy-1(S)-indanyl]-N4-hydroxy-2(R)-[3-(hydroxy-phenyl)methyl]-3(S)-(bis-cyclopropylmethyamino)-butanediamide Prepared by the method described in example 53 to give the desired material. ESI-MS (M+H)$^+$: calcd 494.6, found 494.6.

Example 118

N1-[2(R)-Hydroxy-1(S)-indanyl]-N4-hydroxy-2(R)-[3-(hydroxy-phenyl)methyl]-3(S)-(2-thiophenemethylamino)-butanediamide Prepared by the method described in example 53 to give the desired material. ESI-MS (M+H)$^+$: calcd 482.6, found 482.6.

Example 119

N1-[2(R)-Hydroxy-1(S)-indanyl]-N4-hydroxy-2(R)-[3-(hydroxy-phenyl)methyl]-3(S)-(2-methyl-propylamino)-butanediamide Prepared by the method described in example 53 to give the desired material. ESI-MS (M+H)$^+$: calcd 556.6, found 556.6.

TABLE 1

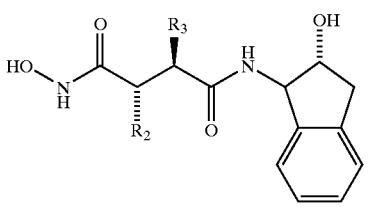

| Ex # | R$_2$ | R$_3$ | M + H |
|---|---|---|---|
| 1 | H | iso-butyl | 321 |
| 2 | CH$_2$CH$_2$CO$_2$H | iso-butyl | 393 |
| 3 | methyl | iso-butyl | 335 |
| 4 | n-propyl | iso-butyl | 363 |
| 5 | n-propyl | n-C$_6$H$_{13}$ | 391 |
| 6 | H | 4-hydroxyphenylmethyl | 371 |
| 7 | H | 4-methoxyphenylmethyl | 385 |

TABLE 1-continued

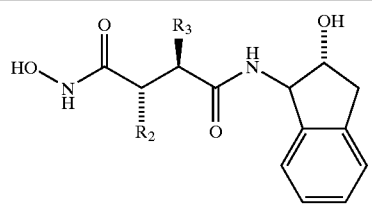

| Ex # | R$_2$ | R$_3$ | M + H |
|---|---|---|---|
| 8 | H | 4-hydroxyphenylmethyl | 355 |
| 9 | H | 3-phenylpropyl | 383 |
| 10 | H | 4-benzyloxyphenylmethyl | 461 |
| 11 | H | 3-benzyloxyphenylmethyl | 461 |
| 12 | H | 3-hydroxyphenylmethyl | 371 |
| 13 | H | 4-fluorophenylmethyl | 373 |
| 14 | H | 3,4-methylenedioxy phenylmethyl | 379 |
| 15 | H | 3-methoxyphenylmethyl | 385 |
| 16 | H | 4-phenyl-phenylmethyl | 431 |
| 17 | H | 4-(2-(tert-butylaminosulfonyl)-phenylphenylmethyl | 566 |
| 18 | H | 4-(2-methoxyphenyl)-phenylmethyl | 461 |
| 19 | H | 4-(3-trifluoromethyl-phenyl)-phenylmethyl | 499 |
| 20 | H | (3-hydroxy-4-methoxy)phenylmethyl | 401 |
| 21 | H | 3-(3-thiophene)-isoxazoline-methyl | 429 |
| 22 | H | 4-(2-chlorophenyl)-phenylmethyl | 465 |
| 23 | H | 4-(2-benzofuran)-phenylmethyl | 471 |
| 24 | H | 4-(2-methylphenyl)-phenyl-methyl | 445 |
| 25 | H | (3,4-methylene-dioxyphenyl)phenyl-methyl | 475 |
| 26 | H | 4-(2-tetrazolephenyl)-phenyl-methyl | 499 |
| 27 | H | 3-phenylphenylmethyl | 431 |
| 28 | H | (3-methyl-phenyl)-phenylmethyl | 445 |
| 29 | H | 4-amino-phenylmethyl | 370 |
| 30 | | 4-benzyloxy-carbonyl-amino-phenylmethyl | 504 |
| 31 | H | 4-(2-hydroxymethylene-phenyl)phenylmethyl | 461 |
| 32 | H | 4-(3,4,5-trimethoxy-phenyl)phenylmethyl | 521 |
| 33 | H | 4-(2,4-dimethoxy-phenyl)phenylmethyl | 491 |
| 34 | H | 4-(3,5-dichloro-phenyl)-phenylmethyl | 499 |
| 35 | H | 4-(2-trifluoromethyl-phenyl)phenylmethyl | 499 |
| 36 | H | 4-(3-isopropyl-phenyl)phenyl-methyl | 473 |
| 37 | H | 4-(2,4-dichloro-phenyl)phenyl-methyl | 499 |
| 38 | H | 4-(3-chloro,4-fluoro-phenyl)phenylmethyl | 483 |
| 39 | H | 4-(p-toluenesulfonyl-amino)-phenylmethyl | 524 |
| 40 | BocNH | phenylmethyl | 470 |
| 41 | BocNH | 4-(3,4-methylenedioxy-phenyl)phenylmethyl | 588 |
| 42 | H | 4-(3-methoxy-phenyl)phenylmethyl | 461 |
| 43 | H | 4-(3-fluoro-phenyl)phenylmethyl | 449 |
| 44 | BocNH | 3-fluorophenylmethyl | 488 |
| 45 | BocNH | 3-hydroxyphenylmethyl | 486 |

TABLE 1-continued

| Ex # | R₂ | R₃ | M + H |
|---|---|---|---|
| 46 | H | 4-(3-nitro-phenyl)phenylmethyl | 476 |
| 47 | H | 4-(3-methylsulfonylamino-phenyl)phenylmethyl | 524 |
| 48 | 2,2-dimethylpropionamido | 3-hydroxyphenylmethyl | 470 |
| 49 | ethoxycarbonylamino | 3-hydroxyphenylmethyl | 458 |
| 50 | iso-butoxy-carbonyl-amino | 3-hydroxyphenylmethyl | 486 |
| 51 | propionamido | 3-hydroxyphenylmethyl | 458 |
| 52 | 1-methylcyclopropane carboxamido-1-yl | 3-hydroxyphenylmethyl | 452 |
| 53 | 2,2-dimethylpropylamino | 3-hydroxyphenylmethyl | 455 |
| 54 | methylsulfonylamino | 3-hydroxyphenylmethyl | 464 |
| 55 | amino | 3-hydroxyphenylmethyl | 386 |
| 56 | H | 4-(methylsulfonyl-amino)phenylmethyl | 448 |
| 57 | cyclobutane carboxamido-1-yl | 3-hydroxyphenylmethyl | 468.5 |
| 58 | 2-hydroxymethyl-isobutanamide | 3-hydroxyphenylmethyl | 486.5 |
| 59 | 1-hydroxyl-cyclopropane carboxyamido-1-yl | 3-hydroxyphenylmethyl | 470.5 |
| 60 | 1-phenyl-cyclopropane carboxamido-1-yl | 3-hydroxyphenylmethyl | 530.6 |
| 61 | bezene carboxamido | 3-hydroxyphenylmethyl | 490.5 |
| 62 | 1-cyano-cyclopropane carboxamido-1-yl | 3-hydroxyphenylmethyl | 479.5 |
| 63 | 1-phenyl-cyclopentane carboxamido-1-yl | 3-hydroxyphenylmethyl | 558.6 |
| 64 | 1-methyl-cyclohexane carboxamido-1-yl | 3-hydroxyphenylmethyl | 510.6 |
| 65 | 2-indole carboxamido | 3-hydroxyphenylmethyl | 529.6 |
| 66 | 2-furan carboxamido | 3-hydroxyphenylmethyl | 480.5 |
| 67 | 2-quinoline carboxamido | 3-hydroxyphenylmethyl | 541.6 |
| 68 | 3,4,5-trimethoxy benzene carboxamido-1-yl | 3-hydroxyphenylmethyl | 580.6 |
| 69 | 2-methyl-3-amino-benzene carboxamido-1-yl | 3-hydroxyphenylmethyl | 519.6 |
| 70 | 2-methyl-6-amino-benzene carboxamido-1-yl | 3-hydroxyphenylmethyl | 619.6 |
| 71 | 3-pyridine carboxamido-1-yl | 3-hydroxyphenylmethyl | 491.5 |
| 72 | 1-(2,4-dichloro-phenyl)-cyclopropane carboxamido-1-yl | 3-hydroxyphenylmethyl | 599.6 |
| 73 | 1-(4-chloro-phenyl)-cyclopropane carboxamido-1-yl | 3-hydroxyphenylmethyl | 565 |
| 74 | 3-methylsulfonyl)-benzene carboxamido-1-yl | 3-hydroxyphenylmethyl | 568.6 |
| 75 | 2-methylsulfonyl-benzene carboxamido-1-yl | 3-hydroxyphenylmethyl | 568.6 |
| 76 | 3-cyano-benzene carboxamido-1-yl | 3-hydroxyphenylmethyl | 515.6 |
| 77 | 6-quinoline carboxamido | 3-hydroxyphenylmethyl | 541.6 |
| 78 | 1-ethyl,3-methyl-pyrazole 5-carboxamido | 3-hydroxyphenylmethyl | 522.6 |
| 79 | 4-morpholino-benzene carboxamido-1-yl | 3-hydroxyphenylmethyl | 575.6 |
| 80 | 2-chloro-4-methylsulfonyl-benzene carboxamido-1-yl | 3-hydroxyphenylmethyl | 603 |
| 81 | 4-(imidazol-1-yl)benzene carboxamido-1-yl | 3-hydroxyphenylmethyl | 556.6 |
| 82 | 2-thiophene carboxamido-1-yl | 3-hydroxyphenylmethyl | 496.6 |
| 83 | 1-tert-butyl,3-methyl-pyrazole 5-carboxamido | 3-hydroxyphenylmethyl | 550.6 |
| 84 | 4-aminomethyl benzene carboxamido-1-yl | 3-hydroxyphenylmethyl | 519.6 |
| 85 | 2-hydroxyl-isobutanamido | 3-hydroxyphenylmethyl | 472.6 |
| 86 | cyclopropane carboxamido-1-yl | 3-hydroxyphenylmethyl | 454.6 |
| 87 | cyclopentane carboxamido-1-yl | 3-hydroxyphenylmethyl | 482.6 |
| 88 | 2-cyclopentyl acetamido | 3-hydroxyphenylmethyl | 496.6 |
| 89 | cyclohexane carboxamido-1-yl | 3-hydroxyphenylmethyl | 496.6 |
| 90 | 4-(4-N-Boc-piperazinyl-1-yl)benzene carboxamido-1-yl | 3-hydroxyphenylmethyl | 674.8 |
| 91 | 4-(piperazinyl-1-yl)benzene carboxamido-1-yl | 3-hydroxyphenylmethyl | 574.6 |
| 92 | 2-Fluoro-6-chloro-benzene carboxamido-1-yl | 3-hydroxyphenylmethyl | 542.6 |
| 93 | 1-amino-cyclohexane carboxamido-1-yl | 3-hydroxyphenylmethyl | 511.6 |
| 94 | 2-methylthio-acetamido | 3-hydroxyphenylmethyl | 474.6 |
| 95 | 2-methoxy-acetamido | 3-hydroxyphenylmethyl | 458.5 |
| 96 | 1-allyl-cyclopentane carboxamido-1-yl | 3-hydroxyphenylmethyl | 522.6 |
| 97 | 1-n-propyl-cyclopentane carboxamido-1-yl | 3-hydroxyphenylmethyl | 524.6 |
| 98 | 1-allyl-cyclopropane carboxamido-1-yl | 3-hydroxyphenylmethyl | 494.6 |
| 99 | 8-quinoline-sulfonamido | 3-hydroxyphenylmethyl | 577.6 |
| 100 | 4-nitro-benzene sulfonamido | 3-hydroxyphenylmethyl | 571.6 |
| 101 | 1,4-di-methyl-2-chloro-pyrazole-3-sulfonamido | 3-hydroxyphenylmethyl | 579 |
| 102 | 1,5-dimethyl-isooxazole 3-sulfonamido | 3-hydroxyphenylmethyl | 545.6 |
| 103 | 1-methyl-imidazole 3-sulfonamido | 3-hydroxyphenylmethyl | 530.6 |
| 104 | benzene sulfonamido | 3-hydroxyphenylmethyl | 526.6 |
| 105 | 1,4-dimethyl pyrazole 3-sulfonamido | 3-hydroxyphenylmethyl | 544.6 |
| 106 | 2-methylsulfonyl benzene sulfonamido-1-yl | 3-hydroxyphenylmethyl | 604.7 |
| 107 | cyclohexylamino | 3-hydroxyphenylmethyl | 468 |
| 108 | iso-propylamino | 3-hydroxyphenylmethyl | 428 |
| 109 | 2,2-dimethylpropyl-amino | 3-hydroxyphenylmethyl | 584 |
| 110 | cyclopentylamino | 3-hydroxyphenylmethyl | 454.5 |
| 111 | cyclopropylmethylamino | 3-hydroxyphenylmethyl | 440.5 |
| 112 | benzylamine | 3-hydroxyphenylmethyl | 476.5 |
| 113 | 2-furanmethylamino | 3-hydroxyphenylmethyl | 466.5 |
| 114 | 3-cyanophenylmethylamino | 3-hydroxyphenylmethyl | 501.5 |
| 115 | 2,2-dimethylpropyl-amino | 3-(hydroxy-4-methylphenyl)methyl | 470.6 |
| 116 | 2-pentylamino | 3-hydroxyphenylmethyl | 456.6 |
| 117 | bis-cyclopropylmethyamino | 3-hydroxyphenylmethyl | 494.6 |
| 118 | 2-thiophenemethylamino | 3-hydroxyphenylmethyl | 482.6 |
| 119 | 2-methyl-propylamino | 3-hydroxyphenylmethyl | 556.6 |

The following tables contain representative examples of the present invention. Each entry in each table is intended to be paired with the formula at the start of the table.

TABLE 2
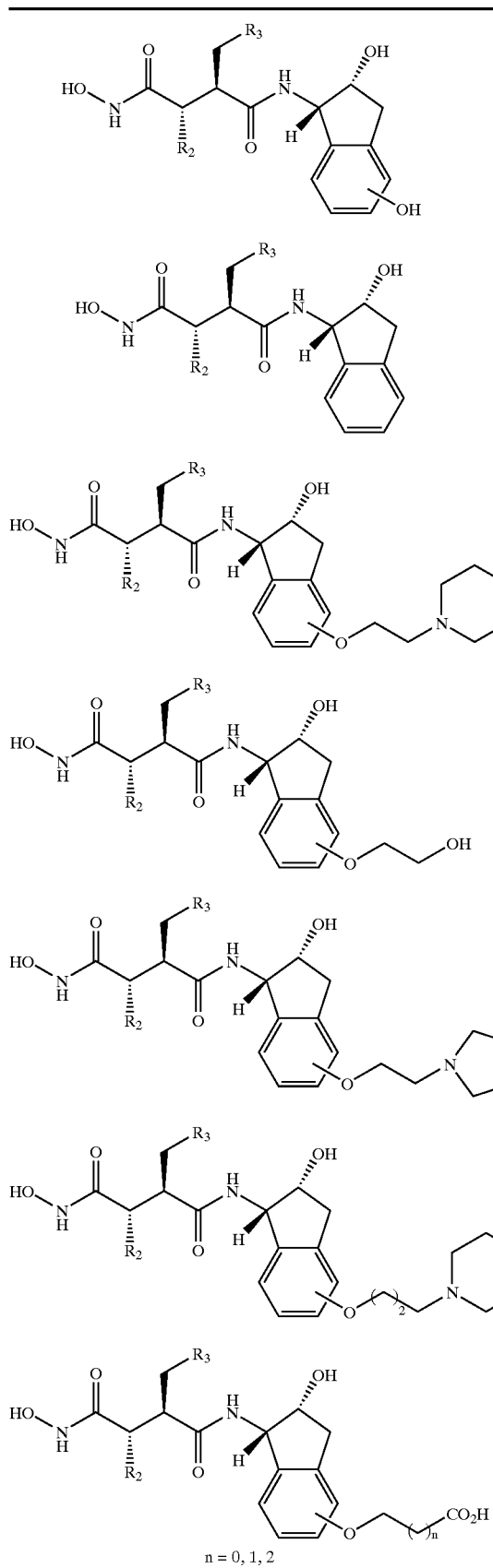
TABLE 2-continued
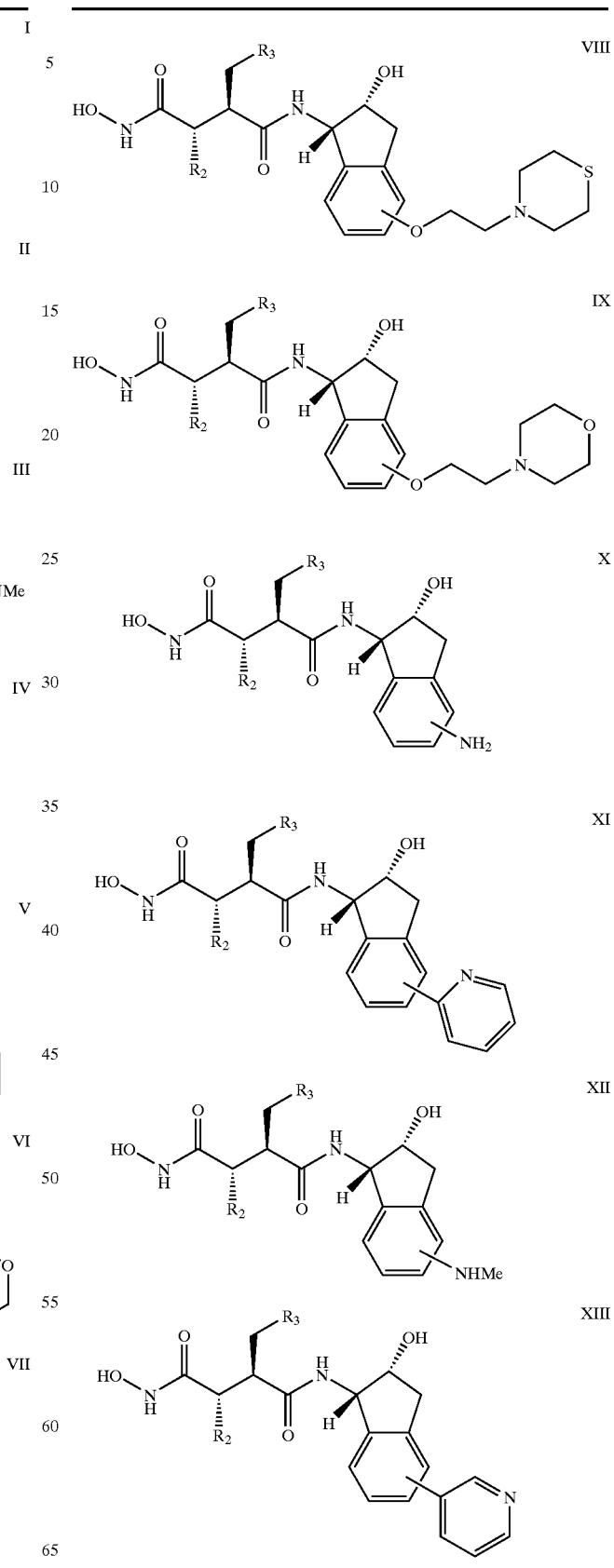

TABLE 2-continued
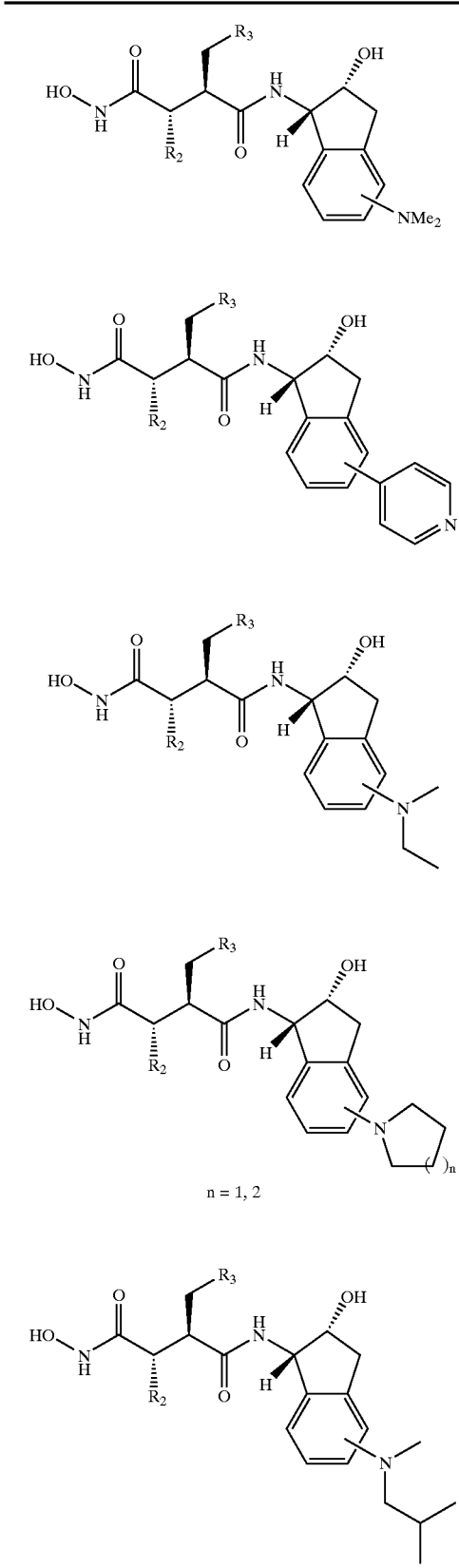
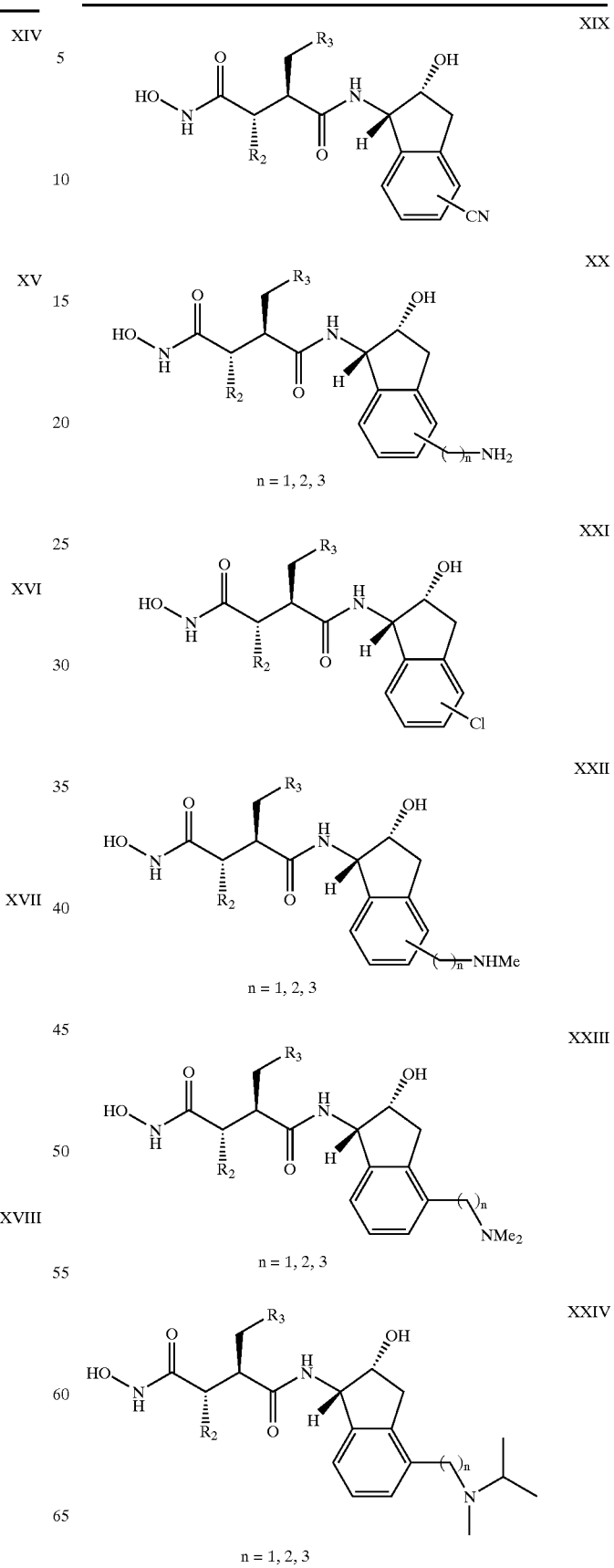

TABLE 2-continued

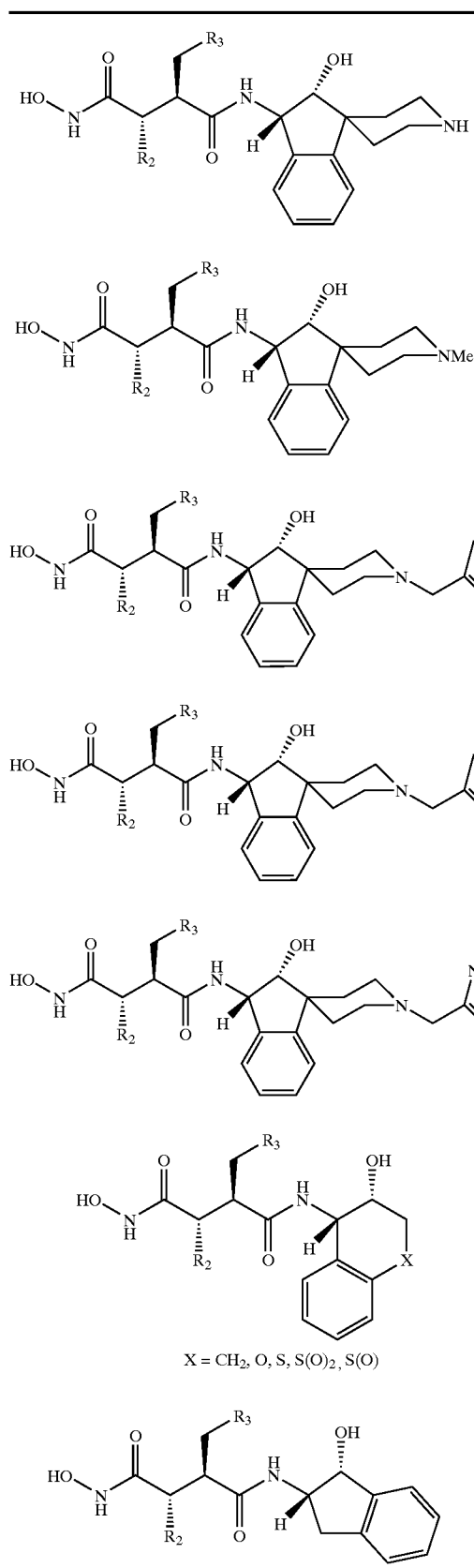

| Ex # | R2 | R3 | Ms |
|---|---|---|---|
| 200 | H | H | |
| 201 | H | methyl | |
| 202 | H | ethyl | |
| 203 | H | n-propyl | |
| 204 | H | n-butyl | |
| 205 | H | n-pentyl | |
| 206 | H | n-hexanyl | |
| 207 | H | n-heptanyl | |
| 208 | H | isopropyl | |
| 209 | H | tert-butyl | |
| 210 | H | cyclopropyl | |
| 211 | H | cyclobutanyl | |
| 212 | H | cyclopentanyl | |
| 213 | H | cyclohexanyl | |
| 214 | H | cycloheptanyl | |
| 215 | H | phenyl | |
| 216 | H | phenylmethyl | |
| 217 | H | 3-hydroxyphenyl | |
| 218 | H | 3-hydroxy-4-methoxyphenyl | |
| 219 | H | 3-fluorophenyl | |
| 220 | H | 3-chlorophenyl | |
| 221 | H | 3-nitrophenyl | |
| 222 | H | 3-aminophenyl | |
| 223 | H | 3-methylsulfonamidephenyl | |
| 224 | H | 3-trifluoro-methylsulfonamidephenyl | |
| 225 | H | 3-Ac—NHphenyl | |
| 226 | H | 3-Boc—NHphenyl | |
| 227 | H | 3-Cbz—NHphenyl | |
| 228 | H | 3-aminomethylenephenyl | |
| 229 | H | 3-aminoethylenephenyl | |
| 230 | H | 3-cyanophenyl | |
| 231 | H | 3-cyanomethylphenyl | |
| 232 | H | 3-hydroxymethylenephenyl | |
| 233 | H | 3-carboxylphenyl | |
| 234 | H | 3-mercaptophenyl | |
| 235 | H | 3-methoxyphenyl | |
| 236 | H | 3,4-methylenedioxophenyl | |
| 237 | H | 3-tetrazolephenyl | |
| 238 | H | 3-aminosulfonylphenyl | |
| 239 | H | 3-methylamino-sulfonylphenyl | |
| 240 | H | 3-ethylamino-sulfonylphenyl | |
| 241 | H | 3-tert-butylamino-sulfonylphenyl | |
| 242 | H | 3-methylsulfonylphenyl | |
| 243 | H | 4-methoxyphenyl | |
| 244 | H | 4-phenylphenyl | |
| 245 | H | (2-hydroxy-methylenephenyl)-phenyl | |
| 246 | H | (2-tert-butylamino-sufonylphenyl)-phenyl | |
| 247 | H | (2-methylamino-sufonylphenyl)-phenyl | |
| 248 | H | (2-ethylamino-sufonylphenyl)-phenyl | |
| 249 | H | (2-amino-sufonylphenyl)-phenyl | |
| 250 | H | (2-chlorophenyl)-phenyl | |
| 251 | H | (2-fluorophenyl)-phenyl | |
| 252 | H | (2,4-dichlorophenyl)-phenyl | |
| 253 | H | (2,6-dichlorophenyl)-phenyl | |
| 254 | H | (3,5-dichlorophenyl)-phenyl | |
| 256 | H | (2,3-dichlorophenyl)-phenyl | |
| 257 | H | (2-methylphenyl)-phenyl | |
| 258 | H | (2-tetrazole-phenyl)-phenyl | |
| 259 | H | (2-methoxy-phenyl)-phenyl | |

TABLE 2-continued

| | | |
|---|---|---|
| 260 | H | (2-tmethyl-phenyl)-phenyl |
| 261 | H | (2-formyl-phenyl)-phenyl |
| 262 | H | (2-amino-phenyl)-phenyl |
| 263 | H | (2-methylamino-phenyl)-phenyl |
| 264 | H | (2-ethylamino-phenyl)-phenyl |
| 265 | H | (2-propylamino-phenyl)-phenyl |
| 266 | H | (2-methylsulfonylamino-phenyl)-phenyl |
| 267 | H | (2-trifluoromethyl-sulfonyl-amino-phenyl)-phenyl |
| 268 | H | (3-methylphenyl)-phenyl |
| 269 | H | (3-isopropylphenyl)-phenyl |
| 270 | H | (3-trifluoromethyl-sulfonyl-amino-phenyl)-phenyl |
| 271 | H | (3-methylsulfonylamino-phenyl)-phenyl |
| 272 | H | (3-amino-phenyl)-phenyl |
| 273 | H | (3-nitro-phenyl)-phenyl |
| 274 | H | 2-pyridyl |
| 275 | H | 3-pyridyl |
| 276 | H | 4-pyridyl |
| 277 | H | 3-amino-4-pyridyl |
| 278 | H | 3-hydroxy-4-pyridyl |
| 279 | H | 3-imidazole |
| 280 | H | 2-nitro-3-imidazole |
| 281 | H | 5-thiazole |
| 282 | H | 5-oxazole |
| 283 | H | 4-pyazole |
| 284 | H | phenylethyl |
| 285 | H | 2-aminophenylethyl |
| 286 | H | 2-methylsulfonylamino-phenylethyl |
| 287 | H | 2-trifluoromethylsulfonyl-amino-phenylethyl |
| 288 | H | 2-hydroxymethylene-phenylethyl |
| 289 | H | 2-aminomethylene-phenylethyl |
| 290 | H | 2-tetrazolephenylethyl |
| 291 | H | 2-tert-butylamino-sulfonylphenylethyl |
| 292 | H | 2-aminosulfonyl-phenylethyl |
| 293 | H | 2-methoxyphenylethyl |
| 294 | H | 3-aminophenylethyl |
| 295 | H | 3-methylsulfonylamino-phenylethyl |
| 296 | H | 3-trifluoromethylsulfonyl-amino-phenylethyl |
| 297 | H | 3-hydroxymethylene-phenylethyl |
| 298 | H | 3-aminomethylene-phenylethyl |
| 299 | H | 3-tetrazolephenylethyl |
| 300 | H | 3-tert-butylamino-sulfonylphenylethyl |
| 301 | H | 3-aminosulfonyl-phenylethyl |
| 302 | H | 3-methoxyphenylethyl |
| 303 | methyl | H |
| 304 | methyl | methyl |
| 305 | methyl | ethyl |
| 306 | methyl | n-propyl |
| 307 | methyl | n-butyl |
| 308 | methyl | n-pentyl |
| 309 | methyl | n-hexanyl |
| 310 | methyl | n-heptanyl |
| 311 | methyl | isopropyl |
| 312 | methyl | tert-butyl |
| 313 | methyl | cyclopropyl |
| 314 | methyl | cyclobutanyl |
| 315 | methyl | cyclpentanyl |
| 316 | methyl | cyclohexanyl |
| 317 | methyl | cycloheptanyl |
| 318 | methyl | phenyl |
| 319 | methyl | phenylmethyl |
| 320 | methyl | 3-hydroxyphenyl |
| 321 | methyl | 3-hydroxy-4-methoxyphenyl |
| 322 | methyl | 3-fluorophenyl |
| 323 | methyl | 3-chlorophenyl |
| 324 | methyl | 3-nitrophenyl |
| 325 | methyl | 3-aminophenyl |
| 326 | methyl | 3-methylsulfonamidephenyl |
| 327 | methyl | 3-trifluoro-methylsulfonamidephenyl |
| 328 | methyl | 3-Ac—NHphenyl |
| 329 | methyl | 3-Boc—NHphenyl |
| 330 | methyl | 3-Cbz—NHphenyl |
| 331 | Methyl | 3-aminomethylenephenyl |
| 332 | methyl | 3-aminoethylenephenyl |
| 333 | methyl | 3-cyanophenyl |
| 334 | methyl | 3-cyanomethylphenyl |
| 335 | methyl | 3-hydroxymethylenephenyl |
| 336 | methyl | 3-carboxylphenyl |
| 337 | methyl | 3-mercaptophenyl |
| 338 | methyl | 3-methoxyphenyl |
| 339 | methyl | 3,4-methylenedioxophenyl |
| 340 | methyl | 3-tetrazolephenyl |
| 341 | methyl | 3-aminosulfonylphenyl |
| 342 | methyl | 3-methylamino-sulfonylphenyl |
| 343 | methyl | 3-ethylamino-sulfonylphenyl |
| 344 | methyl | 3-tert-butylamino-sulfonylphenyl |
| 345 | methyl | 3-methylsulfonylphenyl |
| 346 | methyl | 4-methoxyphenyl |
| 347 | methyl | 4-phenylphenyl |
| 348 | methyl | (2-hydroxy-methylenephenyl)-phenyl |
| 349 | methyl | (2-tert-butylamino-sufonylphenyl)-phenyl |
| 350 | methyl | (2-methylamino-sufonylphenyl)-phenyl |
| 351 | methyl | (2-ethylamino-sufonylphenyl)-phenyl |
| 352 | methyl | (2-aminosufonyl-phenyl)-phenyl |
| 353 | methyl | (2-chlorophenyl)-phenyl |
| 354 | methyl | (2-fluorophenyl)-phenyl |
| 355 | methyl | (2,4-dichlorophenyl)-phenyl |
| 356 | methyl | (2,6-dichlorophenyl)-phenyl |
| 357 | methyl | (3,5-dichlorophenyl)-phenyl |
| 358 | methyl | (2,3-dichlorophenyl)-phenyl |
| 359 | methyl | (2-methylphenyl)-phenyl |
| 360 | methyl | (2-tetrazole-phenyl)-phenyl |
| 361 | methyl | (2-methoxy-phenyl)-phenyl |
| 362 | methyl | (2-tmethyl-phenyl)-phenyl |
| 363 | methyl | (2-formyl-phenyl)-phenyl |
| 364 | methyl | (2-amino-phenyl)-phenyl |
| 365 | methyl | (2-methylamino-phenyl)-phenyl |
| 366 | methyl | (2-ethylamino-phenyl)-phenyl |
| 367 | methyl | (2-propylamino-phenyl)-phenyl |
| 368 | methyl | (2-methylsulfonylamino-phenyl)-phenyl |
| 369 | methyl | (2-trifluoromethyl-sulfonyl-amino-phenyl)-phenyl |
| 370 | methyl | (3-methylphenyl)-phenyl |
| 371 | methyl | (3-isopropylphenyl)-phenyl |
| 372 | methyl | (3-trifluoromethyl-sulfonyl-amino-phenyl)-phenyl |
| 373 | methyl | (3-methylsulfonylamino-phenyl)-phenyl |
| 374 | methyl | (3-amino-phenyl)-phenyl |
| 375 | methyl | (3-nitro-phenyl)-phenyl |
| 376 | methyl | 2-pyridyl |
| 377 | methyl | 3-pyridyl |
| 378 | methyl | 4-pyridyl |
| 379 | methyl | 3-amino-4-pyridyl |
| 380 | methyl | 3-hydroxy-4-pyridyl |
| 381 | methyl | 3-imidazole |

TABLE 2-continued

| | | |
|---|---|---|
| 382 | methyl | 2-nitro-3-imidazole |
| 383 | methyl | 5-thiazole |
| 384 | methyl | 5-oxazole |
| 385 | methyl | 4-pyazole |
| 386 | methyl | phenylethyl |
| 387 | methyl | 2-aminophenylethyl |
| 388 | methyl | 2-methylsulfonylamino-phenylethyl |
| 389 | methyl | 2-trifluoromethylsulfonyl-amino-phenylethyl |
| 390 | methyl | 2-hydroxymethylene-phenylethyl |
| 391 | methyl | 2-aminomethylene-phenylethyl |
| 392 | methyl | 2-tetrazolephenylethyl |
| 393 | methyl | 2-tert-butylamino-sulfonylphenylethyl |
| 394 | methyl | 2-aminosulfonyl-phenylethyl |
| 395 | methyl | 2-methoxyphenylethyl |
| 396 | methyl | 3-aminophenylethyl |
| 397 | methyl | 3-methylsulfonylamino-phenylethyl |
| 398 | methyl | 3-trifluoromethylsulfonyl-amino-phenylethyl |
| 399 | methyl | 3-hydroxymethylene-phenylethyl |
| 400 | methyl | 3-aminomethylene-phenylethyl |
| 401 | methyl | 3-tetrazolephenylethyl |
| 402 | methyl | 3-tert-butylamino-sulfonylphenylethyl |
| 403 | methyl | 3-aminosulfonyl-phenylethyl |
| 404 | methyl | 3-methoxyphenylethyl |
| 405 | OH | H |
| 406 | OH | methyl |
| 407 | OH | ethyl |
| 408 | OH | n-propyl |
| 409 | OH | n-butyl |
| 410 | OH | n-pentyl |
| 411 | OH | n-hexanyl |
| 412 | OH | n-heptanyl |
| 413 | OH | isopropyl |
| 414 | OH | tert-butyl |
| 415 | OH | cyclopropyl |
| 416 | OH | cyclobutanyl |
| 417 | OH | cyclpentanyl |
| 418 | OH | cyclohexanyl |
| 419 | OH | cycloheptanyl |
| 420 | OH | phenyl |
| 421 | OH | phenylmethyl |
| 422 | OH | 3-hydroxyphenyl |
| 423 | OH | 3-hydroxy-4-methoxyphenyl |
| 424 | OH | 3-fluorophenyl |
| 425 | OH | 3-chlorophenyl |
| 426 | OH | 3-nitrophenyl |
| 427 | OH | 3-aminophenyl |
| 428 | OH | 3-methylsulfonamidephenyl |
| 429 | OH | 3-trifluoro-methylsulfonamidephenyl |
| 430 | OH | 3-Ac—NHphenyl |
| 431 | OH | 3-Boc—NHphenyl |
| 432 | OH | 3-Cbz—NHphenyl |
| 433 | OH | 3-aminomethylenephenyl |
| 434 | OH | 3-aminoethylenephenyl |
| 435 | OH | 3-cyanophenyl |
| 436 | OH | 3-cyanomethylphenyl |
| 437 | OH | 3-hydroxymethylenephenyl |
| 438 | OH | 3-carboxylphenyl |
| 439 | OH | 3-mercaptophenyl |
| 440 | OH | 3-methoxyphenyl |
| 441 | OH | 3,4-methylenedioxophenyl |
| 442 | OH | 3-tetrazolephenyl |
| 443 | OH | 3-aminosulfonylphenyl |
| 444 | OH | 3-methylamino-sulfonylphenyl |
| 445 | OH | 3-ethylamino-sulfonylphenyl |
| 446 | OH | 3-tert-butylamino-sulfonylphenyl |
| 447 | OH | 3-methylsulfonylphenyl |
| 448 | OH | 4-methoxyphenyl |
| 449 | OH | 4-phenylphenyl |
| 450 | OH | (2-hydroxy-methylenephenyl)-phenyl |
| 451 | OH | (2-tert-butylamino-sufonylphenyl)-phenyl |
| 452 | OH | (2-methylamino-sufonylphenyl)-phenyl |
| 453 | OH | (2-ethylamino-sufonylphenyl)-phenyl |
| 454 | OH | (2-aminosufonyl-phenyl)-phenyl |
| 455 | OH | (2-chlorophenyl)-phenyl |
| 456 | OH | (2-fluorophenyl)-phenyl |
| 457 | OH | (2,4-dichlorophenyl)-phenyl |
| 458 | OH | (2,6-dichlorophenyl)-phenyl |
| 459 | OH | (3,5-dichlorophenyl)-phenyl |
| 460 | OH | (2,3-dichlorophenyl)-phenyl |
| 461 | OH | (2-methylphenyl)-phenyl |
| 462 | OH | (2-tetrazole-phenyl)-phenyl |
| 463 | OH | (2-methoxy-phenyl)-phenyl |
| 464 | OH | (2-tmethyl-phenyl)-phenyl |
| 465 | OH | (2-formyl-phenyl)-phenyl |
| 466 | OH | (2-amino-phenyl)-phenyl |
| 467 | OH | (2-methylamino-phenyl)-phenyl |
| 468 | OH | (2-ethylamino-phenyl)-phenyl |
| 469 | OH | (2-propylamino-phenyl)-phenyl |
| 470 | OH | (2-methylsulfonylamino-phenyl)-phenyl |
| 471 | OH | (2-trifluoromethyl-sulfonyl-amino-phenyl)-phenyl |
| 472 | OH | (3-methylphenyl)-phenyl |
| 473 | OH | (3-isopropylphenyl)-phenyl |
| 474 | OH | (3-trifluoromethyl-sulfonyl-amino-phenyl)-phenyl |
| 475 | OH | (3-methylsulfonylamino-phenyl)-phenyl |
| 476 | OH | (3-amino-phenyl)-phenyl |
| 477 | OH | (3-nitro-phenyl)-phenyl |
| 478 | OH | 2-pyridyl |
| 479 | OH | 3-pyridyl |
| 480 | OH | 4-pyridyl |
| 481 | OH | 3-amino-4-pyridyl |
| 482 | OH | 3-hydroxy-4-pyridyl |
| 483 | OH | 3-imidazole |
| 484 | OH | 2-nitro-3-imidazole |
| 485 | OH | 5-thiazole |
| 486 | OH | 5-oxazole |
| 487 | OH | 4-pyazole |
| 488 | OH | phenylethyl |
| 489 | OH | 2-aminophenylethyl |
| 490 | OH | 2-methylsulfonylamino-phenylethyl |
| 491 | OH | 2-trifluoromethylsulfonyl-amino-phenylethyl |
| 492 | OH | 2-hydroxymethylene-phenylethyl |
| 493 | OH | 2-aminomethylene-phenylethyl |
| 494 | OH | 2-tetrazolephenylethyl |
| 495 | OH | 2-tert-butylamino-sulfonylphenylethyl |
| 496 | OH | 2-aminosulfonyl-phenylethyl |
| 497 | OH | 2-methoxyphenylethyl |
| 498 | OH | 3-aminophenylethyl |
| 499 | OH | 3-methylsulfonylamino-phenylethyl |
| 500 | OH | 3-trifluoromethylsulfonyl-amino-phenylethyl |
| 501 | OH | 3-hydroxymethylene-phenylethyl |
| 502 | OH | 3-aminomethylene-phenylethyl |
| 503 | OH | 3-tetrazolephenylethyl |

TABLE 2-continued

| | | |
|---|---|---|
| 504 | OH | 3-tert-butylamino-sulfonylphenylethyl |
| 505 | OH | 3-aminosulfonyl-phenylethyl |
| 506 | OH | 3-methoxyphenylethyl |
| 507 | NH(CO)CH$_3$ | H |
| 508 | NH(CO)CH$_3$ | methyl |
| 509 | NH(CO)CH$_3$ | ethyl |
| 510 | NH(CO)CH$_3$ | n-propyl |
| 511 | NH(CO)CH$_3$ | n-butyl |
| 512 | NH(CO)CH$_3$ | n-pentyl |
| 513 | NH(CO)CH$_3$ | n-hexanyl |
| 514 | NH(CO)CH$_3$ | n-heptanyl |
| 515 | NH(CO)CH$_3$ | isopropyl |
| 516 | NH(CO)CH$_3$ | tert-butyl |
| 517 | NH(CO)CH$_3$ | cyclopropyl |
| 518 | NH(CO)CH$_3$ | cyclobutanyl |
| 519 | NH(CO)CH$_3$ | cyclpentanyl |
| 520 | NH(CO)CH$_3$ | cyclohexanyl |
| 521 | NH(CO)CH$_3$ | cycloheptanyl |
| 522 | NH(CO)CH$_3$ | phenyl |
| 523 | NH(CO)CH$_3$ | phenylmethyl |
| 524 | NH(CO)CH$_3$ | 3-hydroxyphenyl |
| 525 | NH(CO)CH$_3$ | 3-hydroxy-4-methoxyphenyl |
| 526 | NH(CO)CH$_3$ | 3-fluorophenyl |
| 527 | NH(CO)CH$_3$ | 3-chlorophenyl |
| 528 | NH(CO)CH$_3$ | 3-nitrophenyl |
| 529 | NH(CO)CH$_3$ | 3-aminophenyl |
| 530 | NH(CO)CH$_3$ | 3-methyl-sulfonamidephenyl |
| 531 | NH(CO)CH$_3$ | 3-trifluoro-methylsulfonamidephenyl |
| 532 | NH(CO)CH$_3$ | 3-Ac—NHphenyl |
| 533 | NH(CO)CH$_3$ | 3-Boc—NHphenyl |
| 534 | NH(CO)CH$_3$ | 3-Cbz—NHphenyl |
| 535 | NH(CO)CH$_3$ | 3-aminomethylenephenyl |
| 536 | NH(CO)CH$_3$ | 3-aminoethylenephenyl |
| 537 | NH(CO)CH$_3$ | 3-cyanophenyl |
| 538 | NH(CO)CH$_3$ | 3-cyanomethylphenyl |
| 539 | NH(CO)CH$_3$ | 3-hydroxymethylenephenyl |
| 540 | NH(CO)CH$_3$ | 3-carboxylphenyl |
| 541 | NH(CO)CH$_3$ | 3-mercaptophenyl |
| 542 | NH(CO)CH$_3$ | 3-methoxyphenyl |
| 543 | NH(CO)CH$_3$ | 3,4-methylenedioxophenyl |
| 544 | NH(CO)CH$_3$ | 3-tetrazolephenyl |
| 545 | NH(CO)CH$_3$ | 3-aminosulfonylphenyl |
| 546 | NH(CO)CH$_3$ | 3-methylamino-sulfonylphenyl |
| 547 | NH(CO)CH$_3$ | 3-ethylamino-sulfonylphenyl |
| 548 | NH(CO)CH$_3$ | 3-tert-butylamino-sulfonylphenyl |
| 549 | NH(CO)CH$_3$ | 3-methylsulfonylphenyl |
| 550 | NH(CO)CH$_3$ | 4-methoxyphenyl |
| 551 | NH(CO)CH$_3$ | 4-phenylphenyl |
| 552 | NH(CO)CH$_3$ | (2-hydroxy-methylenephenyl)-phenyl |
| 553 | NH(CO)CH$_3$ | (2-tert-butylamino-sufonylphenyl)-phenyl |
| 554 | NH(CO)CH$_3$ | (2-methylamino-sufonylphenyl)-phenyl |
| 555 | NH(CO)CH$_3$ | (2-ethylamino-sufonylphenyl)-phenyl |
| 556 | NH(CO)CH$_3$ | (2-aminosufonyl-phenyl)-phenyl |
| 557 | NH(CO)CH$_3$ | (2-chlorophenyl)-phenyl |
| 558 | NH(CO)CH$_3$ | (2-fluorophenyl)-phenyl |
| 559 | NH(CO)CH$_3$ | (2,4-dichlorophenyl)-phenyl |
| 560 | NH(CO)CH$_3$ | (2,6-dichlorophenyl)-phenyl |
| 561 | NH(CO)CH$_3$ | (3,5-dichlorophenyl)-phenyl |
| 562 | NH(CO)CH$_3$ | (2,3-dichlorophenyl)-phenyl |
| 563 | NH(CO)CH$_3$ | (2-methylphenyl)-phenyl |
| 564 | NH(CO)CH$_3$ | (2-tetrazole-phenyl)-phenyl |
| 565 | NH(CO)CH$_3$ | (2-methoxy-phenyl)-phenyl |
| 566 | NH(CO)CH$_3$ | (2-tmethyl-phenyl)-phenyl |
| 567 | NH(CO)CH$_3$ | (2-formyl-phenyl)-phenyl |
| 568 | NH(CO)CH$_3$ | (2-amino-phenyl)-phenyl |
| 569 | NH(CO)CH$_3$ | (2-methylamino-phenyl)-phenyl |
| 570 | NH(CO)CH$_3$ | (2-ethylamino-phenyl)-phenyl |
| 571 | NH(CO)CH$_3$ | (2-propylamino-phenyl)-phenyl |
| 572 | NH(CO)CH$_3$ | (2-methylsulfonylamino-phenyl)-phenyl |
| 573 | NH(CO)CH$_3$ | (2-trifluoromethyl-sulfonyl-amino-phenyl)-phenyl |
| 574 | NH(CO)CH$_3$ | (3-methylphenyl)-phenyl |
| 575 | NH(CO)CH$_3$ | (3-isopropylphenyl)-phenyl |
| 576 | NH(CO)CH$_3$ | (3-trifluoromethyl-sulfonyl-amino-phenyl)-phenyl |
| 577 | NH(CO)CH$_3$ | (3-methylsulfonylamino-phenyl)-phenyl |
| 578 | NH(CO)CH$_3$ | (3-amino-phenyl)-phenyl |
| 579 | NH(CO)CH$_3$ | (3-nitro-phenyl)-phenyl |
| 580 | NH(CO)CH$_3$ | 2-pyridyl |
| 581 | NH(CO)CH$_3$ | 3-pyridyl |
| 582 | NH(CO)CH$_3$ | 4-pyridyl |
| 583 | NH(CO)CH$_3$ | 3-amino-4-pyridyl |
| 584 | NH(CO)CH$_3$ | 3-hydroxy-4-pyridyl |
| 585 | NH(CO)CH$_3$ | 3-imidazole |
| 586 | NH(CO)CH$_3$ | 2-nitro-3-imidazole |
| 587 | NH(CO)CH$_3$ | 5-thiazole |
| 588 | NH(CO)CH$_3$ | 5-oxazole |
| 589 | NH(CO)CH$_3$ | 4-pyazole |
| 590 | NH(CO)CH$_3$ | phenylethyl |
| 591 | NH(CO)CH$_3$ | 2-aminophenylethyl |
| 592 | NH(CO)CH$_3$ | 2-methylsulfonylamino-phenylethyl |
| 593 | NH(CO)CH$_3$ | 2-trifluoromethylsulfonyl-amino-phenylethyl |
| 594 | NH(CO)CH$_3$ | 2-hydroxymethylene-phenylethyl |
| 595 | NH(CO)CH$_3$ | 2-aminomethylene-phenylethyl |
| 596 | NH(CO)CH$_3$ | 2-tetrazolephenylethyl |
| 597 | NH(CO)CH$_3$ | 2-tert-butylamino-sulfonylphenylethyl |
| 598 | NH(CO)CH$_3$ | 2-aminosulfonyl-phenylethyl |
| 599 | NH(CO)CH$_3$ | 2-methoxyphenylethyl |
| 600 | NH(CO)CH$_3$ | 3-aminophenylethyl |
| 601 | NH(CO)CH$_3$ | 3-methylsulfonylamino-phenylethyl |
| 602 | NH(CO)CH$_3$ | 3-trifluoromethylsulfonyl-amino-phenylethyl |
| 603 | NH(CO)CH$_3$ | 3-hydroxymethylene-phenylethyl |
| 604 | NH(CO)CH$_3$ | 3-aminomethylene-phenylethyl |
| 605 | NH(CO)CH$_3$ | 3-tetrazolephenylethyl |
| 606 | NH(CO)CH$_3$ | 3-tert-butylamino-sulfonylphenylethyl |
| 607 | NH(CO)CH$_3$ | 3-aminosulfonyl-phenylethyl |
| 608 | NH(CO)CH$_3$ | 3-methoxyphenylethyl |
| 609 | | |
| 610 | NH(CO)C$_2$H$_5$ | H |
| 611 | NH(CO)C$_2$H$_5$ | methyl |
| 612 | NH(CO)C$_2$H$_5$ | ethyl |
| 613 | NH(CO)C$_2$H$_5$ | n-propyl |
| 614 | NH(CO)C$_2$H$_5$ | n-butyl |
| 615 | NH(CO)C$_2$H$_5$ | n-pentyl |
| 616 | NH(CO)C$_2$H$_5$ | n-hexanyl |
| 617 | NH(CO)C$_2$H$_5$ | n-heptanyl |
| 618 | NH(CO)C$_2$H$_5$ | isopropyl |
| 619 | NH(CO)C$_2$H$_5$ | tert-butyl |
| 620 | NH(CO)C$_2$H$_5$ | cyclopropyl |
| 621 | NH(CO)C$_2$H$_5$ | cyclobutanyl |
| 622 | NH(CO)C$_2$H$_5$ | cyclpentanyl |
| 623 | NH(CO)C$_2$H$_5$ | cyclohexanyl |
| 624 | NH(CO)C$_2$H$_5$ | cycloheptanyl |
| 625 | NH(CO)C$_2$H$_5$ | phenyl |
| 626 | NH(CO)C$_2$H$_5$ | phenylmethyl |
| 627 | NH(CO)C$_2$H$_5$ | 3-hydroxyphenyl |
| 628 | NH(CO)C$_2$H$_5$ | 3-hydroxy-4-methoxyphenyl |
| 629 | NH(CO)C$_2$H$_5$ | 3-fluorophenyl |
| 630 | NH(CO)C$_2$H$_5$ | 3-chlorophenyl |
| 631 | NH(CO)C$_2$H$_5$ | 3-nitrophenyl |
| 632 | NH(CO)C$_2$H$_5$ | 3-aminophenyl |

TABLE 2-continued

| | | |
|---|---|---|
| 633 | NH(CO)C$_2$H$_5$ | 3-methylsulfonamidephenyl |
| 634 | NH(CO)C$_2$H$_5$ | 3-trifluoro-methylsulfonamidephenyl |
| 635 | NH(CO)C$_2$H$_5$ | 3-Ac—NHphenyl |
| 636 | NH(CO)C$_2$H$_5$ | 3-Boc—NHphenyl |
| 637 | NH(CO)C$_2$H$_5$ | 3-Cbz—NHphenyl |
| 638 | NH(CO)C$_2$H$_5$ | 3-aminomethylenephenyl |
| 639 | NH(CO)C$_2$H$_5$ | 3-aminoethylenephenyl |
| 640 | NH(CO)C$_2$H$_5$ | 3-cyanophenyl |
| 641 | NH(CO)C$_2$H$_5$ | 3-cyanomethylphenyl |
| 642 | NH(CO)C$_2$H$_5$ | 3-hydroxymethylenephenyl |
| 643 | NH(CO)C$_2$H$_5$ | 3-carboxylphenyl |
| 644 | NH(CO)C$_2$H$_5$ | 3-mercaptophenyl |
| 645 | NH(CO)C$_2$H$_5$ | 3-methoxyphenyl |
| 646 | NH(CO)C$_2$H$_5$ | 3,4-methylenedioxophenyl |
| 647 | NH(CO)C$_2$H$_5$ | 3-tetrazolephenyl |
| 648 | NH(CO)C$_2$H$_5$ | 3-aminosulfonylphenyl |
| 649 | NH(CO)C$_2$H$_5$ | 3-methylamino-sulfonylphenyl |
| 650 | NH(CO)C$_2$H$_5$ | 3-ethylamino-sulfonylphenyl |
| 651 | NH(CO)C$_2$H$_5$ | 3-tert-butylamino-sulfonylphenyl |
| 652 | NH(CO)C$_2$H$_5$ | 3-methylsulfonylphenyl |
| 653 | NH(CO)C$_2$H$_5$ | 4-methoxyphenyl |
| 654 | NH(CO)C$_2$H$_5$ | 4-phenylphenyl |
| 655 | NH(CO)C$_2$H$_5$ | 4-(2-hydroxy-methylenephenyl)-phenyl |
| 656 | NH(CO)C$_2$H$_5$ | 4-(2-tert-butylamino-sufonylphenyl)-phenyl |
| 657 | NH(CO)C$_2$H$_5$ | 4-(2-methylamino-sufonylphenyl)-phenyl |
| 658 | NH(CO)C$_2$H$_5$ | 4-(2-ethylamino-sufonylphenyl)-phenyl |
| 659 | NH(CO)C$_2$H$_5$ | 4-(2-amino-sufonylphenyl)-phenyl |
| 660 | NH(CO)C$_2$H$_5$ | 4-(2-chlorophenyl)-phenyl |
| 661 | NH(CO)C$_2$H$_5$ | 4-(2-fluorophenyl)-phenyl |
| 662 | NH(CO)C$_2$H$_5$ | 4-(2,4-dichlorophenyl)-phenyl |
| 663 | NH(CO)C$_2$H$_5$ | 4-(2,6-dichlorophenyl)-phenyl |
| 664 | NH(CO)C$_2$H$_5$ | 4-(3,5-dichlorophenyl)-phenyl |
| 665 | NH(CO)C$_2$H$_5$ | 4-(2,3-dichlorophenyl)-phenyl |
| 666 | NH(CO)C$_2$H$_5$ | 4-(2-methylphenyl)-phenyl |
| 667 | NH(CO)C$_2$H$_5$ | 4-(2-tetrazole-phenyl)-phenyl |
| 668 | NH(CO)C$_2$H$_5$ | 4-(2-methoxy-phenyl)-phenyl |
| 669 | NH(CO)C$_2$H$_5$ | 4-(2-tmethyl-phenyl)-phenyl |
| 670 | NH(CO)C$_2$H$_5$ | 4-(2-formyl-phenyl)-phenyl |
| 671 | NH(CO)C$_2$H$_5$ | 4-(2-amino-phenyl)-phenyl |
| 672 | NH(CO)C$_2$H$_5$ | 4-(2-methylamino-phenyl)-phenyl |
| 673 | NH(CO)C$_2$H$_5$ | 4-(2-ethylamino-phenyl)-phenyl |
| 674 | NH(CO)C$_2$H$_5$ | 4-(2-propylamino-phenyl)-phenyl |
| 675 | NH(CO)C$_2$H$_5$ | 4-(2-methylsulfonylamino-phenyl)-phenyl |
| 676 | NH(CO)C$_2$H$_5$ | 4-(2-trifluoromethyl-sulfonyl-amino-phenyl)-phenyl |
| 677 | NH(CO)C$_2$H$_5$ | 4-(3-methylphenyl)-phenyl |
| 678 | NH(CO)C$_2$H$_5$ | 4-(3-isopropylphenyl)-phenyl |
| 679 | NH(CO)C$_2$H$_5$ | 4-(3-trifluoromethyl-sulfonyl-amino-phenyl)-phenyl |
| 680 | NH(CO)C$_2$H$_5$ | 4-(3-methylsulfonylamino-phenyl)-phenyl |
| 681 | NH(CO)C$_2$H$_5$ | 4-(3-amino-phenyl)-phenyl |
| 682 | NH(CO)C$_2$H$_5$ | 4-(3-nitro-phenyl)-phenyl |
| 683 | NH(CO)C$_2$H$_5$ | 2-pyridyl |
| 684 | NH(CO)C$_2$H$_5$ | 3-pyridyl |
| 685 | NH(CO)C$_2$H$_5$ | 4-pyridyl |
| 686 | NH(CO)C$_2$H$_5$ | 3-amino-4-pyridyl |
| 687 | NH(CO)C$_2$H$_5$ | 3-hydroxy-4-pyridyl |
| 688 | NH(CO)C$_2$H$_5$ | 3-imidazole |
| 689 | NH(CO)C$_2$H$_5$ | 2-nitro-3-imidazole |
| 690 | NH(CO)C$_2$H$_5$ | 5-thiazole |
| 691 | NH(CO)C$_2$H$_5$ | 5-oxazole |
| 692 | NH(CO)C$_2$H$_5$ | 4-pyazole |
| 693 | NH(CO)C$_2$H$_5$ | phenylethyl |
| 694 | NH(CO)C$_2$H$_5$ | 2-aminophenylethyl |
| 695 | NH(CO)C$_2$H$_5$ | 2-methylsulfonylamino-phenylethyl |
| 696 | NH(CO)C$_2$H$_5$ | 2-trifluoromethylsulfonyl-amino-phenylethyl |
| 697 | NH(CO)C$_2$H$_5$ | 2-hydroxymethylene-phenylethyl |
| 698 | NH(CO)C$_2$H$_5$ | 2-aminomethylene-phenylethyl |
| 699 | NH(CO)C$_2$H$_5$ | 2-tetrazolephenylethyl |
| 700 | NH(CO)C$_2$H$_5$ | 2-tert-butylamino-sulfonylphenylethyl |
| 701 | NH(CO)C$_2$H$_5$ | 2-aminosulfonyl-phenylethyl |
| 702 | NH(CO)C$_2$H$_5$ | 2-methoxyphenylethyl |
| 703 | NH(CO)C$_2$H$_5$ | 3-aminophenylethyl |
| 704 | NH(CO)C$_2$H$_5$ | 3-methylsulfonylamino-phenylethyl |
| 705 | NH(CO)C$_2$H$_5$ | 3-trifluoromethylsulfonyl-amino-phenylethyl |
| 706 | NH(CO)C$_2$H$_5$ | 3-hydroxymethylene-phenylethyl |
| 707 | NH(CO)C$_2$H$_5$ | 3-aminomethylene-phenylethyl |
| 708 | NH(CO)C$_2$H$_5$ | 3-tetrazolephenylethyl |
| 709 | NH(CO)C$_2$H$_5$ | 3-tert-butylamino-sulfonylphenylethyl |
| 710 | NH(CO)C$_2$H$_5$ | 3-aminosulfonyl-phenylethyl |
| 711 | NH(CO)C$_2$H$_5$ | 3-methoxyphenylethyl |
| 712 | NH(CO)OC$_2$H$_5$ | H |
| 713 | NH(CO)OC$_2$H$_5$ | methyl |
| 714 | NH(CO)OC$_2$H$_5$ | ethyl |
| 715 | NH(CO)OC$_2$H$_5$ | n-propyl |
| 716 | NH(CO)OC$_2$H$_5$ | n-butyl |
| 717 | NH(CO)OC$_2$H$_5$ | n-pentyl |
| 718 | NH(CO)OC$_2$H$_5$ | n-hexanyl |
| 719 | NH(CO)OC$_2$H$_5$ | n-heptanyl |
| 720 | NH(CO)OC$_2$H$_5$ | isopropyl |
| 721 | NH(CO)OC$_2$H$_5$ | tert-butyl |
| 722 | NH(CO)OC$_2$H$_5$ | cyclopropyl |
| 723 | NH(CO)OC$_2$H$_5$ | cyclobutanyl |
| 724 | NH(CO)OC$_2$H$_5$ | cyclpentanyl |
| 725 | NH(CO)OC$_2$H$_5$ | cyclohexanyl |
| 726 | NH(CO)OC$_2$H$_5$ | cycloheptanyl |
| 727 | NH(CO)OC$_2$H$_5$ | phenyl |
| 728 | NH(CO)OC$_2$H$_5$ | phenylmethyl |
| 729 | NH(CO)OC$_2$H$_5$ | 3-hydroxyphenyl |
| 730 | NH(CO)OC$_2$H$_5$ | 3-hydroxy-4-methoxyphenyl |
| 731 | NH(CO)OC$_2$H$_5$ | 3-fluorophenyl |
| 732 | NH(CO)OC$_2$H$_5$ | 3-chlorophenyl |
| 733 | NH(CO)OC$_2$H$_5$ | 3-nitrophenyl |
| 734 | NH(CO)OC$_2$H$_5$ | 3-aminophenyl |
| 735 | NH(CO)OC$_2$H$_5$ | 3-methyl-sulfonamidephenyl |
| 736 | NH(CO)OC$_2$H$_5$ | 3-trifluoro-methylsulfonamidephenyl |
| 737 | NH(CO)OC$_2$H$_5$ | 3-Ac—NHphenyl |
| 738 | NH(CO)OC$_2$H$_5$ | 3-Boc—NHphenyl |
| 739 | NH(CO)OC$_2$H$_5$ | 3-Cbz—NHphenyl |
| 740 | NH(CO)OC$_2$H$_5$ | 3-aminomethylenephenyl |
| 741 | NH(CO)OC$_2$H$_5$ | 3-aminoethylenephenyl |
| 742 | NH(CO)OC$_2$H$_5$ | 3-cyanophenyl |
| 743 | NH(CO)OC$_2$H$_5$ | 3-cyanomethylphenyl |
| 744 | NH(CO)OC$_2$H$_5$ | 3-hydroxymethylenephenyl |
| 745 | NH(CO)OC$_2$H$_5$ | 3-carboxylphenyl |
| 746 | NH(CO)OC$_2$H$_5$ | 3-mercaptophenyl |
| 747 | NH(CO)OC$_2$H$_5$ | 3-methoxyphenyl |
| 748 | NH(CO)OC$_2$H$_5$ | 3,4-methylenedioxophenyl |
| 749 | NH(CO)OC$_2$H$_5$ | 3-tetrazolephenyl |
| 750 | NH(CO)OC$_2$H$_5$ | 3-aminosulfonylphenyl |
| 751 | NH(CO)OC$_2$H$_5$ | 3-methylamino-sulfonylphenyl |
| 752 | NH(CO)OC$_2$H$_5$ | 3-ethylamino-sulfonylphenyl |
| 753 | NH(CO)OC$_2$H$_5$ | 3-tert-butylamino-sulfonylphenyl |
| 754 | NH(CO)OC$_2$H$_5$ | 3-methylsulfonylphenyl |
| 755 | NH(CO)OC$_2$H$_5$ | 4-methoxyphenyl |
| 756 | NH(CO)OC$_2$H$_5$ | 4-phenylphenyl |
| 757 | NH(CO)OC$_2$H$_5$ | 4-(2-hydroxy-methylenephenyl)-phenyl |
| 758 | NH(CO)OC$_2$H$_5$ | 4-(2-tert-butylamino-sufonylphenyl)-phenyl |

TABLE 2-continued

| | | |
|---|---|---|
| 759 | NH(CO)OC$_2$H$_5$ | 4-(2-methylamino-sufonylphenyl)-phenyl |
| 760 | NH(CO)OC$_2$H$_5$ | 4-(2-ethylamino-sufonylphenyl)-phenyl |
| 761 | NH(CO)OC$_2$H$_5$ | 4-(2-aminosufonyl-phenyl)-phenyl |
| 762 | NH(CO)OC$_2$H$_5$ | 4-(2-chlorophenyl)-phenyl |
| 763 | NH(CO)OC$_2$H$_5$ | 4-(2-fluorophenyl)-phenyl |
| 764 | NH(CO)OC$_2$H$_5$ | 4-(2,4-dichlorophenyl)-phenyl |
| 765 | NH(CO)OC$_2$H$_5$ | 4-(2,6-dichlorophenyl)-phenyl |
| 766 | NH(CO)OC$_2$H$_5$ | 4-(3,5-dichlorophenyl)-phenyl |
| 767 | NH(CO)OC$_2$H$_5$ | 4-(2,3-dichlorophenyl)-phenyl |
| 768 | NH(CO)OC$_2$H$_5$ | 4-(2-methylphenyl)-phenyl |
| 769 | NH(CO)OC$_2$H$_5$ | 4-(2-tetrazole-phenyl)-phenyl |
| 770 | NH(CO)OC$_2$H$_5$ | 4-(2-methoxy-phenyl)-phenyl |
| 771 | NH(CO)OC$_2$H$_5$ | 4-(2-tmethyl-phenyl)-phenyl |
| 772 | NH(CO)OC$_2$H$_5$ | 4-(2-formyl-phenyl)-phenyl |
| 773 | NH(CO)OC$_2$H$_5$ | 4-(2-amino-phenyl)-phenyl |
| 774 | NH(CO)OC$_2$H$_5$ | 4-(2-methylamino-phenyl)-phenyl |
| 775 | NH(CO)OC$_2$H$_5$ | 4-(2-ethylamino-phenyl)-phenyl |
| 776 | NH(CO)OC$_2$H$_5$ | 4-(2-propylamino-phenyl)-phenyl |
| 777 | NH(CO)OC$_2$H$_5$ | 4-(2-methylsulfonylamino-phenyl)-phenyl |
| 778 | NH(CO)OC$_2$H$_5$ | 4-(2-trifluoromethyl-sulfonyl-amino-phenyl)-phenyl |
| 779 | NH(CO)OC$_2$H$_5$ | 4-(3-methylphenyl)-phenyl |
| 780 | NH(CO)OC$_2$H$_5$ | 4-(3-isopropylphenyl)-phenyl |
| 781 | NH(CO)OC$_2$H$_5$ | 4-(3-trifluoromethyl-sulfonyl-amino-phenyl)-phenyl |
| 782 | NH(CO)OC$_2$H$_5$ | 4-(3-methylsulfonylamino-phenyl)-phenyl |
| 783 | NH(CO)OC$_2$H$_5$ | 4-(3-amino-phenyl)-phenyl |
| 784 | NH(CO)OC$_2$H$_5$ | 4-(3-nitro-phenyl)-phenyl |
| 785 | NH(CO)OC$_2$H$_5$ | 2-pyridyl |
| 786 | NH(CO)OC$_2$H$_5$ | 3-pyridyl |
| 787 | NH(CO)OC$_2$H$_5$ | 4-pyridyl |
| 788 | NH(CO)OC$_2$H$_5$ | 3-amino-4-pyridyl |
| 789 | NH(CO)OC$_2$H$_5$ | 3-hydroxy-4-pyridyl |
| 790 | NH(CO)OC$_2$H$_5$ | 3-imidazole |
| 791 | NH(CO)OC$_2$H$_5$ | 2-nitro-3-imidazole |
| 792 | NH(CO)OC$_2$H$_5$ | 5-thiazole |
| 793 | NH(CO)OC$_2$H$_5$ | 5-oxazole |
| 794 | NH(CO)OC$_2$H$_5$ | 4-pyazole |
| 795 | NH(CO)OC$_2$H$_5$ | phenylethyl |
| 796 | NH(CO)OC$_2$H$_5$ | 2-aminophenylethyl |
| 797 | NH(CO)OC$_2$H$_5$ | 2-methylsulfonylamino-phenylethyl |
| 798 | NH(CO)OC$_2$H$_5$ | 2-trifluoromethylsulfonyl-amino-phenylethyl |
| 799 | NH(CO)OC$_2$H$_5$ | 2-hydroxymethylene-phenylethyl |
| 800 | NH(CO)OC$_2$H$_5$ | 2-aminomethylene-phenylethyl |
| 801 | NH(CO)OC$_2$H$_5$ | 2-tetrazolephenylethyl |
| 802 | NH(CO)OC$_2$H$_5$ | 2-tert-butylamino-sulfonylphenylethyl |
| 803 | NH(CO)OC$_2$H$_5$ | 2-aminosulfonyl-phenylethyl |
| 804 | NH(CO)OC$_2$H$_5$ | 2-methoxyphenylethyl |
| 805 | NH(CO)OC$_2$H$_5$ | 3-aminophenylethyl |
| 806 | NH(CO)OC$_2$H$_5$ | 3-methylsulfonylamino-phenylethyl |
| 807 | NH(CO)OC$_2$H$_5$ | 3-trifluoromethylsulfonyl-amino-phenylethyl |
| 808 | NH(CO)OC$_2$H$_5$ | 3-hydroxymethylene-phenylethyl |
| 809 | NH(CO)OC$_2$H$_5$ | 3-aminomethylene-phenylethyl |
| 810 | NH(CO)OC$_2$H$_5$ | 3-tetrazolephenylethyl |
| 811 | NH(CO)OC$_2$H$_5$ | 3-tert-butylamino-sulfonylphenylethyl |
| 812 | NH(CO)OC$_2$H$_5$ | 3-aminosulfonyl-phenylethyl |
| 813 | NH(CO)OC$_2$H$_5$ | 3-methoxyphenylethyl |
| 814 | NH(CO)OCH$_3$ | H |
| 815 | NH(CO)OCH$_3$ | methyl |
| 816 | NH(CO)OCH$_3$ | ethyl |
| 817 | NH(CO)OCH$_3$ | n-propyl |
| 818 | NH(CO)OCH$_3$ | n-butyl |
| 819 | NH(CO)OCH$_3$ | n-pentyl |
| 820 | NH(CO)OCH$_3$ | n-hexanyl |
| 821 | NH(CO)OCH$_3$ | n-heptanyl |
| 822 | NH(CO)OCH$_3$ | isopropyl |
| 823 | NH(CO)OCH$_3$ | tert-butyl |
| 824 | NH(CO)OCH$_3$ | cyclopropyl |
| 825 | NH(CO)OCH$_3$ | cyclobutanyl |
| 826 | NH(CO)OCH$_3$ | cyclpentanyl |
| 827 | NH(CO)OCH$_3$ | cyclohexanyl |
| 828 | NH(CO)OCH$_3$ | cycloheptanyl |
| 829 | NH(CO)OCH$_3$ | phenyl |
| 830 | NH(CO)OCH$_3$ | phenylmethyl |
| 831 | NH(CO)OCH$_3$ | 3-hydroxyphenyl |
| 832 | NH(CO)OCH$_3$ | 3-hydroxy-4-methoxyphenyl |
| 833 | NH(CO)OCH$_3$ | 3-fluorophenyl |
| 834 | NH(CO)OCH$_3$ | 3-chlorophenyl |
| 835 | NH(CO)OCH$_3$ | 3-nitrophenyl |
| 836 | NH(CO)OCH$_3$ | 3-aminophenyl |
| 837 | NH(CO)OCH$_3$ | 3-methyl-sulfonamidephenyl |
| 838 | NH(CO)OCH$_3$ | 3-trifluoro-methylsulfonamidephenyl |
| 839 | NH(CO)OCH$_3$ | 3-Ac—NHphenyl |
| 840 | NH(CO)OCH$_3$ | 3-Boc—NHphenyl |
| 841 | NH(CO)OCH$_3$ | 3-Cbz—NHphenyl |
| 842 | NH(CO)OCH$_3$ | 3-aminomethylenephenyl |
| 843 | NH(CO)OCH$_3$ | 3-aminoethylenephenyl |
| 844 | NH(CO)OCH$_3$ | 3-cyanophenyl |
| 845 | NH(CO)OCH$_3$ | 3-cyanomethylphenyl |
| 846 | NH(CO)OCH$_3$ | 3-hydroxymethylenephenyl |
| 847 | NH(CO)OCH$_3$ | 3-carboxylphenyl |
| 848 | NH(CO)OCH$_3$ | 3-mercaptophenyl |
| 849 | NH(CO)OCH$_3$ | 3-methoxyphenyl |
| 850 | NH(CO)OCH$_3$ | 3,4-methylenedioxophenyl |
| 851 | NH(CO)OCH$_3$ | 3-tetrazolephenyl |
| 852 | NH(CO)OCH$_3$ | 3-aminosulfonylphenyl |
| 853 | NH(CO)OCH$_3$ | 3-methylamino-sulfonylphenyl |
| 854 | NH(CO)OCH$_3$ | 3-ethylamino-sulfonylphenyl |
| 855 | NH(CO)OCH$_3$ | 3-tert-butylamino-sulfonylphenyl |
| 856 | NH(CO)OCH$_3$ | 3-methylsulfonylphenyl |
| 857 | NH(CO)OCH$_3$ | 4-methoxyphenyl |
| 858 | NH(CO)OCH$_3$ | 4-phenylphenyl |
| 859 | NH(CO)OCH$_3$ | 4-(2-hydroxy-methylenephenyl)-phenyl |
| 860 | NH(CO)OCH$_3$ | 4-(2-tert-butylamino-sufonylphenyl)-phenyl |
| 861 | NH(CO)OCH$_3$ | 4-(2-methylamino-sufonylphenyl)-phenyl |
| 862 | NH(CO)OCH$_3$ | 4-(2-ethylamino-sufonylphenyl)-phenyl |
| 863 | NH(CO)OCH$_3$ | 4-(2-aminosufonyl-phenyl)-phenyl |
| 864 | NH(CO)OCH$_3$ | 4-(2-chlorophenyl)-phenyl |
| 865 | NH(CO)OCH$_3$ | 4-(2-fluorophenyl)-phenyl |
| 866 | NH(CO)OCH$_3$ | 4-(2,4-dichlorophenyl)-phenyl |
| 867 | NH(CO)OCH$_3$ | 4-(2,6-dichlorophenyl)-phenyl |
| 868 | NH(CO)OCH$_3$ | 4-(3,5-dichlorophenyl)-phenyl |
| 869 | NH(CO)OCH$_3$ | 4-(2,3-dichlorophenyl)-phenyl |
| 870 | NH(CO)OCH$_3$ | 4-(2-methylphenyl)-phenyl |
| 871 | NH(CO)OCH$_3$ | 4-(2-tetrazole-phenyl)-phenyl |
| 872 | NH(CO)OCH$_3$ | 4-(2-methoxy-phenyl)-phenyl |
| 873 | NH(CO)OCH$_3$ | 4-(2-tmethyl-phenyl)-phenyl |
| 874 | NH(CO)OCH$_3$ | 4-(2-formyl-phenyl)-phenyl |
| 875 | NH(CO)OCH$_3$ | 4-(2-amino-phenyl)-phenyl |
| 876 | NH(CO)OCH$_3$ | 4-(2-methylamino-phenyl)-phenyl |
| 877 | NH(CO)OCH$_3$ | 4-(2-ethylamino-phenyl)-phenyl |
| 878 | NH(CO)OCH$_3$ | 4-(2-propylamino-phenyl)-phenyl |
| 879 | NH(CO)OCH$_3$ | 4-(2-methylsulfonylamino-phenyl)-phenyl |
| 880 | NH(CO)OCH$_3$ | 4-(2-trifluoromethyl-sulfonyl-amino-phenyl)-phenyl |

TABLE 2-continued

| | | |
|---|---|---|
| 881 | NH(CO)OCH₃ | 4-(3-methylphenyl)-phenyl |
| 882 | NH(CO)OCH₃ | 4-(3-isopropylphenyl)-phenyl |
| 883 | NH(CO)OCH₃ | 4-(3-trifluoromethyl-sulfonyl-amino-phenyl)-phenyl |
| 884 | NH(CO)OCH₃ | 4-(3-methylsulfonylamino-phenyl)-phenyl |
| 885 | NH(CO)OCH₃ | 4-(3-amino-phenyl)-phenyl |
| 886 | NH(CO)OCH₃ | 4-(3-nitro-phenyl)-phenyl |
| 887 | NH(CO)OCH₃ | 2-pyridyl |
| 888 | NH(CO)OCH₃ | 3-pyridyl |
| 889 | NH(CO)OCH₃ | 4-pyridyl |
| 890 | NH(CO)OCH₃ | 3-amino-4-pyridyl |
| 891 | NH(CO)OCH₃ | 3-hydroxy-4-pyridyl |
| 892 | NH(CO)OCH₃ | 3-imidazole |
| 893 | NH(CO)OCH₃ | 2-nitro-3-imidazole |
| 894 | NH(CO)OCH₃ | 5-thiazole |
| 895 | NH(CO)OCH₃ | 5-oxazole |
| 896 | NH(CO)OCH₃ | 4-pyazole |
| 897 | NH(CO)OCH₃ | phenylethyl |
| 898 | NH(CO)OCH₃ | 2-aminophenylethyl |
| 899 | NH(CO)OCH₃ | 2-methylsulfonylamino-phenylethyl |
| 900 | NH(CO)OCH₃ | 2-trifluoromethylsulfonyl-aminophenylethyl |
| 901 | NH(CO)OCH₃ | 2-hydroxymethylene-phenylethyl |
| 902 | NH(CO)OCH₃ | 2-aminomethylene-phenylethyl |
| 903 | NH(CO)OCH₃ | 2-tetrazolephenylethyl |
| 904 | NH(CO)OCH₃ | 2-tert-butylamino-sulfonylphenylethyl |
| 905 | NH(CO)OCH₃ | 2-aminosulfonyl-phenylethyl |
| 906 | NH(CO)OCH₃ | 2-methoxyphenylethyl |
| 907 | NH(CO)OCH₃ | 3-aminophenylethyl |
| 908 | NH(CO)OCH₃ | 3-methylsulfonylamino-phenylethyl |
| 909 | NH(CO)OCH₃ | 3-trifluoromethylsulfonyl-amino-phenylethyl |
| 910 | NH(CO)OCH₃ | 3-hydroxymethylene-phenylethyl |
| 911 | NH(CO)OCH₃ | 3-aminomethylene-phenylethyl |
| 912 | NH(CO)OCH₃ | 3-tetrazolephenylethyl |
| 913 | NH(CO)OCH₃ | 3-tert-butylamino-sulfonylphenylethyl |
| 914 | NH(CO)OCH₃ | 3-aminosulfonyl-phenylethyl |
| 915 | NH(CO)OCH₃ | 3-methoxyphenylethyl |
| 916 | NHBoc | H |
| 917 | NHBoc | methyl |
| 918 | NHBoc | ethyl |
| 919 | NHBoc | n-propyl |
| 920 | NHBoc | n-butyl |
| 921 | NHBoc | n-pentyl |
| 922 | NHBoc | n-hexanyl |
| 923 | NHBoc | n-heptanyl |
| 924 | NHBoc | isopropyl |
| 925 | NHBoc | tert-butyl |
| 926 | NHBoc | cyclopropyl |
| 927 | NHBoc | cyclobutanyl |
| 928 | NHBoc | cyclpentanyl |
| 929 | NHBoc | cyclohexanyl |
| 930 | NHBoc | cycloheptanyl |
| 931 | NHBoc | phenyl |
| 932 | NHBoc | phenylmethyl |
| 933 | NHBoc | 3-hydroxyphenyl |
| 934 | NHBoc | 3-hydroxy-4-methoxyphenyl |
| 935 | NHBoc | 3-fluorophenyl |
| 936 | NHBoc | 3-chlorophenyl |
| 937 | NHBoc | 3-nitrophenyl |
| 938 | NHBoc | 3-aminophenyl |
| 939 | NHBoc | 3-methyl-sulfonamidephenyl |
| 940 | NHBoc | 3-trifluoro-methylsulfonamidephenyl |
| 941 | NHBoc | 3-Ac—NHphenyl |
| 942 | NHBoc | 3-Boc—NHphenyl |
| 943 | NHBoc | 3-Cbz—NHphenyl |
| 944 | NHBoc | 3-aminomethylenephenyl |
| 945 | NHBoc | 3-aminoethylenephenyl |
| 946 | NHBoc | 3-cyanophenyl |
| 947 | NHBoc | 3-cyanomethylphenyl |
| 948 | NHBoc | 3-hydroxymethylenephenyl |
| 949 | NHBoc | 3-carboxylphenyl |
| 950 | NHBoc | 3-mercaptophenyl |
| 951 | NHBoc | 3-methoxyphenyl |
| 952 | NHBoc | 3,4-methylenedioxophenyl |
| 953 | NHBoc | 3-tetrazolephenyl |
| 954 | NHBoc | 3-aminosulfonylphenyl |
| 955 | NHBoc | 3-methylamino-sulfonylphenyl |
| 956 | NHBoc | 3-ethylamino-sulfonylphenyl |
| 957 | NHBoc | 3-tert-butylamino-sulfonylphenyl |
| 958 | NHBoc | 3-methylsulfonylphenyl |
| 959 | NHBoc | 4-methoxyphenyl |
| 960 | NHBoc | 4-phenylphenyl |
| 961 | NHBoc | 4-(2-hydroxy-methylenephenyl)-phenyl |
| 962 | NHBoc | 4-(2-tert-butylamino-sufonylphenyl)-phenyl |
| 963 | NHBoc | 4-(2-methylamino-sufonylphenyl)-phenyl |
| 964 | NHBoc | 4-(2-ethylamino-sufonylphenyl)-phenyl |
| 965 | NHBoc | 4-(2-aminosufonyl-phenyl)-phenyl |
| 966 | NHBoc | 4-(2-chlorophenyl)-phenyl |
| 967 | NHBoc | 4-(2-fluorophenyl)-phenyl |
| 968 | NHBoc | 4-(2,4-dichlorophenyl)-phenyl |
| 969 | NHBoc | 4-(2,6-dichlorophenyl)-phenyl |
| 970 | NHBoc | 4-(3,5-dichlorophenyl)-phenyl |
| 971 | NHBoc | 4-(2,3-dichlorophenyl)-phenyl |
| 972 | NHBoc | 4-(2-methylphenyl)-phenyl |
| 973 | NHBoc | 4-(2-tetrazole-phenyl)-phenyl |
| 974 | NHBoc | 4-(2-methoxy-phenyl)-phenyl |
| 975 | NHBoc | 4-(2-tmethyl-phenyl)-phenyl |
| 976 | NHBoc | 4-(2-formyl-phenyl)-phenyl |
| 977 | NHBoc | 4-(2-amino-phenyl)-phenyl |
| 978 | NHBoc | 4-(2-methylamino-phenyl)-phenyl |
| 979 | NHBoc | 4-(2-ethylamino-phenyl)-phenyl |
| 980 | NHBoc | 4-(2-propylamino-phenyl)-phenyl |
| 981 | NHBoc | 4-(2-methylsulfonylamino-phenyl)-phenyl |
| 982 | NHBoc | 4-(2-trifluoromethyl-sulfonyl-amino-phenyl)-phenyl |
| 983 | NHBoc | 4-(3-methylphenyl)-phenyl |
| 984 | NHBoc | 4-(3-isopropylphenyl)-phenyl |
| 985 | NHBoc | 4-(3-trifluoromethyl-sulfonyl-amino-phenyl)-phenyl |
| 986 | NHBoc | 4-(3-methylsulfonylamino-phenyl)-phenyl |
| 987 | NHBoc | 4-(3-amino-phenyl)-phenyl |
| 988 | NHBoc | 4-(3-nitro-phenyl)-phenyl |
| 989 | NHBoc | 2-pyridyl |
| 990 | NHBoc | 3-pyridyl |
| 991 | NHBoc | 4-pyridyl |
| 992 | NHBoc | 3-amino-4-pyridyl |
| 993 | NHBoc | 3-hydroxy-4-pyridyl |
| 994 | NHBoc | 3-imidazole |
| 995 | NHBoc | 2-nitro-3-imidazole |
| 996 | NHBoc | 5-thiazole |
| 997 | NHBoc | 5-oxazole |
| 998 | NHBoc | 4-pyazole |
| 999 | NHBoc | phenylethyl |
| 1000 | NHBoc | 2-aminophenylethyl |
| 1001 | NHBoc | 2-methylsulfonylamino-phenylethyl |
| 1002 | NHBoc | 2-trifluoromethylsulfonyl-amino-phenylethyl |
| 1003 | NHBoc | 2-hydroxymethylene-phenylethyl |
| 1004 | NHBoc | 2-aminomethylene-phenylethyl |

TABLE 2-continued

| | | |
|---|---|---|
| 1005 | NHBoc | 2-tetrazolephenylethyl |
| 1006 | NHBoc | 2-tert-butylamino-sulfonylphenylethyl |
| 1007 | NHBoc | 2-aminosulfonyl-phenylethyl |
| 1008 | NHBoc | 2-methoxyphenylethyl |
| 1009 | NHBoc | 3-aminophenylethyl |
| 1010 | NHBoc | 3-methylsulfonylamino-phenylethyl |
| 1011 | NHBoc | 3-trifluoromethylsulfonyl-amino-phenylethyl |
| 1012 | NHBoc | 3-hydroxymethylene-phenylethyl |
| 1013 | NHBoc | 3-aminomethylene-phenylethyl |
| 1014 | NHBoc | 3-tetrazolephenylethyl |
| 1015 | NHBoc | 3-tert-butylamino-sulfonylphenylethyl |
| 1016 | NHBoc | 3-aminosulfonyl-phenylethyl |
| 1017 | NHBoc | 3-methoxyphenylethyl |
| 1018 | NH(CO)OCH$_2$-4-pyridyl | H |
| 1019 | NH(CO)OCH$_2$-4-pyridyl | methyl |
| 1020 | NH(CO)OCH$_2$-4-pyridyl | ethyl |
| 1021 | NH(CO)OCH$_2$-4-pyridyl | n-propyl |
| 1022 | NH(CO)OCH$_2$-4-pyridyl | n-butyl |
| 1023 | NH(CO)OCH$_2$-4-pyridyl | n-pentyl |
| 1024 | NH(CO)OCH$_2$-4-pyridyl | n-hexanyl |
| 1025 | NH(CO)OCH$_2$-4-pyridyl | n-heptanyl |
| 1026 | NH(CO)OCH$_2$-4-pyridyl | isopropyl |
| 1027 | NH(CO)OCH$_2$-4-pyridyl | tert-butyl |
| 1028 | NH(CO)OCH$_2$-4-pyridyl | cyclopropyl |
| 1029 | NH(CO)OCH$_2$-4-pyridyl | cyclobutanyl |
| 1030 | NH(CO)OCH$_2$-4-pyridyl | cyclpentanyl |
| 1031 | NH(CO)OCH$_2$-4-pyridyl | cyclohexanyl |
| 1032 | NH(CO)OCH$_2$-4-pyridyl | cycloheptanyl |
| 1033 | NH(CO)OCH$_2$-4-pyridyl | phenyl |
| 1034 | NH(CO)OCH$_2$-4-pyridyl | phenylmethyl |
| 1035 | NH(CO)OCH$_2$-4-pyridyl | 3-hydroxyphenyl |
| 1036 | NH(CO)OCH$_2$-4-pyridyl | 3-hydroxy-4-methoxyphenyl |
| 1037 | NH(CO)OCH$_2$-4-pyridyl | 3-fluorophenyl |
| 1038 | NH(CO)OCH$_2$-4-pyridyl | 3-chlorophenyl |
| 1039 | NH(CO)OCH$_2$-4-pyridyl | 3-nitrophenyl |
| 1040 | NH(CO)OCH$_2$-4-pyridyl | 3-aminophenyl |
| 1041 | NH(CO)OCH$_2$-4-pyridyl | 3-methyl-sulfonamidephenyl |
| 1042 | NH(CO)OCH$_2$-4-pyridyl | 3-trifluoro-methylsulfonamidephenyl |
| 1043 | NH(CO)OCH$_2$-4-pyridyl | 3-Ac—NHphenyl |
| 1044 | NH(CO)OCH$_2$-4-pyridyl | 3-Boc—NHphenyl |
| 1045 | NH(CO)OCH$_2$-4-pyridyl | 3-Cbz—NHphenyl |
| 1046 | NH(CO)OCH$_2$-4-pyridyl | 3-aminomethylenephenyl |
| 1047 | NH(CO)OCH$_2$-4-pyridyl | 3-aminoethylenephenyl |
| 1048 | NH(CO)OCH$_2$-4-pyridyl | 3-cyanophenyl |
| 1049 | NH(CO)OCH$_2$-4-pyridyl | 3-cyanomethylphenyl |
| 1050 | NH(CO)OCH$_2$-4-pyridyl | 3-hydroxymethylenephenyl |
| 1051 | NH(CO)OCH$_2$-4-pyridyl | 3-carboxylphenyl |
| 1052 | NH(CO)OCH$_2$-4-pyridyl | 3-mercaptophenyl |
| 1053 | NH(CO)OCH$_2$-4-pyridyl | 3-methoxphenyl |
| 1054 | NH(CO)OCH$_2$-4-pyridyl | 3,4-methylenedioxophenyl |
| 1055 | NH(CO)OCH$_2$-4-pyridyl | 3-tetrazolephenyl |
| 1056 | NH(CO)OCH$_2$-4-pyridyl | 3-aminosulfonylphenyl |
| 1057 | NH(CO)OCH$_2$-4-pyridyl | 3-methylamino-sulfonylphenyl |
| 1058 | NH(CO)OCH$_2$-4-pyridyl | 3-ethylamino-sulfonylphenyl |
| 1059 | NH(CO)OCH$_2$-4-pyridyl | 3-tert-butylamino-sulfonylphenyl |
| 1060 | NH(CO)OCH$_2$-4-pyridyl | 3-methylsulfonylphenyl |
| 1061 | NH(CO)OCH$_2$-4-pyridyl | 4-methoxyphenyl |
| 1062 | NH(CO)OCH$_2$-4-pyridyl | 4-phenylphenyl |
| 1063 | NH(CO)OCH$_2$-4-pyridyl | 4-(2-hydroxy-methylenephenyl)-phenyl |
| 1064 | NH(CO)OCH$_2$-4-pyridyl | 4-(2-tert-butylamino-sufonylphenyl)-phenyl |
| 1065 | NH(CO)OCH$_2$-4-pyridyl | 4-(2-methylamino-sufonylphenyl)-phenyl |
| 1066 | NH(CO)OCH$_2$-4-pyridyl | 4-(2-ethylamino-sufonylphenyl)-phenyl |
| 1067 | NH(CO)OCH$_2$-4-pyridyl | 4-(2-aminosufonyl-phenyl)-phenyl |
| 1068 | NH(CO)OCH$_2$-4-pyridyl | 4-(2-chlorophenyl)-phenyl |
| 1069 | NH(CO)OCH$_2$-4-pyridyl | 4-(2-fluorophenyl)-phenyl |
| 1070 | NH(CO)OCH$_2$-4-pyridyl | 4-(2,4-dichlorophenyl)-phenyl |
| 1071 | NH(CO)OCH$_2$-4-pyridyl | 4-(2,6-dichlorophenyl)-phenyl |
| 1072 | NH(CO)OCH$_2$-4-pyridyl | 4-(3,5-dichlorophenyl)-phenyl |
| 1073 | NH(CO)OCH$_2$-4-pyridyl | 4-(2,3-dichlorophenyl)-phenyl |
| 1074 | NH(CO)OCH$_2$-4-pyridyl | 4-(2-methylphenyl)-phenyl |
| 1075 | NH(CO)OCH$_2$-4-pyridyl | 4-(2-tetrazole-phenyl)-phenyl |
| 1076 | NH(CO)OCH$_2$-4-pyridyl | 4-(2-methoxy-phenyl)-phenyl |
| 1077 | NH(CO)OCH$_2$-4-pyridyl | 4-(2-tmethyl-phenyl)-phenyl |
| 1078 | NH(CO)OCH$_2$-4-pyridyl | 4-(2-formyl-phenyl)-phenyl |
| 1079 | NH(CO)OCH$_2$-4-pyridyl | 4-(2-amino-phenyl)-phenyl |
| 1080 | NH(CO)OCH$_2$-4-pyridyl | 4-(2-methylamino-phenyl)-phenyl |
| 1081 | NH(CO)OCH$_2$-4-pyridyl | 4-(2-ethylamino-phenyl)-phenyl |
| 1082 | NH(CO)OCH$_2$-4-pyridyl | 4-(2-propylamino-phenyl)-phenyl |
| 1083 | NH(CO)OCH$_2$-4-pyridyl | 4-(2-methylsulfonylamino-phenyl)-phenyl |
| 1084 | NH(CO)OCH$_2$-4-pyridyl | 4-(2-trifluoromethyl-sulfonyl-amino-phenyl)-phenyl |
| 1085 | NH(CO)OCH$_2$-4-pyridyl | 4-(3-methylphenyl)-phenyl |
| 1086 | NH(CO)OCH$_2$-4-pyridyl | 4-(3-isopropylphenyl)-phenyl |
| 1087 | NH(CO)OCH$_2$-4-pyridyl | 4-(3-trifluoromethyl-sulfonyl-amino-phenyl)-phenyl |
| 1088 | NH(CO)OCH$_2$-4-pyridyl | 4-(3-methylsulfonylamino-phenyl)-phenyl |
| 1089 | NH(CO)OCH$_2$-4-pyridyl | 4-(3-amino-phenyl)-phenyl |
| 1090 | NH(CO)OCH$_2$-4-pyridyl | 4-(3-nitro-phenyl)-phenyl |
| 1091 | NH(CO)OCH$_2$-4-pyridyl | 2-pyridyl |
| 1092 | NH(CO)OCH$_2$-4-pyridyl | 3-pyridyl |
| 1093 | NH(CO)OCH$_2$-4-pyridyl | 4-pyridyl |
| 1094 | NH(CO)OCH$_2$-4-pyridyl | 3-amino-4-pyridyl |
| 1095 | NH(CO)OCH$_2$-4-pyridyl | 3-hydroxy-4-pyridyl |
| 1096 | NH(CO)OCH$_2$-4-pyridyl | 3-imidazole |
| 1097 | NH(CO)OCH$_2$-4-pyridyl | 2-nitro-3-imidazole |
| 1098 | NH(CO)OCH$_2$-4-pyridyl | 5-thiazole |
| 1099 | NH(CO)OCH$_2$-4-pyridyl | 5-oxazole |
| 1100 | NH(CO)OCH$_2$-4-pyridyl | 4-pyazole |
| 1101 | NH(CO)OCH$_2$-4-pyridyl | phenylethyl |
| 1102 | NH(CO)OCH$_2$-4-pyridyl | 2-aminophenylethyl |
| 1103 | NH(CO)OCH$_2$-4-pyridyl | 2-methylsulfonylamino-phenylethyl |
| 1104 | NH(CO)OCH$_2$-4-pyridyl | 2-trifluoromethylsulfonyl-amino-phenylethyl |
| 1105 | NH(CO)OCH$_2$-4-pyridyl | 2-hydroxymethylene-phenylethyl |
| 1106 | NH(CO)OCH$_2$-4-pyridyl | 2-aminomethylene-phenylethyl |
| 1107 | NH(CO)OCH$_2$-4-pyridyl | 2-tetrazolephenylethyl |
| 1108 | NH(CO)OCH$_2$-4-pyridyl | 2-tert-butylamino-sulfonylphenylethyl |
| 1109 | NH(CO)OCH$_2$-4-pyridyl | 2-aminosulfonyl-phenylethyl |
| 1110 | NH(CO)OCH$_2$-4-pyridyl | 2-methoxyphenylethyl |
| 1111 | NH(CO)OCH$_2$-4-pyridyl | 3-aminophenylethyl |
| 1112 | NH(CO)OCH$_2$-4-pyridyl | 3-methylsulfonylamino-phenylethyl |
| 1113 | NH(CO)OCH$_2$-4-pyridyl | 3-trifluoromethylsulfonyl-amino-phenylethyl |
| 1114 | NH(CO)OCH$_2$-4-pyridyl | 3-hydroxymethylene-phenylethyl |
| 1115 | NH(CO)OCH$_2$-4-pyridyl | 3-aminomethylene-phenylethyl |
| 1116 | NH(CO)OCH$_2$-4-pyridyl | 3-tetrazolephenylethyl |
| 1117 | NH(CO)OCH$_2$-4-pyridyl | 3-tert-butylamino-sulfonylphenylethyl |
| 1118 | NH(CO)OCH$_2$-4-pyridyl | 3-aminosulfonyl-phenylethyl |
| 1119 | NH(CO)OCH$_2$-4-pyridyl | 3-methoxyphenylethyl |
| 1120 | NHS(O$_2$)CH$_3$ | H |
| 1121 | NHS(O$_2$)CH$_3$ | methyl |
| 1122 | NHS(O$_2$)CH$_3$ | ethyl |
| 1123 | NHS(O$_2$)CH$_3$ | n-propyl |
| 1124 | NHS(O$_2$)CH$_3$ | n-butyl |
| 1125 | NHS(O$_2$)CH$_3$ | n-pentyl |
| 1126 | NHS(O$_2$)CH$_3$ | n-hexanyl |
| 1127 | NHS(O$_2$)CH$_3$ | n-heptanyl |
| 1128 | NHS(O$_2$)CH$_3$ | isopropyl |
| 1129 | NHS(O$_2$)CH$_3$ | tert-butyl |

TABLE 2-continued

| | | |
|---|---|---|
| 1130 | NHS(O$_2$)CH$_3$ | cyclopropyl |
| 1131 | NHS(O$_2$)CH$_3$ | cyclobutanyl |
| 1132 | NHS(O$_2$)CH$_3$ | cyclpentanyl |
| 1133 | NHS(O$_2$)CH$_3$ | cyclohexanyl |
| 1134 | NHS(O$_2$)CH$_3$ | cycloheptanyl |
| 1135 | NHS(O$_2$)CH$_3$ | phenyl |
| 1136 | NHS(O$_2$)CH$_3$ | phenylmethyl |
| 1137 | NHS(O$_2$)CH$_3$ | 3-hydroxyphenyl |
| 1138 | NHS(O$_2$)CH$_3$ | 3-hydroxy-4-methoxyphenyl |
| 1139 | NHS(O$_2$)CH$_3$ | 3-fluorophenyl |
| 1140 | NHS(O$_2$)CH$_3$ | 3-chlorophenyl |
| 1141 | NHS(O$_2$)CH$_3$ | 3-nitrophenyl |
| 1142 | NHS(O$_2$)CH$_3$ | 3-aminophenyl |
| 1143 | NHS(O$_2$)CH$_3$ | 3-methyl-sulfonamidephenyl |
| 1144 | NHS(O$_2$)CH$_3$ | 3-trifluoro-methylsulfonamidephenyl |
| 1145 | NHS(O$_2$)CH$_3$ | 3-Ac—NHphenyl |
| 1146 | NHS(O$_2$)CH$_3$ | 3-Boc—NHphenyl |
| 1147 | NHS(O$_2$)CH$_3$ | 3-Cbz—NHphenyl |
| 1148 | NHS(O$_2$)CH$_3$ | 3-aminomethylenephenyl |
| 1149 | NHS(O$_2$)CH$_3$ | 3-aminoethylenephenyl |
| 1150 | NHS(O$_2$)CH$_3$ | 3-cyanophenyl |
| 1151 | NHS(O$_2$)CH$_3$ | 3-cyanomethylphenyl |
| 1152 | NHS(O$_2$)CH$_3$ | 3-hydroxymethylenephenyl |
| 1153 | NHS(O$_2$)CH$_3$ | 3-carboxylphenyl |
| 1154 | NHS(O$_2$)CH$_3$ | 3-mercaptophenyl |
| 1155 | NHS(O$_2$)CH$_3$ | 3-methoxyphenyl |
| 1156 | NHS(O$_2$)CH$_3$ | 3,4-methylenedioxophenyl |
| 1157 | NHS(O$_2$)CH$_3$ | 3-tetrazolephenyl |
| 1158 | NHS(O$_2$)CH$_3$ | 3-aminosulfonylphenyl |
| 1159 | NHS(O$_2$)CH$_3$ | 3-methylamino-sulfonylphenyl |
| 1160 | NHS(O$_2$)CH$_3$ | 3-ethylamino-sulfonylphenyl |
| 1161 | NHS(O$_2$)CH$_3$ | 3-tert-butylamino-sulfonylphenyl |
| 1162 | NHS(O$_2$)CH$_3$ | 3-methylsulfonylphenyl |
| 1163 | NHS(O$_2$)CH$_3$ | 4-methoxyphenyl |
| 1164 | NHS(O$_2$)CH$_3$ | 4-phenylphenyl |
| 1165 | NHS(O$_2$)CH$_3$ | 4-(2-hydroxy-methylenephenyl)-phenyl |
| 1166 | NHS(O$_2$)CH$_3$ | 4-(2-tert-butylamino-sufonylphenyl)-phenyl |
| 1167 | NHS(O$_2$)CH$_3$ | 4-(2-methylamino-sufonylphenyl)-phenyl |
| 1168 | NHS(O$_2$)CH$_3$ | 4-(2-ethylamino-sufonylphenyl)-phenyl |
| 1169 | NHS(O$_2$)CH$_3$ | 4-(2-aminosufonyl-phenyl)-phenyl |
| 1170 | NHS(O$_2$)CH$_3$ | 4-(2-chlorophenyl)-phenyl |
| 1171 | NHS(O$_2$)CH$_3$ | 4-(2-fluorophenyl)-phenyl |
| 1172 | NHS(O$_2$)CH$_3$ | 4-(2,4-dichlorophenyl)-phenyl |
| 1173 | NHS(O$_2$)CH$_3$ | 4-(2,6-dichlorophenyl)-phenyl |
| 1174 | NHS(O$_2$)CH$_3$ | 4-(3,5-dichlorophenyl)-phenyl |
| 1175 | NHS(O$_2$)CH$_3$ | 4-(2,3-dichlorophenyl)-phenyl |
| 1176 | NHS(O$_2$)CH$_3$ | 4-(2-methylphenyl)-phenyl |
| 1177 | NHS(O$_2$)CH$_3$ | 4-(2-tetrazole-phenyl)-phenyl |
| 1178 | NHS(O$_2$)CH$_3$ | 4-(2-methoxy-phenyl)-phenyl |
| 1179 | NHS(O$_2$)CH$_3$ | 4-(2-tmethyl-phenyl)-phenyl |
| 1180 | NHS(O$_2$)CH$_3$ | 4-(2-formyl-phenyl)-phenyl |
| 1181 | NHS(O$_2$)CH$_3$ | 4-(2-amino-phenyl)-phenyl |
| 1182 | NHS(O$_2$)CH$_3$ | 4-(2-methylamino-phenyl)-phenyl |
| 1183 | NHS(O$_2$)CH$_3$ | 4-(2-ethylamino-phenyl)-phenyl |
| 1184 | NHS(O$_2$)CH$_3$ | 4-(2-propylamino-phenyl)-phenyl |
| 1185 | NHS(O$_2$)CH$_3$ | 4-(2-methylsulfonylamino-phenyl)-phenyl |
| 1186 | NHS(O$_2$)CH$_3$ | 4-(2-trifluoromethyl-sulfonyl-amino-phenyl)-phenyl |
| 1187 | NHS(O$_2$)CH$_3$ | 4-(3-methylphenyl)-phenyl |
| 1188 | NHS(O$_2$)CH$_3$ | 4-(3-isopropylphenyl)-phenyl |
| 1189 | NHS(O$_2$)CH$_3$ | 4-(3-trifluoromethyl-sulfonyl-amino-phenyl)-phenyl |
| 1190 | NHS(O$_2$)CH$_3$ | 4-(3-methylsulfonylamino-phenyl)-phenyl |
| 1191 | NHS(O$_2$)CH$_3$ | 4-(3-amino-phenyl)-phenyl |
| 1192 | NHS(O$_2$)CH$_3$ | 4-(3-nitro-phenyl)-phenyl |
| 1193 | NHS(O$_2$)CH$_3$ | 2-pyridyl |
| 1194 | NHS(O$_2$)CH$_3$ | 3-pyridyl |
| 1195 | NHS(O$_2$)CH$_3$ | 4-pyridyl |
| 1196 | NHS(O$_2$)CH$_3$ | 3-amino-4-pyridyl |
| 1197 | NHS(O$_2$)CH$_3$ | 3-hydroxy-4-pyridyl |
| 1198 | NHS(O$_2$)CH$_3$ | 3-imidazole |
| 1199 | NHS(O$_2$)CH$_3$ | 2-nitro-3-imidazole |
| 1200 | NHS(O$_2$)CH$_3$ | 5-thiazole |
| 1201 | NHS(O$_2$)CH$_3$ | 5-oxazole |
| 1202 | NHS(O$_2$)CH$_3$ | 4-pyazole |
| 1203 | NHS(O$_2$)CH$_3$ | phenylethyl |
| 1204 | NHS(O$_2$)CH$_3$ | 2-aminophenylethyl |
| 1205 | NHS(O$_2$)CH$_3$ | 2-methylsulfonylamino-phenylethyl |
| 1206 | NHS(O$_2$)CH$_3$ | 2-trifluoromethylsulfonyl-amino-phenylethyl |
| 1207 | NHS(O$_2$)CH$_3$ | 2-hydroxymethylene-phenylethyl |
| 1208 | NHS(O$_2$)CH$_3$ | 2-aminomethylene-phenylethyl |
| 1209 | NHS(O$_2$)CH$_3$ | 2-tetrazolephenylethyl |
| 1210 | NHS(O$_2$)CH$_3$ | 2-tert-butylamino-sulfonylphenylethyl |
| 1211 | NHS(O$_2$)CH$_3$ | 2-aminosulfonyl-phenylethyl |
| 1212 | NHS(O$_2$)CH$_3$ | 2-methoxyphenylethyl |
| 1213 | NHS(O$_2$)CH$_3$ | 3-aminophenylethyl |
| 1214 | NHS(O$_2$)CH$_3$ | 3-methylsulfonylamino-phenylethyl |
| 1215 | NHS(O$_2$)CH$_3$ | 3-trifluoromethylsulfonyl-amino-phenylethyl |
| 1216 | NHS(O$_2$)CH$_3$ | 3-hydroxymethylene-phenylethyl |
| 1217 | NHS(O$_2$)CH$_3$ | 3-aminomethylene-phenylethyl |
| 1218 | NHS(O$_2$)CH$_3$ | 3-tetrazolephenylethyl |
| 1219 | NHS(O$_2$)CH$_3$ | 3-tert-butylamino-sulfonylphenylethyl |
| 1220 | NHS(O$_2$)CH$_3$ | 3-aminosulfonyl-phenylethyl |
| 1221 | NHS(O$_2$)CH$_3$ | 3-methoxyphenylethyl |
| 1222 | NHS(O$_2$)CF$_3$ | H |
| 1223 | NHS(O$_2$)CF$_3$ | methyl |
| 1224 | NHS(O$_2$)CF$_3$ | ethyl |
| 1225 | NHS(O$_2$)CF$_3$ | n-propyl |
| 1226 | NHS(O$_2$)CF$_3$ | n-butyl |
| 1227 | NHS(O$_2$)CF$_3$ | n-pentyl |
| 1228 | NHS(O$_2$)CF$_3$ | n-hexanyl |
| 1229 | NHS(O$_2$)CF$_3$ | n-heptanyl |
| 1230 | NHS(O$_2$)CF$_3$ | isopropyl |
| 1231 | NHS(O$_2$)CF$_3$ | tert-butyl |
| 1232 | NHS(O$_2$)CF$_3$ | cyclopropyl |
| 1233 | NHS(O$_2$)CF$_3$ | cyclobutanyl |
| 1234 | NHS(O$_2$)CF$_3$ | cyclpentanyl |
| 1235 | NHS(O$_2$)CF$_3$ | cyclohexanyl |
| 1236 | NHS(O$_2$)CF$_3$ | cycloheptanyl |
| 1237 | NHS(O$_2$)CF$_3$ | phenyl |
| 1238 | NHS(O$_2$)CF$_3$ | phenylmethyl |
| 1239 | NHS(O$_2$)CF$_3$ | 3-hydroxyphenyl |
| 1240 | NHS(O$_2$)CF$_3$ | 3-hydroxy-4-methoxyphenyl |
| 1241 | NHS(O$_2$)CF$_3$ | 3-fluorophenyl |
| 1242 | NHS(O$_2$)CF$_3$ | 3-chlorophenyl |
| 1243 | NHS(O$_2$)CF$_3$ | 3-nitrophenyl |
| 1244 | NHS(O$_2$)CF$_3$ | 3-aminophenyl |
| 1245 | NHS(O$_2$)CF$_3$ | 3-methyl-sulfonamidephenyl |
| 1246 | NHS(O$_2$)CF$_3$ | 3-trifluoro-methylsulfonamidephenyl |
| 1247 | NHS(O$_2$)CF$_3$ | 3-Ac—NHphenyl |
| 1248 | NHS(O$_2$)CF$_3$ | 3-Boc—NHphenyl |
| 1249 | NHS(O$_2$)CF$_3$ | 3-Cbz—NHphenyl |
| 1250 | NHS(O$_2$)CF$_3$ | 3-aminomethylenephenyl |
| 1251 | NHS(O$_2$)CF$_3$ | 3-aminoethylenephenyl |
| 1252 | NHS(O$_2$)CF$_3$ | 3-cyanophenyl |
| 1253 | NHS(O$_2$)CF$_3$ | 3-cyanomethylphenyl |
| 1254 | NHS(O$_2$)CF$_3$ | 3-hydroxymethylenephenyl |
| 1255 | NHS(O$_2$)CF$_3$ | 3-carboxylphenyl |
| 1256 | NHS(O$_2$)CF$_3$ | 3-mercaptophenyl |
| 1257 | NHS(O$_2$)CF$_3$ | 3-methoxyphenyl |
| 1258 | NHS(O$_2$)CF$_3$ | 3,4-methylenedioxophenyl |
| 1259 | NHS(O$_2$)CF$_3$ | 3-tetrazolephenyl |

TABLE 2-continued

| | | |
|---|---|---|
| 1260 | NHS(O$_2$)CF$_3$ | 3-aminosulfonylphenyl |
| 1261 | NHS(O$_2$)CF$_3$ | 3-methylamino-sulfonylphenyl |
| 1262 | NHS(O$_2$)CF$_3$ | 3-ethylamino-sulfonylphenyl |
| 1263 | NHS(O$_2$)CF$_3$ | 3-tert-butylamino-sulfonylphenyl |
| 1264 | NHS(O$_2$)CF$_3$ | 3-methylsulfonylphenyl |
| 1265 | NHS(O$_2$)CF$_3$ | 4-methoxyphenyl |
| 1266 | NHS(O$_2$)CF$_3$ | 4-phenylphenyl |
| 1267 | NHS(O$_2$)CF$_3$ | 4-(2-hydroxy-methylenephenyl)-phenyl |
| 1268 | NHS(O$_2$)CF$_3$ | 4-(2-tert-butylamino-sufonylphenyl)-phenyl |
| 1269 | NHS(O$_2$)CF$_3$ | 4-(2-methylamino-sufonylphenyl)-phenyl |
| 1270 | NHS(O$_2$)CF$_3$ | 4-(2-ethylamino-sufonylphenyl)-phenyl |
| 1271 | NHS(O$_2$)CF$_3$ | 4-(2-aminosufonyl-phenyl)-phenyl |
| 1272 | NHS(O$_2$)CF$_3$ | 4-(2-chlorophenyl)-phenyl |
| 1273 | NHS(O$_2$)CF$_3$ | 4-(2-fluorophenyl)-phenyl |
| 1274 | NHS(O$_2$)CF$_3$ | 4-(2,4-dichlorophenyl)-phenyl |
| 1275 | NHS(O$_2$)CF$_3$ | 4-(2,6-dichlorophenyl)-phenyl |
| 1276 | NHS(O$_2$)CF$_3$ | 4-(3,5-dichlorophenyl)-phenyl |
| 1277 | NHS(O$_2$)CF$_3$ | 4-(2,3-dichlorophenyl)-phenyl |
| 1278 | NHS(O$_2$)CF$_3$ | 4-(2-methylphenyl)-phenyl |
| 1279 | NHS(O$_2$)CF$_3$ | 4-(2-tetrazole-phenyl)-phenyl |
| 1280 | NHS(O$_2$)CF$_3$ | 4-(2-methoxy-phenyl)-phenyl |
| 1281 | NHS(O$_2$)CF$_3$ | 4-(2-tmethyl-phenyl)-phenyl |
| 1282 | NHS(O$_2$)CF$_3$ | 4-(2-formyl-phenyl)-phenyl |
| 1283 | NHS(O$_2$)CF$_3$ | 4-(2-amino-phenyl)-phenyl |
| 1284 | NHS(O$_2$)CF$_3$ | 4-(2-methylamino-phenyl)-phenyl |
| 1285 | NHS(O$_2$)CF$_3$ | 4-(2-ethylamino-phenyl)-phenyl |
| 1286 | NHS(O$_2$)CF$_3$ | 4-(2-propylamino-phenyl)-phenyl |
| 1287 | NHS(O$_2$)CF$_3$ | 4-(2-methylsulfonylamino-phenyl)-phenyl |
| 1288 | NHS(O$_2$)CF$_3$ | 4-(2-trifluoromethyl-sulfonyl-amino-phenyl)-phenyl |
| 1289 | NHS(O$_2$)CF$_3$ | 4-(3-methylphenyl)-phenyl |
| 1290 | NHS(O$_2$)CF$_3$ | 4-(3-isopropylphenyl)-phenyl |
| 1291 | NHS(O$_2$)CF$_3$ | 4-(3-trifluoromethyl-sulfonyl-amino-phenyl)-phenyl |
| 1292 | NHS(O$_2$)CF$_3$ | 4-(3-methylsulfonylamino-phenyl)-phenyl |
| 1293 | NHS(O$_2$)CF$_3$ | 4-(3-amino-phenyl)-phenyl |
| 1294 | NHS(O$_2$)CF$_3$ | 4-(3-nitro-phenyl)-phenyl |
| 1295 | NHS(O$_2$)CF$_3$ | 2-pyridyl |
| 1296 | NHS(O$_2$)CF$_3$ | 3-pyridyl |
| 1297 | NHS(O$_2$)CF$_3$ | 4-pyridyl |
| 1298 | NHS(O$_2$)CF$_3$ | 3-amino-4-pyridyl |
| 1299 | NHS(O$_2$)CF$_3$ | 3-hydroxy-4-pyridyl |
| 1300 | NHS(O$_2$)CF$_3$ | 3-imidazole |
| 1301 | NHS(O$_2$)CF$_3$ | 2-nitro-3-imidazole |
| 1302 | NHS(O$_2$)CF$_3$ | 5-thiazole |
| 1303 | NHS(O$_2$)CF$_3$ | 5-oxazole |
| 1304 | NHS(O$_2$)CF$_3$ | 4-pyazole |
| 1305 | NHS(O$_2$)CF$_3$ | phenylethyl |
| 1306 | NHS(O$_2$)CF$_3$ | 2-aminophenylethyl |
| 1307 | NHS(O$_2$)CF$_3$ | 2-methylsulfonylamino-phenylethyl |
| 1308 | NHS(O$_2$)CF$_3$ | 2-trifluoromethylsulfonyl-amino-phenylethyl |
| 1309 | NHS(O$_2$)CF$_3$ | 2-hydroxymethylene-phenylethyl |
| 1310 | NHS(O$_2$)CF$_3$ | 2-aminomethylene-phenylethyl |
| 1311 | NHS(O$_2$)CF$_3$ | 2-tetrazolephenylethyl |
| 1312 | NHS(O$_2$)CF$_3$ | 2-tert-butylamino-sulfonylphenylethyl |
| 1313 | NHS(O$_2$)CF$_3$ | 2-aminosulfonyl-phenylethyl |
| 1314 | NHS(O$_2$)CF$_3$ | 2-methoxyphenylethyl |
| 1315 | NHS(O$_2$)CF$_3$ | 3-aminophenylethyl |
| 1316 | NHS(O$_2$)CF$_3$ | 3-methylsulfonylamino-phenylethyl |
| 1317 | NHS(O$_2$)CF$_3$ | 3-trifluoromethylsulfonyl-amino-phenylethyl |
| 1318 | NHS(O$_2$)CF$_3$ | 3-hydroxymethylene-phenylethyl |
| 1319 | NHS(O$_2$)CF$_3$ | 3-aminomethylene-phenylethyl |
| 1320 | NHS(O$_2$)CF$_3$ | 3-tetrazolephenylethyl |
| 1321 | NHS(O$_2$)CF$_3$ | 3-tert-butylamino-sulfonylphenylethyl |
| 1322 | NHS(O$_2$)CF$_3$ | 3-aminosulfonyl-phenylethyl |
| 1323 | NHS(O$_2$)CF$_3$ | 3-methoxyphenylethyl |
| 1324 | 4-aminophenylS(O)2NH | H |
| 1325 | 4-aminophenylS(O)2NH | methyl |
| 1326 | 4-aminophenylS(O)2NH | ethyl |
| 1327 | 4-aminophenylS(O)2NH | n-propyl |
| 1328 | 4-aminophenylS(O)2NH | n-butyl |
| 1329 | 4-aminophenylS(O)2NH | n-pentyl |
| 1330 | 4-aminophenylS(O)2NH | n-hexanyl |
| 1331 | 4-aminophenylS(O)2NH | n-heptanyl |
| 1332 | 4-aminophenylS(O)2NH | isopropyl |
| 1333 | 4-aminophenylS(O)2NH | tert-butyl |
| 1334 | 4-aminophenylS(O)2NH | cyclopropyl |
| 1335 | 4-aminophenylS(O)2NH | cyclobutanyl |
| 1336 | 4-aminophenylS(O)2NH | cyclpentanyl |
| 1337 | 4-aminophenylS(O)2NH | cyclohexanyl |
| 1338 | 4-aminophenylS(O)2NH | cycloheptanyl |
| 1339 | 4-aminophenylS(O)2NH | phenyl |
| 1340 | 4-aminophenylS(O)2NH | phenylmethyl |
| 1341 | 4-aminophenylS(O)2NH | 3-hydroxyphenyl |
| 1342 | 4-aminophenylS(O)2NH | 3-hydroxy-4-methoxyphenyl |
| 1343 | 4-aminophenylS(O)2NH | 3-fluorophenyl |
| 1344 | 4-aminophenylS(O)2NH | 3-chlorophenyl |
| 1345 | 4-aminophenylS(O)2NH | 3-nitrophenyl |
| 1346 | 4-aminophenylS(O)2NH | 3-aminophenyl |
| 1347 | 4-aminophenylS(O)2NH | 3-methyl-sulfonamidephenyl |
| 1348 | 4-aminophenylS(O)2NH | 3-trifluoro-methylsulfonamidephenyl |
| 1349 | 4-aminophenylS(O)2NH | 3-Ac—NHphenyl |
| 1350 | 4-aminophenylS(O)2NH | 3-Boc—NHphenyl |
| 1351 | 4-aminophenylS(O)2NH | 3-Cbz—NHphenyl |
| 1352 | 4-aminophenylS(O)2NH | 3-aminomethylenephenyl |
| 1353 | 4-aminophenylS(O)2NH | 3-aminoethylenephenyl |
| 1354 | 4-aminophenylS(O)2NH | 3-cyanophenyl |
| 1355 | 4-aminophenylS(O)2NH | 3-cyanomethylphenyl |
| 1356 | 4-aminophenylS(O)2NH | 3-hydroxymethylenephenyl |
| 1357 | 4-aminophenylS(O)2NH | 3-carboxylphenyl |
| 1358 | 4-aminophenylS(O)2NH | 3-mercaptophenyl |
| 1359 | 4-aminophenylS(O)2NH | 3-methoxyphenyl |
| 1360 | 4-aminophenylS(O)2NH | 3,4-methylenedioxophenyl |
| 1361 | 4-aminophenylS(O)2NH | 3-tetrazolephenyl |
| 1362 | 4-aminophenylS(O)2NH | 3-aminosulfonylphenyl |
| 1363 | 4-aminophenylS(O)2NH | 3-methylamino-sulfonylphenyl |
| 1364 | 4-aminophenylS(O)2NH | 3-ethylamino-sulfonylphenyl |
| 1365 | 4-aminophenylS(O)2NH | 3-tert-butylamino-sulfonylphenyl |
| 1366 | 4-aminophenylS(O)2NH | 3-methylsulfonylphenyl |
| 1367 | 4-aminophenylS(O)2NH | 4-methoxyphenyl |
| 1368 | 4-aminophenylS(O)2NH | 4-phenylphenyl |
| 1369 | 4-aminophenylS(O)2NH | 4-(2-hydroxy-methylenephenyl)-phenyl |
| 1370 | 4-aminophenylS(O)2NH | 4-(2-tert-butylamino-sufonylphenyl)-phenyl |
| 1371 | 4-aminophenylS(O)2NH | 4-(2-methylamino-sufonylphenyl)-phenyl |
| 1372 | 4-aminophenylS(O)2NH | 4-(2-ethylamino-sufonylphenyl)-phenyl |
| 1373 | 4-aminophenylS(O)2NH | 4-(2-aminosufonyl-phenyl)-phenyl |
| 1374 | 4-aminophenylS(O)2NH | 4-(2-chlorophenyl)-phenyl |
| 1375 | 4-aminophenylS(O)2NH | 4-(2-fluorophenyl)-phenyl |
| 1376 | 4-aminophenylS(O)2NH | 4-(2,4-dichlorophenyl)-phenyl |
| 1377 | 4-aminophenylS(O)2NH | 4-(2,6-dichlorophenyl)-phenyl |
| 1378 | 4-aminophenylS(O)2NH | 4-(3,5-dichlorophenyl)-phenyl |
| 1379 | 4-aminophenylS(O)$_2$NH | 4-(2,3-dichlorophenyl)-phenyl |
| 1380 | 4-aminophenylS(O)$_2$NH | 4-(2-methylphenyl)-phenyl |
| 1381 | 4-aminophenylS(O)$_2$NH | 4-(2-tetrazole-phenyl)-phenyl |
| 1382 | 4-aminophenylS(O)$_2$NH | 4-(2-methoxy-phenyl)-phenyl |
| 1383 | 4-aminophenylS(O)$_2$NH | 4-(2-tmethyl-phenyl)-phenyl |

TABLE 2-continued

| | | |
|---|---|---|
| 1384 | 4-aminophenylS(O)$_2$NH | 4-(2-formyl-phenyl)-phenyl |
| 1385 | 4-aminophenylS(O)$_2$NH | 4-(2-amino-phenyl)-phenyl |
| 1386 | 4-aminophenylS(O)$_2$NH | 4-(2-methylamino-phenyl)-phenyl |
| 1387 | 4-aminophenylS(O)$_2$NH | 4-(2-ethylamino-phenyl)-phenyl |
| 1388 | 4-aminophenylS(O)$_2$NH | 4-(2-propylamino-phenyl)-phenyl |
| 1389 | 4-aminophenylS(O)$_2$NH | 4-(2-methylsulfonylamino-phenyl)-phenyl |
| 1390 | 4-aminophenylS(O)$_2$NH | 4-(2-trifluoromethyl-sulfonyl-amino-phenyl)-phenyl |
| 1391 | 4-aminophenylS(O)$_2$NH | 4-(3-methylphenyl)-phenyl |
| 1392 | 4-aminophenylS(O)$_2$NH | 4-(3-isopropylphenyl)-phenyl |
| 1393 | 4-aminophenylS(O)$_2$NH | 4-(3-trifluoromethyl-sulfonyl-amino-phenyl)-phenyl |
| 1394 | 4-aminophenylS(O)$_2$NH | 4-(3-methylsulfonylamino-phenyl)-phenyl |
| 1395 | 4-aminophenylS(O)$_2$NH | 4-(3-amino-phenyl)-phenyl |
| 1396 | 4-aminophenylS(O)$_2$NH | 4-(3-nitro-phenyl)-phenyl |
| 1397 | 4-aminophenylS(O)$_2$NH | 2-pyridyl |
| 1398 | 4-aminophenylS(O)$_2$NH | 3-pyridyl |
| 1399 | 4-aminophenylS(O)$_2$NH | 4-pyridyl |
| 1400 | 4-aminophenylS(O)$_2$NH | 3-amino-4-pyridyl |
| 1401 | 4-aminophenylS(O)$_2$NH | 3-hydroxy-4-pyridyl |
| 1402 | 4-aminophenylS(O)$_2$NH | 3-imidazole |
| 1403 | 4-aminophenylS(O)$_2$NH | 2-nitro-3-imidazole |
| 1404 | 4-aminophenylS(O)$_2$NH | 5-thiazole |
| 1405 | 4-aminophenylS(O)$_2$NH | 5-oxazole |
| 1406 | 4-aminophenylS(O)$_2$NH | 4-pyazole |
| 1407 | 4-aminophenylS(O)$_2$NH | phenylethyl |
| 1408 | 4-aminophenylS(O)$_2$NH | 2-aminophenylethyl |
| 1409 | 4-aminophenylS(O)$_2$NH | 2-methylsulfonylamino-phenylethyl |
| 1410 | 4-aminophenylS(O)$_2$NH | 2-trifluoromethylsulfonyl-amino-phenylethyl |
| 1411 | 4-aminophenylS(O)$_2$NH | 2-hydroxymethylene-phenylethyl |
| 1412 | 4-aminophenylS(O)$_2$NH | 2-aminomethylene-phenylethyl |
| 1413 | 4-aminophenylS(O)$_2$NH | 2-tetrazolephenylethyl |
| 1414 | 4-aminophenylS(O)$_2$NH | 2-tert-butylamino-sulfonylphenylethyl |
| 1415 | 4-aminophenylS(O)$_2$NH | 2-aminosulfonyl-phenylethyl |
| 1416 | 4-aminophenylS(O)$_2$NH | 2-methoxyphenylethyl |
| 1417 | 4-aminophenylS(O)$_2$NH | 3-aminophenylethyl |
| 1418 | 4-aminophenylS(O)$_2$NH | 3-methylsulfonylamino-phenylethyl |
| 1419 | 4-aminophenylS(O)$_2$NH | 3-trifluoromethylsulfonyl-amino-phenylethyl |
| 1420 | 4-aminophenylS(O)$_2$NH | 3-hydroxymethylene-phenylethyl |
| 1421 | 4-aminophenylS(O)$_2$NH | 3-aminomethylene-phenylethyl |
| 1422 | 4-aminophenylS(O)$_2$NH | 3-tetrazolephenylethyl |
| 1423 | 4-aminophenylS(O)$_2$NH | 3-tert-butylamino-sulfonylphenylethyl |
| 1424 | 4-aminophenylS(O)$_2$NH | 3-aminosulfonyl-phenylethyl |
| 1425 | 4-aminophenylS(O)$_2$NH | 3-methoxyphenylethyl |
| 1426 | NH(CO)NMe$_2$ | H |
| 1427 | NH(CO)NMe$_2$ | methyl |
| 1428 | NH(CO)NMe$_2$ | ethyl |
| 1429 | NH(CO)NMe$_2$ | n-propyl |
| 1430 | NH(CO)NMe$_2$ | n-butyl |
| 1431 | NH(CO)NMe$_2$ | n-pentyl |
| 1432 | NH(CO)NMe$_2$ | n-hexanyl |
| 1433 | NH(CO)NMe$_2$ | n-heptanyl |
| 1434 | NH(CO)NMe$_2$ | isopropyl |
| 1435 | NH(CO)NMe$_2$ | tert-butyl |
| 1436 | NH(CO)NMe$_2$ | cyclopropyl |
| 1437 | NH(CO)NMe$_2$ | cyclobutanyl |
| 1438 | NH(CO)NMe$_2$ | cyclpentanyl |
| 1439 | NH(CO)NMe$_2$ | cyclohexanyl |
| 1440 | NH(CO)NMe$_2$ | cycloheptanyl |
| 1441 | NH(CO)NMe$_2$ | phenyl |
| 1442 | NH(CO)NMe$_2$ | phenylmethyl |
| 1443 | NH(CO)NMe$_2$ | 3-hydroxyphenyl |

TABLE 2-continued

| | | |
|---|---|---|
| 1444 | NH(CO)NMe$_2$ | 3-hydroxy-4-methoxyphenyl |
| 1445 | NH(CO)NMe$_2$ | 3-fluorophenyl |
| 1446 | NH(CO)NMe$_2$ | 3-chlorophenyl |
| 1447 | NH(CO)NMe$_2$ | 3-nitrophenyl |
| 1448 | NH(CO)NMe$_2$ | 3-aminophenyl |
| 1449 | NH(CO)NMe$_2$ | 3-methylsulfonamidephenyl |
| 1450 | NH(CO)NMe$_2$ | 3-trifluoro-methylsulfonamidephenyl |
| 1451 | NH(CO)NMe$_2$ | 3-Ac—NHphenyl |
| 1452 | NH(CO)NMe$_2$ | 3-Boc—NHphenyl |
| 1453 | NH(CO)NMe$_2$ | 3-Cbz—NHphenyl |
| 1454 | NH(CO)NMe$_2$ | 3-aminomethylenephenyl |
| 1455 | NH(CO)NMe$_2$ | 3-aminoethylenephenyl |
| 1456 | NH(CO)NMe$_2$ | 3-cyanophenyl |
| 1457 | NH(CO)NMe$_2$ | 3-cyanomethylphenyl |
| 1458 | NH(CO)NMe$_2$ | 3-hydroxymethylenephenyl |
| 1459 | NH(CO)NMe$_2$ | 3-carboxylphenyl |
| 1460 | NH(CO)NMe$_2$ | 3-mercaptophenyl |
| 1461 | NH(CO)NMe$_2$ | 3-methoxyphenyl |
| 1462 | NH(CO)NMe$_2$ | 3,4-methylenedioxophenyl |
| 1463 | NH(CO)NMe$_2$ | 3-tetrazolephenyl |
| 1464 | NH(CO)NMe$_2$ | 3-aminosulfonylphenyl |
| 1465 | NH(CO)NMe$_2$ | 3-methylamino-sulfonylphenyl |
| 1466 | NH(CO)NMe$_2$ | 3-ethylamino-sulfonylphenyl |
| 1467 | NH(CO)NMe$_2$ | 3-tert-butylamino-sulfonylphenyl |
| 1468 | NH(CO)NMe$_2$ | 3-methylsulfonylphenyl |
| 1469 | NH(CO)NMe$_2$ | 4-methoxyphenyl |
| 1470 | NH(CO)NMe$_2$ | 4-phenylphenyl |
| 1471 | NH(CO)NMe$_2$ | 4-(2-hydroxy-methylenephenyl)-phenyl |
| 1472 | NH(CO)NMe$_2$ | 4-(2-tert-butylamino-sufonylphenyl)-phenyl |
| 1473 | NH(CO)NMe$_2$ | 4-(2-methylamino-sufonylphenyl)-phenyl |
| 1474 | NH(CO)NMe$_2$ | 4-(2-ethylamino-sufonylphenyl)-phenyl |
| 1475 | NH(CO)NMe$_2$ | 4-(2-aminosufonyl-phenyl)-phenyl |
| 1476 | NH(CO)NMe$_2$ | 4-(2-chlorophenyl)-phenyl |
| 1477 | NH(CO)NMe$_2$ | 4-(2-fluorophenyl)-phenyl |
| 1478 | NH(CO)NMe$_2$ | 4-(2,4-dichlorophenyl)-phenyl |
| 1479 | NH(CO)NMe$_2$ | 4-(2,6-dichlorophenyl)-phenyl |
| 1480 | NH(CO)NMe$_2$ | 4-(3,5-dichlorophenyl)-phenyl |
| 1481 | NH(CO)NMe$_2$ | 4-(2,3-dichlorophenyl)-phenyl |
| 1482 | NH(CO)NMe$_2$ | 4-(2-methylphenyl)-phenyl |
| 1483 | NH(CO)NMe$_2$ | 4-(2-tetrazole-phenyl)-phenyl |
| 1484 | NH(CO)NMe$_2$ | 4-(2-methoxy-phenyl)-phenyl |
| 1485 | NH(CO)NMe$_2$ | 4-(2-tmethyl-phenyl)-phenyl |
| 1486 | NH(CO)NMe$_2$ | 4-(2-formyl-phenyl)-phenyl |
| 1487 | NH(CO)NMe$_2$ | 4-(2-amino-phenyl)-phenyl |
| 1488 | NH(CO)NMe$_2$ | 4-(2-methylamino-phenyl)-phenyl |
| 1489 | NH(CO)NMe$_2$ | 4-(2-ethylamino-phenyl)-phenyl |
| 1490 | NH(CO)NMe$_2$ | 4-(2-propylamino-phenyl)-phenyl |
| 1491 | NH(CO)NMe$_2$ | 4-(2-methylsulfonylamino-phenyl)-phenyl |
| 1492 | NH(CO)NMe$_2$ | 4-(2-trifluoromethyl-sulfonyl-amino-phenyl)-phenyl |
| 1493 | NH(CO)NMe$_2$ | 4-(3-methylphenyl)-phenyl |
| 1494 | NH(CO)NMe$_2$ | 4-(3-isopropylphenyl)-phenyl |
| 1495 | NH(CO)NMe$_2$ | 4-(3-trifluoromethyl-sulfonyl-amino-phenyl)-phenyl |
| 1496 | NH(CO)NMe$_2$ | 4-(3-methylsulfonylamino-phenyl)-phenyl |
| 1497 | NH(CO)NMe$_2$ | 4-(3-amino-phenyl)-phenyl |
| 1498 | NH(CO)NMe$_2$ | 4-(3-nitro-phenyl)-phenyl |
| 1499 | NH(CO)NMe$_2$ | 2-pyridyl |
| 1500 | NH(CO)NMe$_2$ | 3-pyridyl |
| 1501 | NH(CO)NMe$_2$ | 4-pyridyl |
| 1502 | NH(CO)NMe$_2$ | 3-amino-4-pyridyl |
| 1503 | NH(CO)NMe$_2$ | 3-hydroxy-4-pyridyl |
| 1504 | NH(CO)NMe$_2$ | 3-imidazole |
| 1505 | NH(CO)NMe$_2$ | 2-nitro-3-imidazole |

TABLE 2-continued

| | | |
|---|---|---|
| 1506 | NH(CO)NMe$_2$ | 5-thiazole |
| 1507 | NH(CO)NMe$_2$ | 5-oxazole |
| 1508 | NH(CO)NMe$_2$ | 4-pyazole |
| 1509 | NH(CO)NMe$_2$ | phenylethyl |
| 1510 | NH(CO)NMe$_2$ | 2-aminophenylethyl |
| 1511 | NH(CO)NMe$_2$ | 2-methylsulfonylamino-phenylethyl |
| 1512 | NH(CO)NMe$_2$ | 2-trifluoromethylsulfonyl-amino-phenylethyl |
| 1513 | NH(CO)NMe$_2$ | 2-hydroxymethylene-phenylethyl |
| 1514 | NH(CO)NMe$_2$ | 2-aminomethylene-phenylethyl |
| 1515 | NH(CO)NMe$_2$ | 2-tetrazolephenylethyl |
| 1516 | NH(CO)NMe$_2$ | 2-tert-butylamino-sulfonylphenylethyl |
| 1517 | NH(CO)NMe$_2$ | 2-aminosulfonyl-phenylethyl |
| 1518 | NH(CO)NMe$_2$ | 2-methoxyphenylethyl |
| 1519 | NH(CO)NMe$_2$ | 3-aminophenylethyl |
| 1520 | NH(CO)NMe$_2$ | 3-methylsulfonylamino-phenylethyl |
| 1521 | NH(CO)NMe$_2$ | 3-trifluoromethylsulfonyl-amino-phenylethyl |
| 1522 | NH(CO)NMe$_2$ | 3-hydroxymethylene-phenylethyl |
| 1523 | NH(CO)NMe$_2$ | 3-aminomethylene-phenylethyl |
| 1524 | NH(CO)NMe$_2$ | 3-tetrazolephenylethyl |
| 1525 | NH(CO)NMe$_2$ | 3-tert-butylamino-sulfonylphenylethyl |
| 1526 | NH(CO)NMe$_2$ | 3-aminosulfonyl-phenylethyl |
| 1527 | NH(CO)NMe$_2$ | 3-methoxyphenylethyl |
| 1528 | NH(CO)N(CH$_2$CH$_2$)$_2$O | H |
| 1529 | NH(CO)N(CH$_2$CH$_2$)$_2$O | methyl |
| 1530 | NH(CO)N(CH$_2$CH$_2$)$_2$O | ethyl |
| 1531 | NH(CO)N(CH$_2$CH$_2$)$_2$O | n-propyl |
| 1532 | NH(CO)N(CH$_2$CH$_2$)$_2$O | n-butyl |
| 1533 | NH(CO)N(CH$_2$CH$_2$)$_2$O | n-pentyl |
| 1534 | NH(CO)N(CH$_2$CH$_2$)$_2$O | n-hexanyl |
| 1535 | NH(CO)N(CH$_2$CH$_2$)$_2$O | n-heptanyl |
| 1536 | NH(CO)N(CH$_2$CH$_2$)$_2$O | isopropyl |
| 1537 | NH(CO)N(CH$_2$CH$_2$)$_2$O | tert-butyl |
| 1538 | NH(CO)N(CH$_2$CH$_2$)$_2$O | cyclopropyl |
| 1539 | NH(CO)N(CH$_2$CH$_2$)$_2$O | cyclobutanyl |
| 1540 | NH(CO)N(CH$_2$CH$_2$)$_2$O | cyclpentanyl |
| 1541 | NH(CO)N(CH$_2$CH$_2$)$_2$O | cyclohexanyl |
| 1542 | NH(CO)N(CH$_2$CH$_2$)$_2$O | cycloheptanyl |
| 1543 | NH(CO)N(CH$_2$CH$_2$)$_2$O | phenyl |
| 1544 | NH(CO)N(CH$_2$CH$_2$)$_2$O | phenylmethyl |
| 1545 | NH(CO)N(CH$_2$CH$_2$)$_2$O | 3-hydroxyphenyl |
| 1546 | NH(CO)N(CH$_2$CH$_2$)$_2$O | 3-hydroxy-4-methoxyphenyl |
| 1547 | NH(CO)N(CH$_2$CH$_2$)$_2$O | 3-fluorophenyl |
| 1548 | NH(CO)N(CH$_2$CH$_2$)$_2$O | 3-chlorophenyl |
| 1549 | NH(CO)N(CH$_2$CH$_2$)$_2$O | 3-nitrophenyl |
| 1550 | NH(CO)N(CH$_2$CH$_2$)$_2$O | 3-aminophenyl |
| 1551 | NH(CO)N(CH$_2$CH$_2$)$_2$O | 3-methyl-sulfonamidephenyl |
| 1552 | NH(CO)N(CH$_2$CH$_2$)$_2$O | 3-trifluoro-methylsulfonamidephenyl |
| 1553 | NH(CO)N(CH$_2$CH$_2$)$_2$O | 3-Ac—NHphenyl |
| 1554 | NH(CO)N(CH$_2$CH$_2$)$_2$O | 3-Boc—NHphenyl |
| 1555 | NH(CO)N(CH$_2$CH$_2$)$_2$O | 3-Cbz—NHphenyl |
| 1556 | NH(CO)N(CH$_2$CH$_2$)$_2$O | 3-aminomethylenephenyl |
| 1557 | NH(CO)N(CH$_2$CH$_2$)$_2$O | 3-aminoethylenephenyl |
| 1558 | NH(CO)N(CH$_2$CH$_2$)$_2$O | 3-cyanophenyl |
| 1559 | NH(CO)N(CH$_2$CH$_2$)$_2$O | 3-cyanomethylphenyl |
| 1560 | NH(CO)N(CH$_2$CH$_2$)$_2$O | 3-hydroxymethylenephenyl |
| 1561 | NH(CO)N(CH$_2$CH$_2$)$_2$O | 3-carboxylphenyl |
| 1562 | NH(CO)N(CH$_2$CH$_2$)$_2$O | 3-mercaptophenyl |
| 1563 | NH(CO)N(CH$_2$CH$_2$)$_2$O | 3-methoxyphenyl |
| 1564 | NH(CO)N(CH$_2$CH$_2$)$_2$O | 3,4-methylenedioxophenyl |
| 1565 | NH(CO)N(CH$_2$CH$_2$)$_2$O | 3-tetrazolephenyl |
| 1566 | NH(CO)N(CH$_2$CH$_2$)$_2$O | 3-aminosulfonylphenyl |
| 1567 | NH(CO)N(CH$_2$CH$_2$)$_2$O | 3-methylamino-sulfonylphenyl |
| 1568 | NH(CO)N(CH$_2$CH$_2$)$_2$O | 3-ethylamino-sulfonylphenyl |
| 1569 | NH(CO)N(CH$_2$CH$_2$)$_2$O | 3-tert-butylamino-sulfonylphenyl |
| 1570 | NH(CO)N(CH$_2$CH$_2$)$_2$O | 3-methylsulfonylphenyl |
| 1571 | NH(CO)N(CH$_2$CH$_2$)$_2$O | 4-methoxyphenyl |
| 1572 | NH(CO)N(CH$_2$CH$_2$)$_2$O | 4-phenylphenyl |
| 1573 | NH(CO)N(CH$_2$CH$_2$)$_2$O | 4-(2-hydroxy-methylenephenyl)-phenyl |
| 1574 | NH(CO)N(CH$_2$CH$_2$)$_2$O | 4-(2-tert-butylamino-sufonylphenyl)-phenyl |
| 1575 | NH(CO)N(CH$_2$CH$_2$)$_2$O | 4-(2-methylamino-sufonylphenyl)-phenyl |
| 1576 | NH(CO)N(CH$_2$CH$_2$)$_2$O | 4-(2-ethylamino-sufonylphenyl)-phenyl |
| 1577 | NH(CO)N(CH$_2$CH$_2$)$_2$O | 4-(2-aminosufonyl-phenyl)-phenyl |
| 1578 | NH(CO)N(CH$_2$CH$_2$)$_2$O | 4-(2-chlorophenyl)-phenyl |
| 1579 | NH(CO)N(CH$_2$CH$_2$)$_2$O | 4-(2-fluorophenyl)-phenyl |
| 1580 | NH(CO)N(CH$_2$CH$_2$)$_2$O | 4-(2,4-dichlorophenyl)-phenyl |
| 1581 | NH(CO)N(CH$_2$CH$_2$)$_2$O | 4-(2,6-dichlorophenyl)-phenyl |
| 1582 | NH(CO)N(CH$_2$CH$_2$)$_2$O | 4-(3,5-dichlorophenyl)-phenyl |
| 1583 | NH(CO)N(CH$_2$CH$_2$)$_2$O | 4-(2,3-dichlorophenyl)-phenyl |
| 1584 | NH(CO)N(CH$_2$CH$_2$)$_2$O | 4-(2-methylphenyl)-phenyl |
| 1585 | NH(CO)N(CH$_2$CH$_2$)$_2$O | 4-(2-tetrazole-phenyl)-phenyl |
| 1586 | NH(CO)N(CH$_2$CH$_2$)$_2$O | 4-(2-methoxy-phenyl)-phenyl |
| 1587 | NH(CO)N(CH$_2$CH$_2$)$_2$O | 4-(2-tmethyl-phenyl)-phenyl |
| 1588 | NH(CO)N(CH$_2$CH$_2$)$_2$O | 4-(2-formyl-phenyl)-phenyl |
| 1589 | NH(CO)N(CH$_2$CH$_2$)$_2$O | 4-(2-amino-phenyl)-phenyl |
| 1590 | NH(CO)N(CH$_2$CH$_2$)$_2$O | 4-(2-methylamino-phenyl)-phenyl |
| 1591 | NH(CO)N(CH$_2$CH$_2$)$_2$O | 4-(2-ethylamino-phenyl)-phenyl |
| 1592 | NH(CO)N(CH$_2$CH$_2$)$_2$O | 4-(2-propylamino-phenyl)-phenyl |
| 1593 | NH(CO)N(CH$_2$CH$_2$)$_2$O | 4-(2-methylsulfonylamino-phenyl)-phenyl |
| 1594 | NH(CO)N(CH$_2$CH$_2$)$_2$O | 4-(2-trifluoromethyl-sulfonyl-amino-phenyl)-phenyl |
| 1595 | NH(CO)N(CH$_2$CH$_2$)$_2$O | 4-(3-methylphenyl)-phenyl |
| 1596 | NH(CO)N(CH$_2$CH$_2$)$_2$O | 4-(3-isopropylphenyl)-phenyl |
| 1597 | NH(CO)N(CH$_2$CH$_2$)$_2$O | 4-(3-trifluoromethyl-sulfonyl-amino-phenyl)-phenyl |
| 1598 | NH(CO)N(CH$_2$CH$_2$)$_2$O | 4-(3-methylsulfonylamino-phenyl)-phenyl |
| 1599 | NH(CO)N(CH$_2$CH$_2$)$_2$O | 4-(3-amino-phenyl)-phenyl |
| 1600 | NH(CO)N(CH$_2$CH$_2$)$_2$O | 4-(3-nitro-phenyl)-phenyl |
| 1601 | NH(CO)N(CH$_2$CH$_2$)$_2$O | 2-pyridyl |
| 1602 | NH(CO)N(CH$_2$CH$_2$)$_2$O | 3-pyridyl |
| 1603 | NH(CO)N(CH$_2$CH$_2$)$_2$O | 4-pyridyl |
| 1604 | NH(CO)N(CH$_2$CH$_2$)$_2$O | 3-amino-4-pyridyl |
| 1605 | NH(CO)N(CH$_2$CH$_2$)$_2$O | 3-hydroxy-4-pyridyl |
| 1606 | NH(CO)N(CH$_2$CH$_2$)$_2$O | 3-imidazole |
| 1607 | NH(CO)N(CH$_2$CH$_2$)$_2$O | 2-nitro-3-imidazole |
| 1608 | NH(CO)N(CH$_2$CH$_2$)$_2$O | 5-thiazole |
| 1609 | NH(CO)N(CH$_2$CH$_2$)$_2$O | 5-oxazole |
| 1610 | NH(CO)N(CH$_2$CH$_2$)$_2$O | 4-pyazole |
| 1611 | NH(CO)N(CH$_2$CH$_2$)$_2$O | phenylethyl |
| 1612 | NH(CO)N(CH$_2$CH$_2$)$_2$O | 2-aminophenylethyl |
| 1613 | NH(CO)N(CH$_2$CH$_2$)$_2$O | 2-methylsulfonylamino-phenylethyl |
| 1614 | NH(CO)N(CH$_2$CH$_2$)$_2$O | 2-trifluoromethylsulfonyl-amino-phenylethyl |
| 1615 | NH(CO)N(CH$_2$CH$_2$)$_2$O | 2-hydroxymethylene-phenylethyl |
| 1616 | NH(CO)N(CH$_2$CH$_2$)$_2$O | 2-aminomethylene-phenylethyl |
| 1617 | NH(CO)N(CH$_2$CH$_2$)$_2$O | 2-tetrazolephenylethyl |
| 1618 | NH(CO)N(CH$_2$CH$_2$)$_2$O | 2-tert-butylamino-sulfonylphenylethyl |
| 1619 | NH(CO)N(CH$_2$CH$_2$)$_2$O | 2-aminosulfonyl-phenylethyl |
| 1620 | NH(CO)N(CH$_2$CH$_2$)$_2$O | 2-methoxyphenylethyl |
| 1621 | NH(CO)N(CH$_2$CH$_2$)$_2$O | 3-aminophenylethyl |
| 1622 | NH(CO)N(CH$_2$CH$_2$)$_2$O | 3-methylsulfonylamino-phenylethyl |
| 1623 | NH(CO)N(CH$_2$CH$_2$)$_2$O | 3-trifluoromethylsulfonyl-amino-phenylethyl |
| 1624 | NH(CO)N(CH$_2$CH$_2$)$_2$O | 3-hydroxymethylene-phenylethyl |
| 1625 | NH(CO)N(CH$_2$CH$_2$)$_2$O | 3-aminomethylene-phenylethyl |
| 1626 | NH(CO)N(CH$_2$CH$_2$)$_2$O | 3-tetrazolephenylethyl |

TABLE 2-continued

| | | |
|---|---|---|
| 1627 | NH(CO)N(CH$_2$CH$_2$)$_2$O | 3-tert-butylamino-sulfonylphenylethyl |
| 1628 | NH(CO)N(CH$_2$CH$_2$)$_2$O | 3-aminosulfonyl-phenylethyl |
| 1629 | NH(CO)N(CH$_2$CH$_2$)$_2$O | 3-methoxyphenylethyl |
| 1630 | tert-BuCONH | H |
| 1631 | tert-BuCONH | methyl |
| 1632 | tert-BuCONH | ethyl |
| 1633 | tert-BuCONH | n-propyl |
| 1634 | tert-BuCONH | n-butyl |
| 1635 | tert-BuCONH | n-pentyl |
| 1636 | tert-BuCONH | n-hexanyl |
| 1637 | tert-BuCONH | n-heptanyl |
| 1638 | tert-BuCONH | isopropyl |
| 1639 | tert-BuCONH | tert-butyl |
| 1640 | tert-BuCONH | cyclopropyl |
| 1641 | tert-BuCONH | cyclobutanyl |
| 1642 | tert-BuCONH | cyclpentanyl |
| 1643 | tert-BuCONH | cyclohexanyl |
| 1644 | tert-BuCONH | cycloheptanyl |
| 1645 | tert-BuCONH | phenyl |
| 1646 | tert-BuCONH | phenylmethyl |
| 1647 | tert-BuCONH | 3-hydroxyphenyl |
| 1648 | tert-BuCONH | 3-hydroxy-4-methoxyphenyl |
| 1649 | tert-BuCONH | 3-fluorophenyl |
| 1650 | tert-BuCONH | 3-chlorophenyl |
| 1651 | tert-BuCONH | 3-nitrophenyl |
| 1652 | tert-BuCONH | 3-aminophenyl |
| 1653 | tert-BuCONH | 3-methyl-sulfonamidephenyl |
| 1654 | tert-BuCONH | 3-trifluoro-methylsulfonamidephenyl |
| 1655 | tert-BuCONH | 3-Ac—NHphenyl |
| 1656 | tert-BuCONH | 3-Boc—NHphenyl |
| 1657 | tert-BuCONH | 3-Cbz—NHphenyl |
| 1658 | tert-BuCONH | 3-aminomethylenephenyl |
| 1659 | tert-BuCONH | 3-aminoethylenephenyl |
| 1660 | tert-BuCONH | 3-cyanophenyl |
| 1661 | tert-BuCONH | 3-cyanomethylphenyl |
| 1662 | tert-BuCONH | 3-hydroxymethylenephenyl |
| 1663 | tert-BuCONH | 3-carboxylphenyl |
| 1664 | tert-BuCONH | 3-mercaptophenyl |
| 1665 | tert-BuCONH | 3-methoxyphenyl |
| 1666 | tert-BuCONH | 3,4-methylenedioxophenyl |
| 1667 | tert-BuCONH | 3-tetrazolephenyl |
| 1668 | tert-BuCONH | 3-aminosulfonylphenyl |
| 1669 | tert-BuCONH | 3-methylamino-sulfonylphenyl |
| 1670 | tert-BuCONH | 3-ethylamino-sulfonylphenyl |
| 1671 | tert-BuCONH | 3-tert-butylamino-sulfonylphenyl |
| 1672 | tert-BuCONH | 3-methylsulfonylphenyl |
| 1673 | tert-BuCONH | 4-methoxyphenyl |
| 1674 | tert-BuCONH | 4-phenylphenyl |
| 1675 | tert-BuCONH | 4-(2-hydroxy-methylenephenyl)-phenyl |
| 1676 | tert-BuCONH | 4-(2-tert-butylamino-sufonylphenyl)-phenyl |
| 1677 | tert-BuCONH | 4-(2-methylamino-sufonylphenyl)-phenyl |
| 1678 | tert-BuCONH | 4-(2-ethylamino-sufonylphenyl)-phenyl |
| 1679 | tert-BuCONH | 4-(2-aminosufonyl-phenyl)-phenyl |
| 1680 | tert-BuCONH | 4-(2-chlorophenyl)-phenyl |
| 1681 | tert-BuCONH | 4-(2-fluorophenyl)-phenyl |
| 1682 | tert-BuCONH | 4-(2,4-dichlorophenyl)-phenyl |
| 1683 | tert-BuCONH | 4-(2,6-dichlorophenyl)-phenyl |
| 1684 | tert-BuCONH | 4-(3,5-dichlorophenyl)-phenyl |
| 1685 | tert-BuCONH | 4-(2,3-dichlorophenyl)-phenyl |
| 1686 | tert-BuCONH | 4-(2-methylphenyl)-phenyl |
| 1687 | tert-BuCONH | 4-(2-tetrazole-phenyl)-phenyl |
| 1688 | tert-BuCONH | 4-(2-methoxy-phenyl)-phenyl |
| 1689 | tert-BuCONH | 4-(2-tmethyl-phenyl)-phenyl |
| 1690 | tert-BuCONH | 4-(2-formyl-phenyl)-phenyl |
| 1691 | tert-BuCONH | 4-(2-amino-phenyl)-phenyl |
| 1692 | tert-BuCONH | 4-(2-methylamino-phenyl)-phenyl |
| 1693 | tert-BuCONH | 4-(2-ethylamino-phenyl)-phenyl |
| 1694 | tert-BuCONH | 4-(2-propylamino-phenyl)-phenyl |
| 1695 | tert-BuCONH | 4-(2-methylsulfonylamino-phenyl)-phenyl |
| 1696 | tert-BuCONH | 4-(2-trifluoromethyl-sulfonyl-amino-phenyl)-phenyl |
| 1697 | tert-BuCONH | 4-(3-methylphenyl)-phenyl |
| 1698 | tert-BuCONH | 4-(3-isopropylphenyl)-phenyl |
| 1699 | tert-BuCONH | 4-(3-trifluoromethyl-sulfonyl-amino-phenyl)-phenyl |
| 1700 | tert-BuCONH | 4-(3-methylsulfonylamino-phenyl)-phenyl |
| 1701 | tert-BuCONH | 4-(3-amino-phenyl)-phenyl |
| 1702 | tert-BuCONH | 4-(3-nitro-phenyl)-phenyl |
| 1703 | tert-BuCONH | 2-pyridyl |
| 1704 | tert-BuCONH | 3-pyridyl |
| 1705 | tert-BuCONH | 4-pyridyl |
| 1706 | tert-BuCONH | 3-amino-4-pyridyl |
| 1707 | tert-BuCONH | 3-hydroxy-4-pyridyl |
| 1708 | tert-BuCONH | 3-imidazole |
| 1709 | tert-BuCONH | 2-nitro-3-imidazole |
| 1710 | tert-BuCONH | 5-thiazole |
| 1711 | tert-BuCONH | 5-oxazole |
| 1712 | tert-BuCONH | 4-pyazole |
| 1713 | tert-BuCONH | phenylethyl |
| 1714 | tert-BuCONH | 2-aminophenylethyl |
| 1715 | tert-BuCONH | 2-methylsulfonylamino-phenylethyl |
| 1716 | tert-BuCONH | 2-trifluoromethylsulfonyl-amino-phenylethyl |
| 1717 | tert-BuCONH | 2-hydroxymethylene-phenylethyl |
| 1718 | tert-BuCONH | 2-aminomethylene-phenylethyl |
| 1719 | tert-BuCONH | 2-tetrazolephenylethyl |
| 1720 | tert-BuCONH | 2-tert-butylamino-sulfonylphenylethyl |
| 1721 | tert-BuCONH | 2-aminosulfonyl-phenylethyl |
| 1722 | tert-BuCONH | 2-methoxyphenylethyl |
| 1723 | tert-BuCONH | 3-aminophenylethyl |
| 1724 | tert-BuCONH | 3-methylsulfonylamino-phenylethyl |
| 1725 | tert-BuCONH | 3-trifluoromethylsulfonyl-amino-phenylethyl |
| 1726 | tert-BuCONH | 3-hydroxymethylene-phenylethyl |
| 1727 | tert-BuCONH | 3-aminomethylene-phenylethyl |
| 1728 | tert-BuCONH | 3-tetrazolephenylethyl |
| 1729 | tert-BuCONH | 3-tert-butylamino-sulfonylphenylethyl |
| 1730 | tert-BuCONH | 3-aminosulfonyl-phenylethyl |
| 1731 | tert-BuCONH | 3-methoxyphenylethyl |
| 1732 | c-C$_3$H$_5$CONH | H |
| 1733 | c-C$_3$H$_5$CONH | methyl |
| 1734 | c-C$_3$H$_5$CONH | ethyl |
| 1735 | c-C$_3$H$_5$CONH | n-propyl |
| 1736 | c-C$_3$H$_5$CONH | n-butyl |
| 1737 | c-C$_3$H$_5$CONH | n-pentyl |
| 1738 | c-C$_3$H$_5$CONH | n-hexanyl |
| 1739 | c-C$_3$H$_5$CONH | n-heptanyl |
| 1740 | c-C$_3$H$_5$CONH | isopropyl |
| 1741 | c-C$_3$H$_5$CONH | tert-butyl |
| 1742 | c-C$_3$H$_5$CONH | cyclopropyl |
| 1743 | c-C$_3$H$_5$CONH | cyclobutanyl |
| 1744 | c-C$_3$H$_5$CONH | cyclpentanyl |
| 1745 | c-C$_3$H$_5$CONH | cyclohexanyl |
| 1746 | c-C$_3$H$_5$CONH | cycloheptanyl |
| 1747 | c-C$_3$H$_5$CONH | phenyl |
| 1748 | c-C$_3$H$_5$CONH | phenylmethyl |
| 1749 | c-C$_3$H$_5$CONH | 3-hydroxyphenyl |
| 1750 | c-C$_3$H$_5$CONH | 3-hydroxy-4-methoxyphenyl |
| 1751 | c-C$_3$H$_5$CONH | 3-fluorophenyl |
| 1752 | c-C$_3$H$_5$CONH | 3-chlorophenyl |
| 1753 | c-C$_3$H$_5$CONH | 3-nitrophenyl |
| 1754 | c-C$_3$H$_5$CONH | 3-aminophenyl |
| 1755 | c-C$_3$H$_5$CONH | 3-methyl-sulfonamidephenyl |

TABLE 2-continued

| | | |
|---|---|---|
| 1756 | c-C$_3$H$_5$CONH | 3-trifluoro-methylsulfonamidephenyl |
| 1757 | c-C$_3$H$_5$CONH | 3-Ac—NHphenyl |
| 1758 | c-C$_3$H$_5$CONH | 3-Boc—NHphenyl |
| 1759 | c-C$_3$H$_5$CONH | 3-Cbz—NHphenyl |
| 1760 | c-C$_3$H$_5$CONH | 3-aminomethylenephenyl |
| 1761 | c-C$_3$H$_5$CONH | 3-aminoethylenephenyl |
| 1762 | c-C$_3$H$_5$CONH | 3-cyanophenyl |
| 1763 | c-C$_3$H$_5$CONH | 3-cyanomethylphenyl |
| 1764 | c-C$_3$H$_5$CONH | 3-hydroxymethylenephenyl |
| 1765 | c-C$_3$H$_5$CONH | 3-carboxylphenyl |
| 1766 | c-C$_3$H$_5$CONH | 3-mercaptophenyl |
| 1767 | c-C$_3$H$_5$CONH | 3-methoxyphenyl |
| 1768 | c-C$_3$H$_5$CONH | 3,4-methylenedioxophenyl |
| 1769 | c-C$_3$H$_5$CONH | 3-tetrazolephenyl |
| 1770 | c-C$_3$H$_5$CONH | 3-aminosulfonylphenyl |
| 1771 | c-C$_3$H$_5$CONH | 3-methylamino-sulfonylphenyl |
| 1772 | c-C$_3$H$_5$CONH | 3-ethylamino-sulfonylphenyl |
| 1773 | c-C$_3$H$_5$CONH | 3-tert-butylamino-sulfonylphenyl |
| 1774 | c-C$_3$H$_5$CONH | 3-methylsulfonylphenyl |
| 1775 | c-C$_3$H$_5$CONH | 4-methoxyphenyl |
| 1776 | c-C$_3$H$_5$CONH | 4-phenylphenyl |
| 1777 | c-C$_3$H$_5$CONH | 4-(2-hydroxy-methylenephenyl)-phenyl |
| 1778 | c-C$_3$H$_5$CONH | 4-(2-tert-butylamino-sufonylphenyl)-phenyl |
| 1779 | c-C$_3$H$_5$CONH | 4-(2-methylamino-sufonylphenyl)-phenyl |
| 1780 | c-C$_3$H$_5$CONH | 4-(2-ethylamino-sufonylphenyl)-phenyl |
| 1781 | c-C$_3$H$_5$CONH | 4-(2-aminosufonyl-phenyl)-phenyl |
| 1782 | c-C$_3$H$_5$CONH | 4-(2-chlorophenyl)-phenyl |
| 1783 | c-C$_3$H$_5$CONH | 4-(2-fluorophenyl)-phenyl |
| 1784 | c-C$_3$H$_5$CONH | 4-(2,4-dichlorophenyl)-phenyl |
| 1785 | c-C$_3$H$_5$CONH | 4-(2,6-dichlorophenyl)-phenyl |
| 1786 | c-C$_3$H$_5$CONH | 4-(3,5-dichlorophenyl)-phenyl |
| 1787 | c-C$_3$H$_5$CONH | 4-(2,3-dichlorophenyl)-phenyl |
| 1788 | c-C$_3$H$_5$CONH | 4-(2-methylphenyl)-phenyl |
| 1789 | c-C$_3$H$_5$CONH | 4-(2-tetrazole-phenyl)-phenyl |
| 1790 | c-C$_3$H$_5$CONH | 4-(2-methoxy-phenyl)-phenyl |
| 1791 | c-C$_3$H$_5$CONH | 4-(2-tmethyl-phenyl)-phenyl |
| 1792 | c-C$_3$H$_5$CONH | 4-(2-formyl-phenyl)-phenyl |
| 1793 | c-C$_3$H$_5$CONH | 4-(2-amino-phenyl)-phenyl |
| 1794 | c-C$_3$H$_5$CONH | 4-(2-methylamino-phenyl)-phenyl |
| 1795 | c-C$_3$H$_5$CONH | 4-(2-ethylamino-phenyl)-phenyl |
| 1796 | c-C$_3$H$_5$CONH | 4-(2-propylamino-phenyl)-phenyl |
| 1797 | c-C$_3$H$_5$CONH | 4-(2-methylsulfonylamino-phenyl)-phenyl |
| 1798 | c-C$_3$H$_5$CONH | 4-(2-trifluoromethyl-sulfonyl-amino-phenyl)-phenyl |
| 1799 | c-C$_3$H$_5$CONH | 4-(3-methylphenyl)-phenyl |
| 1800 | c-C$_3$H$_5$CONH | 4-(3-isopropylphenyl)-phenyl |
| 1801 | c-C$_3$H$_5$CONH | 4-(3-trifluoromethyl-sulfonyl-amino-phenyl)-phenyl |
| 1802 | c-C$_3$H$_5$CONH | 4-(3-methylsulfonylamino-phenyl)-phenyl |
| 1803 | c-C$_3$H$_5$CONH | 4-(3-amino-phenyl)-phenyl |
| 1804 | c-C$_3$H$_5$CONH | 4-(3-nitro-phenyl)-phenyl |
| 1805 | c-C$_3$H$_5$CONH | 2-pyridyl |
| 1806 | c-C$_3$H$_5$CONH | 3-pyridyl |
| 1807 | c-C$_3$H$_5$CONH | 4-pyridyl |
| 1808 | c-C$_3$H$_5$CONH | 3-amino-4-pyridyl |
| 1809 | c-C$_3$H$_5$CONH | 3-hydroxy-4-pyridyl |
| 1810 | c-C$_3$H$_5$CONH | 3-imidazole |
| 1811 | c-C$_3$H$_5$CONH | 2-nitro-3-imidazole |
| 1812 | c-C$_3$H$_5$CONH | 5-thiazole |
| 1813 | c-C$_3$H$_5$CONH | 5-oxazole |
| 1814 | c-C$_3$H$_5$CONH | 4-pyazole |
| 1815 | c-C$_3$H$_5$CONH | phenylethyl |
| 1816 | c-C$_3$H$_5$CONH | 2-aminophenylethyl |
| 1817 | c-C$_3$H$_5$CONH | 2-methylsulfonylamino-phenylethyl |
| 1818 | c-C$_3$H$_5$CONH | 2-trifluoromethylsulfonyl-amino-phenylethyl |
| 1819 | c-C$_3$H$_5$CONH | 2-hydroxymethylene-phenylethyl |
| 1820 | c-C$_3$H$_5$CONH | 2-aminomethylene-phenylethyl |
| 1821 | c-C$_3$H$_5$CONH | 2-tetrazolephenylethyl |
| 1822 | c-C$_3$H$_5$CONH | 2-tert-butylamino-sulfonylphenylethyl |
| 1823 | c-C$_3$H$_5$CONH | 2-aminosulfonyl-phenylethyl |
| 1824 | c-C$_3$H$_5$CONH | 2-methoxyphenylethyl |
| 1825 | c-C$_3$H$_5$CONH | 3-aminophenylethyl |
| 1826 | c-C$_3$H$_5$CONH | 3-methylsulfonylamino-phenylethyl |
| 1827 | c-C$_3$H$_5$CONH | 3-trifluoromethylsulfonyl-amino-phenylethyl |
| 1828 | c-C$_3$H$_5$CONH | 3-hydroxymethylene-phenylethyl |
| 1829 | c-C$_3$H$_5$CONH | 3-aminomethylene-phenylethyl |
| 1830 | c-C$_3$H$_5$CONH | 3-tetrazolephenylethyl |
| 1831 | c-C$_3$H$_5$CONH | 3-tert-butylamino-sulfonylphenylethyl |
| 1832 | c-C$_3$H$_5$CONH | 3-aminosulfonyl-phenylethyl |
| 1833 | c-C$_3$H$_5$CONH | 3-methoxyphenylethyl |
| 1834 | | |
| 1835 | ⊁ | H |
| 1836 | " | methyl |
| 1837 | " | ethyl |
| 1838 | " | n-propyl |
| 1839 | " | n-butyl |
| 1840 | " | n-pentyl |
| 1841 | " | n-hexanyl |
| 1842 | " | n-heptanyl |
| 1843 | " | isopropyl |
| 1844 | " | tert-butyl |
| 1845 | " | cyclopropyl |
| 1846 | " | cyclobutanyl |
| 1847 | " | cyclpentanyl |
| 1848 | " | cyclohexanyl |
| 1849 | " | cycloheptanyl |
| 1850 | " | phenyl |
| 1851 | " | phenylmethyl |
| 1852 | " | 3-hydroxyphenyl |
| 1853 | " | 3-hydroxy-4-methoxyphenyl |
| 1854 | " | 3-fluorophenyl |
| 1855 | " | 3-chlorophenyl |
| 1856 | " | 3-nitrophenyl |
| 1857 | " | 3-aminophenyl |
| 1858 | " | 3-methyl-sulfonamidephenyl |
| 1859 | " | 3-trifluoro-methylsulfonamidephenyl |
| 1860 | " | 3-Ac—NHphenyl |
| 1861 | " | 3-Boc—NHphenyl |
| 1862 | " | 3-Cbz—NHphenyl |
| 1863 | " | 3-aminomethylenephenyl |
| 1864 | " | 3-aminoethylenephenyl |
| 1865 | " | 3-cyanophenyl |
| 1866 | " | 3-cyanomethylphenyl |
| 1867 | " | 3-hydroxymethylenephenyl |
| 1868 | " | 3-carboxylphenyl |
| 1869 | " | 3-mercaptophenyl |
| 1870 | " | 3-methoxyphenyl |
| 1871 | " | 3,4-methylenedioxophenyl |
| 1872 | " | 3-tetrazolephenyl |
| 1873 | " | 3-aminosulfonylphenyl |
| 1874 | " | 3-methylamino-sulfonylphenyl |
| 1875 | " | 3-ethylamino-sulfonylphenyl |
| 1876 | " | 3-tert-butylamino-sulfonylphenyl |
| 1877 | " | 3-methylsulfonylphenyl |
| 1878 | " | 4-methoxyphenyl |
| 1879 | " | 4-phenylphenyl |
| 1880 | " | 4-(2-hydroxy-methylenephenyl)-phenyl |

TABLE 2-continued

| | | |
|---|---|---|
| 1881 | " | 4-(2-tert-butylamino-sufonylphenyl)-phenyl |
| 1882 | " | 4-(2-methylamino-sufonylphenyl)-phenyl |
| 1883 | " | 4-(2-ethylamino-sufonylphenyl)-phenyl |
| 1884 | " | 4-(2-aminosufonyl-phenyl)-phenyl |
| 1885 | " | 4-(2-chlorophenyl)-phenyl |
| 1886 | " | 4-(2-fluorophenyl)-phenyl |
| 1887 | " | 4-(2,4-dichlorophenyl)-phenyl |
| 1888 | " | 4-(2,6-dichlorophenyl)-phenyl |
| 1889 | " | 4-(3,5-dichlorophenyl)-phenyl |
| 1890 | " | 4-(2,3-dichlorophenyl)-phenyl |
| 1891 | " | 4-(2-methylphenyl)-phenyl |
| 1892 | " | 4-(2-tetrazole-phenyl)-phenyl |
| 1893 | " | 4-(2-methoxy-phenyl)-phenyl |
| 1894 | " | 4-(2-tmethyl-phenyl)-phenyl |
| 1895 | " | 4-(2-formyl-phenyl)-phenyl |
| 1896 | " | 4-(2-amino-phenyl)-phenyl |
| 1897 | " | 4-(2-methylamino-phenyl)-phenyl |
| 1898 | " | 4-(2-ethylamino-phenyl)-phenyl |
| 1899 | " | 4-(2-propylamino-phenyl)-phenyl |
| 1900 | " | 4-(2-methylsulfonylamino-phenyl)-phenyl |
| 1901 | " | 4-(2-trifluoromethyl-sulfonyl-amino-phenyl)-phenyl |
| 1902 | " | 4-(3-methylphenyl)-phenyl |
| 1903 | " | 4-(3-isopropylphenyl)-phenyl |
| 1904 | " | 4-(3-trifluoromethyl-sulfonyl-amino-phenyl)-phenyl |
| 1905 | " | 4-(3-methylsulfonylamino-phenyl)-phenyl |
| 1906 | " | 4-(3-amino-phenyl)-phenyl |
| 1907 | " | 4-(3-nitro-phenyl)-phenyl |
| 1908 | " | 2-pyridyl |
| 1909 | " | 3-pyridyl |
| 1910 | " | 4-pyridyl |
| 1911 | " | 3-amino-4-pyridyl |
| 1912 | " | 3-hydroxy-4-pyridyl |
| 1913 | " | 3-imidazole |
| 1914 | " | 2-nitro-3-imidazole |
| 1915 | " | 5-thiazole |
| 1916 | " | 5-oxazole |
| 1917 | " | 4-pyazole |
| 1918 | " | phenylethyl |
| 1919 | " | 2-aminophenylethyl |
| 1920 | " | 2-methylsulfonylamino-phenylethyl |
| 1921 | " | 2-trifluoromethylsulfonyl-amino-phenylethyl |
| 1922 | " | 2-hydroxymethylene-phenylethyl |
| 1923 | " | 2-aminomethylene-phenylethyl |
| 1924 | " | 2-tetrazolephenylethyl |
| 1925 | " | 2-tert-butylamino-sulfonylphenylethyl |
| 1926 | " | 2-aminosulfonyl-phenylethyl |
| 1927 | " | 2-methoxyphenylethyl |
| 1928 | " | 3-aminophenylethyl |
| 1929 | " | 3-methylsulfonylamino-phenylethyl |
| 1930 | " | 3-trifluoromethylsulfonyl-amino-phenylethyl |
| 1931 | " | 3-hydroxymethylene-phenylethyl |
| 1932 | " | 3-aminomethylene-phenylethyl |
| 1933 | " | 3-tetrazolephenylethyl |
| 1934 | " | 3-tert-butylamino-sulfonylphenylethyl |
| 1935 | " | 3-aminosulfonyl-phenylethyl |
| 1936 | " | 3-methoxyphenylethyl |

TABLE 3

TABLE 3-continued
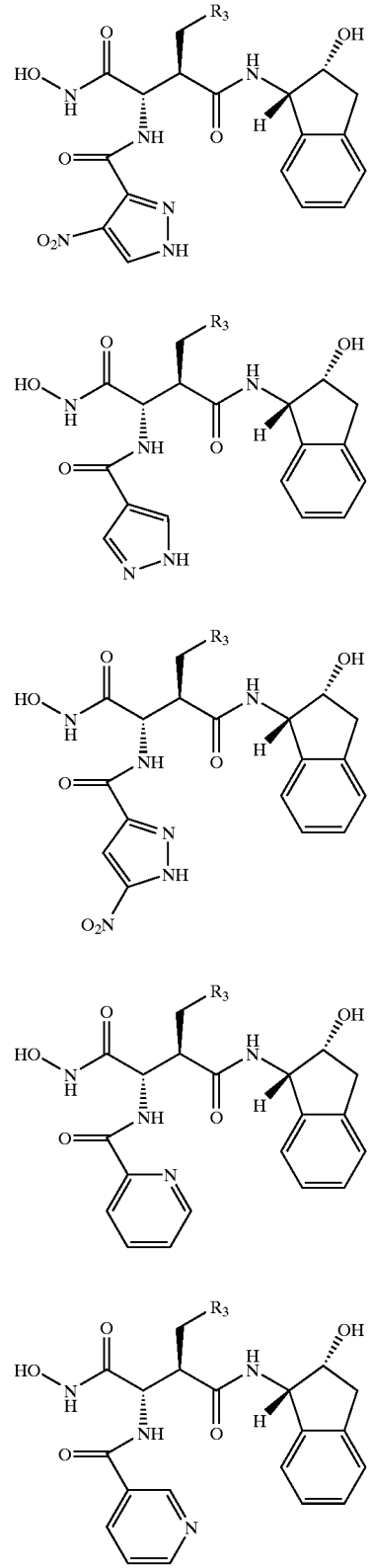
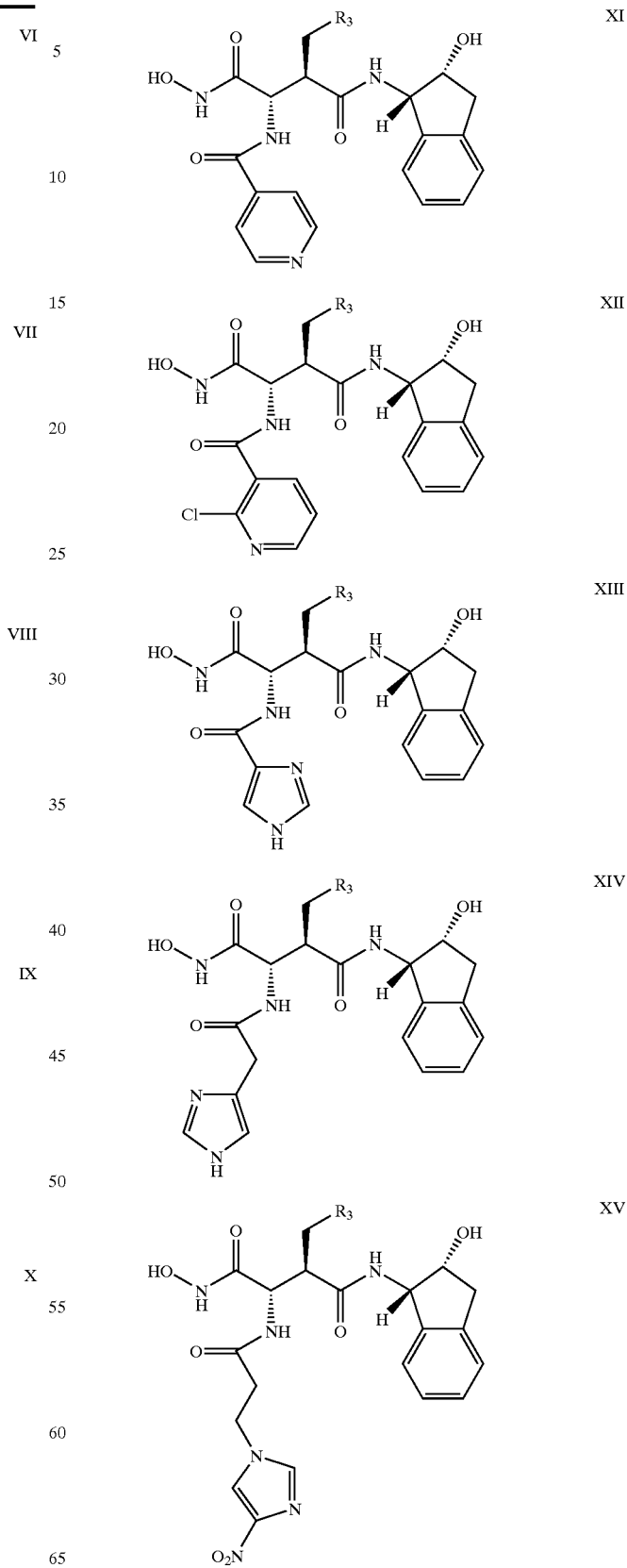

TABLE 3-continued
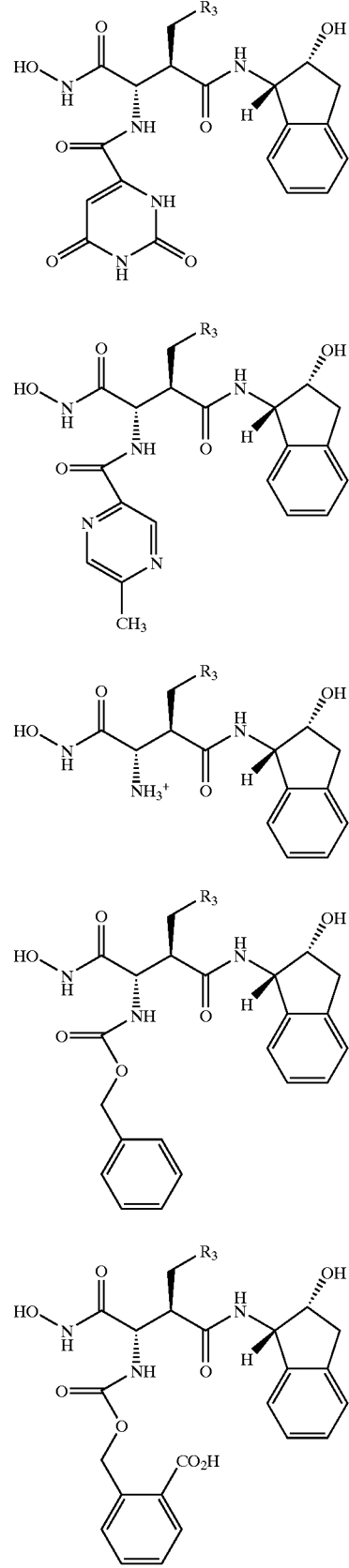
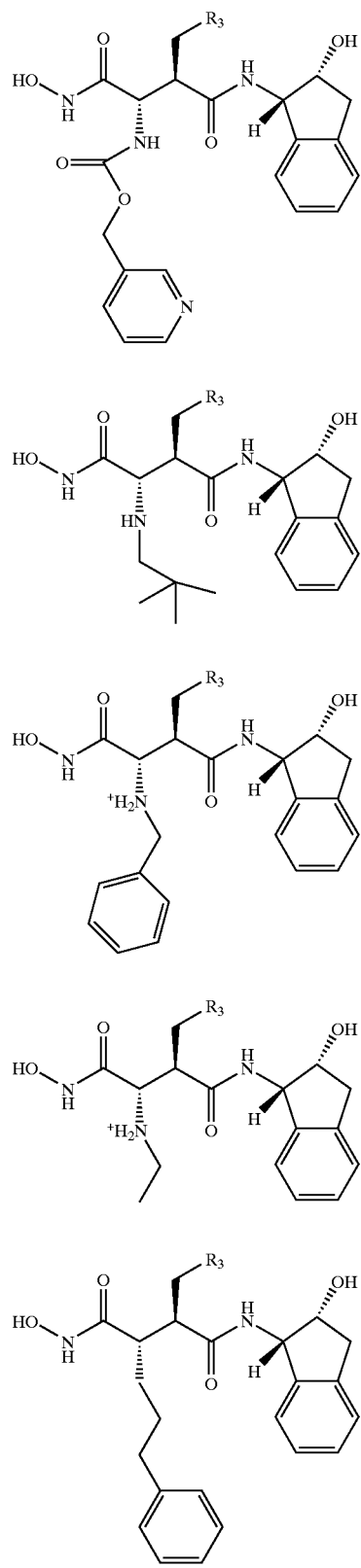

TABLE 3-continued

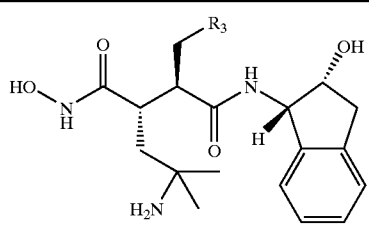

XXVI

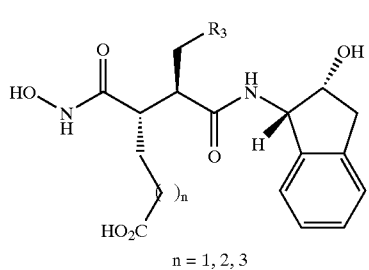

XXVII n = 1, 2, 3

| Ex # | R3 | Ms | Ex # | R3 | Ms |
|---|---|---|---|---|---|
| 2000 | H | | 2001 | 4-(2-aminosufonylphenyl)-phenyl | |
| 2002 | methyl | | 2003 | 4-(2-chlorophenyl)-phenyl | |
| 2004 | ethyl | | 2005 | 4-(2-fluorophenyl)-phenyl | |
| 2006 | n-propyl | | 2007 | 4-(2,4-dichlorophenyl)-phenyl | |
| 2008 | n-butyl | | 2009 | 4-(2,6-dichlorophenyl)-phenyl | |
| 2010 | n-pentyl | | 2011 | 4-(3,5-dichlorophenyl)-phenyl | |
| 2012 | n-hexanyl | | 2013 | 4-(2,3-dichlorophenyl)-phenyl | |
| 2014 | n-heptanyl | | 2015 | 4-(2-methylphenyl)-phenyl | |
| 2016 | isopropyl | | 2017 | 4-(2-tetrazole-phenyl)-phenyl | |
| 2018 | tert-butyl | | 2019 | 4-(2-methoxy-phenyl)-phenyl | |
| 2020 | cyclopropyl | | 2021 | 4-(2-tmethyl-phenyl)-phenyl | |
| 2022 | cyclobutanyl | | 2023 | 4-(2-formyl-phenyl)-phenyl | |
| 2024 | cyclpentanyl | | 2025 | 4-(2-amino-phenyl)-phenyl | |
| 2026 | cyclohexanyl | | 2027 | 4-(2-methylamino-phenyl)-phenyl | |
| 2028 | cycloheptanyl | | 2029 | 4-(2-ethylamino-phenyl)-phenyl | |
| 2030 | phenyl | | 2031 | 4-(2-propylamino-phenyl)-phenyl | |
| 2032 | phenylmethyl | | 2033 | 4-(2-methylsulfonylamino-phenyl)-phenyl | |
| 2034 | 3-hydroxyphenyl | | 2035 | 4-(2-trifluoromethylsulfonyl-amino-phenyl)-phenyl | |
| 2036 | 3-hydroxy-4-methoxyphenyl | | 2037 | 4-(3-methylphenyl)-phenyl | |
| 2038 | 3-fluorophenyl | | 2039 | 4-(3-isopropylphenyl)-phenyl | |
| 2040 | 3-chlorophenyl | | 2041 | 4-(3-trifluoromethylsulfonyl-amino-phenyl)-phenyl | |
| 2042 | 3-nitrophenyl | | 2043 | 4-(3-methylsulfonylamino-phenyl)-phenyl | |
| 2044 | 3-aminophenyl | | 2045 | 4-(3-amino-phenyl)-phenyl | |
| 2046 | 3-methylsulfonamidephenyl | | 2047 | 4-(3-nitro-phenyl)-phenyl | |
| 2048 | 3-trifluoro-methyl-sulfonamidephenyl | | 2049 | 2-pyridyl | |
| 2050 | 3-Ac—NHphenyl | | 2051 | 3-pyridyl | |
| 2052 | 3-Boc—NHphenyl | | 2053 | 4-pyridyl | |
| 2054 | 3-Cbz—NHphenyl | | 2055 | 3-amino-4-pyridyl | |
| 2056 | 3-aminomethylenephenyl | | 2057 | 3-hydroxy-4-pyridyl | |
| 2058 | 3-aminoethylenephenyl | | 2059 | 3-imidazole | |
| 2060 | 3-cyanophenyl | | 2061 | 2-nitro-3-imidazole | |
| 2062 | 3-cyanomethylphenyl | | 2063 | 5-thiazole | |
| 2064 | 3-hydroxymethylenephenyl | | 2065 | 5-oxazole | |
| 2066 | 3-carboxylphenyl | | 2067 | 4-pyazole | |
| 2068 | 3-mercaptophenyl | | 2069 | phenylethyl | |
| 2070 | 3-methoxyphenyl | | 2071 | 2-aminophenylethyl | |
| 2072 | 3,4-methylenedioxo-phenyl | | 2073 | 2-methylsulfonyl-amino-phenylethyl | |
| 2074 | 3-tetrazolephenyl | | 2075 | 2-trifluoromethylsulfonyl-amino-phenylethyl | |
| 2076 | 3-aminosulfonylphenyl | | 2077 | 2-hydroxymethylene-phenylethyl | |
| 2078 | 3-methylamino-sulfonylphenyl | | 2079 | 2-aminomethylene-phenylethyl | |
| 2080 | 3-ethylamino-sulfonylphenyl | | 2081 | 2-tetrazole-phenylethyl | |
| 2082 | 3-tert-butylamino-sulfonylphenyl | | 2083 | 2-tertbutylamino-sulfonylphenylethyl | |
| 2084 | 3-methylsulfonyl-phenyl | | 2085 | 2-aminosulfonyl-phenylethyl | |
| 2086 | 4-methoxyphenyl | | 2087 | 2-methoxy-phenylethyl | |
| 2088 | 4-phenylphenyl | | 2089 | 3-aminophenylethyl | |
| 2090 | 4-(2-hydroxymethyl-enephenyl)-phenyl | | 2091 | 3-methylsulfonyl-amino-phenylethyl | |
| 2092 | 4-(2-tert-butyl-aminosufonylphenyl)-phenyl | | 2093 | 3-trifluoromethylsulfonyl-amino-phenylethyl | |
| 2094 | 4-(2-methylamino-sufonylphenyl)-phenyl | | 2095 | 3-hydroxymethylene-phenylethyl | |
| 2096 | 4-(2-ethylamino-sufonylphenyl)-phenyl | | 2097 | 3-aminomethylene-phenylethyl | |
| 2098 | | | 2099 | 3-tetrazole-phenylethyl | |
| 2100 | | | 2101 | 3-tert-butylamino-sulfonylphenylethyl | |
| 2102 | | | 2103 | 3-aminosulfonyl-phenylethyl | |
| 2104 | | | 2105 | 3-methoxy-phenylethyl | |

TABLE 4

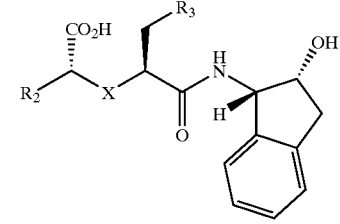

I

X = NH, CH₂

TABLE 4-continued

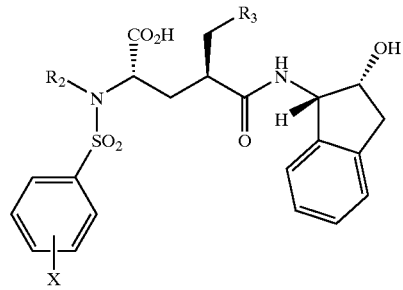

II

X = H, NH$_2$, CO$_2$H, CH$_2$CO$_2$H, Cl, F,

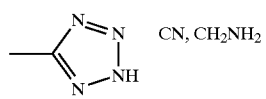 CN, CH$_2$NH$_2$

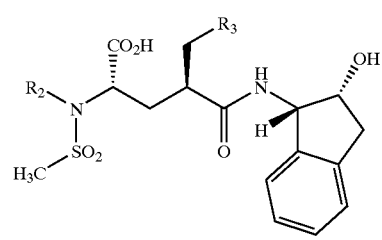

III

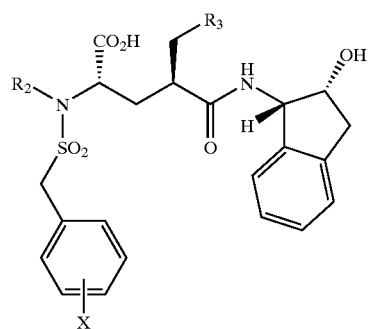

IV

X = H, NH$_2$, CO$_2$H, CH$_2$CO$_2$H, Cl, F,

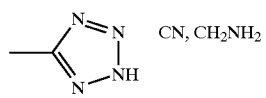 CN, CH$_2$NH$_2$

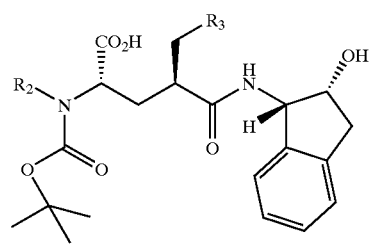

V

TABLE 4-continued

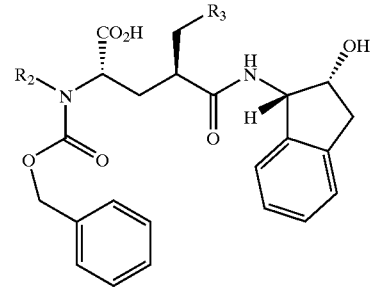

VI

| Ex # | R2 | R3 |
|---|---|---|
| 2500 | n-Bu | H |
| 2501 | " | methyl |
| 2502 | " | ethyl |
| 2503 | " | n-propyl |
| 2504 | " | n-butyl |
| 2505 | " | n-pentyl |
| 2506 | " | n-hexanyl |
| 2507 | " | n-heptanyl |
| 2508 | " | isopropyl |
| 2509 | " | tert-butyl |
| 2510 | " | cyclopropyl |
| 2511 | " | cyclobutanyl |
| 2512 | " | cyclpentanyl |
| 2513 | " | cyclohexanyl |
| 2514 | " | cycloheptanyl |
| 2515 | " | phenyl |
| 2516 | " | phenylmethyl |
| 2517 | " | 3-hydroxyphenyl |
| 2518 | " | 3-hydroxy-4-methoxyphenyl |
| 2519 | " | 3-fluorophenyl |
| 2520 | " | 3-chlorophenyl |
| 2521 | " | 3-nitrophenyl |
| 2522 | " | 3-aminophenyl |
| 2523 | " | 3-methyl-sulfonamidephenyl |
| 2524 | " | 3-trifluoro-methyl-sulfonamidephenyl |
| 2525 | " | 3-Ac—NHphenyl |
| 2526 | " | 3-Boc—NHphenyl |
| 2527 | " | 3-Cbz—NHphenyl |
| 2528 | " | 3-aminomethylenephenyl |
| 2529 | " | 3-aminoethylenephenyl |
| 2530 | " | 3-cyanophenyl |
| 2531 | " | 3-cyanomethylphenyl |
| 2532 | " | 3-hydroxy-methylenephenyl |
| 2533 | " | 3-carboxylphenyl |
| 2534 | " | 3-mercaptophenyl |
| 2535 | " | 3-methoxyphenyl |
| 2536 | " | 3,4-methylene-dioxophenyl |
| 2537 | " | 3-tetrazolephenyl |
| 2538 | " | 3-aminosulfonylphenyl |
| 2539 | " | 3-methylamino-sulfonylphenyl |
| 2540 | " | 3-ethylamino-sulfonylphenyl |
| 2541 | " | 3-tertbutylamino-sulfonylphenyl |
| 2542 | " | 3-methylsulfonylphenyl |
| 2543 | " | 4-methoxyphenyl |
| 2544 | " | 4-phenylphenyl |
| 2545 | " | 4-(2-hydroxymethylene-phenyl)-phenyl |
| 2546 | " | 4-(2-tertbutylamino-sufonylphenyl)-phenyl |
| 2547 | " | 4-(2-methylamino-sufonylphenyl)-phenyl |
| 2548 | " | 4-(2-ethylamino-sufonylphenyl)-phenyl |
| 2549 | " | 4-(2-aminosufonyl-phenyl)-phenyl |
| 2550 | " | 4-(2-chlorophenyl)-phenyl |
| 2551 | " | 4-(2-fluorophenyl)-phenyl |
| 2552 | " | 4-(2,4-dichlorophenyl)-phenyl |

TABLE 4-continued

| | | |
|---|---|---|
| 2553 | " | 4-(2,6-dichlorophenyl)-phenyl |
| 2554 | " | 4-(3,5-dichlorophenyl)-phenyl |
| 2555 | " | 4-(2,3-dichlorophenyl)-phenyl |
| 2556 | " | 4-(2-methylphenyl)-phenyl |
| 2557 | " | 4-(2-tetrazole-phenyl)-phenyl |
| 2558 | " | 4-(2-methoxy-phenyl)-phenyl |
| 2559 | " | 4-(2-tmethyl-phenyl)-phenyl |
| 2560 | " | 4-(2-formyl-phenyl)-phenyl |
| 2561 | " | 4-(2-amino-phenyl)-phenyl |
| 2562 | " | 4-(2-methylamino-phenyl)-phenyl |
| 2563 | " | 4-(2-ethylamino-phenyl)-phenyl |
| 2564 | " | 4-(2-propylamino-phenyl)-phenyl |
| 2565 | " | 4-(2-methylsulfonylamino-phenyl)-phenyl |
| 2566 | " | 4-(2-trifluoromethylsulfonyl-amino-phenyl)-phenyl |
| 2567 | " | 4-(3-methylphenyl)-phenyl |
| 2568 | " | 4-(3-isopropylphenyl)-phenyl |
| 2569 | " | 4-(3-trifluoromethylsulfonyl-amino-phenyl)-phenyl |
| 2570 | " | 4-(3-methylsulfonylamino-phenyl)-phenyl |
| 2571 | " | 4-(3-amino-phenyl)-phenyl |
| 2572 | " | 4-(3-nitro-phenyl)-phenyl |
| 2573 | " | 2-pyridyl |
| 2574 | " | 3-pyridyl |
| 2575 | " | 4-pyridyl |
| 2576 | " | 3-amino-4-pyridyl |
| 2577 | " | 3-hydroxy-4-pyridyl |
| 2578 | " | 3-imidazole |
| 2579 | " | 2-nitro-3-imidazole |
| 2580 | " | 5-thiazole |
| 2581 | " | 5-oxazole |
| 2582 | " | 4-pyazole |
| 2583 | " | phenylethyl |
| 2584 | " | 2-aminophenylethyl |
| 2585 | " | 2-methylsulfonylamino-phenylethyl |
| 2586 | " | 2-trifluoromethyl-sulfonylamino-phenylethyl |
| 2587 | " | 2-hydroxy-methylenephenylethyl |
| 2588 | " | 2-aminomethylene-phenylethyl |
| 2589 | " | 2-tetrazolephenylethyl |
| 2590 | " | 2-tertbutylamino-sulfonylphenylethyl |
| 2591 | " | 2-aminosulfonyl-phenylethyl |
| 2592 | " | 2-methoxyphenylethyl |
| 2593 | " | 3-aminophenylethyl |
| 2594 | " | 3-methylsulfonylamino-phenylethyl |
| 2595 | " | 3-trifluoromethyl-sulfonylamino-phenylethyl |
| 2596 | " | 3-hydroxymethylene-phenylethyl |
| 2597 | " | 3-aminomethylene-phenylethyl |
| 2598 | " | 3-tetrazolephenylethyl |
| 2599 | " | 3-tertbutylamino-sulfonylphenylethyl |
| 2600 | " | 3-aminosulfonyl-phenylethyl |
| 2601 | " | 3-methoxyphenylethyl |
| 2602 | " | 4-phenylphenylmethyl |
| 2603 | " | 4-(2-hydroxymethylenephenyl)-phenylmethyl |
| 2604 | " | 4-(2-tert-butyl-aminosufonyl-phenyl)-phenylmethyl |
| 2605 | " | 4-(2-methylamino-sufonylphenyl)-phenylmethyl |
| 2606 | " | 4-(2-ethylamino-sufonylphenyl)-phenylmethyl |
| 2607 | " | 4-(2-aminosufonylphenyl)-phenylmethyl |
| 2608 | " | 4-(2-chlorophenyl)-phenylmethyl |
| 2609 | " | 4-(2-fluorophenyl)-phenylmethyl |
| 2610 | " | 4-(2,4-dichlorophenyl)-phenylmethyl |
| 2611 | " | 4-(2,6-dichlorophenyl)-phenylmethyl |
| 2612 | " | 4-(3,5-dichlorophenyl)-phenylmethyl |
| 2613 | " | 4-(2,3-dichlorophenyl)-phenylmethyl |
| 2614 | " | 4-(2-methylphenyl)-phenylmethyl |
| 2615 | " | 4-(2-tetrazole-phenyl)-phenylmethyl |
| 2616 | " | 4-(2-methoxy-phenyl)-phenylmethyl |
| 2617 | " | 4-(2-tmethyl-phenyl)-phenylmethyl |
| 2618 | " | 4-(2-formyl-phenyl)-phenylmethyl |
| 2619 | " | 4-(2-amino-phenyl)-phenylmethyl |
| 2620 | " | 4-(2-methylamino-phenyl)-phenylmethyl |
| 2621 | " | 4-(2-ethylamino-phenyl)-phenylmethyl |
| 2622 | " | 4-(2-propylamino-phenyl)-phenylmethyl |
| 2623 | " | 4-(2-methylsulfonylamino-phenyl)-phenylmethyl |
| 2624 | " | 4-(2-trifluoromethylsulfonyl-amino-phenyl)-phenylmethyl |
| 2625 | " | 4-(3-methylphenyl)-phenylmethyl |
| 2626 | " | 4-(3-isopropylphenyl)-phenylmethyl |
| 2627 | " | 4-(3-trifluoromethylsulfonyl-amino-phenyl)-phenylmethyl |
| 2628 | " | 4-(3-methylsulfonylamino-phenyl)-phenylmethyl |
| 2629 | " | 4-(3-amino-phenyl)-phenylmethyl |
| 2630 | " | 4-(3-nitro-phenyl)-phenylmethyl |
| 2631 | | |
| 2632 | $CH_3$ | H |
| 2633 | " | methyl |
| 2634 | " | ethyl |
| 2635 | " | n-propyl |
| 2636 | " | n-butyl |
| 2637 | " | n-pentyl |
| 2638 | " | n-hexanyl |
| 2639 | " | n-heptanyl |
| 2640 | " | isopropyl |
| 2641 | " | tert-butyl |
| 2642 | " | cyclopropyl |
| 2643 | " | cyclobutanyl |
| 2644 | " | cyclpentanyl |
| 2645 | " | cyclohexanyl |
| 2646 | " | cycloheptanyl |
| 2647 | " | phenyl |
| 2648 | " | phenylmethyl |
| 2649 | " | 3-hydroxphenyl |
| 2650 | " | 3-hydroxy-4-methoxyphenyl |
| 2651 | " | 3-fluorophenyl |
| 2652 | " | 3-chlorophenyl |

TABLE 4-continued

| | | |
|---|---|---|
| 2653 | " | 3-nitrophenyl |
| 2654 | " | 3-aminophenyl |
| 2655 | " | 3-methyl-sulfonamidephenyl |
| 2656 | " | 3-trifluoro-methylsulfonamidephenyl |
| 2657 | " | 3-Ac—NHphenyl |
| 2658 | " | 3-Boc—NHphenyl |
| 2659 | " | 3-Cbz—NHphenyl |
| 2660 | " | 3-aminomethylenephenyl |
| 2661 | " | 3-aminoethylenephenyl |
| 2662 | " | 3-cyanophenyl |
| 2663 | " | 3-cyanomethylphenyl |
| 2664 | " | 3-hydroxy-methylenephenyl |
| 2665 | " | 3-carboxylphenyl |
| 2666 | " | 3-mercaptophenyl |
| 2667 | " | 3-methoxyphenyl |
| 2668 | " | 3,4-methylene-dioxophenyl |
| 2669 | " | 3-tetrazolephenyl |
| 2670 | " | 3-aminosulfonylphenyl |
| 2671 | " | 3-methylamino-sulfonylphenyl |
| 2672 | " | 3-ethylamino-sulfonylphenyl |
| 2673 | " | 3-tertbutylamino-sulfonylphenyl |
| 2674 | " | 3-methylsulfonylphenyl |
| 2675 | " | 4-methoxyphenyl |
| 2676 | " | 4-phenylphenyl |
| 2677 | " | 4-(2-hydroxymethylene-phenyl)-phenyl |
| 2678 | " | 4-(2-tert-butylamino-sufonylphenyl)-phenyl |
| 2679 | " | 4-(2-methylamino-sufonylphenyl)-phenyl |
| 2680 | " | 4-(2-ethylamino-sufonylphenyl)-phenyl |
| 2681 | " | 4-(2-aminosufonyl-phenyl)-phenyl |
| 2682 | " | 4-(2-chlorophenyl)-phenyl |
| 2683 | " | 4-(2-fluorophenyl)-phenyl |
| 2684 | " | 4-(2,4-dichlorophenyl)-phenyl |
| 2685 | " | 4-(2,6-dichlorophenyl)-phenyl |
| 2686 | " | 4-(3,5-dichlorophenyl)-phenyl |
| 2687 | " | 4-(2,3-dichlorophenyl)-phenyl |
| 2688 | " | 4-(2-methylphenyl)-phenyl |
| 2689 | " | 4-(2-tetrazole-phenyl)-phenyl |
| 2690 | " | 4-(2-methoxy-phenyl)-phenyl |
| 2691 | " | 4-(2-tmethyl-phenyl)-phenyl |
| 2692 | " | 4-(2-formyl-phenyl)-phenyl |
| 2693 | " | 4-(2-amino-phenyl)-phenyl |
| 2694 | " | 4-(2-methylamino-phenyl)-phenyl |
| 2695 | " | 4-(2-ethylamino-phenyl)-phenyl |
| 2696 | " | 4-(2-propylamino-phenyl)-phenyl |
| 2697 | " | 4-(2-methylsulfonylamino-phenyl)-phenyl |
| 2698 | " | 4-(2-trifluoromethylsulfonyl-amino-phenyl)-phenyl |
| 2699 | " | 4-(3-methylphenyl)-phenyl |
| 2700 | " | 4-(3-isopropylphenyl)-phenyl |
| 2701 | " | 4-(3-trifluoromethylsulfonyl-amino-phenyl)-phenyl |
| 2702 | " | 4-(3-methylsulfonyl-amino-phenyl)-phenyl |
| 2703 | " | 4-(3-amino-phenyl)-phenyl |
| 2704 | " | 4-(3-nitro-phenyl)-phenyl |
| 2705 | " | 2-pyridyl |
| 2706 | " | 3-pyridyl |
| 2707 | " | 4-pyridyl |
| 2708 | " | 3-amino-4-pyridyl |
| 2709 | " | 3-hydroxy-4-pyridyl |
| 2710 | " | 3-imidazole |
| 2711 | " | 2-nitro-3-imidazole |
| 2712 | " | 5-thiazole |
| 2713 | " | 5-oxazole |
| 2714 | " | 4-pyazole |
| 2715 | " | phenylethyl |
| 2716 | " | 2-aminophenylethyl |
| 2717 | " | 2-methylsulfonylamino-phenylethyl |
| 2718 | " | 2-trifluoromethylsulfonylamino-phenylethyl |
| 2719 | " | 2-hydroxymethylene-phenylethyl |
| 2720 | " | 2-aminomethylene-phenylethyl |
| 2721 | " | 2-tetrazolephenylethyl |
| 2722 | " | 2-tertbutylamino-sulfonylphenylethyl |
| 2723 | " | 2-aminosulfonyl-phenylethyl |
| 2724 | " | 2-methoxyphenylethyl |
| 2725 | " | 3-aminophenylethyl |
| 2726 | " | 3-methylsulfonylamino-phenylethyl |
| 2727 | " | 3-trifluoromethyl-sulfonylamino-phenylethyl |
| 2728 | " | 3-hydroxy-methylenephenylethyl |
| 2729 | " | 3-aminomethylene-phenylethyl |
| 2730 | " | 3-tetrazolephenylethyl |
| 2731 | " | 3-tertbutylamino-sulfonylphenylethyl |
| 2732 | " | 3-aminosulfonyl-phenylethyl |
| 2733 | " | 3-methoxyphenylethyl |
| 2734 | " | 4-phenylphenylmethyl |
| 2735 | " | 4-(2-hydroxy-methylenephenyl)-phenylmethyl |
| 2736 | " | 4-(2-tert-butylaminosufonyl-phenyl)-phenylmethyl |
| 2737 | " | 4-(2-methylamino-sufonylphenyl)-phenylmethyl |
| 2738 | " | 4-(2-ethylamino-sufonylphenyl)-phenylmethyl |
| 2739 | " | 4-(2-aminosufonyl-phenyl)-phenylmethyl |
| 2740 | " | 4-(2-chlorophenyl)-phenylmethyl |
| 2741 | " | 4-(2-fluorophenyl)-phenylmethyl |
| 2742 | " | 4-(2,4-dichlorophenyl)-phenylmethyl |
| 2743 | " | 4-(2,6-dichlorophenyl)-phenylmethyl |
| 2744 | " | 4-(3,5-dichlorophenyl)-phenylmethyl |
| 2745 | " | 4-(2,3-dichlorophenyl)-phenylmethyl |
| 2746 | " | 4-(2-methylphenyl)-phenylmethyl |
| 2747 | " | 4-(2-tetrazole-phenyl)-phenylmethyl |
| 2748 | " | 4-(2-methoxy-phenyl)-phenylmethyl |
| 2749 | " | 4-(2-tmethyl-phenyl)-phenylmethyl |
| 2750 | " | 4-(2-formyl-phenyl)-phenylmethyl |
| 2751 | " | 4-(2-amino-phenyl)-phenylmethyl |
| 2752 | " | 4-(2-methylamino-phenyl)-phenylmethyl |
| 2753 | " | 4-(2-ethylamino-phenyl)-phenylmethyl |
| 2754 | " | 4-(2-propylamino-phenyl)-phenylmethyl |

TABLE 4-continued

| | | |
|---|---|---|
| 2755 | " | 4-(2-methylsulfonylamino-phenyl)-phenylmethyl |
| 2756 | " | 4-(2-trifluoromethylsulfonyl-amino-phenyl)-phenylmethyl |
| 2757 | " | 4-(3-methylphenyl)-phenylmethyl |
| 2758 | " | 4-(3-isopropylphenyl)-phenylmethyl |
| 2759 | " | 4-(3-trifluoromethylsulfonyl-amino-phenyl)-phenylmethyl |
| 2760 | " | 4-(3-methylsulfonyl-amino-phenyl)-phenylmethyl |
| 2761 | " | 4-(3-amino-phenyl)-phenylmethyl |
| 2762 | " | 4-(3-nitro-phenyl)-phenylmethyl |
| 2763 | | |
| 2764 | 3-phenylpropyl | H |
| 2765 | " | methyl |
| 2766 | " | ethyl |
| 2767 | " | n-propyl |
| 2768 | " | n-butyl |
| 2769 | " | n-pentyl |
| 2770 | " | n-hexanyl |
| 2771 | " | n-heptanyl |
| 2772 | " | isopropyl |
| 2773 | " | tert-butyl |
| 2774 | " | cyclopropyl |
| 2775 | " | cyclobutanyl |
| 2776 | " | cyclpentanyl |
| 2777 | " | cyclohexanyl |
| 2778 | " | cycloheptanyl |
| 2779 | " | phenyl |
| 2780 | " | phenylmethyl |
| 2781 | " | 3-hydroxyphenyl |
| 2782 | " | 3-hydroxy-4-methoxyphenyl |
| 2783 | " | 3-fluorophenyl |
| 2784 | " | 3-chlorophenyl |
| 2785 | " | 3-nitrophenyl |
| 2786 | " | 3-aminophenyl |
| 2787 | " | 3-methyl-sulfonamidephenyl |
| 2788 | " | 3-trifluoro-methylsulfonamidephenyl |
| 2789 | " | 3-Ac—NHphenyl |
| 2790 | " | 3-Boc—NHphenyl |
| 2791 | " | 3-Cbz—NHphenyl |
| 2792 | " | 3-aminomethylenephenyl |
| 2793 | " | 3-aminoethylenephenyl |
| 2794 | " | 3-cyanophenyl |
| 2795 | " | 3-cyanomethylphenyl |
| 2796 | " | 3-hydroxy-methylenephenyl |
| 2797 | " | 3-carboxyphenyl |
| 2798 | " | 3-mercaptophenyl |
| 2799 | " | 3-methoxyphenyl |
| 2800 | " | 3,4-methylene-dioxophenyl |
| 2801 | " | 3-tetrazolephenyl |
| 2802 | " | 3-aminosulfonylphenyl |
| 2803 | " | 3-methylamino-sulfonylphenyl |
| 2804 | " | 3-ethylamino-sulfonylphenyl |
| 2805 | " | 3-tertbutylamino-sulfonylphenyl |
| 2806 | " | 3-methylsulfonylphenyl |
| 2807 | " | 4-methoxyphenyl |
| 2808 | " | 4-phenylphenyl |
| 2809 | " | 4-(2-hydroxy-methylenephenyl)-phenyl |
| 2810 | " | 4-(2-tert-butylamino-sufonylphenyl)-phenyl |
| 2811 | " | 4-(2-methylamino-sufonylphenyl)-phenyl |
| 2812 | " | 4-(2-ethylamino-sufonylphenyl)-phenyl |
| 2813 | " | 4-(2-aminosufonyl-phenyl)-phenyl |
| 2814 | " | 4-(2-chlorophenyl)-phenyl |
| 2815 | " | 4-(2-fluorophenyl)-phenyl |
| 2816 | " | 4-(2,4-dichlorophenyl)-phenyl |
| 2817 | " | 4-(2,6-dichlorophenyl)-phenyl |
| 2818 | " | 4-(3,5-dichlorophenyl)-phenyl |
| 2819 | " | 4-(2,3-dichlorophenyl)-phenyl |
| 2820 | " | 4-(2-methylphenyl)-phenyl |
| 2821 | " | 4-(2-tetrazole-phenyl)-phenyl |
| 2822 | " | 4-(2-methoxy-phenyl)-phenyl |
| 2823 | " | 4-(2-tmethyl-phenyl)-phenyl |
| 2824 | " | 4-(2-formyl-phenyl)-phenyl |
| 2825 | " | 4-(2-amino-phenyl)-phenyl |
| 2826 | " | 4-(2-methylamino-phenyl)-phenyl |
| 2827 | " | 4-(2-ethylamino-phenyl)-phenyl |
| 2828 | " | 4-(2-propylamino-phenyl)-phenyl |
| 2829 | " | 4-(2-methylsulfonyl-amino-phenyl)-phenyl |
| 2830 | " | 4-(2-trifluoromethylsulfonyl-amino-phenyl)-phenyl |
| 2831 | " | 4-(3-methylphenyl)-phenyl |
| 2832 | " | 4-(3-isopropylphenyl)-phenyl |
| 2833 | " | 4-(3-trifluoromethylsulfonyl-amino-phenyl)-phenyl |
| 2834 | " | 4-(3-methylsulfonyl-amino-phenyl)-phenyl |
| 2835 | " | 4-(3-amino-phenyl)-phenyl |
| 2836 | " | 4-(3-nitro-phenyl)-phenyl |
| 2837 | " | 2-pyridyl |
| 2838 | " | 3-pyridyl |
| 2839 | " | 4-pyridyl |
| 2840 | " | 3-amino-4-pyridyl |
| 2841 | " | 3-hydroxy-4-pyridyl |
| 2842 | " | 3-imidazole |
| 2843 | " | 2-nitro-3-imidazole |
| 2844 | " | 5-thiazole |
| 2845 | " | 5-oxazole |
| 2846 | " | 4-pyazole |
| 2847 | " | phenylethyl |
| 2848 | " | 2-aminophenylethyl |
| 2849 | " | 2-methylsulfonylamino-phenylethyl |
| 2850 | " | 2-trifluoromethylsulfonylamino-phenylethyl |
| 2851 | " | 2-hydroxymethylene-phenylethyl |
| 2852 | " | 2-aminomethylene-phenylethyl |
| 2853 | " | 2-tetrazolephenylethyl |
| 2854 | " | 2-tert-butylamino-sulfonylphenylethyl |
| 2855 | " | 2-aminosulfonyl-phenylethyl |
| 2856 | " | 2-methoxyphenyl |
| 2857 | " | 3-aminophenylethyl |
| 2858 | " | 3-methylsulfonylamino-phenylethyl |
| 2859 | " | 3-trifluoromethylsulfonylamino-phenylethyl |
| 2860 | " | 3-hydroxymethylene-phenylethyl |
| 2861 | " | 3-aminomethylene-phenylethyl |
| 2862 | " | 3-tetrazolephenylethyl |
| 2863 | " | 3-tertbutylamino-sulfonylphenylethyl |
| 2864 | " | 3-aminosulfonyl-phenylethyl |
| 2865 | " | 3-methoxyphenylethyl |
| 2866 | " | 4-phenylphenylmethyl |

TABLE 4-continued

| | | |
|---|---|---|
| 2867 | " | 4-(2-hydroxymethylene-phenyl)-phenylmethyl |
| 2868 | " | 4-(2-tert-butylaminosufonyl-phenyl)-phenylmethyl |
| 2869 | " | 4-(2-methylaminosufonyl-phenyl)-phenylmethyl |
| 2870 | " | 4-(2-ethylaminosufonyl-phenyl)-phenylmethyl |
| 2871 | " | 4-(2-aminosufonylphenyl)-phenylmethyl |
| 2872 | " | 4-(2-chlorophenyl)-phenylmethyl |
| 2873 | " | 4-(2-fluorophenyl)-phenylmethyl |
| 2874 | " | 4-(2,4-dichlorophenyl)-phenylmethyl |
| 2875 | " | 4-(2,6-dichlorophenyl)-phenylmethyl |
| 2876 | " | 4-(3,5-dichlorophenyl)-phenylmethyl |
| 2877 | " | 4-(2,3-dichlorophenyl)-phenylmethyl |
| 2878 | " | 4-(2-methylphenyl)-phenylmethyl |
| 2879 | " | 4-(2-tetrazole-phenyl)-phenylmethyl |
| 2880 | " | 4-(2-methoxy-phenyl)-phenylmethyl |
| 2881 | " | 4-(2-tmethyl-phenyl)-phenylmethyl |
| 2882 | " | 4-(2-formyl-phenyl)-phenylmethyl |
| 2883 | " | 4-(2-amino-phenyl)-phenylmethyl |
| 2884 | " | 4-(2-methylamino-phenyl)-phenylmethyl |
| 2885 | " | 4-(2-ethylamino-phenyl)-phenylmethyl |
| 2886 | " | 4-(2-propylamino-phenyl)-phenylmethyl |
| 2887 | " | 4-(2-methylsulfonylamino-phenyl)-phenylmethyl |
| 2888 | " | 4-(2-trifluoromethylsulfonyl-amino-phenyl)-phenylmethyl |
| 2889 | " | 4-(3-methylphenyl)-phenylmethyl |
| 2890 | " | 4-(3-isopropylphenyl)-phenylmethyl |
| 2891 | " | 4-(3-trifluoromethylsulfonyl-amino-phenyl)-phenylmethyl |
| 2892 | " | 4-(3-methylsulfonylamino-phenyl)-phenylmethyl |
| 2893 | " | 4-(3-amino-phenyl)-phenylmethyl |
| 2894 | " | 4-(3-nitro-phenyl)-phenylmethyl |

What is claimed:

1. A compound of the formula II:

Formula II or a pharmaceutically acceptable salt form or a steroisomer thereof, wherein:

$R^1$ is selected from: —$CO_2H$, —C(O)NHOH, —C(O)NHOR$^7$, —SH, and —$CH_2CO_2R^7$;

$R^2$ is selected from the formula:

$$U—X—Y—Z—U^a—X^a—Y^a—Z^a$$

wherein:

U is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X is absent or selected from $C_{1-10}$ alkylene, $C_{2-10}$ alkenylene, and $C_{2-10}$ alkynylene;

Y is absent or selected from O, NR$^a$, S(O)$_p$, and C(O);

Z is absent or selected from a $C_{3-13}$ carbocyclic residue substituted with 0–5 R$^b$ and a 5–14 membered heterocyclic system containing from 1–4 heteroatoms selected from the group consisting of N, O, and S substituted with 0–5 R$^b$;

U$^a$ is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X$^a$ is absent or selected from $C_{1-10}$ alkylene, $C_{2-10}$ alkenylene, and $C_{2-10}$ alkynylene;

Y$^a$ is absent or selected from O, NR$^a$, S(O)$_p$, and C(O);

Z$^a$ is selected from H, a $C_{3-13}$ carbocyclic residue substituted with 0–5 R$^c$ and a 5–14 membered heterocyclic system containing from 1–4 heteroatoms selected from the group consisting of N, O, and S substituted with 0–5 R$^c$;

R$^a$, at each occurrence, is independently selected from H, $C_{1-4}$ alkyl, phenyl and benzyl;

R$^{a'}$, at each occurrence, is independently selected from H, $C_{1-4}$ alkyl, phenyl and benzyl;

alternatively, R$^a$ and R$^{a'}$ taken together with the nitrogen to which they are attached form a 5 or 6 membered ring containing from 0–1 additional heteroatoms selected from the group consisting of N, O, and S;

R$^b$, at each occurrence, is independently selected from $C_{1-6}$ alkyl, OR$^a$, $C_1$, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, and CF$_2$CF$_3$;

R$^c$, at each occurrence, is independently selected from $C_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, NR$^a$S(O)$_2$R$^{a'}$, S(O)$_2$NR$^a$R$^{a'}$, S(O)$_p$R$^a$, CF$_3$, CF$_2$CF$_3$, and a 5–14 membered heterocyclic system containing from 1–4 heteroatoms selected from the group consisting of N, O, and S;

R$^3$ is selected from the formula:

$$U^1—X^1—Y^1—Z^1—U^{1a}—X^{1a}—Y^{1a}—Z^{1a}$$

wherein:

U$^1$ is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X$^1$ is absent or selected from $C_{1-10}$ alkylene, $C_{2-10}$ alkenylene, and $C_{2-10}$ alkynylene;

Y$^1$ is absent or selected from O, NR$^a$, S(O)$_p$, and C(O);

Z$^1$ is absent or selected from a $C_{3-13}$ carbocyclic residue substituted with 0–5 R$^b$ and piperidinyl substituted with 0–5 R$^b$;

U$^{1a}$ is absent or is selected from: O, NR$^a$, C(O), C(O)O, OC(O), C(O)NR$^a$, NR$^a$C(O), OC(O)O, OC(O)NR$^a$, $NR^aC(O)O$, $NR^aC(O)NR^a$, $S(O)_p$, $S(O)_pNR^a$, $NR^aS(O)_p$, and $NR^aSO_2NR^a$;

$X^{1a}$ is absent or selected from $C_{1-10}$ alkylene, $C_{2-10}$ alkenylene, and $C_{2-10}$ alkynylene;

$Y^{1a}$ is absent or selected from O, $NR^a$, $S(O)_p$, and C(O);

$Z^{1a}$ is selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl and benzyl;

$R^{a'}$, at each occurrence, is independently selected from H, $C_{1-4}$ alkyl, phenyl and benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^5$ is selected from:

$$U^2-X^2-Y^2-Z^2-U^{2a}-X^{2a}-Y^{2a}-Z^{2a}$$

wherein:

$U^2$ is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^2$ is absent or selected from $C_{1-10}$ alkylene, $C_{2-10}$ alkenylene, and $C_{2-10}$ alkynylene;

$Y^2$ is absent or selected from O, $NR^a$, $S(O)_p$, and C(O);

$Z^2$ is absent or selected from a $C_{3-13}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^{2a}$ is absent or is selected from: O, $NR^a$, C(O), C(O)O, OC(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^{2a}$ is absent or selected from $C_{1-10}$ alkylene, $C_{2-10}$ alkenylene, and $C_{2-10}$ alkynylene;

$Y^{2a}$ is absent or selected from O, $NR^a$, $S(O)_p$, and C(O);

$Z^{2a}$ is selected from H, a $C_{3-13}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^a$, at each occurrence, is independently selected from H, $C_{1-4}$ alkyl, phenyl and benzyl;

$R^{a'}$, at each occurrence, is independently selected from H, $C_{1-4}$ alkyl, phenyl and benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aS(O)_2R^{a'}$, $S(O)_2NR^aR^{a'}$, $S(O)_pR^a$, $CF_3$, $CF_2CF_3$, and a 5–14 membered heterocyclic system containing from 1–4 heteroatoms selected from the group consisting of N, O, and S;

$R^7$ is selected from: $C_1$–$C_{10}$ alkyl, alkylaryl, and

E is $CH_2$ or CO.

2. A pharmaceutical composition comprising a pharmaceutically acceptable carrier and a therapeutically effective amount of a compound of claim 1.

3. A method of treating an inflammatory disease in a mammal comprising administering to the mammal in need of such treatment a therapeutically effective amount of a compound of claim 1.

4. A method of treating a condition or disease mediated by MMPs and/or TNF and/or aggrecanase in a mammal comprising administering to the mammal in need of such treatment a therapeutically effective amount of a compound of claim 1.

5. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 1.

6. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 1.

7. A compound of claim 1, wherein:

$R^1$ is selected from: —C(O)NHOH.

8. A pharmaceutical composition comprising a pharmaceutically acceptable carrier and a therapeutically effective amount of a compound of claim 7.

9. A method of treating an inflammatory disease in a mammal comprising administering to the mammal in need of such treatment a therapeutically effective amount of a compound of claim 7.

10. A method of treating a condition or disease mediated by MMPs and/or TNF and/or aggrecanase in a mammal comprising administering to the mammal in need of such treatment a therapeutically effective amount of a compound of claim 7.

11. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 7.

12. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 7.

13. A compound of claim 7, wherein:

$R^1$ is —C(O)NHOH;

$R^2$ is selected from the formula:

$$U-X-Y-Z-U^a-X^a-Y^a-Z^a$$

wherein:

U is absent or is selected from: O, $NR^a$, C(O), C(O)O, C(O)$NR^a$, $NR^a$C(O), S(O)$_p$, S(O)$_p NR^a$, and $NR^a$S(O)$_p$;

X is absent or selected from $C_{1-4}$ alkylene, $C_{2-4}$ alkenylene, and $C_{2-4}$ alkynylene;

Y is absent or selected from O, $NR^a$, S(O)$_p$, and C(O);

Z is absent or selected from a $C_{3-10}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^a$ is absent or is selected from: O, $NR^a$, C(O), C(O)O, C(O)$NR^a$, $NR^a$C(O), S(O)$_p$, S(O)$_p NR^a$, and $NR^a$S(O)$_p$;

$X^a$ is absent or selected from $C_{1-4}$ alkylene, $C_{2-4}$ alkenylene, and $C_{2-4}$ alkynylene;

$Y^a$ is absent or selected from O, $NR^a$, S(O)$_p$, and C(O);

$Z^a$ is selected from H, a $C_{3-10}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^3$ is selected from the formula:

$$U^1-X^1-Y^1-Z^1-U^{1a}-X^{1a}-Y^{1a}-Z^{1a}$$

wherein:

$U^1$ is absent or is selected from: O, $NR^a$, C(O), C(O)O, C(O)$NR^a$, $NR^a$C(O), S(O)$_p$, S(O)$_p NR^a$, and $NR^a$S(O)$_p$;

$X^1$ is absent or selected from $C_{1-4}$ alkylene, $C_{2-4}$ alkenylene, and $C_{2-4}$ alkynylene;

$Y^1$ is absent or selected from O, $NR^a$, S(O)$_p$, and C(O);

$Z^1$ is phenyl substituted with 0–5 $R^b$;

$U^{1a}$ is absent or is selected from: O, $NR^a$, C(O), C(O)O, C(O)$NR^a$, $NR^a$C(O), S(O)$_p$, S(O)$_p NR^a$, and $NR^a$S(O)$_p$;

$X^{1a}$ is absent or selected from $C_{1-4}$ alkylene, $C_{2-4}$ alkenylene, and $C_{2-4}$ alkynylene;

$Y^{1a}$ is absent or selected from O, $NR^a$, S(O)$_p$, and C(O);

$Z^{1a}$ is selected from H, a $C_{3-10}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^5$ is selected from:

$$U^2-X^2-Y^2-Z^2-U^{2a}-X^{2a}-Y^{2a}-Z^{2a}$$

wherein:

$U^2$ is absent or is selected from: O, $NR^a$, C(O), C(O)O, C(O)$NR^a$, $NR^a$C(O), S(O)$_p$, S(O)$_p NR^a$, and $NR^a$S(O)$_p$;

$X^2$ is absent or selected from $C_{1-4}$ alkylene, $C_{2-4}$ alkenylene, and $C_{2-4}$ alkynylene;

$Y^2$ is absent or selected from O, $NR^a$, S(O)$_p$, and C(O);

$Z^2$ is absent or selected from a $C_{3-10}$ carbocyclic residue substituted with 0–5 $R^b$ and a 5–14 membered heterocyclic system containing from 1–4 heteroatoms selected from the group consisting of N, O, and S substituted with 0–5 $R^b$;

$U^{2a}$ is absent or is selected from: O, $NR^a$, C(O), C(O)O, C(O)$NR^a$, $NR^a$C(O), S(O)$_p$, S(O)$_p NR^a$, and $NR^a$S(O)$_p$;

$X^{2a}$ is absent or selected from $C_{1-4}$ alkylene, $C_{2-4}$ alkenylene, and $C_{2-4}$ alkynylene;

$Y^{2a}$ is absent or selected from O, $NR^a$, S(O)$_p$, and C(O);

$Z^{2a}$ is selected from H, a $C_{3-10}$ carbocyclic residue substituted with 0–5 $R^c$ and a 5–14 membered heterocyclic system containing from 1–4 heteroatoms selected from the group consisting of N, O, and S substituted with 0–5 $R^c$;

E is $CH_2$.

14. A pharmaceutical composition comprising a pharmaceutically acceptable carrier and a therapeutically effective amount of a compound of claim 13.

15. A method of treating an inflammatory disease in a mammal comprising administering to the mammal in need of such treatment a therapeutically effective amount of a compound of claim 13.

16. A method of treating a condition or disease mediated by MMPs and/or TNF and/or aggrecanase in a mammal comprising administering to the mammal in need of such treatment a therapeutically effective amount of a compound of claim 13.

17. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 13.

18. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 13.

19. A compound of claim 13 wherein:

$R^5$ is selected from:

$$U^2-X^2-Y^2-Z^2-U^{2a}-X^{2a}-Y^{2a}-Z^{2a}$$

wherein:

$U^2$ is absent;

$X^2$ is absent or is $C_{1-4}$ alkylene;

$Y^2$ is absent;

$Z^2$ is absent or phenyl substituted with 0–3 $R^b$;

$U^{2a}$ is absent or is selected from: O and $NR^a$;

$X^{2a}$ is absent or is $C_{1-4}$ alkylene;

$Y^{2a}$ is absent or selected from O and $NR^a$; and $Z^{2a}$ is selected from H, a $C_{3-10}$ carbocyclic residue substituted with 0–3 $R^c$ and a 5–6 membered heterocyclic system containing from 1–2 heteroatoms selected from the group consisting of N, O, and S substituted with 0–3 $R^c$.

20. A pharmaceutical composition comprising a pharmaceutically acceptable carrier and a therapeutically effective amount of a compound of claim 19.

21. A method of treating an inflammatory disease in a mammal comprising administering to the mammal in need of such treatment a therapeutically effective amount of a compound of claim 19.

22. A method of treating a condition or disease mediated by MMPs and/or TNF and/or aggrecanase in a mammal comprising administering to the mammal in need of such treatment a therapeutically effective amount of a compound of claim 19.

23. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 19.

24. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 19.

25. A compound of claim 19 wherein:

$R^1$ is —C(O)NHOH;

$R^2$ is selected from the formula:

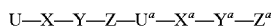

wherein:

U is absent or is selected from: $NR^a$, $C(O)NR^a$, $NR^aC(O)$, $S(O)_pNR^a$, and $NR^aS(O)_p$;

X is absent or is $C_{1-4}$ alkylene;

Y is absent;

Z is absent or selected from a $C_{3-7}$ cycloalkyl residue substituted with 0–3 $R^b$, phenyl substituted with 0–3 $R^b$, and a 5–10 membered heterocyclic system containing from 1–4 heteroatoms selected from the group consisting of N, O, and S substituted with 0–3 $R^b$;

$U^a$ is absent or is selected from: O and $NR^a$;

$X^a$ is absent or is $C_{1-4}$ alkylene;

$Y^a$ is absent or selected from O, $NR^a$, $S(O)_p$, and C(O);

$Z^a$ is selected from H, a $C_{3-7}$ cycloalkyl residue substituted with 0–3 $R^c$, phenyl substituted with 0–3 $R^c$, and a 5–10 membered heterocyclic system containing from 1–4 heteroatoms selected from the group consisting of N, O, and S substituted with 0–3 $R^c$;

$R^3$ is selected from the formula:

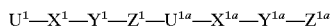

wherein:

$U^1$ is absent or is selected from: O, $NR^a$, C(O), C(O)O, $C(O)NR^a$, $NR^aC(O)$, $S(O)_p$, $S(O)_pNR^a$, and $NR^aS(O)_p$;

$X^1$ is absent or selected from $C_{1-4}$ alkylene, $C_{2-4}$ alkenylene, and $C_{2-4}$ alkynylene;

$Y^1$ is absent or selected from O, $NR^a$, $S(O)_p$, and C(O);

$Z^1$ is phenyl substituted with 0–5 $R^b$;

$U^{1a}$ is absent or is selected from: O, $NR^a$, C(O), C(O)O, $C(O)NR^a$, $NR^aC(O)$, $S(O)_p$, $S(O)_pNR^a$, and $NR^aS(O)_p$;

$X^{1a}$ is absent or selected from $C_{1-4}$ alkylene, $C_{2-4}$ alkenylene, and $C_{2-4}$ alkynylene;

$Y^{1a}$ is absent or selected from O, $NR^a$, $S(O)_p$, and C(O);

$Z^{1a}$ is selected from H, a $C_{5-10}$ carbocyclic residue substituted with 0–5 $R^c$ and a 5–14 membered heterocyclic system containing from 1–4 heteroatoms selected from the group consisting of N, O, and S substituted with 0–5 $R^c$;

$R^5$ is selected from:

wherein:

$U^2$ is absent;

$X^2$ is absent or is $C_{1-4}$ alkylene;

$Y^2$ is absent;

$Z^2$ is absent or phenyl substituted with 0–3 $R^b$;

$U^{2a}$ is absent or is selected from: O and $NR^a$;

$X^{2a}$ is absent or is $C_{1-4}$ alkylene;

$Y^{2a}$ is absent or selected from O and $NR^a$; and $Z^{2a}$ is selected from H, a $C_{5-10}$ carbocyclic residue substituted with 0–3 $R^c$ and a 5–6 membered heterocyclic system containing from 1–2 heteroatoms selected from the group consisting of N, O, and S substituted with 0–3 $R^c$.

26. A pharmaceutical composition comprising a pharmaceutically acceptable carrier and a therapeutically effective amount of a compound of claim 25.

27. A method of treating an inflammatory disease in a mammal comprising administering to the mammal in need of such treatment a therapeutically effective amount of a compound of claim 25.

28. A method of treating a condition or disease mediated by MMPs and/or TNF and/or aggrecanase in a mammal comprising administering to the mammal in need of such treatment a therapeutically effective amount of a compound of claim 25.

29. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 25.

30. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 25.

31. A compound is selected from the group consisting of:

N1-(2(R)-hydroxy-1(S)-indanyl)-N4-hydroxy-2(R)-isobutyl-butanediamide;

N1-(2(R)-hydroxy-1(S)-indanyl)-N4-hydroxy-2(R)-isobutyl-3(S)-(5-hydroxycarbonyl)-pentanamide;

N1-(2(R)-hydroxy-1(S)-indanyl)-N4-hydroxy-2(R)-isobutyl-3(S)-methyl-butanediamide;

N1-(2(R)-hydroxy-1(S)-indanyl)-N4-hydroxy-2(R)-isobutyl-3(S)-propyl-butanediamide;

N1-(2(R)-hydroxy-1(S)-indanyl)-N4-hydroxy-2(R)-hexyl-3(S)-propyl-butanediamide;

N1-[2(R)-hydroxy-1(S)-indanyl]-N4-hydroxy-2(R)-[(4-hydroxy-phenyl)methyl]butanediamide;

N1-[2(R)-hydroxy-1(S)-indanyl]-N4-hydroxy-2(R)-[(4-methoxy-phenyl)methyl]butanediamide;

N1-[1(S)-indanyl]-N4-hydroxy-2(R)-[(4-hydroxy-phenyl)methyl]butanediamide;

N1-[2(R)-hydroxy-1(S)-indanyl]-N4-hydroxy-2(R)-[3-phenyl-propyl]butanediamide;

N1-[2(R)-hydroxy-1(S)-indanyl]-N4-hydroxy-2(R)-[[4-(benzyloxy)-phenyl]methyl]butanediamide;

N1-[2(R)-hydroxy-1(S)-indanyl]-N4-hydroxy-2(R)-[[3-(benzyloxy)-phenyl]methyl]butanediamide;

N1-[2(R)-hydroxy-1(S)-indanyl]-N4-hydroxy-2(R)-[(3-hydroxy-phenyl)methyl]butanediamide;

N1-[2(R)-hydroxy-1(S)-indanyl]-N4-hydroxy-2(R)-[(4-fluoro-phenyl)methyl]butanediamide;

N1-[2(R)-hydroxy-1(S)-indanyl]-N4-hydroxy-2(R)-[(3,4-methylenedioxy-phenyl)methyl]butanediamide;

N1-[2(R)-hydroxy-1(S)-indanyl]-N4-hydroxy-2(R)-[(3-methoxy-phenyl)methyl]butanediamide;

N1-[2(R)-hydroxy-1(S)-indanyl]-N4-hydroxy-2(R)-[[4-(3-trifluoromethyl-phenyl)phenyl]methyl]butanediamide;

N1-[2(R)-hydroxy-1(S)-indanyl]-N4-hydroxy-2(R)-[[4-(2-tert-butylaminosulfonyl-phenyl)phenyl]methyl]-butanediamide;

N1-[2(R)-hydroxy-1(S)-indanyl]-N4-hydroxy-2(R)-[[4-(2-methoxy-phenyl)phenyl]methyl]butanediamide;

N1-[2(R)-hydroxy-1(S)-indanyl]-N4-hydroxy-2(R)-[[4-phenylphenyl]methyl]butanediamide;

N1-[2(R)-hydroxy-1(S)-indanyl]-N4-hydroxy-2(R)-[(3-hydroxy-4-methoxy-phenyl)methyl]butanediamide;

N1-[2(R)-hydroxy-1(S)-indanyl]-N4-hydroxy-2(R)-[[4-(2-chloro-phenyl)phenyl]methyl]butanediamide;

N1-[2(R)-hydroxy-1(S)-indanyl]-N4-hydroxy-2(R)-[[4-(benzofuran-2-yl)phenyl]methyl]butanediamide;

N1-[2(R)-hydroxy-1(S)-indanyl]-N4-hydroxy-2(R)-[[4-(2-methyl-phenyl)phenyl]methyl]butanediamide;

N1-[2(R)-hydroxy-1(S)-indanyl]-N4-hydroxy-2(R)-[[(3,4-methylenedioxy-phenyl)phenyl]methyl]butanediamide;

N1-[2(R)-hydroxy-1(S)-indanyl]-N4-hydroxy-2(R)-[[4-((tetrazol-2-yl-phenyl)phenyl]methyl]butanediamide;

N1-[2(R)-hydroxy-1(S)-indanyl]-N4-hydroxy-2(R)-[[3-phenylphenyl]methyl]butanediamide;

N1-[2(R)-hydroxy-1(S)-indanyl]-N4-hydroxy-2(R)-[[(3-methyl-phenyl)phenyl]methyl]butanediamide;

N1-[2(R)-hydroxy-1(S)-indanyl]-N4-hydroxy-2(R)-[(4-amino-phenyl)methyl]butanediamide;

N1-[2(R)-hydroxy-1(S)-indanyl]-N4-hydroxy-2(R)-[[((4-benzyloxy-carbonyl)amino)phenyl]methyl]butanediamide;

N1-[2(R)-hydroxy-1(S)-indanyl]-N4-hydroxy-2(R)-[[4-(2-hydroxymethylphenyl)phenyl]methyl]butanediamide;

N1-[2(R)-hydroxy-1(S)-indanyl]-N4-hydroxy-2(R)-[[4-(3,4,5-trimethoxy-phenyl)phenyl]methyl]butanediamide;

N1-[2(R)-hydroxy-1(S)-indanyl]-N4-hydroxy-2(R)-[[4-(2,4-di-methoxy-phenyl)phenyl]methyl]butanediamide;

N1-[2(R)-hydroxy-1(S)-indanyl]-N4-hydroxy-2(R)-[[4-(3,5-di-chloro-phenyl)phenyl]methyl]butanediamide;

N1-[2(R)-hydroxy-1(S)-indanyl]-N4-hydroxy-2(R)-[[4-(2-trifluoromethyl-phenyl)phenyl]methyl]butanediamide;

N1-[2(R)-hydroxy-1(S)-indanyl]-N4-hydroxy-2(R)-[[4-(3-isopropyl-phenyl)phenyl]methyl]butanediamide;

N1-[2(R)-hydroxy-1(S)-indanyl]-N4-hydroxy-2(R)-[[4-(2,4-dichloro-phenyl)phenyl]methyl]butanediamide;

N1-[2(R)-hydroxy-1(S)-indanyl]-N4-hydroxy-2(R)-[[4-(3-chloro-4-fluoro-phenyl)phenyl]methyl]butanediamide;

N1-[2(R)-hydroxy-1(S)-indanyl]-N4-hydroxy-2(R)-[[4-(p-toluenesulfonyl-amino)phenyl]methyl]butanediamide;

N1-[2(R)-hydroxy-1S)-indanyl]-N4-hydroxy-2(R)-phenylmethyl-3(S)-(tert-butyloxy-carbonyl-amino)-butanediamide;

N1-[2(R)-hydroxy-1(S)-indanyl]-N4-hydroxy-2(R)-[[4-(3,4-methylenedioxyphenyl)phenyl]methyl]-3(S)-(tert-butyloxy-carbonyl-amino)-butanediamide;

N1-[2(R)-hydroxy-1(S)-indanyl]-N4-hydroxy-2(R)-[[4-(3-methoxyphenyl)phenyl]methyl]butanediamide;

N1-[2(R)-hydroxy-1(S)-indanyl]-N4-hydroxy-2(R)-[[4-(3-fluorophenyl)phenyl]methyl]butanediamide;

N1-[2(R)-hydroxy-1(S)-indanyl]-N4-hydroxy-2(R)-[(3-fluoro-phenyl)methyl]-3(S)-(tert-butyloxy-carbonyl-amino)-butanediamide;

N1-[2(R)-hydroxy-1(S)-indanyl]-N4-hydroxy-2(R)-[(3-hydroxy-phenyl)methyl]-3(S)-(tert-butyloxy-carbonyl-amino)-butanediamide;

N1-[2(R)-hydroxy-1(S)-indanyl]-N4-hydroxy-2(R)-[[4-(3-nitrophenyl)phenyl]methyl]butanediamide;

N1-[2(R)-hydroxy-1(S)-indanyl]-N4-hydroxy-2(R)-[[4-(3-(methylsulfonyl-amino)-phenyl)phenyl]methyl]-butanediamide;

N1-[2(R)-hydroxy-1(S)-indanyl]-N4-hydroxy-2(R)-[(3-hydroxy-phenyl)methyl]-3(S)-(3-trimethylsilyl-propyl)-butanediamide;

N1-[2(R)-hydroxy-1(S)-indanyl]-N4-hydroxy-2(R)-[(3-hydroxy-phenyl)methyl]-3(S)-(2,2-dimethyl-propionamido)-butanediamide;

N1-[2(R)-hydroxy-1(S)-indanyl]-N4-hydroxy-2(R)-[(3-hydroxy-phenyl)methyl]-3(S)-(ethyloxy-carbonyl-amino)-butanediamide;

N1-[2(R)-hydroxy-1(S)-indanyl]-N4-hydroxy-2(R)-[(3-hydroxy-phenyl)methyl]-3(S)-(iso-butyloxy-carbonyl-amino)-butanediamide;

N1-[2(R)-hydroxy-1(S)-indanyl]-N4-hydroxy-2(R)-[(3-hydroxy-phenyl)methyl]-3(S)-(propionamido)-butanediamide;

N1-[2(R)-hydroxy-1(S)-indanyl]-N4-hydroxy-2(R)-[(3-hydroxy-phenyl)methyl]-3(S)-(1-methyl-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(2,2-dimethylpropyl-amino)-butanediamide;

N1-[2(R)-hydroxy-1(S)-indanyl]-N4-hydroxy-2(R)-[(3-hydroxy-phenyl)methyl]-3(S)-(methylsulfonyl-amino)-butanediamide;

N1-[2(R)-hydroxy-1(S)-indanyl]-N4-hydroxy-2(R)-[(3-hydroxy-phenyl)methyl]-3(S)-amino-butanediamide;

N1-[2(R)-hydroxy-1(S)-indanyl]-N4-hydroxy-2(R)-[(4-(methylsulfonylamino)-phenyl)methyl]-butanediamide;

N1-[2(R)-hydroxy-1(S)-indanyl]-N4-hydroxy-2(R)-[(3-hydroxy-phenyl)methyl]-3(S)-(cyclobutane Carboxamido-1-yl)-butanediamide;

N1-[2(R)-hydroxy-1(S)-indanyl]-N4-hydroxy-2(R)-[(3-hydroxy-phenyl)methyl]-3(S)-(2-hydroxymethyl-isobutanamide)-butanediamide;

N1-[2(R)-hydroxy-1(S)-indanyl]-N4-hydroxy-2(R)-[(3-hydroxy-phenyl)methyl]-3(S)-(1-hydroxyl-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(1-phenyl-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(bezene Carboxamido-1-yl)-butanediamide;

N1-[2(R)-hydroxy-1(S)-indanyl]-N4-hydroxy-2(R)-[(3-hydroxy-phenyl)methyl]-3(S)-(1-cyano-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(1-phenyl-cyclopentane Carboxamido-1-yl)-butanediamide;

N1-[2(R)-hydroxy-1(S)-indanyl]-N4-hydroxy-2(R)-[(3-hydroxy-phenyl)methyl]-3(S)-(1-methyl-cyclohexane Carboxamido-1-yl)-butanediamide;

N1-[2(R)-hydroxy-1(S)-indanyl]-N4-hydroxy-2(R)-[(3-hydroxy-phenyl)methyl]-3(S)-(2-indole carboxamido)-butanediamide;

N1-[2(R)-hydroxy-1(S)-indanyl]-N4-hydroxy-2(R)-[(3-hydroxy-phenyl)methyl]-3(S)-(2-furan carboxamido)-butanediamide;

N1-[2(R)-hydroxy-1(S)-indanyl]-N4-hydroxy-2(R)-[(3-hydroxy-phenyl)methyl]-3(S)-(2-quinoline carboxamido)-butanediamide;

N1-[2(R)-hydroxy-1(S)-indanyl]-N4-hydroxy-2(R)-[(3-hydroxy-phenyl)methyl]-3(S)-(3,4,5-trimethoxy benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-methyl-3-amino-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-methyl-6-amino-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(3-pyridine Carboxamido-1-yl)-butanediamide;

N1-[2(R)-hydroxy-1(S)-indanyl]-N4-hydroxy-2(R)-[(3-hydroxy-phenyl)methyl]-3(S)-(1-(2,4-dichloro-phenyl)-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(1-(4-chloro-phenyl)-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(3-methylsulfonyl)-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-methylsulfonyl-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(3-cyano-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(6-quinoline carboxamido)-butanediamide;

N1-[2(R)-hydroxy-1(S)-indanyl]-N4-hydroxy-2(R)-[(3-hydroxy-phenyl)methyl]-3(S)-(1-ethyl,3-methyl-pyrazole 5-carboxamido)-butanediamide;

N1-[2(R)-hydroxy-1(S)-indanyl]-N4-hydroxy-2(R)-[(3-hydroxy-phenyl)methyl]-3-(4-morpholino-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-chloro-4-methylsulfonyl-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(4-(imidazol-1-yl) benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-thiophene Carboxamido-1-yl)-butanediamide;

N1-[2(R)-hydroxy-1(S)-indanyl]-N4-hydroxy-2(R)-[(3-hydroxy-phenyl)methyl]-3(S)-(1-tert-butyl, 3-methyl-pyrazole 5-carboxamido)-butanediamide;

N1-[2(R)-hydroxy-1(S)-indanyl]-N4-hydroxy-2(R)-[(3-hydroxy-phenyl)methyl]-3(S)-(4-aminomethyl benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-hydroxyl-isobutanamido)-butanediamide;

N1-[2(R)-hydroxy-1(S)-indanyl]-N4-hydroxy-2(R)-[(3-hydroxy-phenyl)methyl]-3(S)-(cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(cyclopentane Carboxamido-1-yl)-butanediamide;

N1-[2(R)-hydroxy-1(S)-indanyl]-N4-hydroxy-2(R)-[(3-hydroxy-phenyl)methyl]-3(S)-(2-cyclopentyl acetamido)-butanediamide;

N1-[2(R)-hydroxy-1(S)-indanyl]-N4-hydroxy-2(R)-[(3-hydroxy-phenyl)methyl]-3(S)-(cyclohexane Carboxamido-1-yl)-butanediamide;

N1-[2(R)-hydroxy-1(S)-indanyl]-N4-hydroxy-2(R)-[(3-hydroxy-phenyl)methyl]-3(S)-(4-(4-N-Boc-piperazinyl-1-yl)benzene Carboxamido-1-yl)-butanediamide;

N1-[2(R)-hydroxy-1(S)-indanyl]-N4-hydroxy-2(R)-[(3-hydroxy-phenyl)methyl]-3(S)-(4-(piperazinyl-1-yl) benzene Carboxamido-1-yl)-butanediamide;

N1-[2(R)-hydroxy-1(S)-indanyl]-N4-hydroxy-2(R)-[(3-hydroxy-phenyl)methyl]-3(S)-(2-fluoro-6-chloro-benzene Carboxamido-1-yl)-butanediamide;

N1-[2(R)-hydroxy-1(S)-indanyl]-N4-hydroxy-2(R)-[(3-hydroxy-phenyl)methyl]-3(S)-(1-amino-cyclohexane Carboxamido-1-yl)-butanediamide;

N1-[2(R)-hydroxy-1(S)-indanyl]-N4-hydroxy-2(R)-[(3-hydroxy-phenyl)methyl]-3(S)-(2-methylthio-acetamido)-butanediamide;

N1-[2(R)-hydroxy-1(S)-indanyl]-N4-hydroxy-2(R)-[(3-hydroxy-phenyl)methyl]-3(S)-(2-methoxy-acetamido)-butanediamide;

N1-[2(R)-hydroxy-1(S)-indanyl]-N4-hydroxy-2(R)-[(3-hydroxy-phenyl)methyl]-3(S)-(1-allyl-cyclopentane Carboxamido-1-yl)-butanediamide;

N1-[2(R)-hydroxy-1(S)-indanyl]-N4-hydroxy-2(R)-[(3-hydroxy-phenyl)methyl]-3(S)-(1-n-propyl-cyclopentane Carboxamido-1-yl)-butanediamide;

N1-[2(R)-hydroxy-1(S)-indanyl]-N4-hydroxy-2(R)-[(3-hydroxy-phenyl)methyl]-3(S)-(1-allyl-cyclopropane Carboxamido-1-yl)-butanediamide;

N1-[2(R)-hydroxy-1(S)-indanyl]-N4-hydroxy-2(R)-[(3-hydroxy-phenyl)methyl]-3(S)-(8-quinoline-sulfonamido)-butanediamide;

N1-[2(R)-hydroxy-1(S)-indanyl]-N4-hydroxy-2(R)-[(3-hydroxy-phenyl)methyl]-3(S)-(4-nitro-benzene sulfonamido)-butanediamide;

N1-[2(R)-hydroxy-1(S)-indanyl]-N4-hydroxy-2(R)-[(3-hydroxy-phenyl)methyl]-3(S)-(1,4-di-methyl-2-chloro-pyrazole-3-sulfonamido)-butanediamide;

N1-[2(R)-hydroxy-1(S)-indanyl]-N4-hydroxy-2(R)-[(3-hydroxy-phenyl)methyl]-3(S)-(1,5-dimethyl-isoxazole 3-sulfonamido)-butanediamide;

N1-[2(R)-hydroxy-1(S)-indanyl]-N4-hydroxy-2(R)-[(3-hydroxy-phenyl)methyl]-3(S)-(1-methyl-imidazole 3-sulfonamido)-butanediamide;

N1-[2(R)-hydroxy-1(S)-indanyl]-N4-hydroxy-2(R)-[(3-hydroxy-phenyl)methyl]-3(S)-(benzene sulfonamido)-butanediamide;

N1-[2(R)-hydroxy-1(S)-indanyl]-N4-hydroxy-2(R)-[(3-hydroxy-phenyl)methyl]-3(S)-(1,4-dimethyl pyrazole 3-sulfonamido)-butanediamide;

N1-[2(R)-hydroxy-1(S)-indanyl]-N4-hydroxy-2(R)-[(3-hydroxy-phenyl)methyl]-3(S)-(2-methylsulfonyl benzene sulfonamido-1-yl)-butanediamide;

N1-[2(R)-hydroxy-1(S)-indanyl]-N4-hydroxy-2(R)-[(3-hydroxy-phenyl)methyl]-3(S)-(cyclohexylamino)-butanediamide;

N1-[2(R)-hydroxy-1(S)-indanyl]-N4-hydroxy-2(R)-[(3-hydroxy-phenyl)methyl]-3(S)-(iso-propylamino)-butanediamide;

N1-[2(R)-hydroxy-1(S)-indanyl]-N4-hydroxy-2(R)-[4-(2-trifluoromethylphenyl)-phenylmethyl]-3(S)-(2,2-dimethylpropyl-amino)-butanediamide;

N1-[2(R)-hydroxy-1(S)-indanyl]-N4-hydroxy-2(R)-[(3-hydroxy-phenyl)methyl]-3(S)-(cyclopentylamino)-butanediamide;

N1-[2(R)-hydroxy-1(S)-indanyl]-N4-hydroxy-2(R)-[(3-hydroxy-phenyl)methyl]-3(S)-(cyclopropylmethyl)-butanediamide;

N1-[2(R)-hydroxy-1(S)-indanyl]-N4-hydroxy-2(R)-[(3-hydroxy-phenyl)methyl]-3(S)-(benzylamino)-butanediamide;

N1-[2(R)-hydroxy-1(S)-indanyl]-N4-hydroxy-2(R)-[(3-hydroxy-phenyl)methyl]-3(S)-(2-furanylmethylamino)-butanediamide;

N1-[2(R)-hydroxy-1(S)-indanyl]-N4-hydroxy-2(R)-[(3-hydroxy-4-methylphenyl)methyl]-3(S)-(3-cyanophenylmethylamino)-butanediamide;

N1-[2(R)-hydroxy-1(S)-indanyl]-N4-hydroxy-2(R)-[(3-hydroxy-phenyl)methyl]-3(S)-(2,2-dimethylpropyl-amino)-butanediamide;

N1-[2(R)-hydroxy-1(S)-indanyl]-N4-hydroxy-2(R)-[(3-hydroxy-phenyl)methyl]-3(S)-(2-pentylamino)-butanediamide;

N1-[2(R)-hydroxy-1(S)-indanyl]-N4-hydroxy-2(R)-[(3-hydroxy-phenyl)methyl]-3(S)-(bis-cyclopropylmethylamino)-butanediamide;

N1-[2(R)-hydroxy-1(S)-indanyl]-N4-hydroxy-2(R)-[(3-hydroxy-phenyl)methyl]-3(S)-(2-thiophenylmethylamino)-butanediamide;

N1-[2(R)-hydroxy-1(S)-indanyl]-N4-hydroxy-2(R)-[(3-hydroxy-phenyl)methyl]-3()-(2-methyl-propylamino)-butanediamide;

or a pharmaceutically acceptable salt form or a steroisomer thereof.

32. A pharmaceutical composition comprising a pharmaceutically acceptable carrier and a therapeutically effective amount of a compound of claim 31.

33. A method of treating an inflammatory disease in a mammal comprising administering to the mammal in need of such treatment a therapeutically effective amount of a compound of claim 31.

34. A method of treating a condition or disease mediated by MMPs and/or TNF and/or aggrecanase in a mammal comprising administering to the mammal in need of such treatment a therapeutically effective amount of a compound of claim 31.

35. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal comprising administering to the mammal in need of such treatment a therapeutically effective amount of a compound of claim 31.

36. A method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 31.

* * * * *